United States Patent
Valentin et al.

(10) Patent No.: US 7,112,717 B2
(45) Date of Patent: Sep. 26, 2006

(54) HOMOGENTISATE PRENYL TRANSFERASE GENE (HPT2) FROM ARABIDOPSIS AND USES THEREOF

(75) Inventors: Henry E. Valentin, Chesterfield, MO (US); Tyamagondlu V. Venkatesh, St. Louis, MO (US); Karunanandaa Balasulojini, Creve Coeur, MO (US)

(73) Assignee: Monsanto Technology LLC, St. Louis, MO (US)

( * ) Notice: Subject to any disclaimer, the term of this patent is extended or adjusted under 35 U.S.C. 154(b) by 404 days.

(21) Appl. No.: 10/391,363

(22) Filed: Mar. 18, 2003

(65) Prior Publication Data

US 2003/0213017 A1  Nov. 13, 2003

Related U.S. Application Data

(60) Provisional application No. 60/365,202, filed on Mar. 19, 2002.

(51) Int. Cl.
C12N 15/82 (2006.01)
C12N 15/29 (2006.01)
C12N 5/14 (2006.01)

(52) U.S. Cl. ............. 800/278; 536/23.2; 536/23.6; 435/419; 435/468

(58) Field of Classification Search ............... None
See application file for complete search history.

(56) References Cited

U.S. PATENT DOCUMENTS

| | | | |
|---|---|---|---|
| 4,727,219 A | 2/1988 | Brar et al. |
| 5,304,478 A | 4/1994 | Bird et al. |
| 5,429,939 A | 7/1995 | Misawa et al. |
| 5,432,069 A | 7/1995 | Grüninger et al. |
| 5,545,816 A | 8/1996 | Ausich et al. |
| 5,618,988 A | 4/1997 | Hauptmann et al. |
| 5,684,238 A | 11/1997 | Ausich et al. |
| 5,693,507 A | 12/1997 | Daniell et al. |
| 5,750,865 A | 5/1998 | Bird et al. |
| 5,792,903 A | 8/1998 | Hirschberg et al. |
| 5,876,964 A | 3/1999 | Croteau et al. |
| 5,908,940 A | 6/1999 | Lane et al. |
| 6,281,017 B1 | 8/2001 | Croteau et al. |
| 6,303,365 B1 | 10/2001 | Martin et al. |
| 6,541,259 B1 | 4/2003 | Lassner et al. |
| 2002/0069426 A1 | 6/2002 | Boronat et al. |
| 2002/0108148 A1 | 8/2002 | Boronat et al. |
| 2003/0148300 A1 | 8/2003 | Valentin et al. |
| 2003/0150015 A1 | 8/2003 | Norris et al. |
| 2003/0154513 A1 | 8/2003 | van Eenennaam et al. |
| 2003/0166205 A1 | 9/2003 | van Eenennaam et al. |
| 2003/0170833 A1 | 9/2003 | Lassner et al. |
| 2003/0176675 A1 | 9/2003 | Valentin et al. |
| 2003/0213017 A1 | 11/2003 | Valentin et al. |
| 2004/0018602 A1 | 1/2004 | Lassner et al. |
| 2004/0045051 A1 | 3/2004 | Norris et al. |

FOREIGN PATENT DOCUMENTS

| | | |
|---|---|---|
| CA | 2339519 | 2/2000 |
| CA | 2343919 | 3/2000 |
| CA | 2372332 | 11/2000 |
| DE | 198 35 219 A1 | 8/1998 |
| EP | 0 531 639 A2 | 3/1993 |
| EP | 0 531 639 A3 | 3/1993 |
| EP | 0 674 000 A2 | 9/1995 |
| EP | 0 723 017 A2 | 7/1996 |
| EP | 0 763 542 A2 | 3/1997 |
| EP | 1 033 405 A2 | 9/2000 |
| EP | 1 063 297 A1 | 12/2000 |
| FR | 2 778 527 | 11/1999 |
| GB | 560529 | 4/1944 |
| WO | WO 91/02059 | 2/1991 |
| WO | WO 91/09128 | 6/1991 |
| WO | WO 91/13078 | 9/1991 |
| WO | WO 93/18158 | 9/1993 |
| WO | WO 94/11516 | 5/1994 |
| WO | WO 94/12014 | 6/1994 |
| WO | WO 94/18337 | 8/1994 |
| WO | WO 95/08914 | 4/1995 |
| WO | WO 95/18220 | 7/1995 |
| WO | WO 95/23863 | 9/1995 |
| WO | WO 95/34668 | 12/1995 |
| WO | WO 96/02650 | 2/1996 |
| WO | WO 96/06172 | 2/1996 |
| WO | WO 96/13149 | 5/1996 |
| WO | WO 96/13159 | 5/1996 |
| WO | WO 96/36717 A2 | 11/1996 |
| WO | WO 96/36717 A3 | 11/1996 |
| WO | WO 96/38567 | 12/1996 |
| WO | WO 97/17447 | 5/1997 |
| WO | WO 97/27285 | 7/1997 |
| WO | WO 97/49816 | 12/1997 |

(Continued)

OTHER PUBLICATIONS

Blastn database search results, AAC40232.

(Continued)

*Primary Examiner*—Ashwin D. Mehta
*Assistant Examiner*—Cathy Kingdon Worley
(74) *Attorney, Agent, or Firm*—Fulbright & Jaworski L.L.P.

(57) ABSTRACT

The present invention is in the field of plant genetics and biochemistry. More specifically, the present invention relates to genes and polypeptides associated with the tocopherol biosynthesis pathway, namely those encoding homogentisate prenyl transferase activity, and uses thereof. In particular, the sequence of the HPT2 gene from *Arabidopsis thaliana* is disclosed for expression in any plant species to increase the levels of tocopherol.

31 Claims, 47 Drawing Sheets

FOREIGN PATENT DOCUMENTS

| | | |
|---|---|---|
| WO | WO 98/04685 | 2/1998 |
| WO | WO 98/06862 | 2/1998 |
| WO | WO 98/18910 | 5/1998 |
| WO | WO 99/04021 | 1/1999 |
| WO | WO 99/04622 | 2/1999 |
| WO | WO 99/06580 | 2/1999 |
| WO | WO 99/07867 | 2/1999 |
| WO | WO 99/11757 | 3/1999 |
| WO | WO 99/19460 | 4/1999 |
| WO | WO 99/55889 | 11/1999 |
| WO | WO 99/58649 | 11/1999 |
| WO | WO 00/01650 | 1/2000 |
| WO | WO 00/08169 | 2/2000 |
| WO | WO 00/08187 | 2/2000 |
| WO | WO 00/10380 | 3/2000 |
| WO | WO 00/11165 | 3/2000 |
| WO | WO 00/14207 | 3/2000 |
| WO | WO 00/17233 | 3/2000 |
| WO | WO 00/22150 A3 | 4/2000 |
| WO | WO 00/28005 | 5/2000 |
| WO | WO 00/32757 A2 | 6/2000 |
| WO | WO 00/32757 A3 | 6/2000 |
| WO | WO 00/34448 | 6/2000 |
| WO | WO 00/42205 A2 | 7/2000 |
| WO | WO 00/42205 A3 | 7/2000 |
| WO | WO 00/46346 | 8/2000 |
| WO | WO 00/61771 | 10/2000 |
| WO | WO 00/63389 | 10/2000 |
| WO | WO 00/63391 | 10/2000 |
| WO | WO 00/65036 A2 | 11/2000 |
| WO | WO 00/65036 A3 | 11/2000 |
| WO | WO 00/68393 | 11/2000 |
| WO | WO 01/04330 | 1/2001 |
| WO | WO 01/09341 | 2/2001 |
| WO | WO 01/12827 | 2/2001 |
| WO | WO 01/21650 | 3/2001 |
| WO | WO 01/44276 | 6/2001 |
| WO | WO 01/62781 | 8/2001 |
| WO | WO 01/79472 | 10/2001 |
| WO | WO 01/88169 A2 | 11/2001 |
| WO | WO 01/88169 A3 | 11/2001 |
| WO | WO 02/00901 A1 | 1/2002 |
| WO | WO 02/26933 | 4/2002 |
| WO | WO 02/29022 | 4/2002 |
| WO | WO 02/31173 | 4/2002 |
| WO | WO 02/33060 | 4/2002 |
| WO | WO 02/46441 | 6/2002 |
| WO | WO 02/072848 | 9/2002 |
| WO | WO 02/089561 | 11/2002 |
| WO | WO 03/034812 | 5/2003 |
| WO | WO 03/047547 | 6/2003 |

OTHER PUBLICATIONS

Blastn database search results, AAG24033.
Blastn database search results.
Blastn database search results.
Blastn database search results.
Blastn database search results.
International Search Report, PCT /US03/08468, pp. 1-5 (Jan. 11, 2005).
Subramaniam et al., Database STIC, Accession No. AX360884 (Feb. 2002).
Bowie et al., "Deciphering the Message in Protein Sequences: Tolerance to Amino Acid Substitutions", Science, 247:1306-1310 (1990).
McConnell et al., "Role of Phabulosa and Phavoluta in determining radial patterning in shoots", Nature, 411(6838): 709-713 (2001).
Baker et al., NCBI Accession No. X64451 (Dec. 1993).
Addlesee et al., "Cloning, sequencing and functional assignment of the chlorophyll biosyntheses gene, chlP, of Synechocystis sp. PCC 6803", FEBS Letters 389 (1996) 126-130.
Arango et al., "Tocopherol synthesis from homogentisate in Capsicum anuum L. (yellow pepper) chromoplast membranes: evidence for tocopherol cyclase", Biochem J., 336:531-533 (1998).
Arigoni et al., "Terpenoid biosynthesis from 1-deoxy-o-xylulose in higher plants by intramolecular skeletal rearrangement", Proc. Natl. Acad. Sci. USA, 94:10600-10605 (1997).
Baker et al., "Sequence and characterization of the gcpE gene of Escherichia coli", FEMS Microbiology Letters, 94:175-180 (1992).
Bayley et al., "Engineering 2,4-D resistance into cotton," Theor Appl Genet, 83:645-649 (1992).
Bentley, R., "The Shikimate Pathway—A Metabolic Tree with Many Branches," Critical Reviews™ in Biochemistry and Molecular Biology; vol. 25, Issue 5, 307-384 (1990).
Bevan, M., "Binary Agrobacterium vectors for plant transformation", Nucleic Acids Research, 12:8711-8721 (1984).
Beyer et al., "Phytoene-forming activities in wild-type and transformed rice endosperm," IRRN 21:2-3, p. 44-45 (Aug.-Dec. 1996).
Bork et al., "Go hunting in sequence databases but watch out for the traps", TIG 12, 10:425-427 (Oct. 1996).
Bouvier et al., "Dedicated Roles of Plastid Transketolases during the Early Onset of Isoprenoid Biogenesis in Pepper Fruits", Plant Physiol., 117:1423-1431 (1998).
Bramley et al., "Biochemical characterization of transgenic tomato plants in which carotenoid synthesis has been inhibited through the expression of antisense RNA to pTOM5," The Plant Journal, 2(3), 343-349 (1992).
Breitenbach et al., "Expression in Escherichia coli and properties of the carotene ketolase from Haematococcus pluvialis, " FEMS Microbiology Letters 140, 241-246 (1996).
Broun et al., "Catalytic Plasticity of Fatty Acid Modification Enzymes Underlying Chemical Diversity of Plant Lipids," Science, 282:1315-1317 (1998).
Buckner et al., "The y1 Gene of Maize Codes for Phytoene Synthase," Genetics 143:479-488 (May 1996).
Burkhardt et al., "Genetic engineering of provitamin A biosynthesis in rice endosperm," Experientia, 818-821.
Burkhardt et al., "Transgenic rice (Oryza sativa) endosperm expressing daffodil (Narcissus pseudonarcissus) phytoene synthase accumulates phytoene, a key intermediate of provitamin A biosynthesis" The Plant Journal, 11(5), 1071-1078 (1997).
Cahoon et al., "Production of Fatty Acid Components of Meadowfoam Oil in Somatic Soybean Embryos," Plant Physiology, 124:243-251 (2000).
Chaudhuri et al., "The purification of shikimate dehydrogenase from Escherichia coli," Biochem. J., 226:217-223 (1985).
Cheng et al., "Highly Divergent Methyltransferases Catalyze a Conserved Reaction in Tocopherol and Plastoquinone Synthesis in Cyanobacteria and Photosynthetic Eukaryotes", The Plant Cell, 15:2343-2356 (2003).
Collakova et al., "Isolation and Functional Analysis of Homogentisate Phytyltransferase from Synechocystis sp. PCC 6803 and Arabidopsis", Plant Physiology, 127:1113-1124 (2001).
Collakova et al., "Homogentisate Phytyltransferase Activity is Limiting for Tocopherol Biosynthesis in Arabidopsis", Plant Physiology, 131:632-642 (Feb. 2003).
Collakova et al., "Isolation and Characterization of Tocopherol Prenyl Transferase From Synechocystis and Arabidopsis", Poster Abstract see REN-01-026.
Cook et al., "Nuclear Mutations affecting plastoquinone accumulation in maize", Photosynthesis Research, 31:99-111 (1992).
Cunillera et al., "Characterization of dehydrodolichyl diphosphate synthase of Arabidopsis thaliana, a key enzyme in dolichol biosynthesis", FEBS Letters, 477:170-174 (2000).
d'Amato et al., "Subcellular localization of chorismate-mutase isoenzymes in protoplasts from mesophyll and suspension-cultured cells of Nicotiana silvestris," Planta, 162:104-108 (1984).
Doerks et al., "Protein annotation: detective work for function prediction", TIG, 14:248-250 (1998).
d'Harlingue et al., "Plastid Enzymes of Terpenoid Biosynthesis, Purification and Characterization of Tocopherol Methyltransferase from *Capsicum* Chromoplasts," The Journal of Biological Chemistry, vol. 260, No. 28, pp. 15200-15203, Dec. 5, 1985.

De Luca, Vincenzo, "Molecular characterization of secondary metabolic pathways", AgBiotech News and Information, 5(6):225N-229N (1993).

Duncan et al., "The overexpression and complete amino acid sequence of *Escherichia coli* 3-dehydroquinase", Biochem. J., 238:475-483 (1986).

Duvold et al., "Incorporation of 2-C-Methyl-D-erythritol, a Putative Isoprenoid Precursor in the Mevalonate-Independent Pathway, into Ubiquinone and Menaquinone of *Escherichia coli*", Tetrahedron Letters, 38(35):6181-6184 (1997).

Elliott, Thomas, "A Method for Constructing Single-Copy *lac* Fusions in *Salmonella typhimurium* and Its Application to the *hemA-prfA* Operon", Journal of Bacteriology, 174:245-253 (1992).

Eisenreich et al., "The deoxyxylulose phosphate pathway of terpenoid biosynthesis in plants and microorganisms", Chemistry & Biology, 5(9):R221-R233 (1998).

Ericson et al., "Analysis of the promoter region of napin genes from *Brassica napus* demonstrates binding of nuclear protein *in vitro* to a conserved sequence motif", Eur. J. Biochem., 197:741-746 (1991).

Estévez et al., "1-Deoxy-D-xylulose-5-phosphate Synthase, a Limiting Enzyme for Plastidic Isoprenoid Biosynthesis in Plants", The Journal of Biological Chemistry, 276(25):22901-22909 (2001).

Fellermeier et al., "Cell-free conversion of 1-deoxy-D-xylulose 5-phosphate and 2-C-methyl-D-erythritol 4-phosphate into β-carotene in higher plants and its inhibition by fosmidomycin", Tetrahedron Letters, 40:2743-2746 (1999).

Fiedler et al., "The formation of homogentisate in the biosynthesis of tocopherol and plastoquinone in spinach chloroplasts", Planta, 155:511-515 (1982).

Fourgoux-Nicol et al., "Isolation of rapeseed genes expressed early and specifically during development of the male gametophyte", Plant Molecular Biology, 40:857-872 (1999).

Fraser et al., "Enzymic confirmation of reactions involved in routes to astaxanthin formation, elucidated using a direct substrate *in vitro* assay", Eur. J. Biochem., 252:229-236 (1998).

Fraser et al., "*In Vitro* Characterization of Astaxanthin Biosynthetic Enzymes", The Journal of Biological Chemistry, 272(10) 6128-6135 (1997).

Fray et al., "Constitutive expression of a fruit phytoene synthase gene in transgenic tomatoes causes dwarfism by redirecting metabolites from the gibberellin pathway", The Plant Journal, 8(5):693-701 (1995).

Fray et al., "Identification and genetic analysis of normal and mutant phytoene synthase genes of tomato by sequencing, complementation and co-suppression", Plant Molecular Biology, 22:589-602 (1993).

Fuqua et al., "Characterization of *melA*: a gene encoding melanin biosynthesis from the marine bacterium *Shewanella colwelliana*", Gene, 109:131-136 (1991).

Furuya et al., "Production of Tocopherols by Cell Culture of Safflower", Phytochemistry, 26(10):2741-2747 (1987).

Garcia et al., "Subcellular localization and purification of a *p*-hydroxyphenylpyruvate dioxygenase from cultured carrot cells and characterization of the corresponding cDNA", Biochem. J., 325:761-769 (1997).

Gaubier et al., "A chlorophyll synthetase gene from *Arabidopsis thaliana*", Mol. Gen. Genet., 249:58-64 (1995).

Goers et al., "Separation and characterization of two chorismate-mutase isoenzymes from *Nicotiana silvestris*", Planta, 162:109-116 (1984).

Graβse et al., "Loss of α-tocopherol in tobacco plants with decreased geranylgeranyl reductase activity does not modify photosynthesis in optimal growth conditions but increases sensitivity to high-light stress", Planta, 213:620-628 (2001).

Harker et al., "Biosynthesis of ketocarotenoids in transgenic cyanobacteria expressing the algal gene for β-C-4-oxygenase, *crtO*", FEBS Letters, 404:129-134 (1997).

Harker et al., "Expression of prokaryotic 1-deoxy-D-xylulose-5-phosphatases in *Escherichia coli* increases carotenoid and ubiquinone biosynthesis", FEBS Letters, 448:115-119 (1999).

Hecht et al., "Studies of the nonmevalonate pathway to terpenes: The role of the GcpE (IspG) protein", PNAS, 98(26):14837-14842 (2001).

Herrmann, K.M., "The Shikimate Pathway as an Entry to Aromatic Secondary Metabolism", Plan Physiol., 107:7-12 (1995).

Herz et al., "Biosynthesis of terpenoids: YgbB protein converts 4-diphosphocytidyl-2C-methyl-D-erythritol 2-phosphate to 2C-methyl-D-erythritol 2,4-cyclodiphosphate", Proc. Natl. Acad. Sci. USA, 97(6):2486-2490 (2000).

Kajiwara et al., "Isolation and functional identification of a novel cDNA for astaxanthin biosynthesis from *Haematococcus pluvialis*, and astaxanthin synthesis in *Escherichia coli*", Plant Molecular Biology, 29:343-352 (1995).

Kaneko et al., "Complete Genomic Sequence of the Filamentous Nitrogen-fixing Cyanobacterium *Anabaena* sp. Strain PCC 7120", DNA Research, 8(5):205-213 (2001).

Keegstra, K., "Transport and Routing of Proteins into Chloroplasts", Cell, 56(2):247-253 (1989).

Keller et al., "Metabolic compartmentation of plastid prenyllipid biosynthesis Evidence for the involvement of a multifunctional geranylgeranyl reductase", Eur. J. Biochem., 251:413-417 (1998).

Kishore et al., "Amino Acid Biosynthesis Inhibitors as Herbicides", Ann. Rev. Biochem., 57:627-663 (1988).

Koziel et al., "Optimizing expression of transgenes with an emphasis on post-transcriptional events", Plant Molecular Biology, 32:393-405 (1996).

Kumagai et al., "Cytoplasmic inhibition of carotenoid biosynthesis with virus-derived RNA", Proc. Natl. Acad. Sci. USA, 92:1679-1683 (1995).

Kuntz et al., "Identification of a cDNA for the plastid-located geranylgeranyl pyrophosphate synthase from *Capsicum annuum*: correlative increase in enzyme activity and transcript level during fruit ripening", The Plant Journal, 2(1):25-34 (1992).

Lange et al., "A Family of transketolases that directs isoprenoid biosynthesis via a mevalonate-independent pathway", Proc. Natl. Acad. Sci. USA, 95:2100-2104 (1998).

Lange et al., "Isoprenoid Biosyntheis via a Mevalonate-Independent Pathway in Plants: Cloning and Heterologous Expression of 1-Deoxy-D-xylulose-5-phosphate Reductoisomerase from Peppermint", Archives of Biochemistry and Biophysics, 365(1):170-174 (1999).

Li et al., "Identification of a maize endosperm-specific cDNA encoding farnesyl pyrophosphate synthetase", Gene, 171:193-196 (1996).

Linthorst et al., "Constitutive Expression of Pathogenesis-Related Proteins PR-1,GRP, and PR-S in Tobacco Has No Effect on Virus Infection", The Plant Cell, 1:285-291 (1989).

Lois et al., "Cloning and characterization of a gene from *Escherichia coli* encoding a transketolase-like enzyme that catalyzes the synthesis of D-1-deoxyxylulose 5-phosphate, a common precursor for isoprenoid, thiamin, and pyridoxol biosynthesis", Proc. Natl. Acad. Sci. USA, 95(5):2105-2110 (1998).

Lopez et al., "Sequence of the *bchG* Gene from *Chloroflexus aurantiacus*: Relationship between Chlorophyll Synthase and other Polyprenyltransferases", Journal of Bacteriology, 178(11):3369-3373 (1996).

Lotan et al., "Cloning and expression in *Escherichia coli* of the gene encoding β-C-4-oxygenase, that converts β-carotene to the ketocarotenoid canthaxanthin in *Haematococcus pluvialis*", FEBS Letters, 364:125-128 (1995).

Mahmoud et al., "Metabolic engineering of essential oil yield and composition in mint by altering expression of deoxyxylulose phosphate reductoisomerase and menthofuran synthase", PNAS, 98(15):8915-8920 (2001).

Mandel et al., "*CLA1*, a novel gene required for chloroplast development, is highly conserved in evolution", The Plant Journal, 9(5):649-658 (1996).

Marshall et al., "Biosynthesis of Tocopherols: A Re-Examination of the Biosynthesis and Metabolism of 2-Methyl-6-Phytyl-1,4-Benzoquinol", Phytochemistry, 24(8):1705-1711 (1985).

Misawa et al., "Expression of an *Erwinia* phytoene desaturase gene not only confers multiple resistance to herbicides interfering with carotenoid biosynthesis but also alters xanthophyll metabolism in transgenic plants", The Plant Journal, 6(4):481-489 (1994).
Misawa et al., "Elucidation of the *Erwinia uredovora* Carotenoid Biosynthetic Pathway by Functional Analysis of Gene Products Expressed in *Escherichia coli*", Journal of Bacteriology, 172(12):6704-6712 (1990).
Misawa et al., "Functional expression of the *Erwinia uredovora* carotenoid biosynthesis gene *crtl* in transgenic plants showing an increase of β-carotene biosynthesis activity and resistance to the bleaching herbicide norflurazon", The Plant Journal, 4(5):833-840 (1993).
Misawa et al., "Structure and Functional Analysis of a Marine Bacterial Carotenoid Biosynthesis Gene Cluster and Astaxanthin Biosynthetic Pathway Proposed at the Gene Level", Journal of Bacteriology, 177(22):6575-6584 (1995).
Nakamura et al., "Structural Analysis of *Arabidopsis thaliana* Chromosome 5. III. Sequence Features of the Regions of 1,191,918 bp Covered by Seventeen Physically Assigned P1 Clones", DNA Research, 4(6):401-414 (1997).
Nawrath et al., "Targeting of the polyhydroxybutyrate biosynthetic pathway to the plastids of *Arabidopsis thaliana* results in high levels of polymer accumulation", Proc. Natl. Acad. Sci. USA, 91:12760-12764 (1994).
Norris et al., "Genetic Dissection of Carotenoid Synthesis in Arabidopsis Defines Plastoquinone as an Essential Component of Phytoene Desaturation", The Plant Cell, 7:2139-2149 (1995).
Norris et al., "Complementation of the Arabidopsis *pds1* Mutation with the Gene Encoding *p*-Hydroxyphenylpyruvate Dioxygenase", Plant Physiol., 117:1317-1323 (1998).
Oh et al., "Molecular Cloning, Expression, and Functional Analysis of a *cis*-Prenyltransferase from *Arabidopsis thaliana*", The Journal of Biological Chemistry, 275(24):18482-18488 (2000).
Okada et al., "Five Geranylgeranyl Diphosphate Synthases Expressed in Different Organs Are Localized into Three Subcellular Compartments in Arabidopsis", Plant Physiology, 122:1045-1056 (2000).
Oommen et al., "The Elicitor-Inducible Alfalfa Isoflavone Reductase Promoter Confers Different Patterns of Developmental Expression in Homologous and Heterologous Transgenic Plants", The Plant Cell, 6:1789-1803 (1994).
Oster et al., "The G4 Gene of *Arabidopsis thaliana* Encodes a Chlorophyll Synthase of Etiolated Plants", Bot. Acta, 110:420-423 (1997).
Peisker et al., "Phytol and the Breakdown of Chlorophyll in Senescent Leaves", J. Plant Physiol., 135:428-432 (1989).
Pompliano et al., "Probing Lethal Metabolic Perturbations in Plants with Chemical Inhibition of Dehydroquinate Synthase", J. Am. Chem. Soc., 111:1866-1871 (1989).
Porfirova et al., "Isolation of an *Arabidopsis* mutant lacking vitamin E and identification of a cyclase essential for all tocopherol biosynthesis", PNAS, 99(19):12495-12500 (2002).
Querol et al., "Functional analysis of the *Arabidopsis thaliana* GCPE protein involved in plastid isoprenoid biosynthesis", FEBS Letters, 514:343-346 (2002).
Rippert et al., "Molecular and biochemical characterization of an *Arabidopsis thaliana* arogenate dehydrogenase with two highly similar and active protein domains", Plant Mol. Biol., 48:361-368 (2002).
Rippert et al., "Engineering Plant Shikimate Pathway for Production of Tocotrienol and Improving Herbicide Resistance", Plant Physiology, 134:92-100 (2004).
Rodriguez -Concepción et al., "Elucidation of the Methylerythritol Phosphate Pathway for Isoprenoid Biosynthesis in Bacteria and Plastids. A Metabolic Milestone Achieved through Genomics", Plant Physiology, 130:1079-1089 (2002).
Rodriguez -Concepción et al., "1-Deoxy-D-xylulose 5-phosphate reductoisomerase and plastid isoprenoid biosynthesis during tomato fruit ripening", The Plant Journal, 27(3):213-222 (2001).
Rohdich et al., "Cytidine 5'-triphosphate-dependent biosynthesis of isoprenoids: YgbP protein of *Escherichia coli* catalyzes the formation of 4-diphosphocytidyl-2-C-methylerythritol", Proc. Natl. Acad. Sci. USA, 96(21):11758-11763 (1999).

Rohmer et al., "Glyceraldehyde 3-Phosphate and Pyruvate as Precursors of Isoprenic Units in an Alternative Non-mevalonate Pathway for Terpenoid Biosynthesis", J. Am. Chem. Soc., 118:2564-2566 (1996).
Rohmer et al., "Isoprenoid biosynthesis in bacteria: a novel pathway for the early steps leading to isopentenyl diphosphate", Biochem. J., 295:517-524 (1993).
Rohmer, M., "A Mevalonate-independent Route to Isopentenyl Diphosphate", Comprehensive Natural Products Chemistry, 2:45-67 (1999).
Rohmer, M., "Isoprenoid biosynthesis via the mevalonate-independent route, a novel target for antibacterial drugs?", Progress in Drug Research, 50:136-154 (1998).
R ömer et al., "Expression of the Genes Encoding the Early Carotenoid Biosynthetic Enzymes in *Capsicum Annuum*", Biochemical and Biophysical Research Communications, 196(3):1414-1421 (1993).
Ruzafa et al., "The protein encoded by the *Shewanella colwelliana melA* gene is a *p*-hydroxyphenylpyruvate dioxygenase", FEMS Microbiology Letters, 124:179-184 (1994).
Saint-Guily et al., "Complementary DNA Sequence of an Adenylate Translocator from *Arabidopsis thaliana*", Plant Physiol., 100(2):1069-1071 (1992).
Sandmann et al., "New functional assignment of the carotenogenic genes *crtB* and *crtE* with constructs of these genes from *Erwinia* species", FEMS Microbiology Letters, 90:253-258 (1992).
Sato et al., "Structural Analysis of *Arabidopsis thaliana* Chromosome 5. X. Sequence Features of the Regions of 3,076,755 bp Covered by Sixty P1 and TAC Clones", DNA Research, 7(1):31-63 (2000).
Sato et al., "Structural Analysis of *Arabidopsis thaliana* Chromosome 5. IV. Sequence Features of the Regions of 1,456,315 bp Covered by Nineteen Physically Assigned P1 and TAC Clones", DNA Research, 5:41-54 (1998).
Savidge et al., "Isolation and Characterization of Homogentisate Phytyltransferase Genes from *Synechocystis* sp. PCC 6803 and Arabidopsis", Plant Physiology, 129:321-332 (2002).
Schwender et al., "Cloning and heterologous expression of a cDNA encoding 1-deoxy-D-xylulose-5-phosphate reductoisomerase of *Arabidopsis thaliana*", FEBS Letters, 455:140-144 (1999).
Scolnik et al., "Nucleotide Sequence of an *Arabidopsis* cDNA for Geranylgeranyl Pyrophosphate Synthase", Plant Physiol., 104(4):1469-1470 (1994).
Shewmaker et al., "Seed-specific overexpression of phytoene synthase: increase in carotenoids and other metabolic effects", The Plant Journal, 20(4):401-412 (1999).
Shigeoka et al., "Isolation and properties of γ-tocopherol methyltransferase in *Euglena gracilis*", Biochimica et Biophysica Acta, 1128:220-226 (1992).
Shintani et al., "Elevating the Vitamin E Content of Plants Through Metabolic Engineering", Science, 282:2098-2100 (1998).
Singh et al., "Chorismate Mutase Isoenzymes from *Sorghum bicolor*. Purification and Properties", Archives of Biochemistry and Biophysics, 243(2):374-384 (1985).
Smith, F.W. et al., "The cloning of two *Arabidopsis* genes belonging to a phosphate transporter family", Plant Journal, 11(1):83-92 (1997).
Smith, C.J.S. et al., "Antisense RNA inhibition of polygalacturonase gene expression in transgenic tomatoes", Nature, 334:724-726 (1998).
Smith, T.F. et al., "The challenges of genome sequence annotation or the devil is in the details", Nature Biotechnology, 15:1222-1223 (1997).
Soll et al., "Hydrogenation of Geranylgeraniol", Plant Physiol., 71:849-854 (1983).
Soll et al., "Tocopherol and Plastoquinone Synthesis in Spinach Chloroplasts Subfractions", Archives of Biochemistry and Biophysics, 204(2):544-550 (1980).
Soll et al., "2-Methyl-6-Phytylquinol and 2,3-Dimethyl-5-Phytylquinol as Precursors of Tocopherol Synthesis in Spinach Chloroplasts", Phytochemistry, 19:215-218 (1980).
Sprenger et al., "Identification of a thiamin-dependent synthase in *Escherichia coli* required for the formation of the 1-deoxy-D- xylulose 5-phosphate precursor to isoprenoids, thiamin, and pyridoxol", Proc. Natl. Acad. Sci. USA, 94:12857-12862 (1997).
Spurgeon et al., "Biosynthesis of Isoprenoid Compounds", 1:1-45 (1981).
Stam et al.., "The Silence of Genes in Transgenic Plants", Annals of Botany, 79:3-12 (1997).
Stocker et al., "Identification of the Tocopherol-Cyclase in the Blue-Green Algae *Anabaena variabilis* Kützing (Cyanobacteria)", Helvetica Chimica Acta, 76:1729-1738 (1993).
Stocker et al., "The Substrate Specifically of Tocopherol Cyclase", Bioorganic & Medicinal Chemistry, 4(7):1129-1134 (1996).
Sun et al., "Cloning and Functional Analysis of the β-Carotene Hydroxylase of *Arabidopsis thaliana*", The Journal of Biological Chemistry, 271(40):24349-24352 (1996).
Suzich et al., "3-Deoxy-D-*arabino*-Heptulosonate 7-Phosphate Synthase from Carrot Root (*Daucus carota*) Is a Hysteretic Enzyme", Plant Physiol., 79:765-770 (1985).
Svab et al., "High-frequency plastid transformation in tobacco by selection for a chimeric *aadA* gene", Proc. Natl. Acad. Sci. USA, 90:913-917 (1993).
Svab et al., "Stable transformation of plastids in higher plants", Proc. Natl. Acad. Sci. USA, 87:8526-8530 (1990).
Takahashi et al., "A 1-deoxy-D-xylulose 5-phosphate reductoisomerase catalyzing the formation of 2-C-methyl-D-erythritol 4-phosphate in an alternative nonmevalonate pathway for terpenoid biosynthesis", Proc. Natl. Acad. Sci. USA, 95:9879-9884 (1998).
Takatsuji, H., "Zinc-finger transcription factors in plants", CMLS Cell. Mol. Life Sci., Birkhauser Verlag Basel CH, 54(6):582-596 (1998).
Tjaden et al., "Altered plastidic ATP/ADP-transporter activity influences potato (*Solanum tubersomum* L.) tuber morphology, yield and composition of tuber starch", The Plant Journal, 16(5):531-540 (1998).
Town et al., "Whole genome shotgun sequencing of Brassica oleracea, BOGKS71TR BOGK Brassica oleracea genomic clone BOGKS71, DNA sequence", Database EMBL Accession No. BH534089 (Dec. 2001).
Town et al., "Whole genome shotgun sequencing of Brassica oleracea, BOGAU46, DNA sequence", Database EMBL Accession No. BH248880 (Nov. 2001).
Verwoert et al., "Developmental specific expression and organelle targeting of the *Escherichia coli fabD* gene, encoding malonyl coenzyme A-acyl carrier protein transacylase in transgenic rape and tobacco seeds", Plant Molecular Biology, 26:189-202 (1994).
Xia et al., "A monofunctional prephenate dehydrogenase created by cleavage of the 5' 109 bp of the *tyrA* gene from *Erwinia herbicola*", Journal of General Microbiology, 138(7):1309-1316 (1992).
Xia et al., "The *pheA I tyrA I aroF* Region from *Erwinia herbicola*: An Emerging Comparative Basis for Analysis of Gene Organization and Regulation in Enteric Bacteria", Database GENBANK on STN, GenBank Acc. No. (GBN): M74133, J. Mol. Evol., 36(2):107-120 Abstract (1993).
Yamamoto, E., "Purification and Metal Requirements of 3-Dehydroquinate Synthase from *Phaseolus Mungo* Seedlings", Phytochemistry, 19:779-781 (1980).
Zaka et al., "Changes in Carotenoids and Tocopherols During Maturation of *Cassia* Seeds", Pakistan J. Sci. Ind. Res., 30(11): 812-814 (1987).
Zeidler et al., "Inhibition of the Non-Mevalonate 1-Deoxy-D-xylulose-5-phosphate Pathway of Plant Isoprenoid Biosynthesis by Fosmidomycin", A Journal of Biosciences, Zeitschrift fuer Naturforschung, Section C, 53(11/12):980-986 (Nov./Dec. 1998).
Zhu et al., "Geranylgeranyl pyrophosphate synthase encoded by the newly isolated gene *GGPS6* from *Arabidopsis thaliana* is localized in mitochondria", Plant Molecular Biology, 35:331-341 (1997).
Zhu et al., "Cloning and Functional Expression of a Novel Geranylgeranyl Pyrophosphate Synthase Gene from *Arabidopsis thaliana* in *Escherichia coli*", Plant Cell Physiol., 38(3):357-361 (1997).
Kaneko et al., NCBI General Identifier No. 1653572, Accession No. BAA18485 (Jul. 2001).
Kaneko et al., NCBI General Identifier No. 1001725, Accession No. BAA10562 (Feb. 2003).
Alcala et al., Genbank Accession No. Al 897027 (Jul. 1999).
Bevan et al., Database EMBL, Accession No. AL035394 (Feb. 1999).
Bevan et al., TREMBL Database Accession No. O65524 (Aug. 1998).
Campos et al., NCBI General Identifier BAA 18485, Database EMBL, Accession No.: AF148852, (2000).
Chen et al., EMBL Sequence Database Accession No. Al995392 (Sep. 1999).
Desprez et al., Database EMBL, Accession No. Z34566 (Jun. 1994).
Fedenko et al., Abstract: RU 2005353, Derwent Accession No. 1994-253787.
Gaubier et al., Database EMBL, Accession No. Q38833 (Nov. 1996).
Kaneko et al., Database EMBL, Accession No. P73726 (Feb. 1997).
Kaneko et al., Database EMBL, Accession No. P73962 (Jul. 1998).
Kaneko et al., EMBL Sequence Database Accession No. D90909 (Oct. 1996).
Kaneko et al., TREMBL Database Accession No. P73727 (Feb. 1997).
Lange et al., "Mentha x Piperita 1-deoxy-D-xylulose-5-phosphate Reductoisomerase (DXR) mRNA", complete cds, Entrez Report, Accession No. AF116825 (Apr. 1999).
Lin et al., Database EMBL, Accession No. AC003672 (Dec. 1997).
Lin et al., Database EMBL, Accession No. AC003673 (Dec. 1997).
Lin et al., Database EMBL, Accession No. AC004077 (Feb. 1998).
Malakhov et al., Database TREMBL, Accession No. Q55207 (Nov. 1996).
Murata et al., EMBL Sequence Database Accession No. D13960 (Mar. 1996).
Nakamura et al., Database EMBL, Accession No.: AB009053, Abstract (Dec. 1997) (1998)(2000).
Nakamura et al., Database EMBL, Acccession No.: AB005246 (Jul. 1997).
Newman et al., Database EMBL, Accession No.: AA586087, Abstract (Sep. 1997).
Newman et al., Database EMBL, Accession No. R30625 (Aug. 1995).
Newman et al., Database EMBL, Accession No. T44803 (Feb. 1995).
Newman et al., DEBEST ID:1262303, Entrez Report, Accession No.: AA586087 (Sep. 1997).
Oster et al., Database Biosis, Accession No. PREV199800047824 (Oct. 1997).
Ouyang et al., Database EMBL, Accession No. AF381248 (Jan. 2003).
Rounsley et al., Database EMBL, Accession No. B24116 (Oct. 1997).
Rounsley et al., Database EMBL, Accession No. B29398 (Oct. 1997).
Rounsley et al., Database TREMBL, Accession No. O64684 (Aug. 1998).
Schwender et al., Arabidopsis thaliana mRNA for Partial 1-deoxy-d-xylulose-5-phosphate Reductoisomerase (dxr gene), Entrez Report, Accession No.: AJ242588 (Aug. 1999).
Scolnik et al., Database EMBL, Accession No. L40577 (Apr. 1995).
Shintani et al., Database NCBI, Accession No. AF104220 (Jan. 1999).
Shoemaker et al., Database EMBL, Accession No. Al748688 (Jun. 1999).
Shoemaker et al., Database EMBL, Accession No. Al938569 (Aug. 1999).
Shoemaker et al., Database EMBL, Accession No. Al988542 (Sep. 1999).
Shoemaker et al., Database EMBL, Accession No.AW306617 (Jan. 2000).
Tabata et al., Database EMBL, Accession No. D64001 (Sep. 1995).
Tabata et al., Database EMBL, Accession No. D64006 (Sep. 1995).
Tabata et al., Database EMBL, Accession No. D90909 (Oct. 1996).
Tabata et al., Database EMBL, Accession No. D90911 (Oct. 1996).
Tabata et al., Database EMBL, Accession No. Q55145 (Nov. 1996).

Tabata et al., Database EMBL, Accession No. Q55500 (Nov. 1996).
Walbot, V., Database EMBL, Accession No. AI795655 (Jul. 1999).
Wing et al., Database EMBL, Accession No. AQ690643 (Jul. 1999).
Xia et al., Database EMBL, Accession No. M74133 (Jun. 1993).
Bevan et al., Accession T4 8445.
International Search Report, PCT/US00/10367, pp. 1-5 (Sep. 15, 2000).
International Search Report, PCT/US00/10368, pp. 1-14 (Jun. 15, 2001).
Written Opinion, PCT/US00/10368, pp. 1-6 (May 9, 2002).
IPER, PCT/US00/10368, pp. 1-5 (Aug. 16, 2002).
Examination Report, New Zealand Patent Application No. 514600, based on PCT/US/00/10368, pp. 1-2 (Apr. 24, 2003).
Communication pursuant to Article 96(2) EPC, EP Application 00922287.8, based on PCT/US00/10368, pp. 1-6 (Oct. 17, 2003).
Examiner's Report No. 2, Australia Patent Application No. 42492/00, based on PCT/US00/10368, pp. 1-4 (Nov. 12, 2003).
International Search Report, PCT/US01/12334, pp. 1-5 (Apr. 5, 2002).
International Search Report, PCT/US01/24335, pp. 1-8 (Mar. 6, 2003).
International Search Report, PCT/US01/42673, pp. 1-4.
International Search Report, PCT/US02/03294, pp. 1-4 (Mar. 19, 2003).
International Search Report, PCT/US02/13898, pp. 1-3 (Sep. 13, 2002).
IPER, PCT/US02/13898, pp. 1-4 (Apr. 24, 2003).
International Search Report, PCT/US02/14445, pp. 1-6 (Oct. 30, 2003).
International Search Report, PCT/US02/26047, pp. 1-5 (Dec. 5, 2003).
International Search Report, PCT/US02/34079, pp. 1-5 (Jul. 28, 2003).
Written Opinion, PCT/US02/34079, pp. 1-4 (Oct. 23, 2003).
Response to Written Opinion, PCT/US02/34079, pp. 1-6 (Dec. 22, 2003).
slr 1736 cyanobase www.kazusa.com.

```
                           *         20         *         40         *         60         *         80
Nostoc_ppt    : ------------------------------------------------------------------------------------ :   -
anabaena_p    : ------------------------------------------------------------------------------------ :   -
Synechocys    : ------------------------------------------------------------------------------------ :   -
Corn_ppt      : ------MDAIRLRPSLLPVRPGAARPRDHFLPPCCS---IQRNGEGRIC---FSSQRTQGPTLHHHQKFFEWKSSYCRISHRSLN :  73
soy-ppt2      : MDSLLLRSFPNINNASLTTTGANFSRTKSFANIYHASSYPNASWHNRKIQKEYNFLRFWPSLNHHYKGIE---GACTCKKCNIK :  84
soy-ppt1      : MDSMLLRSFPNINNASLATTG-------SYLPNASWHNRKIQKEYNFLRFWPSLNHHYKSIE---GGCTCKKCNIK :  68
Arabidopsi    : ------MESLLSSSIVSAAGGFCWKKQNLKLHSLSEIRVLRCDSSKVVAKP----KFRNNLVRPDGQG-S---SLLLYPKHKSR :  71
Cuphea_ppt    : ------MRMESLLNSFSPSPAGGKICRADTYKKAYFATARCNTLNSLNKN-TGEYHLSRTR-QRFTFHQNGHR---------T :  67

Motif A
                           *        120         *        140         *        160         *
Nostoc_ppt    : ---------MSQSQNSPLPRKPVQSYFHWEYAFWKFSRPHTIGTSLSVISLYIMIAISNNTASLETTPGSLSPLFGAMIACICG :  78
anabaena_p    : ---------MNQSSQDRPLRPKPLQSSFQWLYAFWKFSRPHTIGTSLSVEGLYISIAVSSTGFAL---TQINSVGAWLACICG :  74
Synechocys    : -------------------------MATLQAFWRFSRPHTIGTLSVWAVYLTILGDGNS---VNSPASLDLVFGAWLACLLG :  57
Corn_ppt      : TSVNASGQQ-LQSEPETHDSTTIWRAISSSLDAFYRFSRPHTVIGTALSIVSVSLEAVSDISPLF----LIGLLEAVVAALFM : 154
soy-ppt2      : FVVKATSEKSLESEPQAFDPKSILDSVKNSIDAFYRFSRPHTVIGTALSIESVSLEAVEKISDISPLF----FIGVLEAVVAALFM : 166
soy-ppt1      : FVVKATSEKSFESEPQAFDPKSILDSVKNSIDAFYRFSRPHTVIGTALSIRSVSLEAVEKISDISPEL----FLGILEAVVAALFM : 150
Arabidopsi    : FRVNATA----GQPEAFDSNSKQKSFRDSIDAFYRFSRPHTVIGTVLSIVSVSFLAVEKVSDISPLL-----FLGTLEAVVAALMM : 148
Cuphea_ppt    : YLVKAVSGQSLESEPESY-PNNRWDYVKSAADAFYRFSRPHTIIGTALSIVSVSLLAVEKLPELNSWF-----FLGLEEVILAALFM : 148
                                          AF54FSRPHT6IGT LS6 s6 16a6    61 a 6A a L
```

```
                                                       Motif D
              *           360           *           380           *           400           *           420           *
Nostoc_ppt   : TVCYLGITVGVLRIASVNPIFLITALLVWMIWRSLAVDLQDKSAIAQFYQFIWCFEIEYLIFPIACFLA~~~~~ : 322
anabaena_p   : TVCYLGMYIEGVLRLGTINSVFLVVTILVWMMQSLAVDIHDKTAIAQFYQFIWKFFLEYIMFPIACLLA~~~~~ : 318
Synechocys   : TGCYLAMATWGLWAAMPLNTAFLIVSLCPLALITWRSRDVHESKTEIASFYQTSKAATYPLALWLPNFSNTIF* : 308
Corn_ppt     : EMAVSVAIIWGATSSCLWSKTATIAGESIPAAILNSCARSVDETSKAATSFYMFIWKLFFLAEMJIIPLVR*  : 399
soy-ppt2     : ELAYGVAILVGAASPCLWSKIFTGLGHAVEASILMFHAKSVDLKSKASITSFYMFIWKLFYAEYLIIPFVR~  : 411
soy-ppt1     : ELAYGVAILVGAASPCLWSKIVTGEGHAVEASILMFHAKSVDIKSKASITSFYMFIWKLFYAEYLIIPFVR~  : 395
Arabidopsi   : QMAVAVAILVGATSPFIWSKVISVVGHVIFATTLMARAKSVDSSKTEITSCYMFIWKLFYAEYLIIPFLK*  : 393
Cuphea_ppt   : EMALAVAGLWVLRARGR-KKHADGVSASEFFLSISGGRKNL*                                 : 362
               Y    6  g                h            6w      6d      k   i  fy fiwklf  eyl  p Nostoc_ppt   : (SEQ ID NO: 1)
anabaena_p   : (SEQ ID NO: 2)
Synechocys   : (SEQ ID NO: 3)
Corn_ppt     : (SEQ ID NO: 4)
soy-ppt2     : (SEQ ID NO: 5)
soy-ppt1     : (SEQ ID NO: 6)
Arabidopsi   : (SEQ ID NO: 7)
Cuphea_ppt   : (SEQ ID NO: 8)
```

*Fig. 2c*

```
                         *         20         *         40         *         60         *         80
Corn         : MDALRLRPSLLPVRP--GAARPRDHFLP-------------PCCSIQRNGEGRICFSSQRTQGPTLHHHQKFFEWKSSYCRISHRSLN :  73
Wheat        : MDSLRLRPSSLRSAPGAAAARRRDHILP-------------SFCSIQRNGKGRVTLSIQASKGPTINHCKKFLDWKYSNHRISHQSIN :  75
Leek         : MLSMDSLLTKPVVIPLPSPVCSLPILRG-------------SSAPGQYSCRNYNPIRIQRCLVNYEHVKPRFTTCSRS-----QKLG :  69
soy-ppt2     : --MDSLLRSFPNINNASSLTTTGANFSRTKSFANIYHASSYVPNASWHNRKIQKEYNFLRFRWPSLNHHYKGIEGACTCKKCNIKF :  85
soy-ppt1     : --MDSMLLRSFPNINNASSLATTGS----------------YLPNASWHNRKIQKEYNFLRFWPSLNHHYKSIEGGCTCKKCNIKF :  69
Cuphea       : MRMESLLLNSFSPSPAGGKICRADT----------------YKKAYFATARCNTLNSLNKNTGEYHLSRTRQRFTFHQNGHRTY :  68
Arabidopsi   : -MESLLSSSSLVSAAGGFCWKKQN-----------------LKLHSLSEIRVLRCDSSKVVAKPKFRNNLVRPDGQGSSLLLYPKHK :  69
Nostoc_ppt   : ------------------------------------------------------------------------------------ :   -
anabaena_p   : ------------------------------------------------------------------------------------ :   -
Synechocys   : ------------------------------------------------------------------------------------ :   -

*        100         *        120         *        140         *        160
                                                             Motif I
Corn         : TSVNASGQQLQSEPETHDSTIIWRAISSSIDAFYRFSRPHTVIGTALSIMSVSLAVQSLSDISPLFLG---LEAVVAALFMN : 155
Wheat        : TSAKAG-QSLQPETEAHDPASFWKPISSSIDAFYRFSRPHTIIGTALSIMSVSLAVESLSDISPLFLG---LEAVVAALFMN : 156
Leek         : HVKATSEHSLESGSEGYTPRSIWEAVLASTNVLYKFSRPHTIIGTAMGIMSVSIESVSDISPLFFVG---LFAVVAALFMN : 151
soy-ppt2     : VVKATSEKSLESEPQAFDPKSILDSVKNSFDAIYRFSRPHTVIGTALSIESVSTAVEKISDISPLFFG---VVEAVVAALFMN : 167
soy-ppt1     : VVKATSEKSFESEPQAFDPKSILDSVKNSLDAIYRFSRPHTVIGTALSIESVSTAVEKLSDISPLFFG---VLEAVVAALFMN : 151
Cuphea       : LVKAVSGQSLESEPESYP-NNRWDYVKSAADAIYRFSRPHTIIGTALSIMSVSVSFLAVEKLPENSMFFG---IIEAVILAALFMN : 149
Arabidopsi   : SRFRVN--ATAGQPEAFDSNSKQKSFRDSEDAIYRFSRPHTIIGTALSIMSVSVSFIAVEKVSDISPLFLG---IIEAVVALMMN : 149
Nostoc_ppt   : MSQSSQNSPLPRKPVQSYFHWIYAWKFSRPHTIIGTVLSLSLVLSLYEIAISNNTASFIPGSLSPLFGAWIACLCGN :  79
anabaena_p   : ------MNQSSQDRPLRPKPLQSSFQWEYAWKFSRPHTIIGTISLSVLGLYLSIAVSSTGFAITQIN--SVCAWIACICGN :  75
Synechocys   : -------MATIQAIWRFSRPHTIIGTISIWAVYLITIILGDGN-----SVNSPASLDLVFCAWIACLLGN :  58
                                     af54FSRPHT6IGT  6s6 s6 16 6       61 a  6A L   N
```

```
             *        20         *        40         *        60
NoHPT    : ------------------------------------------------------------ :   -
AnHPT    : ------------------------------------------------------------ :   -
SyHPT    : ------------------------------------------------------------ :   -
ZmHPT1   : --MDALRLRPSLLPVRPGAARPRDHFLPPCCSIQRNGEGRICFSSQRTQGPTLHHHQKFF : 58
TaHPT1   : MDSLRLRPSSLRSAPGAAAARRRDHILPSFCSIQRNGKGRVTLSIQASKGPTINHCKKFL : 60
ApHPT1   : ----MLSMDSLLTKPVVIPLPSPVCSLPILRGSSAPGQYSCRNYNPIRIQRCLVNYEH : 54
GmHPT1-1 : ------MDSMLLRSFPNINNASSLATTGSYLPNASWHNRKIQKEYNFLRFRWPSLNHHYK : 54
CpHPT1   : -------MRMESLLLNSFSPSPAGGKICRADTYKKAYFATARCNTLNSLNKNTGEYHLSR : 53
AtHPT1   : --------MESLLSSSSLVSAAGGFCWKKQNLKLHSLSEIRVLRCDSSKVVAKPKFRNNL : 52
AtHPT2   : --------------MELSISQSPRVRFSSLAPRFLAASHHHRPSVHLAGKFISLPRDVRF : 46
GmHPT2   : -----------MELSLSPTSHRVPSTIPTLNSAKLSSTKATKSQQPLFLGFSKHFNSIGL : 49
OsHPT2   : --------------------MASLASPPLPCRAAATASRSGRPAPRLLGPPPPPASPLL : 39

Motif V
                                                              ────────
             *        80         *        100        *        120
NoHPT    : --------------------MSQSSQNSPLRKPVQSYFHWLYAEWKFSRPHTIIGT :  37
AnHPT    : --------------------MNQSSQDRPLRPKPLQSSFQWLYAEWKFSRPHTIIGT :  37
SyHPT    : ----------------------------MATIQAFWRFSRPHTIIGT :  19
ZmHPT1   : EWKSSYCRISHRSLNTSVNASGQQLQSEPETHDSTTIWRAISSSLDAFYRFSRPHTVIGT : 118
TaHPT1   : DWKYSNHRISHQSINTSAKAG-QSLQPETEAHDPASFWKPISSSLDAFYRFSRPHTIIGT : 119
ApHPT1   : VKPRFTTCSRSQKLGHVKATSEHSLESGSEGYTPRSIWEAVLASLNVLYKFSRPHTIIGT : 114
GmHPT1-1 : SIEGGCTCKKCNIKFVVKATSEKSFESEPQAFDPKSILDSVKNSLDAFYRFSRPHTVIGT : 114
CpHPT1   : TRQRFTPHQNGHRTYLVKAVSGQSLESEPESYP-NNRWDYVKSAADAFYRFSRPHTIIGT : 112
AtHPT1   : VRPDGQGSSLLLYPKHKSRFRVNATAGQPEAFDSNSKQKSFRDSLDAFYRFSRPHTVIGT : 112
AtHPT2   : TSLSTSRMRSKFVSTNYRKISTRACSQVGAAESDDPVLDRIARFQNACWRFLRPHTIRGT : 106
GmHPT2   : HHHSYRCCSNAVPERPQRPSSIRACTGVGASGSDRPLAERLLDLKDACWRFLRPHTIRGT : 109
OsHPT2   : SSASARFPRAPCNAARWSRRDAVRVCSQAGAAGPAPLSKTLSDLKDSCWRFLRPHTIRGT :  99

Motif VI
                                                       ────────
             *        140        *        160        *        180
NoHPT    : SLSVLSLYLIAIAISNNTASLFTTPGSLSPLFGAWIACLCGNVYIVGLNQLEDVDIDKIN :  97
AnHPT    : SLSVLGLYLLSIAVSSTGFALTQIN----SVLGAWIACLCGNVYIVGLNQLEDIEIDKVN :  93
SyHPT    : TLSVWAVYLLTILGDGNSVNSPASLD---LVPGAWIACLLGNVYIVGLNQLWDVDIDRIN :  76
ZmHPT1   : ALSIVSVSLLAVQSLSDISPLFLTG----LLEAVAALFMNIYIVGLNQLFDIEIDKVN : 173
TaHPT1   : ALSIVSVSLLAVESLSDISPLFLTG----LLHEAVAALFMNIYIVGLNQLFDIEIDKVN : 174
ApHPT1   : AVGIMSVSLLVVESLSDISPLFFVG----LLEAVAALFMNVYIVGLNQLFDIEIDKVN : 169
GmHPT1-1 : ALSIISVSLLAVEKTSDISPLFFTG----VLEAVAALFMNIYIVGLNQLSDVEIDKIN : 169
CpHPT1   : ALSIVSVSLLAVEKLPELNSMFFTG----LLEVLAALFMNIYIVGLNQLSDIDIDKVN : 167
AtHPT1   : VLSTLSVSFLAVEKVSDISPLLFTG----TLHEAVAALMMNIYIVGLNQLSDVEIDKVN : 167
AtHPT2   : ALGSTALVTRALIENTHLIKWSLVLK----ALSGLLALICGNGYIVGINQIYDIGIDKVN : 162
GmHPT2   : ALGSFALVARALIENTNLIKWSLFFK----AFCGLBALICGNGYIVGINQIYDISIDKVN : 165
OsHPT2   : ALGSTALVARALIENPQLINWWLVFK----AFYGLVALICGNGYIVGINQIYDIRIDKVN : 155

──────
             *        200        *        220        *        240
NoHPT    : KPHLPLASGEFSQQTGQLIVASTGIIALVMAWLTG---PLLFGMVTISLAIGTAYSLFPI : 154
AnHPT    : KPHLPLASGEFSRKQGRIIVILTGITAIVLAWLNG---PYLFGMVAVSLAIGTAYSLFPI : 150
SyHPT    : KPNLPLANGDFSIAQGRWIVGLCGVASLAIAWGLG---LWLGLTVGISLIIGTAYSVFPV : 133
ZmHPT1   : KPTLPLASGEYTLATGVAIVSVFAAMSFGLGWAVGSQPLFWALFISFVLGTAYSINLFYL : 233
TaHPT1   : KFTLPLASGEYSPATGVAIVSVFAAMSFGLGWVVGSPPLFWALFISFVLGTAYSVNLFYF : 234
ApHPT1   : KPDLPLASGEYSPRAGTALVIASAIMSFGLGWLVGSWPLFWALFISFVLGTAYSINLFFI : 229
GmHPT1-1 : KPYLPLASGEYSFETGVTIVASFSILSFWLGWVVGSWPLFWALFVSFVLGTAYSINVLLI : 229
CpHPT1   : KPYLPLASGEFSVGTGVTIIVTSFLIMSFWLGWVGSWPLFWALFISFVLGTAYSIDMPML : 227
AtHPT1   : KPYLPLASGEYSVNTGIAIVASFSIMSFWLGWIVGSWPLFWALFVSFMLGTAYSINLPLL : 227
AtHPT2   : KPYLPIAAGDLSVQSAWLLVIFFALAGLLVVGFNFG--PEITSLYSLGIFLGTIYSVPPL : 220
GmHPT2   : KPYLPIAAGDLSVQSAWFLVIFFAAAGLSIAGLNFG--PEIFSLYLLGIFLGTIYSVPPL : 223
OsHPT2   : KPVLPIAAGDLSVQTAWLLVVLFAAAGFSIVVTNFI--LPITSLYCLALFLGTIYSVPPF : 213
```

Motif V (SEQ ID NO: 46)

```
NoHPT     : WKFSRPHTIIGT : 12
AnHPT     : WKFSRPHTIGT  : 12
SyHPT     : WRFSRPHTIIGT : 12
ZmHPT1    : YRFSRPHTVIGT : 12
TaHPT1    : YRFSRPHTIIGT : 12
ApHPT1    : YKFSRPHTIIGT : 12
GmHPT1-1  : YRFSRPHTVIGT : 12
CpHPT1    : YRFSRPHTIIGT : 12
AtHPT1    : YRFSRPHTVIGT : 12
AtHPT2    : WRFLRPHTIRGT : 12
GmHPT2    : WRFLRPHTIRGT : 12
OsHPT2    : WRFLRPHTIRGT : 12
```

Motif VI (SEQ ID NO: 47)

```
NoHPT     : NVYIVGLNQLEDVDIDKINKPHLPLA : 26
AnHPT     : NVYIVGLNQLEDIEIDKVNKPHLPLA : 26
SyHPT     : NVYIVGLNQLWDVDIDRINKPNLPLA : 26
ZmHPT1    : NIYIVGLNQLFDIEIDKVNKPTLPLA : 26
TaHPT1    : NIYIVGLNQLFDIEIDKVNKPTLPLA : 26
ApHPT1    : NVYIVGLNQLFDIEIDKVNKPDLPLA : 26
GmHPT1-1  : NIYIVGLNQLSDVEIDKINKPYLPLA : 26
CpHPT1    : NIYIVGLNQLSDIDIDKVNKPYLPLA : 26
AtHPT1    : NIYIVGLNQLSDVEIDKVNKPYLPLA : 26
AtHPT2    : NGYIVGINQIYDIGIDKVNKPYLPIA : 26
GmHPT2    : NGYIVGINQIYDISIDKVNKPYLPIA : 26
OsHPT2    : NGYIVGINQIYDIRIDKVNKPYLPIA : 26
                      *
```

Motif VII (SEQ ID NO: 48)

```
NoHPT     : IAIFKDIPDIEGDR : 14
AnHPT     : IAIFKDIPDMEGDR : 14
SyHPT     : IAIFKDVPDMEGDR : 14
ZmHPT1    : IALFKDIPDIEGDR : 14
TaHPT1    : IALFKDIPDIEGDR : 14
ApHPT1    : IALFKDIPDIDGDK : 14
GmHPT1-1  : IALFKDIPDIEGDK : 14
CpHPT1    : IALFKDIPDIEGDK : 14
AtHPT1    : IALFKDIPDIEGDK : 14
AtHPT2    : IAITKDLPDVEGDR : 14
GmHPT2    : IAITKDLPDVEGDR : 14
OsHPT2    : IAITKDLPDVEGDR : 14
```

*Fig.25a*

Motif VIII (SEQ ID NO: 49)

```
NoHPT    : KSAIAQFYQFIWKLFFIEYLIFP : 23
AnHPT    : KTAIAQFYQFIWKLFFLEYLMFP : 23
SyHPT    : KTEIASFYQFIWKLFFLEYLLYP : 23
ZmHPT1   : KAAITSFYMFIWKLFYAEYLLIP : 23
TaHPT1   : KAAITSFYMLIWRLFYAEYLLIP : 23
ApHPT1   : KTTITSFYMFVWKLFYAEYLLIP : 23
GmHPT1-1 : KASITSFYMFIWKLFYAEYLLIP : 23
CpHPT1   : KAALTSFYMFIWKLFYAEYLLIP : 23
AtHPT1   : KTEITSCYMFIWKLFYAEYLLLP : 23
AtHPT2   : KEAISGYYRFIWNLFYAEYLLFP : 23
GmHPT2   : KDAISGFYRFIWNLFYAEYALFP : 23
OsHPT2   : KDAISQYYRFIWNLFYAEYIFFP : 23
```

*Fig. 25b*

```
                  *         20          *         40          *         60
NoHPT    : ------------------------------------------------------------ :   -
AnHPT    : ------------------------------------------------------------ :   -
Tricho   : ------------------------------------------------------------ :   -
SyHPT    : ------------------------------------------------------------ :   -
ZmHPT1   : --MDALRLRPSLLPVRPGAARPRDHFLPPCCSIQRNGEGRICFSSQRTQGPTLHHHQKFF :  58
TaHPT1   : MDSLRLRPSSLRSAPGAAAARRRDHILPSFCSIQRNGKGRVTLSIQASKGPTINHCKKFL :  60
ApHPT1   : ----MLSMDSLLTKPVVIPLPSPVCSLPILRGSSAPGQYSCRNYNPIRIQRCLVNYEH   :  54
GmHPT1-1 : -----MDSMLLRSFPNINNASSLATTGSYLPNASWHNRKIQKEYNFLRFWPSLNHHYK   :  54
CpHPT1   : ----MRMESLLLNSFS?SPAGGKICRADTYKKAYFATARCNTLNSLNKNTGEYHLSR    :  53
AtHPT1   : -----MESLLSSSSLVSAAGGFCWKKQNLKLHSLSEIRVLRCDSSKVVAKPKFRNNL    :  52
Chloro   : ------------------------------------------------------------ :   -
AtHPT2   : ------------MELSISQSPRVRFSSLAPRFLAASHHHRPSVHLAGKFISLPRDVRF   :  46
GmHPT2   : -----------MELSLSPTSHRVPSTIPTLNSAKLSSTKATKSQQPLFLGFSKHFNSIGL :  49
OsHPT2   : ----------------MASLASPPLPCRAAATASRSGRPAPRLLGPPPPPASPLL      :  39

Motif IX
                  *         80          *         100         *         120
NoHPT    : -------------------------------EWKSSYCRISHRSLNTSVNASGQQLQSEPETHDSTTIWRAISSSLDAF YAF FSRPHT EGT :  37
AnHPT    : -------------------------------DWKYSNHRISHQSINTSAKAG-QSLQPETEAHDPASFWKPISSSIDAF LVAF KF RPHT LGT :  37
Tricho   : -------------------------------VKPRFTTCSRSQKLGHVKATSEHSLESGSEGYTPRSIWEAVLASINV- QWLVAE R RPHT IGT :  39
SyHPT    : -------------------------------SIEGGCTCKKCNIKFVVKATSEKSFESEPQAFDPKSILDSVKNSLDAF QKYVPWIYSF A RPHTV GT :  19
ZmHPT1   : MSQSQNSPLPRKPVQSYFHWLYAF -------TRQRFTFHQNGHRTYLVKPKHKSRFPVNATAGQPEAFDSNSKQKSFRDSLDAF MATIQAF F SRPHT EGT : 118
TaHPT1   : MNQSSQDRPLRPKPLQSSFQWLVAE ------VRPDGQGSSLLLYPKHKSRFPVNATAGQPEAFDSNSKQKSFRDSLDAF RF SRPHT GT : 119
ApHPT1   : MGKIAGSQQGKITTNWLQKYVPWIYSF ---- -----------------------MRKQLRLLIEF LF RPHTI GT : 114
GmHPT1-1 : MATIQAF ----------------------------------------------- SDLKDSC R RPHTV GT : 114
CpHPT1   : ---------------------------------------------------- R RPHT IGT : 112
AtHPT1   : -----------------------------------------------------MRKQLRLLIEF R RPHIV GT : 20
Chloro   : TSLSTSRMRSKFVSTNYRKISIRACSQVGAAESDDPVLDRIARFQNAC R RPHTV AT : 106
AtHPT2   : HHHSYRCCSNAVPERPQRPSSIRACTGVGASGSDRPLAERLDLKDAC LF LRPHTIR GT : 109
GmHPT2   : SSASARFPRAPCNAARWSRRDAVRVCSQAGAAGPAPLSKTESDLKDSC LF LRPHTIR GT :  99
```

Fig. 33a

| | | Motif X | |
|---|---|---|---|
| NoHPT | SLSVLSLYLIAISNNTASLFTTPGSLSPLFGAMLCLCGNVYIVGLNQLEDVDIDKIN | : | 97 |
| AnHPT | SLSVLGLYLHSIAVSSTGFALTQIN----SYLEGAMVACLCGNVYIVGLNQLEDIEIDKVN | : | 93 |
| Tricho | SLSVLALYLITAMGDRSNFFDKYFFLYSLILLITWSLCLCGNIYICGLNQLEDIEIDRIN | : | 99 |
| SyHPT | TLSWAVYLLTILGDG---NSVNSPASLDLVFGAWLGNVYIVGLNQLWDVDIDRIN | : | 76 |
| ZmHPT1 | ALSLVSVSLLAVQSLSLSDISPLFLTG------LLEAVVAALFMNLYIVGLNQLFDIEIDKVN | : | 173 |
| TaHPT1 | ALSLVSVSLLAVESLSDISPLFLTG------LLEAVVAALFMNLYIVGLNQLFDIEIDKVN | : | 174 |
| ApHPT1 | AMGIMSVSLLEVESLSDSPLFVG------LLEAVVAALFMNIYVGLNQLFEIDKVN | : | 169 |
| GmHPT1-1 | ALSLLSVSLLAVEKISDISPLFFTG------LLEAVVAALFMNIYVGLNQLSDVEIDKVN | : | 169 |
| CpHPT1 | ALSLVSVSLLAVEKLPELNSMFTG------LLEVILAALFMNIYVGLNQLSDIDIDKVAN | : | 167 |
| AtHPT1 | VLSLSVSFLAVEKVSDISPLLFTG------ILEAVVAAIMNVTVGLNQLSDVEIDKVAN | : | 167 |
| Chloro | SVQMLMLIVIGWHPPTLEHVGLVG------VTLMVCIALNLYVVGVNQLTDVAIDRIN | : | 74 |
| AtHPT2 | ALGSTAIVTRALIENTHLIKWSLVLK---ALSGLFALICAINVCLAIICGNGYIVGINYDIGIDKVAN | : | 162 |
| GmHPT2 | ALGSFALVARAIIENTPNLIKWSLFFK---AFCGLFALICGNGYIVGINYDISIDKVAN | : | 165 |
| OsHPT2 | ALGSTALVARAIIENPQLINWWLVFK---AFYGLVLICAINGYIVGINYDIRIDKVAN | : | 155 |

| | | | |
|---|---|---|---|
| NoHPT | KPHLPLASGEFSQQTGQLLVASTGILALVMAWLTC---PLFGMVTISLPAIGTAYSLPPL | : | 154 |
| AnHPT | KPHLPLASGEFSRKQGRLIVILTGITAIVLAWLNG---PYLFGMVAVSLPAIGTAYSLPPL | : | 150 |
| Tricho | KPHLPIAAGEFSRFSGQIIVITGILALSFAGLG---PLLGTVGISLPAIGTAYSLPPL | : | 156 |
| SyHPT | KPNLPLANGDFSIAQGRWIVGLCVASLAIAWGLG---LWLGLTVGISLSFVIIGIAVSVPPM | : | 133 |
| ZmHPT1 | KPTLPLASGEYLATGVAIVSVFAAMSFGLGWAVGSQPLEWALFHSFVGTAYSINLPYL | : | 233 |
| TaHPT1 | KPTLPLASGEYSPATGVAIVSVEAAMSFGLGMVVGSPPLEWALFLSFVGTAYSVNLPYF | : | 234 |
| ApHPT1 | KPDLPLASGEYSPRAGTAIVIASAIMSFGIGWLVGSWPLFWLVGSWPFFWALFWSFVGTAYSINPFE | : | 229 |
| GmHPT1-1 | KPYLPLASGEYSFETGVILVASESILSFWLGWVVGSWPLFWALFWSFVGTAYSINVPLL | : | 229 |
| CpHPT1 | KPYLPLASGEYSVGTGVTIVTSFLIMSFWLGWVVGSWPLFWALFVSFVGTAYSIDMPMS | : | 227 |
| AtHPT1 | KPYLPLASGEYSVNIGIAIVASESIMSFWLGWIVGSWPLFWALFVSFMGTAYSINLPLF | : | 227 |
| Chloro | KPMLPVAAGQLSSDAAQRIVISALFIALTGAAMLG---PPLWWTLVSLIALIGSLVLLP | : | 131 |
| AtHPT2 | KPYLPIAAGDLSVQSAWLLVIFFATAGLLVVGFNFG---PRITSLYSLGFLGHIYSVPPF | : | 220 |
| GmHPT2 | KPYLPIAAGDLSVQSAWFLVIFFAAAGLSIAGLNFG---PRIFSLYTLGFLGHIYSVPPF | : | 223 |
| OsHPT2 | KPYLPIAAGDLSVQTAWLLVVLFAAAGFSLVVTNFI---LHITSLYCLAFLGHIYSVPPF | : | 213 |

Motif IX (SEQ ID NO: 92)

```
                         *
NoHPT    : WKFSRPHTIIGT : 12
AnHPT    : WKFSRPHTIIGT : 12
Tricho   : WKFARPHTIIGT : 12
SyHPT    : WRFSRPHTIIGT : 12
ZmHPT1   : YRFSRPHTVIGT : 12
TaHPT1   : YRFSRPHTIIGT : 12
ApHPT1   : YKFSRPHTIIGT : 12
GmHPT1-1 : YRFSRPHTVIGT : 12
CpHPT1   : YRFSRPHTIIGT : 12
AtHPT1   : YRFSRPHTVIGT : 12
Chloro   : IEFARPHTVLAT : 12
AtHPT2   : WRFLRPHTIRGT : 12
GmHPT2   : WRFLRPHTIRGT : 12
OsHPT2   : WRFLRPHTIRGT : 12
```

Motif X (SEQ ID NO: 93)

```
                 *           20
NoHPT    : NVYIVGLNQLEDVDIDKINKPHLPLA : 26
AnHPT    : NVYIVGLNQLEDIEIDKVNKPHLPLA : 26
Tricho   : NIYIVGLNQLEDIEIDRINKPHLPIA : 26
SyHPT    : NVYIVGLNQLWDVDIDRINKPNLPLA : 26
ZmHPT1   : NIYIVGLNQLFDIEIDKVNKPTLPLA : 26
TaHPT1   : NIYIVGLNQLFDIEIDKVNKPTLPLA : 26
ApHPT1   : NVYIVGLNQLFDIEIDKVNKPDLPLA : 26
GmHPT1-1 : NIYIVGLNQLSDVEIDKINKPYLPLA : 26
CpHPT1   : NIYIVGLNQLSDIDIDKVNKPYLPLA : 26
AtHPT1   : NIYIVGLNQLSDVEIDKVNKPYLPLA : 26
Chloro   : NLYVVGVNQLTDVAIDRINKPWLPVA : 26
AtHPT2   : NGYIVGINQIYDIGIDKVNKPYLPIA : 26
GmHPT2   : NGYIVGINQIYDISIDKVNKPYLPIA : 26
OsHPT2   : NGYIVGINQIYDIRIDKVNKPYLPIA : 26
```

*Fig. 34a*

Motif XI (SEQ ID NO: 94)

```
                          *
NoHPT     : IAIFKDIPDIEGDR : 14
AnHPT     : IAIFKDIPDMEGDR : 14
Tricho    : IAIFKDIPDIEGDR : 14
SyHPT     : IAIFKDVPDMEGDR : 14
ZmHPT1    : IALFKDIPDIEGDR : 14
TaHPT1    : IALFKDIPDIEGDR : 14
ApHPT1    : IALFKDIPDIDGDK : 14
GmHPT1-1  : IALFKDIPDIEGDK : 14
CpHPT1    : IALFKDIPDIEGDK : 14
AtHPT1    : IALFKDIPDIEGDK : 14
Chloro    : IALYKDLPDDRGDR : 14
AtHPT2    : IAITKDLPDVEGDR : 14
GmHPT2    : IAITKDLPDVEGDR : 14
OsHPT2    : IAITKDLPDVEGDR : 14
```

Motif XII (SEQ ID NO: 95)

```
                           *          20
NoHPT     : KSAIAQFYQFIWKLFFIEYLIFP : 23
AnHPT     : KTAIAQFYQFIWKLFFLEYLMFP : 23
Tricho    : KKAIADFYQFIWKLFFLEYLIFP : 23
SyHPT     : KTEIASFYQFIWKLFFLEYLLYP : 23
ZmHPT1    : KAAITSFYMFIWKLFYAEYLLIP : 23
TaHPT1    : KAAITSFYMLIWRLFYAEYLLIP : 23
ApHPT1    : KTTITSFYMFVWKLFYAEYLLIP : 23
GmHPT1-1  : KASITSFYMFIWKLFYAEYLLIP : 23
CpHPT1    : KAALTSFYMFIWKLFYAEYLLIP : 23
AtHPT1    : KTEITSCYMFIWKLFYAEYLLLP : 23
Chloro    : RQSIASFYMFLWGIFYTEFALLS : 23
AtHPT2    : KEAISGYYRFIWNLFYAEYLLFP : 23
GmHPT2    : KDAISGFYRFIWNLFYAEYALFP : 23
OsHPT2    : KDAISQYYRFIWNLFYAEYIFFP : 23
```

*Fig. 34b*

Motif I

```
                         *
Corn        : AEYRFSRPHTVIGT : 14
Wheat       : AEYRFSRPHTIIGT : 14
Leek        : VLYKFSRPHTIIGT : 14
soy-ppt2    : AEYRFSRPHTVIGT : 14
soy-ppt1    : AEYRFSRPHTVIGT : 14
Cuphea      : AEYRFSRPHTIIGT : 14
Arabidopsi  : AEYRFSRPHTVIGT : 14
Nostoc_ppt  : AEWKFSRPHTIIGT : 14
anabaena_p  : AEWKFSRPHTIIGT : 14
Synechocys  : AEWRFSRPHTIIGT : 14
              af54FSRPHT6IGT
```

Motif II

```
                      *         20
Corn        : NIYIVGLNQLFDIEIDKVNKPTLPLA : 26
Wheat       : NIYIVGLNQLFDIEIDKVNKPTLPLA : 26
Leek        : NVYIVGLNQLFDIEIDKVNKPDLPLA : 26
soy-ppt2    : NIYIVGLNQLSDVEIDKINKPYLPLA : 26
soy-ppt1    : NIYIVGLNQLSDVEIDKINKPYLPLA : 26
Cuphea      : NIYIVGLNQLSDIDIDKVNKPYLPLA : 26
Arabidopsi  : NIYIVGLNQLSDVEIDKVNKPYLPLA : 26
Nostoc_ppt  : NVYIVGLNQLEDVDIDKINKPHLPLA : 26
anabaena_p  : NVYIVGLNQLEDIEIDKVNKPHLPLA : 26
Synechocys  : NVYIVGLNQLWDVDIDRINKPNLPLA : 26
              N6YIVGLNQL D6 ID46NKP LPLA
```

Motif III

```
                         *
Corn        : IALFKDIPDIEGDREF : 16
Wheat       : IALFKDIPDIEGDREF : 16
Leek        : IALFKDIPDIDGDKLF : 16
soy-ppt2    : IALFKDIPDIEGDKVF : 16
soy-ppt1    : IALFKDIPDIEGDKVF : 16
Cuphea      : IALFKDIPDIEGDKLF : 16
Arabidopsi  : IALFKDIPDIEGDKTF : 16
Nostoc_ppt  : IAIFKDIPDIEGDRLY : 16
anabaena_p  : IAIFKDIPDMEGDRLY : 16
Synechocys  : IAIFKDVPDMEGDRQF : 16
              IA6FKD6PD6eGD4 5
```

*Fig. 35a*

Motif IV

```
                     *
Corn        : FYMFIWKLFYAEYLLIP : 17
Wheat       : FYMLIWRLFYAEYLLIP : 17
Leek        : FYMFVWKLFYAEYLLIP : 17
soy-ppt2    : FYMFIWKLFYAEYLLIP : 17
soy-ppt1    : LYMFIWKLFYAEYLLIP : 17
Cuphea      : FYMFIWKLFYAEYLLIP : 17
Arabidopsi  : CYMFIWKLFYAEYLLLP : 17
Nostoc_ppt  : FYQFIWKLFFIEYLIFP : 17
anabaena_p  : FYQFIWKLFFLEYLMFP : 17
Synechocys  : FYQFIWKLFFLEYLLYP : 17
              fY f6W4LF5 EYL6 P
```

Fig. 35b

Motif A

```
                          *
Nostoc_ppt  : AFWKFSRPHTIIGT : 14
anabaena_p  : AFWKFSRPHTIIGT : 14
Synechocys  : AFWRFSRPHTIIGT : 14
Corn_ppt    : AFYRFSRPHTVIGT : 14
soy-ppt2    : AFYRFSRPHTVIGT : 14
soy-ppt1    : AFYRFSRPHTVIGT : 14
Arabidopsi  : AFYRFSRPHTVIGT : 14
Cuphea_ppt  : AFYRFSRPHTIIGT : 14
              AF54FSRPHT6IGT
```

Motif B

```
                         *          20
Nostoc_ppt  : NVYIVGLNQLEDVDIDKINKPHLPLA : 26
anabaena_p  : NVYIVGLNQLEDIEIDKVNKPHLPLA : 26
Synechocys  : NVYIVGLNQLWDVDIDRINKPNLPLA : 26
Corn_ppt    : NIYIVGLNQLFDIEIDKVNKPTLPLA : 26
soy-ppt2    : NIYIVGLNQLSDVEIDKINKPYLPLA : 26
soy-ppt1    : NIYIVGLNQLSDVEIDKINKPYLPLA : 26
Arabidopsi  : NIYIVGLNQLSDVEIDKVNKPYLPLA : 26
Cuphea_ppt  : NIYIVGLNQLSDIDIDKVNKPYLPLA : 26
              N6YIVGLNQL D6 ID46NKP LPLA
```

Motif C

```
Nostoc_ppt  : IAIFKDIPDIEGDRIY : 16
anabaena_p  : IAIFKDIPDMEGDRIY : 16
Synechocys  : IAIFKDVPDMEGDRQF : 16
Corn_ppt    : IALFKDIPDIEGDRIF : 16
soy-ppt2    : IALFKDIPDIEGDKVF : 16
soy-ppt1    : IALFKDIPDIEGDKVF : 16
Arabidopsi  : IALFKDIPDIEGDKIF : 16
Cuphea_ppt  : IALFKDIPDIEGDKIF : 16
              IA6FKD6PD6EGD4 5
```

Motif D

```
                    *
Nostoc_ppt  : FYQFTWKLFEIEYTIFP : 17
anabaena_p  : FYQFTWKLFELEYLMFP : 17
Synechocys  : FYQFTWKLFLLEYLLYP : 17
Corn_ppt    : FYMFTWKLFYAEYLLIP : 17
soy-ppt2    : FYMFTWKLFYAEYLLIP : 17
soy-ppt1    : FYMFTWKLFYAEYLLIP : 17
Arabidopsi  : CYMFTWKLFYAEYLLLP : 17
```

*Fig. 36*

HOMOGENTISATE PRENYL TRANSFERASE GENE (HPT2) FROM ARABIDOPSIS AND USES THEREOF

This application claims priority to U.S. No. 60/365,202 filed Mar. 19, 2002, the disclosure of which is incorporated herein by reference in its entirety.

The present invention is in the field of plant genetics and biochemistry. More specifically, the present invention relates to genes and polypeptides associated with the tocopherol biosynthesis pathway, namely those encoding homogentisate prenyl transferase activity, and uses thereof.

Isoprenoids are ubiquitous compounds found in all living organisms. Plants synthesize a diverse array of greater than 22,000 isoprenoids (Connolly and Hill, *Dictionary of Terpenoids*, Chapman and Hall, New York, N.Y. (1992)). In plants, isoprenoids play essential roles in particular cell functions such as production of sterols, contributing to eukaryotic membrane architecture, acyclic polyprenoids found in the side chain of ubiquinone and plastoquinone, growth regulators like abscisic acid, gibberellins, brassinosteroids or the photosynthetic pigments chlorophylls and carotenoids. Although the physiological role of other plant isoprenoids is less evident, like that of the vast array of secondary metabolites, some are known to play key roles mediating the adaptative responses to different environmental challenges. In spite of the remarkable diversity of structure and function, all isoprenoids originate from a single metabolic precursor, isopentenyl diphosphate (IPP) (Wright, (1961) *Annu. Rev. Biochem.*, 20:525–548; and Spurgeon and Porter, In: *Biosynthesis of Isoprenoid Compounds*, Porter and Spurgeon (eds.) John Wiley, NY, Vol. 1, pp. 1–46 (1981)).

A number of unique and interconnected biochemical pathways derived from the isoprenoid pathway leading to secondary metabolites, including tocopherols, exist in chloroplasts of higher plants. Tocopherols not only perform vital functions in plants, but are also important from mammalian nutritional perspectives. In plastids, tocopherols account for up to 40% of the total quinone pool. Tocopherols are an important component of mammalian diets. Epidemiological evidence indicates that tocopherol supplementation can result in decreased risk for cardiovascular disease and cancer, can aid in immune function, and is associated with prevention or retardation of a number of degenerative disease processes in humans (Traber and Sies, *Annu. Rev. Nutr.*, 16:321–347 (1996)). Tocopherol functions, in part, by stabilizing the lipid bilayer of biological membranes (Skrypin and Kagan, *Biochim. Biophys. Acta*, 815:209 (1995); Kagan, *N.Y. Acad. Sci.*, p. 121 (1989); Gomez-Fernandez et al., *Ann. N.Y. Acad. Sci.*, p. 109 (1989)), reducing polyunsaturated fatty acid (PUFA) free radicals generated by lipid oxidation (Fukuzawa et al., *Lipids*, 17:511–513 (1982)), and scavenging oxygen free radicals, lipid peroxy radicals and singlet oxygen species (Diplock et al., *Ann. NY Acad. Sci.*, 570:72 (1989); Fryer, *Plant Cell Environ.*, 15(4):381–392 (1992)).

The compound α-tocopherol, which is often referred to as vitamin E, belongs to a class of lipid-soluble antioxidants that includes α, β, γ, and δ-tocopherols and α, β, γ, and δ-tocotrienols. Although α, β, γ, and δ-tocopherols and α, β, γ, and δ-tocotrienols are sometimes referred to collectively as "vitamin E", vitamin E is more appropriately defined chemically as α-tocopherol. Vitamin E, or α-tocopherol, is significant for human health, in part because it is readily absorbed and retained by the body, and therefore has a higher degree of bioactivity than other tocopherol species (Traber and Sies, *Annu. Rev. Nutr.*, 16:321–347 (1996)). Other tocopherols, however, such as β, γ, and δ-tocopherols also have significant health and nutritional benefits.

Tocopherols are primarily synthesized only by plants and certain other photosynthetic organisms, including cyanobacteria. As a result, mammalian dietary tocopherols are obtained almost exclusively from these sources. Plant tissues vary considerably in total tocopherol content and tocopherol composition, with α-tocopherol the predominant tocopherol species found in green, photosynthetic plant tissues. Leaf tissue can contain from 10–50 μg of total tocopherols per gram fresh weight, but most of the world's major staple crops (e.g., rice, corn, wheat, potato) produce low to extremely low levels of total tocopherols, of which only a small percentage is α-tocopherol (Hess, Vitamin E, α-tocopherol, In: *Antioxidants in Higher Plants*, R. Alscher and J. Hess, (eds.), CRC Press, Boca Raton., pp. 111–134 (1993)). Oil seed crops generally contain much higher levels of total tocopherols, but α-tocopherol is present only as a minor component in most oilseeds (Taylor and Barnes, *Chemy Ind.*, October:722–726 (1981)).

The recommended daily dietary intake of 15–30 mg of vitamin E is quite difficult to achieve from the average American diet. For example, it would take over 750 grams of spinach leaves, in which α-tocopherol comprises 60% of total tocopherols, or 200–400 grams of soybean oil to satisfy this recommended daily vitamin E intake. While it is possible to augment the diet with supplements, most of these supplements contain primarily synthetic vitamin E, having eight stereoisomers, whereas natural vitamin E is predominantly composed of only a single isomer. Furthermore, supplements tend to be relatively expensive, and the general population is disinclined to take vitamin supplements on a regular basis. Therefore, there is a need in the art for compositions and methods that either increase the total tocopherol production or increase the relative percentage of α-tocopherol produced by plants.

In addition to the health benefits of tocopherols, increased α-tocopherol levels in crops have been associated with enhanced stability and extended shelf life of plant products (Peterson, *Cereal-Chem.*, 72(1):21–24 (1995); Ball, *Fat-soluble vitamin assays in food analysis. A comprehensive review*, London, Elsevier Science Publishers Ltd. (1988)). Further, tocopherol supplementation of swine, beef, and poultry feeds has been shown to significantly increase meat quality and extend the shelf life of post-processed meat products by retarding post-processing lipid oxidation, which contributes to the undesirable flavor components (Sante and Lacourt, *J. Sci. Food Agric.*, 65(4):503–507 (1994); Buckley et al., *J. of Animal Science*, 73:3122–3130 (1995)).

Tocopherol Biosynthesis

The plastids of higher plants exhibit interconnected biochemical pathways leading to secondary metabolites including tocopherols. The tocopherol biosynthetic pathway in higher plants involves condensation of homogentisic acid and phytylpyrophosphate to form 2-methylphytylplastoquinol (Fiedler et al., *Planta*, 155:511–515 (1982); Soll et al., *Arch. Biochem. Biophys.*, 204:544–550 (1980); Marshall et al., *Phytochem.*, 24:1705–1711 (1985)). This plant tocopherol pathway can be divided into four parts: 1) synthesis of homogentisic acid (HGA), which contributes to the aromatic ring of tocopherol; 2) synthesis of phytylpyrophosphate, which contributes to the side chain of tocopherol; 3) joining of HGA and phytylpyrophosphate via a homogentisate prenyl transferase followed by a subsequent cyclization; and 4) S-adenosyl methionine dependent methylation of an aromatic ring, which affects the relative abundance of each of the tocopherol species. See FIG. 1.

Various genes and their encoded proteins that are involved in tocopherol biosynthesis include those listed in the table below:

| Gene ID | Enzyme name |
|---|---|
| tyrA | Bifunctional prephenate dehydrogenase |
| slr1736 | Homogentisate prenyl transferase from Synechocystis |
| ATPT2 | Homogentisate prenyl transferase from Arabidopsis thaliana |
| DXS | 1-Deoxyxylulose-5-phosphate synthase |
| DXR | 1-Deoxyxylulose-5-phosphate reductoisomerase |
| GGPPS | Geranylgeranyl pyrophosphate synthase |
| HPPD | p-Hydroxyphenylpyruvate dioxygenase |
| AANT1 | Adenylate transporter |
| slr1737 | Tocopherol cyclase |
| IDI | Isopentenyl diphosphate isomerase |
| GGH | Geranylgeranyl diphosphate reductase |
| GMT | Gamma Methyl Transferase |
| tMT2 | Tocopherol methyl transferase 2 |
| MT1 | Methyl transferase 1 |
| gcpE | (E)-4-hydroxy-3-methylbut-2-enyl diphosphate synthase |

The "Gene IDs" given in the table above identify the gene associated with the listed enzyme. Any of the Gene IDs listed in the table appearing herein in the present disclosure refer to the gene encoding the enzyme with which the Gene ID is associated in the table.

As used herein, HPT, HPT2, PPT, slr1736, and ATPT2 each refer to proteins or genes encoding proteins that have the same activity.

Synthesis of Homogentisic Acid

Homogentisic acid is the common precursor to both tocopherols and plastoquinones. In at least some bacteria the synthesis of homogentisic acid is reported to occur via the conversion of chorismate to prephenate and then to p-hydroxyphenylpyruvate via a bifunctional prephenate dehydrogenase. Examples of bifunctional bacterial prephenate dehydrogenase enzymes include the proteins encoded by the tyrA genes of *Erwinia herbicola* and *Escherichia coli*. The tyrA gene product catalyzes the production of prephenate from chorismate, as well as the subsequent dehydrogenation of prephenate to form p-hydroxyphenylpyruvate (p-HPP), the immediate precursor to homogentisic acid. p-HPP is then converted to homogentisic acid by hydroxyphenylpyruvate dioxygenase (HPPD). In contrast, plants are believed to lack prephenate dehydrogenase activity, and it is generally believed that the synthesis of homogentisic acid from chorismate occurs via the synthesis and conversion of the intermediate arogenate. Since pathways involved in homogentisic acid synthesis are also responsible for tyrosine formation, any alterations in these pathways can also result in the alteration in tyrosine synthesis and the synthesis of other aromatic amino acids.

Synthesis of Phytylpyrophosphate

Tocopherols are a member of the class of compounds referred to as the isoprenoids. Other isoprenoids include carotenoids, gibberellins, terpenes, chlorophyll and abscisic acid. A central intermediate in the production of isoprenoids is isopentenyl diphosphate (IPP). Cytoplasmic and plastid-based pathways to generate IPP have been reported. The cytoplasmic based pathway involves the enzymes acetoacetyl CoA thiolase, HMGCoA synthase, HMGCoA reductase, mevalonate kinase, phosphomevalonate kinase, and mevalonate pyrophosphate decarboxylase.

Recently, evidence for the existence of an alternative, plastid based, isoprenoid biosynthetic pathway emerged from studies in the research groups of Rohmer and Arigoni (Eisenreich et al., *Chem. Bio.*, 5:R221–R233 (1998); Rohmer, *Prog. Drug. Res.*, 50:135–154 (1998); Rohmer, *Comprehensive Natural Products Chemistry*, Vol. 2, pp. 45–68, Barton and Nakanishi (eds.), Pergamon Press, Oxford, England (1999)), who found that the isotope labeling patterns observed in studies on certain eubacterial and plant terpenoids could not be explained in terms of the mevalonate pathway. Arigoni and coworkers subsequently showed that 1-deoxyxylulose, or a derivative thereof, serves as an intermediate of the novel pathway, now referred to as the MEP pathway (Rohmer et al., *Biochem. J.*, 295:517–524 (1993); Schwarz, Ph.D. thesis, Eidgenössiche Technische Hochschule, Zurich, Switzerland (1994)). Recent studies showed the formation of 1-deoxyxylulose 5-phosphate (Broers, Ph.D. thesis, Eidgenössiche Technische Hochschule, Zurich, Switzerland (1994)) from one molecule each of glyceraldehyde 3-phosphate (Rohmer, *Comprehensive Natural Products Chemistry*, Vol. 2, pp. 45–68, Barton and Nakanishi (eds.), Pergamon Press, Oxford, England (1999)) and pyruvate (Eisenreich et al., *Chem. Biol.*, 5:R223–R233 (1998); Schwarz supra; Rohmer et al., *J. Am. Chem. Soc.*, 118:2564–2566 (1996); and Sprenger et al., *Proc. Natl. Acad. Sci. (U.S.A.)*, 94:12857–12862 (1997)) by an enzyme encoded by the dxs gene (Lois et al., *Proc. Natl. Acad. Sci. (U.S.A.)*, 95:2105–2110 (1997); and Lange et al., *Proc. Natl. Acad. Sci. (U.S.A.)*, 95:2100–2104 (1998)). 1-Deoxyxylulose 5-phosphate can be further converted into 2-C-methyl-erythritol 4-phosphate (Arigoni et al., *Proc. Natl. Acad. Sci. (U.S.A.)*, 94:10600–10605 (1997)) by a reductoisomerase encoded by the dxr gene (Bouvier et al., *Plant Physiol*, 117:1421–1431 (1998); and Rohdich et al., *Proc. Natl. Acad. Sci. (U.S.A.)*, 96:11758–11763 (1999)).

Reported genes in the MEP pathway also include ygbP, which catalyzes the conversion of 2-C-methylerythritol 4-phosphate into its respective cytidyl pyrophosphate derivative and ygbB, which catalyzes the conversion of 4-phosphocytidyl-2-C-methyl-D-erythritol into 2-C-methyl-D-erythritol, 3,4-cyclophosphate. These genes are tightly linked on the *E. coli* genome (Herz et al., *Proc. Natl. Acad. Sci. (U.S.A.)*, 97(6):2485–2490 (2000)).

Once IPP is formed by the MEP pathway, it is converted to GGDP by GGPDP synthase, and then to phytylpyrophosphate, which is the central constituent of the tocopherol side chain.

Combination and Cyclization

Homogentisic acid is combined with either phytyl-pyrophosphate or solanyl-pyrophosphate by homogentisate prenyl transferase (HPT) forming 2-methylphytyl plastoquinol or 2-methylsolanyl plastoquinol, respectively. 2-methylsolanyl plastoquinol is a precursor to the biosynthesis of plastoquinones, while 2-methylphytyl plastoquinol is ultimately converted to tocopherol.

Methylation of the Aromatic Ring

The major structural difference between each of the tocopherol subtypes is the position of the methyl groups around the phenyl ring. Both 2-methylphytyl plastoquinol and 2-methylsolanyl plastoquinol serve as substrates for the plant enzyme 2-methylphytylplastoquinol/2-methylsolanylplastoquinol methyltransferase (Tocopherol Methyl Transferase 2; Methyl Transferase 2; MT2; tMT2), which is capable of methylating a tocopherol precursor. Subsequent methylation at the 5 position of γ-tocopherol by γ-tocopherol methyl-transferase (GMT) generates the biologically active α-tocopherol.

Some plants e.g. soy produce substantial amounts of delta and subsequently beta-tocopherol in their seed. The formation of δ-tocopherol or β-tocopherol can be prevented by the overexpression of tMT2, resulting in the methylation of the δ-tocopherol precursor, 2-methyl phytyl plastoquinone to form 2,3-dimethyl-5-phytyl plastoquinone followed by cyclization with tocopherol cyclase to form γ-tocopherol and a subsequent methylation by GMT to form α-tocopherol. In a possible alternative pathway, β-tocopherol is directly converted to α-tocopherol by tMT2 via the methylation of the 3 position (see, for example, *Biochemical Society Transactions*, 11:504–510 (1983); *Introduction to Plant Biochemistry*, 2$^{nd}$ edition, Chapter 11 (1983); *Vitamin Hormone*, 29:153–200 (1971); *Biochemical Journal*, 109:577 (1968); and, *Biochemical and Biophysical Research Communication*, 28(3):295 (1967)). Since all potential mechanisms for the generation of α-tocopherol involve catalysis by tMT2, plants that are deficient in this activity accumulate δ-tocopherol and β-tocopherol. Plants which have increased tMT2 activity tend to accumulate γ-tocopherol and α-tocopherol. Since there is limited GMT activity in the seeds of many plants, these plants tend to accumulate γ-tocopherol.

There is a need in the art for nucleic acid molecules encoding enzymes involved in tocopherol biosysnthesis, as well as related enzymes and antibodies for the enhancement or alteration of tocopherol production in plants. There is a further need for transgenic organisms expressing those nucleic acid molecules involved in tocopherol biosynthesis, which are capable of nutritionally enhancing food and feed sources.

SUMMARY OF THE INVENTION

The present invention includes and provides a substantially purified nucleic acid molecule encoding an amino acid sequence selected from the group consisting of SEQ ID NOs: 5, 9–11, 57–58, and 90.

The present invention includes and provides a substantially purified polypeptide molecule comprising an amino acid sequence selected from the group consisting of SEQ ID NOs: 5, 9–11, 57–58, and 90.

The present invention includes and provides an antibody capable of specifically binding a polypeptide comprising an amino acid sequence selected from the group consisting of SEQ ID NOs: 5, 9–11, 57–58, and 90.

The present invention includes and provides a substantially purified nucleic acid molecule encoding a polypeptide having homogentisate prenyl transferase activity comprising an amino acid sequence selected from the group consisting of SEQ ID NOs: 43 and 44.

The present invention includes and provides a substantially purified polypeptide having homogentisate prenyl transferase activity comprising an amino acid sequence selected from the group consisting of SEQ ID NOs: 43 and 44.

The present invention includes and provides a transformed plant comprising an introduced nucleic acid molecule encoding a polypeptide comprising an amino acid sequence selected from the group consisting of SEQ ID NOs: 5, 9–11, 43–44, 57–58, and 90, and complements thereof.

The present invention includes and provides a transformed plant comprising an introduced first nucleic acid molecule encoding a polypeptide comprising an amino acid sequence selected from the group consisting of SEQ ID NOs: 5, 9–11, 43–44, 57–58, and 90, and complements thereof, and an introduced second nucleic acid molecule encoding an enzyme selected from the group consisting of tyrA, prephenate dehydrogenase, tocopherol cyclase, dxs, dxr, GMT, MT1, tMT2, GCPE, GGPPS, HPPD, AANT1, IDI, GGH, and complements thereof.

The present invention includes and provides a transformed plant comprising a nucleic acid molecule comprising an introduced promoter region which functions in plant cells to cause the production of an mRNA molecule, wherein said introduced promoter region is linked to a transcribed nucleic acid molecule having a transcribed strand and a non-transcribed strand, wherein said transcribed strand is complementary to a nucleic acid molecule encoding a polypeptide selected from the group consisting of SEQ ID NOs: 5, 9–11, 43–44, 57–58, and 90, and wherein said transcribed nucleic acid molecule is linked to a 3' non-translated sequence that functions in the plant cells to cause termination of transcription and addition of polyadenylated ribonucleotides to a 3' end of the mRNA sequence.

The present invention includes and provides a method of producing a plant having a seed with an increased total tocopherol level comprising: (A) transforming said plant with an introduced nucleic acid molecule encoding a polypeptide comprising an amino acid sequence selected from the group consisting of SEQ ID NOs: 5, 9–11, 43–44, 57–58, and 90; and (B) growing said transformed plant.

The present invention includes and provides a method of producing a plant having a seed with an increased total tocopherol level comprising: (A) transforming said plant with an introduced first nucleic acid molecule, wherein said first nucleic acid molecule encodes a polypeptide having an amino acid sequence selected from the group consisting of SEQ ID NOs: 5, 9–11, 43–44, 57–58, and 90, and an introduced second nucleic acid molecule encoding an enzyme selected from the group consisting of tyrA, prephenate dehydrogenase, tocopherol cyclase, dxs, dxr, GMT, MT1, tMT2, GGPPS, GCPE, HPPD, AANT1, IDI, GGH, and complements thereof; and (B) growing said transformed plant.

The present invention includes and provides a seed derived from a transformed plant comprising an introduced nucleic acid molecule encoding a polypeptide comprising an amino acid sequence selected from the group consisting of SEQ ID NOs: 5, 9–11, 43–44, 57–58, and 90.

The present invention includes and provides a seed derived from a transformed plant comprising an introduced first nucleic acid molecule encoding an introduced polypeptide comprising an amino acid sequence selected from the group consisting of SEQ ID NOs: 5, 9–11, 43, 44, 57, 58, and 90 and an introduced second nucleic acid encoding an enzyme selected from the group consisting of tyrA, prephenate dehydrogenase, tocopherol cyclase, dxs, dxr, GMT, MT1, GCPE, tMT2, GGPPS, HPPD, AANT1, IDI, GGH, and complements thereof.

The present invention includes and provides a substantially purified polypeptide comprising an amino acid sequence selected from the group consisting of SEQ ID NOs: 39–42, 46–49, and 92–95 wherein said amino acid sequence is not derived from a nucleic acid molecule that is derived from *Nostoc punctiforme, Anabaena, Synechocystis, Zea mays, Glycine max, Arabidopsis thaliana, Oryza sativa, Trichodesmium erythraeum, Chloroflexus aurantiacus,* wheat, leek, canola, cotton, or tomato. The present invention includes and provides said substantially purified polypeptide wherein more than one more amino acid sequence is selected from the group consisting of SEQ ID NOs: 39–42, 46–49, and 92–95.

The present invention includes and provides a substantially purified nucleic acid molecule encoding a polypeptide comprising an amino acid sequence selected from the group consisting of SEQ ID NOs: 39–42, 46–49, and 92–95 wherein said nucleic acid molecule is not derived from Nostoc punctiforme, Anabaena, Synechocystis, Zea mays, Glycine max, Arabidopsis thaliana, Oryza sativa, Trichodesmium erythraeum, Chloroflexus aurantiacus, wheat, leek, canola, cotton, or tomato. The present invention includes and provides said nucleic acid molecule wherein the polypeptide further comprises more than one amino acid sequence selected from the group consisting of SEQ ID NOs: 39–42, 46–49, and 92–95.

The present invention includes and provides a substantially purified nucleic acid molecule encoding a polypeptide comprising an amino acid sequence selected from the group consisting of SEQ ID NOs: 39–42, 46–49, and 92–95 wherein said nucleic acid molecule is not derived from Nostoc punctiforme, Anabaena, Synechocystis, Zea mays, Glycine max, Arabidopsis thaliana, Oryza sativa, Sulfolobus, Aeropyum, Trichodesmium erythraeum, Chloroflexus aurantiacus, sorghum, wheat, tomato, or leek. The present invention includes and provides said nucleic acid molecule wherein the polypeptide further comprises more than one amino acid sequence selected from the group consisting of SEQ ID NOs: 39–42, 46–49 and 92–95.

The present invention includes and provides a plant transformed with a nucleic acid molecule encoding a polypeptide comprising an amino acid sequence selected from the group consisting of SEQ ID NOs: 39–42, 46–49, and 92–95 wherein said nucleic acid molecule is not derived from Nostoc punctiforme, Anabaena, Synechocystis, Zea mays, Glycine max, Arabidopsis thaliana, Oryza sativa, Sulfolobus, Aeropyum, Trichodesmium erythraeum, Chloroflexus aurantiacus, sorghum, wheat, tomato, or leek. The present invention includes and provides said nucleic acid molecule wherein the polypeptide further comprises more than one amino acid sequence selected from the group consisting of SEQ ID NOs: 39–42, 46–49, and 92–95.

The present invention includes and provides a substantially purified polypeptide comprising an amino acid sequence selected from the group consisting of SEQ ID NOs: 39–42, 46–49, and 92–95 wherein said polypeptide does not comprise any of the amino acid sequences set forth in sequence listings in WO 00/68393 (which sequences are incorporated herein by reference); WO 00/63391 (which sequences are incorporated herein by reference); WO 01/62781 (which sequences are incorporated herein by reference); or WO 02/33060 (which sequences are incorporated herein by reference); and does not comprise SEQ ID NOs: 1–11, 43–45, 57–58, 61–62, or 90 from the present application.

The present invention includes and provides a substantially purified polypeptide comprising more than onean amino acid sequence selected from the group consisting of SEQ ID NOs: 39–42, 46–49, and 92–95.

The present invention includes and provides a substantially purified nucleic acid molecule encoding a polypeptide comprising an amino acid sequence selected from the group consisting of SEQ ID NOs: 39–42, 46–49, and 92–95 wherein said nucleic acid molecule does not comprise any of the nucleic acid sequences set forth in sequence listings in WO 00/68393; WO 00/63391; WO 01/62781; or WO 02/33060; and does not comprise SEQ ID NOs: 27–36; 59–60, 88–89, and 91 from the present application, or the gene with Genebank Accession Nos. AI 897027 or AW 563431 The present invention includes and provides said nucleic acid molecule wherein the polypeptide further comprises more than one amino acid sequence selected from the group consisting of SEQ ID NOs: 39–42, 46–49, and 92–95.

The present invention includes and provides a plant transformed with a nucleic acid molecule encoding a polypeptide comprising an amino acid sequence selected from the group consisting of SEQ ID NOs: 39–42, 46–49, and 92–95 wherein said nucleic acid molecule does not comprise any of the nucleic acid sequences set forth in sequence listings in WO 00/68393; WO 00/63391; WO 01/62781; or WO 02/33060; and does not comprise SEQ ID NOs: 27–36; 59–60, 88–89, and 91 from the present application, or the gene with Genebank Accession Nos. AI 897027 or AW 563431. The present invention includes and provides said nucleic acid molecule wherein the polypeptide further comprises more than one amino acid sequence selected from the group consisting of SEQ ID NOs: 39–42, 46–49, and 92–95.

The present invention includes and provides a substantially purified nucleic acid molecule comprising a nucleic acid sequence selected from the group consisting of SEQ ID NOs: 31, 34–36, 59–60, and 91.

The present invention includes and provides for homogentisate prenyl transferases discovered using one or more of the alignments of FIGS. 2a–2c, 3a–3c, 24a–24b, 25a–25b, 33a–33c, 34a–34b, 35a–35b and 36.

DESCRIPTION OF THE NUCLEIC AND AMINO ACID SEQUENCES

SEQ ID NO: 1 sets forth a Nostoc punctiforme homogentisate prenyl transferase polypeptide.

SEQ ID NO: 2 sets forth an Anabaena homogentisate prenyl transferase polypeptide.

SEQ ID NO: 3 sets forth a Synechocystis homogentisate prenyl transferase polypeptide.

SEQ ID NO: 4 sets forth a Zea mays homogentisate prenyl transferase polypeptide (HPT1).

SEQ ID NO: 5 sets forth a Glycine max homogentisate prenyl transferase polypeptide (HPT1-2).

SEQ ID NO: 6 sets forth a Glycine max homogentisate prenyl transferase polypeptide (HPT1-1).

SEQ ID NO: 7 sets forth an Arabidopsis thaliana homogentisate prenyl transferase polypeptide (HPT1).

SEQ ID NO: 8 sets forth a partial Cuphea pulcherrima homogentisate prenyl transferase polypeptide.

SEQ ID NO: 9 sets forth a leek homogentisate prenyl transferase polypeptide (HPT1).

SEQ ID NO: 10 sets forth a wheat homogentisate prenyl transferase polypeptide (HPT1).

SEQ ID NO: 11 sets forth a Cuphea pulcherrima homogentisate prenyl transferase polypeptide (HPT1).

SEQ ID NOs: 12–15 represent domains from SEQ ID NOs: 1–8.

SEQ ID NOs: 16–26 set forth primer sequences.

SEQ ID NO: 27 sets forth a nucleic acid molecule encoding a Nostoc punctiforme homogentisate prenyl transferase polypeptide.

SEQ ID NO: 28 sets forth a nucleic acid molecule encoding an Anabaena homogentisate prenyl transferase polypeptide.

SEQ ID NO: 29 sets forth a nucleic acid molecule encoding a Synechocystis homogentisate prenyl transferase polypeptide.

SEQ ID NO: 30 sets forth a nucleic acid molecule encoding a Zea mays homogentisate prenyl transferase polypeptide (HPT1).

SEQ ID NO: 31 sets forth a nucleic acid molecule encoding a Glycine max homogentisate prenyl transferase polypeptide (HPT1-2).

SEQ ID NO: 32 sets forth a nucleic acid molecule encoding a *Glycine max* homogentisate prenyl transferase polypeptide (HPT1-1).

SEQ ID NO: 33 sets forth a nucleic acid molecule encoding an *Arabidopsis thaliana* homogentisate prenyl transferase polypeptide (HPT1).

SEQ ID NO: 34 sets forth a nucleic acid molecule encoding a *Cuphea pulcherrima* homogentisate prenyl transferase polypeptide (HPT1).

SEQ ID NO: 35 sets forth a nucleic acid molecule encoding a leek homogentisate prenyl transferase polypeptide (HPT1).

SEQ ID NO: 36 sets forth a nucleic acid molecule encoding a wheat homogentisate prenyl transferase polypeptide (HPT1).

SEQ ID NOs: 37–38 set forth primer sequences.

SEQ ID NOs: 39–42 set forth domains from SEQ ID NOs: 1–7 and 9–11.

SEQ ID NO: 43 sets forth a homogentisate prenyl transferase polypeptide from *Trichodesmium erythraeum*.

SEQ ID NO: 44 sets forth a homogentisate prenyl transferase polypeptide from *Chloroflexus aurantiacus*.

SEQ ID NO: 45 sets forth a putative sequence for an *Arabidopsis thaliana* homogentisate prenyl transferase polypeptide (HPT2).

SEQ ID NOs: 46–49 represent domains from SEQ ID NOs: 1–4, 6–7, 9–11, 57–58 and 91.

SEQ ID NOs: 50–56 set forth primer sequences.

SEQ ID NO: 57 sets forth an *Arabidopsis thaliana* homogentisate prenyl transferase polypeptide (HPT2).

SEQ ID NO: 58 sets forth an *Oryza sativa* homogentisate prenyl transferase polypeptide (HPT2).

SEQ ID NO: 59 sets forth a nucleic acid molecule encoding an *Arabidopsis thaliana* homogentisate prenyl transferase polypeptide (HPT2).

SEQ ID NO: 60 sets forth a nucleic acid molecule encoding an *Oryza sativa* homogentisate prenyl transferase polypeptide (HPT2).

SEQ ID NO: 61 sets forth a putative homogentisate prenyl transferase polypeptide from *Arabidopsis thaliana* (HPT2).

SEQ ID NO: 62 sets forth a putative homogentisate prenyl transferase polypeptide from *Arabidopsis thaliana* (HPT2).

SEQ ID NO: 63 sets forth an EST from *Arabidopsis thaliana*.

SEQ ID NO: 64 sets forth an EST from *Medicago truncatula*.

SEQ ID NO: 65 sets forth an EST from *Medicago truncatula* developing stem.

SEQ ID NO: 66 sets forth an EST from *Medicago truncatula* developing stem.

SEQ ID NO: 67 sets forth an EST from *Medicago truncatula* developing stem.

SEQ ID NO: 68 sets forth an EST from mixed potato tissues.

SEQ ID NO: 69 sets forth an EST from *Arabidopsis thaliana*, Columbia ecotype flower buds.

SEQ ID NO: 70 sets forth an EST from *Arabidopsis thaliana*.

SEQ ID NO: 71 sets forth an EST from *Medicago truncatula*.

SEQ ID NO: 72 sets forth an EST from *Glycine max*.

SEQ ID NOs: 73–83 and 84–87 set forth primer sequences.

SEQ ID NO: 88 sets forth a nucleic acid molecule encoding a homogentisate prenyl transferase polypeptide from cyanobacteria *Trichodesmium erythraeum*.

SEQ ID NO: 89 sets forth a nucleic acid molecule encoding a homogentisate prenyl transferase polypeptide from photobacteria *Chloroflexus aurantiacus*.

SEQ ID NO: 90 sets forth a *Glycine max* homogentisate prenyl transferase polypeptide (HPT2).

SEQ ID NO: 91 sets forth a nucleic acid molecule encoding a homogentisate prenyl transferase polypeptide from *Glycine max* (HPT2).

SEQ ID NOs: 92–95 represent domains from SEQ ID NOs: 1–4, 6–7, 9–11, 43–44, 57–58, and 90.

Note: cyanobacteria and photobbacteria have one HPT. Plants have both HPT1 and HPT2. In soy, there are two variations of HPT1, HPT1-1 and HPT1-2, as well as HPT2.

BRIEF DESCRIPTION OF THE FIGURES

FIGS. 2a–2c depicts a sequence alignment for several homogentisate prenyl transferase polypeptides SEQ ID NOs: 1–8).

FIGS. 3a–3c depicts a sequence alignment for several homogentisate prenyl transferase polypeptides (SEQ ID NOs: 1–7, and 9–11).

Figure 24B:
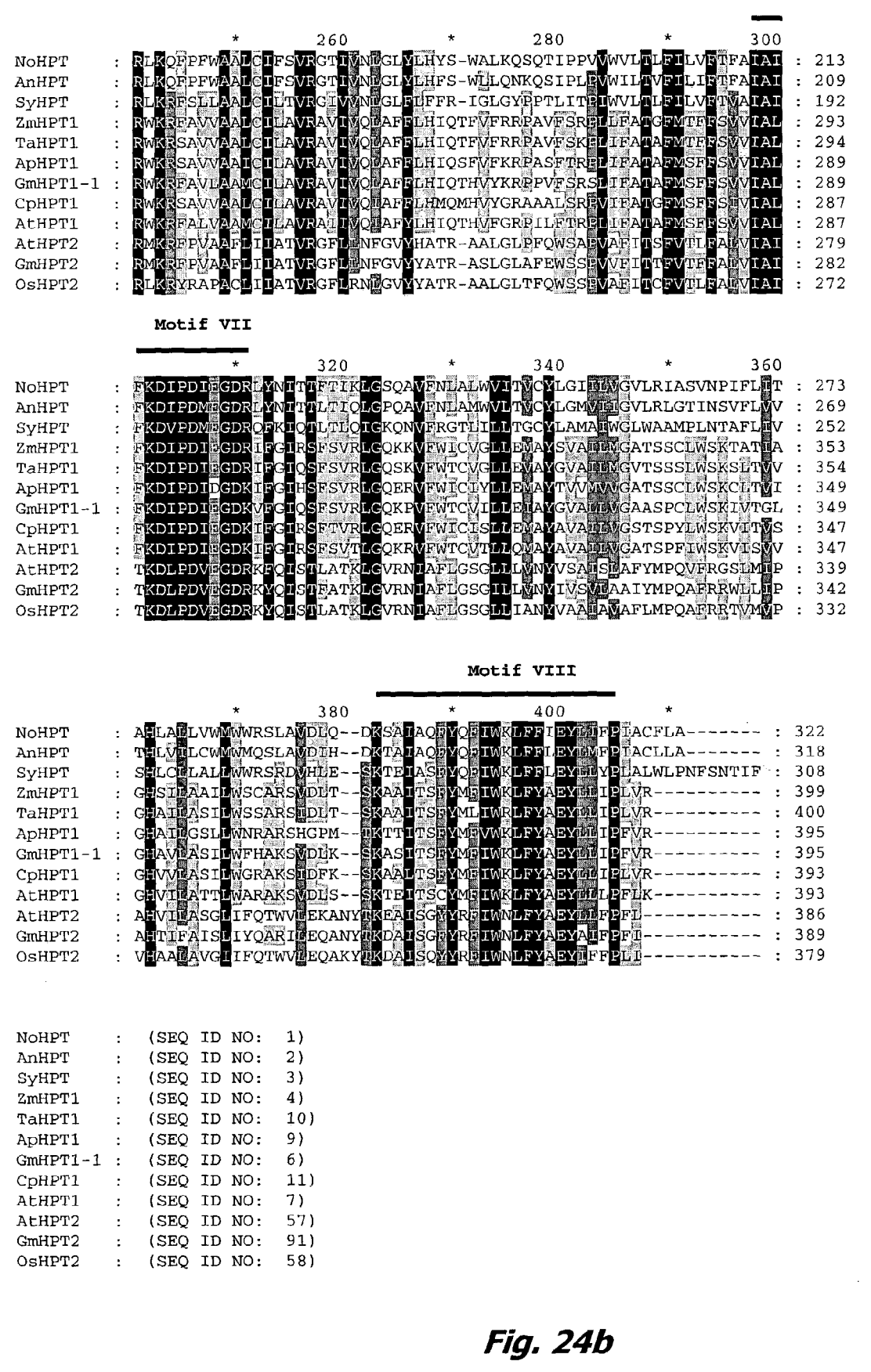

FIG. 24 depicts the alignments of SEQ ID NOs: 1–4, 6–7, 9–11, 57–58, and 91.

FIG. 25 depicts motifs V through VIII, SEQ ID NOs: 46–49.

FIGS. 33*a*–33*d* depicts a sequence alignment for several homogentisate prenyl transferase polypeptide SEQ ID NOs: 1–4, 6–7, 9–11, 43–44, 57–58, and 90.

FIG. 34 depicts motifs IX through XII, SEQ ID NOs: 92–95.

FIG. 35 depicts motifs I–IV, SEQ ID NOs: 39–42.

FIG. 36 depicts motifs A–D, (SEQ ID NOs:1–8, FIGS. 2A–C).

DETAILED DESCRIPTION

Figure 1:
FIG. 1 is a schematic diagram of the tocopherol biosynthetic pathway.

The present invention provides a number of agents, for example, nucleic acid molecules and polypeptides associated with the synthesis of tocopherol, and provides uses of such agents.

Agents

The agents of the present invention will preferably be "biologically active" with respect to either a structural attribute, such as the capacity of a nucleic acid to hybridize to another nucleic acid molecule, or the ability of a protein to be bound by an antibody (or to compete with another molecule for such binding). Alternatively, such an attribute may be catalytic and thus involve the capacity of the agent to mediate a chemical reaction or response. The agents will preferably be "substantially purified". The term "substantially purified", as used herein, refers to a molecule separated from substantially all other molecules normally associated with it in its native environmental conditions. More preferably a substantially purified molecule is the predominant species present in a preparation. A substantially purified molecule may be greater than about 60% free, preferably about 75% free, more preferably about 90% free, and most preferably about 95% free from the other molecules (exclusive of solvent) present in the natural mixture. The term "substantially purified" is not intended to encompass molecules present in their native environmental conditions.

The agents of the present invention may also be recombinant. As used herein, the term recombinant means any agent (e.g., DNA, peptide etc.), that is, or results, however indirectly, from human manipulation of a nucleic acid molecule.

It is understood that the agents of the present invention may be labeled with reagents that facilitate detection of the agent (e.g., fluorescent labels, Prober et al., *Science*, 238: 336–340 (1987); Albarella et al., EP 144 914; chemical labels, Sheldon et al., U.S. Pat. No. 4,582,789; Albarella et al., U.S. Pat. No. 4,563,417; modified bases, Miyoshi et al., EP 119 448).

Nucleic Acid Molecules

Agents of the present invention include nucleic acid molecules. In a preferred aspect of the present invention the nucleic acid molecule comprises a nucleic acid sequence that encodes a homogentisate prenyl transferase. As used herein, a homogentisate prenyl transferase is any plant protein that is capable of specifically catalyzing the formation of 2-methyl-6-phytylbenzoquinol (2-methyl-6-geranylgeranylbenzoquinol) from phytyl-DP (GGDP) and homogentisate.

An example of a more preferred homogentisate prenyl transferase is a polypeptide with the amino acid sequence selected from the group consisting of SEQ ID NOs: 5, 9–11, 43–44, 55, 58, and 90. In a more preferred embodiment, the homogentisate prenyl transferase is encoded by any nucleic acid molecule encoding an amino acid sequence selected from the group consisting of SEQ ID NOs: 5, 9–11, 43–44, 55, 58, and 90.

In another preferred aspect of the present invention the nucleic acid molecule of the present invention comprises a nucleic acid sequence encoding a polypeptide selected from the group consisting of SEQ ID NOs: 5, 9–11, 43–44, 55, 58, and 90, and complements thereof and fragments of either.

In another preferred aspect of the present invention the nucleic acid molecule of the present invention comprises a nucleic acid sequence selected from the group consisting of SEQ ID NOs: 31, 34–36, 59–60, and 91.

In another embodiment, the present invention includes nucleic acid molecules encoding polypeptides having a region of conserved amino acid sequence shown in any of Figures FIGS. 2*a*–2*c*, 3*a*–3*c*, 24*a*–24*b*, 25*a*–25*b*, 33*a*–33*c*, 34*a*–34*b*, 35*a*–*b* and 36, and complements of those nucleic acid molecules. In a preferred embodiment, the present invention includes nucleic acid molecules encoding polypeptides comprising a sequence selected from the group consisting of SEQ ID NOs: 39–42, 46–49, and 92–95, and complements of those nucleic acid molecules. The present invention includes and provides said nucleic acid molecule wherein the polypeptide further comprises more than one amino acid sequence selected from the group consisting of SEQ ID NOs: 39–42, 46–49, and 92–95.

In a further preferred embodiment the present invention includes nucleic acid molecules encoding polypeptides comprising two or more, three or more, or four sequences selected from the group consisting of SEQ ID NOs: 39–42, 46–49, and 92–95, and complements of those nucleic acid molecules. In another embodiment, the present invention includes nucleic acid molecules encoding polypeptides having homogentisate prenyl transferase activity and a region of conserved amino acid sequence shown in any of FIGS. 2*a*–2*c*, 3*a*–3*c*, 24*a*–24*b*, 25*a*–25*b*, 33*a*–33*c*, 34*a*–34*b*, 35*a*–35*b* and 36, and complements of those nucleic acid molecules. In a preferred embodiment, the present invention includes nucleic acid molecules encoding polypeptides having homogentisate prenyl transferase activity and comprising a sequence selected from the group consisting of SEQ ID NOs: 39–42, 46–49, and 92–95 and complements of those nucleic acid molecules. The present invention includes and provides said nucleic acid molecule wherein the polypeptide further comprises more than one amino acid sequence selected from the group consisting of SEQ ID NOs: 39–42, 46–49, and 92–95.

In a further preferred embodiment the present invention includes nucleic acid molecules encoding polypeptides having homogentisate prenyl transferase activity and comprising two or more, three or more, or four sequences selected from the group consisting of SEQ ID NOs: 39–42, 46–49, and 92–95, and complements of those nucleic acid molecules. In another embodiment, the present invention includes nucleic acid molecules, excluding nucleic acid molecules derived from *Nostoc punctiforme, Anabaena, Synechocystis, Zea mays, Glycine max, Arabidopsis thaliana, Oryza sativa, Trichodesmium erythraeum, Chloroflexus aurantiacus*, wheat, leek, canola, cotton, or tomato, encoding polypeptides having a region of conserved amino acid sequence shown in any of FIGS. 2*a*–2*c*, 3*a*–3*c*, 24*a*–24*b*, 25*a*–25*b*, 33*a*–33*c*, 34*a*–34*b*, 35*a*–35*b* and 36, and complements of hose nucleic acid molecules. In a preferred embodiment, the present invention includes nucleic acid molecules, excluding nucleic acid molecules derived from *Nostoc punctiforme, Anabaena, Synechocystis, Zea mays, Glycine max, Arabidopsis thaliana, Oryza sativa, Trichodesmium erythraeum, Chloroflexus aurantiacus*, wheat, leek, canola, cotton, or tomato, encoding polypeptides comprising a sequence selected from the group consisting of SEQ ID NOs: 39–42, 46–49, and 92–95 and complements of those nucleic acid molecules. The present invention includes and provides said nucleic acid molecule wherein the polypeptide further comprises more than one amino acid sequence selected from the group consisting of SEQ ID NOs: 39–42, 46–49, and 92–95.

In a further preferred embodiment the present invention includes nucleic acid molecules, excluding nucleic acid molecules derived from *Nostoc punctiforme, Anabaena, Synechocystis, Zea mays, Glycine max, Arabidopsis thaliana, Oryza sativa, Trichodesmium erythraeum, Chloroflexus aurantiacus*, wheat, leek, canola, cotton, or tomato, encoding polypeptides comprising two or more, three or more, or four sequences selected from the group consisting of SEQ ID NOs: 39–42, 46–49, and 92–95.

In another embodiment, the present invention includes nucleic acid molecules, excluding nucleic acid molecules derived from *Nostoc punctiforme, Anabaena, Synechocystis, Zea mays, Glycine max, Arabidopsis thaliana, Oryza sativa, Trichodesmium erythraeum, Chloroflexus aurantiacus*, wheat, leek, canola, cotton, Sulfolobus, Aeropyum, sorghum, or tomato, encoding polypeptides having homogentisate prenyl transferase activity and a region of conserved amino acid sequence shown in any of FIGS. 2a–2c, 3a–3c, 24a–24b, 25a–25b, 33a–33c, 34a–34b, 35a–35b and 36 and complements of those nucleic acid molecules. In a preferred embodiment, the present invention includes nucleic acid molecules, excluding nucleic acid molecules derived from *Nostoc punctiforme, Anabaena, Synechocystis, Zea mays, Glycine max, Arabidopsis thaliana, Oryza sativa, Trichodesmium erythraeum, Chloroflexus aurantiacus*, wheat, leek, canola, cotton, or tomato, encoding polypeptides having homogentisate prenyl transferase activity and comprising a sequence selected from the group consisting of SEQ ID NOs: 39–42, 46–49, and 92–95. The present invention includes and provides said nucleic acid molecule wherein the polypeptide further comprises more than one amino acid sequence selected from the group consisting of SEQ ID NOs: 39–42, 46–49, and 92–95.

In a further preferred embodiment the present invention includes nucleic acid molecules, excluding nucleic acid molecules derived from *Nostoc punctiforme, Anabaena, Synechocystis, Zea mays, Glycine max, Arabidopsis thaliana, Oryza sativa, Trichodesmium erythraeum, Chloroflexus aurantiacus*, wheat, leek, canola, cotton, or tomato, encoding polypeptides having homogentisate prenyl transferase activity and comprising two or more, three or more, or four sequences selected from the group consisting of SEQ ID NOs: 39–42, 46–49, and 92–95.

In one embodiment of a method of the present invention, any of the nucleic acid sequences or polypeptide sequences, or fragments of either, of the present invention can be used to search for related sequences. In a preferred embodiment, a member selected from the group consisting of SEQ ID NOs: 5, 9–11, 43–44, 57–58, and 90 is used to search for related sequences. In a preferred embodiment, a member selected from the group consisting of SEQ ID NOs: 31, 34–36, 59–60, 88–89, and 91 is used to search for related sequences. In another embodiment, any of the motifs or regions of conserved sequence shown in FIGS. 2a–2c, 3a–3c, 24a–24b, 25a–25l), 33a–33c, 34a–34b, 35a–35b and 36 are used to search for related amino acid sequences. In a preferred embodiment, a member selected from the group consisting of SEQ ID NOs: 39–42 and 46–49 is used to search for related sequences. In one embodiment, one or more of SEQ ID NOs: 39–42, 46–49, and 92–95 is used to search for related sequences. As used herein, "search for related sequences" means any method of determining relatedness between two sequences, including, but not limited to, searches that compare sequence homology: for example, a PBLAST search of a database for relatedness to a single amino acid sequence. Other searches may be counted using profile based methods, such as the HMM (Hidden Markov model) META-MEME [(http://metameme.sdsc.edu/mhmm-links.html), PSI-BLAST (http://www.ncbi.nlm.nih.gov/BLAST/).] (http://followed by metameme.sdsc.edu/mhmm-links.html), PSI-BLAST (on the world wide web at ncbi.nlm.nih.gov/BLAST/).

As used herein, a nucleic acid molecule is said to be "derived from" a particular organism, species, ecotype, etc., when the sequence of the nucleic acid molecule originated from that organism, species, ecotype, etc. "Derived from" therefore includes copies of nucleic acid molecules derived through, for example, PCR, as well as synthetically generated nucleic acid molecules having the same nucleic acid sequence as the original organism, species, ecotype, etc. Likewise, a polypeptide is said to be "derived from" a nucleic acid molecule when that nucleic acid molecule is used to code for the polypeptide, whether the polypeptide is enzymatically generated from the nucleic acid molecule or synthesized based on the sequence information inherent in the nucleic acid molecule.

The present invention includes the use of the above-described conserved sequences and fragments thereof in transgenic plants, other organisms, and for other uses, including, without limitation, as described below.

In another preferred aspect of the present invention a nucleic acid molecule comprises nucleotide sequences encoding a plastid transit peptide operably fused to a nucleic acid molecule that encodes a protein or fragment of the present invention.

In another preferred embodiment of the present invention, the nucleic acid molecules of the present invention encode mutant tocopherol homogentisate prenyl transferase enzymes. As used herein, a mutant enzyme is any enzyme that contains an amino acid that is different from the amino acid in the same position of a wild type enzyme of the same type.

It is understood that in a further aspect of nucleic acid sequences of the present invention, the nucleic acids can encode a protein that differs from any of the proteins in that one or more amino acids have been deleted, substituted or added without altering the function. For example, it is understood that codons capable of coding for such conservative amino acid substitutions are known in the art.

In one aspect of the present invention the nucleic acids of the present invention are said to be introduced nucleic acid molecules. A nucleic acid molecule is said to be "introduced" if it is inserted into a cell or organism as a result of human manipulation, no matter how indirect. Examples of introduced nucleic acid molecules include, without limitation, nucleic acids that have been introduced into cells via transformation, transfection, injection, and projection, and those that have been introduced into an organism via conjugation, endocytosis, phagocytosis, etc.

One subset of the nucleic acid molecules of the present invention is fragment nucleic acids molecules. Fragment nucleic acid molecules may consist of significant portion(s) of, or indeed most of, the nucleic acid molecules of the present invention, such as those specifically disclosed. Alternatively, the fragments may comprise smaller oligonucleotides (having from about 15 to about 400 nucleotide residues and more preferably, about 15 to about 30 nucleotide residues, or about 50 to about 100 nucleotide residues, or about 100 to about 200 nucleotide residues, or about 200 to about 400 nucleotide residues, or about 275 to about 350 nucleotide residues).

A fragment of one or more of the nucleic acid molecules of the present invention may be a probe and specifically a PCR probe. A PCR probe is a nucleic acid molecule capable of initiating a polymerase activity while in a double-stranded structure with another nucleic acid. Various methods for determining the structure of PCR probes and PCR techniques exist in the art. Computer generated searches using programs such as Primer3 (www-genome.wi.mit.edu/cgi-bin/primer/primer3.cgi), STSPipeline (www-genome.wi.mit.edu/cgi-bin/www-STS_Pipeline), or GeneUp (Pesole et al., *BioTechniques*, 25:112–123 (1998)), for example, can be used to identify potential PCR primers.

Nucleic acid molecules or fragments thereof of the present invention are capable of specifically hybridizing to other nucleic acid molecules under certain circumstances. Nucleic acid molecules of the present invention include those that specifically hybridize to those nucleic acid molecules disclosed herein, such as those encoding any of SEQ ID NOs: 5, 9–11, 43–44, 57–58, and 90, and complements thereof. Nucleic acid molecules of the present invention include those that specifically hybridize to a nucleic acid molecules comprising a member selected from the group consisting of SEQ ID NOs: 31, 34–36, 59–60, and 91, and complements thereof.

As used herein, two nucleic acid molecules are said to be capable of specifically hybridizing to one another if the two molecules are capable of forming an anti-parallel, double-stranded nucleic acid structure.

A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., *Molecular Cloning, A Laboratory Manual*, 2nd Ed., Cold Spring Harbor Press, Cold Spring Harbor, N.Y. (1989), and by Haymes et al., *Nucleic Acid Hybridization, A Practical Approach, IRL Press*, Washington, D.C. (1985). Departures from complete complementarity are therefore permissible, as long as such departures do not completely preclude the capacity of the molecules to form a double-stranded structure. Thus, in order for a nucleic acid molecule to serve as a primer or probe it need only be sufficiently complementary in sequence to be able to form a stable double-stranded structure under the particular solvent and salt concentrations employed.

Appropriate stringency conditions which promote DNA hybridization are, for example, 6.0× sodium chloride/sodium citrate (SSC) at about 45° C., followed by a wash of 2.0×SSC at 20–25° C., are known to those skilled in the art or can be found in *Current Protocols in Molecular Biology*, John Wiley & Sons, NY (1989), 6.3.1–6.3.6. For example, the salt concentration in the wash step can be selected from a low stringency of about 2.0×SSC at 50° C. to a high stringency of about 0.2×SSC at 65° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

In a preferred embodiment, a nucleic acid of the present invention will specifically hybridize to one or more of the nucleic acid molecules described herein and complements thereof, such as those encoding any of SEQ ID NOs: 5, 9–11, 43–44, 57–58, and 90, under moderately stringent conditions, for example at about 2.0×SSC and about 65° C.

In a particularly preferred embodiment, a nucleic acid of the present invention will include those nucleic acid molecules that specifically hybridize to one or more nucleic acid molecules encoding any of SEQ ID NOs: 5, 9–11, 43–44, 57–58, and 90, and complements thereof, under high stringency conditions such as 0.2×SSC and about 65° C.

In one aspect of the present invention, the nucleic acid molecules of the present invention have one or more nucleic acid sequences encoding SEQ ID NOs: 5, 9–11, 43–44, 57–58, and 90, or complements thereof. In another aspect of the present invention, one or more of the nucleic acid molecules of the present invention share between about 100% and about 90% sequence identity with one or more of the nucleic acid sequences encoding SEQ ID NOs: 5, 9–11, 43–44, 57–58, and 90, and complements thereof, and fragments of either. In a further aspect of the present invention, one or more of the nucleic acid molecules of the present invention share between about 100% and about 95% sequence identity with one or more of the nucleic acid sequences encoding SEQ ID NOs: 5, 9–11, 43–44, 57–58, and 90, and complements thereof, and fragments of either. In a more preferred aspect of the present invention, one or more of the nucleic acid molecules of the present invention share between about 100% and about 98% sequence identity with one or more of the nucleic acid sequences encoding SEQ ID NOs: 5, 9–11, 43–44, 57–58, and 90, and complements thereof, and fragments of either. In an even more preferred aspect of the present invention, one or more of the nucleic acid molecules of the present invention share between about 100% and about 99% sequence identity with one or more of the sequences encoding SEQ ID NOs: 5, 9–11, 43–44, 57–58, and 90, and complements thereof, and fragments of either.

In a preferred embodiment the percent identity calculations are performed using BLASTN or BLASTP (default, parameters, version 2.0.8, Altschul et al., *Nucleic Acids Res.*, 25:3389–3402 (1997)).

A nucleic acid molecule of the present invention can also encode a homolog polypeptide. As used herein, a homolog polypeptide molecule or fragment thereof is a counterpart protein molecule or fragment thereof in a second species (e.g., corn rubisco small subunit is a homolog of *Arabidopsis* rubisco small subunit). A homolog can also be generated by molecular evolution or DNA shuffling techniques, so that the molecule retains at least one functional or structure characteristic of the original polypeptide (see, for example, U.S. Pat. No. 5,811,238).

In another embodiment, the homolog is selected from the group consisting of alfalfa, *Arabidopsis*, barley, *Brassica campestris, Brassica napus*, oilseed rape, broccoli, cabbage, canola, citrus, cotton, garlic, oat, Allium, flax, an ornamental plant, peanut, pepper, potato, rapeseed, rice, rye, sorghum, strawberry, sugarcane, sugarbeet, tomato, wheat, poplar, pine, fir, eucalyptus, apple, lettuce, lentils, grape, banana, tea, turf grasses, sunflower, soybean, corn, *Phaseolus*, crambe, mustard, castor bean, sesame, cottonseed, linseed, safflower, and oil palm. More particularly, preferred homologs are selected from canola, corn, *Brassica campestris, Brassica napus*, oilseed rape, soybean, crambe, mustard, castor bean, peanut, sesame, cottonseed, linseed, rapeseed, safflower, oil palm, flax, and sunflower. In an even more preferred embodiment, the homolog is selected from the group consisting of canola, rapeseed, corn, *Brassica campestris, Brassica napus*, oilseed rape, soybean, sunflower, safflower, oil palms, and peanut. In a particularly preferred embodiment, the homolog is soybean. In a particularly preferred embodiment, the homolog is canola. In a particularly preferred embodiment, the homolog is oilseed rape.

In a preferred embodiment, nucleic acid molecules encoding SEQ ID NOs: 5, 9–11, 43–44, 57–58, and 90, and complements thereof, and fragments of either; or more preferably encoding SEQ ID NOs: 5, 9–11, 43–44, 57–58, and 90, and complements thereof, can be utilized to obtain such homologs.

In another further aspect of the present invention, nucleic acid molecules of the present invention can comprise sequences that differ from those encoding a polypeptide or fragment thereof due to the fact that a polypeptide can have one or more conservative amino acid changes, and nucleic acid sequences coding for the polypeptide can therefore have sequence differences. It is understood that codons capable of coding for such conservative amino acid substitutions are known in the art.

It is well known in the art that one or more amino acids in a native sequence can be substituted with other amino acid(s), the charge and polarity of which are similar to that of the native amino acid, i.e., a conservative amino acid substitution. Conservative substitutes for an amino acid within the native polypeptide sequence can be selected from other members of the class to which the amino acid belongs. Amino acids can be divided into the following four groups: (1) acidic amino acids; (2) basic amino acids; (3) neutral polar amino acids; and (4) neutral nonpolar amino acids. Representative amino acids within these various groups include, but are not limited to, (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; and (4) neutral nonpolar (hydrophobic) amino acids such as alanine, leucine, isoleucine, valine, proline, phenylalanine, tryptophan, and methionine.

Conservative amino acid substitution within the native polypeptide sequence can be made by replacing one amino acid from within one of these groups with another amino acid from within the same group. In a preferred aspect, biologically functional equivalents of the proteins or fragments thereof of the present invention can have ten or fewer conservative amino acid changes, more preferably seven or fewer conservative amino acid changes, and most preferably five or fewer conservative amino acid changes. The encoding nucleotide sequence will thus have corresponding base substitutions, permitting it to encode biologically functional equivalent forms of the polypeptides of the present invention.

It is understood that certain amino acids may be substituted for other amino acids in a protein structure without appreciable loss of interactive binding capacity with structures such as, for example, antigen-binding regions of antibodies or binding sites on substrate molecules. Because it is the interactive capacity and nature of a protein that defines that protein's biological functional activity, certain amino acid sequence substitutions can be made in a protein sequence and, of course, its underlying DNA coding sequence and, nevertheless, a protein with like properties can still be obtained. It is thus contemplated by the inventors that various changes may be made in the peptide sequences of the proteins or fragments of the present invention, or corresponding DNA sequences that encode said peptides, without appreciable loss of their biological utility or activity. It is understood that codons capable of coding for such amino acid changes are known in the art.

In making such changes, the hydropathic index of amino acids may be considered. The importance of the hydropathic amino acid index in conferring interactive biological function on a protein is generally understood in the art (Kyte and Doolittle, *J. Mol. Biol.*, 157:105–132 (1982)). It is accepted that the relative hydropathic character of the amino acid contributes to the secondary structure of the resultant polypeptide, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, *J. Mol. Biol.*, 157:105–132 (1982)); these are isoleucine (+4.5), valine (+4.2), leucine (+3.8), phenylalanine (+2.8), cysteine/cystine (+2.5), methionine (+1.9), alanine (+1.8), glycine (–0.4), threonine (–0.7), serine (–0.8), tryptophan (–0.9), tyrosine (–1.3), proline (–1.6), histidine (–3.2), glutamate (–3.5), glutamine (–3.5), aspartate (–3.5), asparagine (–3.5), lysine (–3.9), and arginine (–4.5).

In making such changes, the substitution of amino acids whose hydropathic indices are within ±2 is preferred, those that are within ±1 are particularly preferred, and those within ±0.5 are even more particularly preferred.

It is also understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0), lysine (+3.0), aspartate (+3.0±1), glutamate (+3.0±1), serine (+0.3), asparagine (+0.2), glutamine (+0.2), glycine (0), threonine (–0.4), proline (–0.5±1), alanine (–0.5), histidine (–0.5), cysteine (–1.0), methionine (–1.3), valine (–1.5), leucine (–1.8), isoleucine (–1.8), tyrosine (–2.3), phenylalanine (–2.5), and tryptophan (–3.4).

In making such changes, the substitution of amino acids whose hydrophilicity values are within ±2 is preferred, those that are within ±1 are particularly preferred, and those within ±0.5 are even more particularly preferred.

In a further aspect of the present invention, one or more of the nucleic acid molecules of the present invention differ in nucleic acid sequence from those for which a specific sequence is provided herein because one or more codons has been replaced with a codon that encodes a conservative substitution of the amino acid originally encoded.

Agents of the present invention include nucleic acid molecules that encode at least about a contiguous 10 amino acid region of a polypeptide of the present invention, more preferably at least about a contiguous 25, 40, 50, 100, or 125 amino acid region of a polypeptide of the present invention.

In a preferred embodiment, any of the nucleic acid molecules of the present invention can be operably linked to a promoter region that functions in a plant cell to cause the production of an mRNA molecule, where the nucleic acid molecule that is linked to the promoter is heterologous with respect to that promoter. As used herein, "heterologous" means not naturally occurring together.

The nature of the coding sequences of non-plant genes can distinguish them from plant genes as well as many other heterologous genes expressed in plants. For example, the average A+T content of bacteria can be higher than that for plants. The A+T content of the genomes (and thus the genes) of any organism are features of that organism and reflect its evolutionary history. While within any one organism genes have similar A+T content, the A+T content can vary tremendously from organism to organism. For example, some *Bacillus* species have among the most A+T rich genomes while some *Steptomyces* species are among the least A+T rich genomes (about 30 to 35% A+T).

Due to the degeneracy of the genetic code and the limited number of codon choices for any amino acid, most of the "excess" A+T of the structural coding sequences of some *Bacillus* species, for example, are found in the third position of the codons. That is, genes of some *Bacillus* species have A or T as the third nucleotide in many codons. Thus A+T content in part can determine codon usage bias. In addition, it is clear that genes evolve for maximum function in the organism in which they evolve. This means that particular nucleotide sequences found in a gene from one organism, where they may play no role except to code for a particular stretch of amino acids, have the potential to be recognized as gene control elements in another organism (such as transcriptional promoters or terminators, polyA addition sites, intron splice sites, or specific mRNA degradation signals). It is perhaps surprising that such misread signals are not a more common feature of heterologous gene expression, but this can be explained in part by the relatively homogeneous A+T content (about 50%) of many organisms. This A+T content plus the nature of the genetic code put clear constraints on the likelihood of occurrence of any particular oligonucleotide sequence. Thus, a gene from *E. coli* with a 50% A+T content is much less likely to contain any particular A+T rich segment than a gene from *B. thuringiensis*. The same can be true between genes in a bacterium and genes in a plant, for example.

Any of the nucleic acid molecules of the present invention can be altered via any methods known in the art in order to make the codons within the nucleic acid molecule more appropriate for the organism in which the nucleic acid molecule is located. That is, the present invention includes the modification of any of the nucleic acid molecules disclosed herein to improve codon usage in a host organism.

It is preferred that regions comprising many consecutive A+T bases or G+C bases are disrupted since these regions are predicted to have a higher likelihood to form hairpin structure due to self-complementarity. Therefore, insertion of heterogeneous base pairs would reduce the likelihood of self-complementary secondary structure formation which are known to inhibit transcription and/or translation in some organisms. In most cases, the adverse effects may be minimized by using sequences which do not contain more than five consecutive A+T or G+C.

Protein and Peptide Molecules

A class of agents includes one or more of the polypeptide molecules encoded by a nucleic acid agent of the present invention. A particular preferred class of proteins is that having an amino acid sequence selected from the group consisting of SEQ ID NOs: 5, 9–11, 43–44, 57–58, and 90, and fragments thereof.

In another embodiment, the present invention includes polypeptides having a region of conserved amino acid sequence shown in any of FIGS. 2a–2c, 3a–3c, 24a–24b, 25a–25b, 33a–33c, 34a–34b, 35a–35b and 36. In an embodiment, the present invention includes polypeptides comprising a sequence selected from the group consisting of SEQ ID NOs: 39–42, 46–49, and 92–95. The present invention includes and provides said substantially purified polypeptide wherein more than one amino acid sequence is selected from the group consisting of SEQ ID NOs: 39–42, 46–49, and 92–95. In a further preferred embodiment the present invention includes polypeptides comprising two or more, three or more, or four sequences selected from the group consisting of SEQ ID NOs: 39–42, 46–49, and 92–95.

In another embodiment, the present invention includes polypeptides having homogentisate prenyl transferase activity and a region of conserved amino acid sequence shown in any of FIGS. 2a–2c, 3a–3c, 25a–25c, 33a–33c, 34a–34b, 35a–35b embodiment, the present invention includes polypeptides having homogentisate prenyl transferase activity and comprising a sequence selected from the group consisting of SEQ ID NOs: 39–42, 46–49, and 92–95. The present invention includes and provides said substantially purified polypeptide wherein more than one amino acid sequence is selected from the group consisting of SEQ ID NOs: 39–42, 46–49, and 92–95.

In a further preferred embodiment the present invention includes polypeptides having homogentisate prenyl transferase activity and comprising two or more, three or more, or four sequences selected from the group consisting of SEQ ID NOs: 39–42, 46–49, and 92–95.

In another embodiment, the present invention includes polypeptides having a region of conserved amino acid sequence shown in any of FIGS. 2a–2c, 3a–13c, 25a–25c, 33a–33c, 34a–34b, 35a–35b or 36, excluding polypeptides derived from nucleic acid molecules derived from *Nostoc punctiforme, Anabaena, Synechocystis, Zea mays, Glycine max, Arabidopsis thaliana, Oryza sativa, Trichodesmium erythraeum, Chloroflexus aurantiacus*, wheat, leek, canola, cotton, Sulfolobus, Aeropyum, sorghum, or tomato. In a preferred embodiment, the present invention includes polypeptides comprising a sequence selected from the group consisting of SEQ ID NOs: 39–42, 46–49, and 92–95 excluding polypeptides derived from nucleic acid molecules derived from *Nostoc punctiforme, Anabaena, Synechocystis, Zea mays, Glycine max, Arabidopsis thaliana, Oryza sativa, Trichodesmium erythraeum, Chloroflexus aurantiacus*, wheat, leek, canola, cotton, or tomato. The present invention includes and provides said substantially purified polypeptide wherein more than onethe amino acid sequence is selected from the group consisting of SEQ ID NOs: 39–42, 46–49, and 92–95.

In a further preferred embodiment the present invention includes polypeptides comprising two or more, three or more, or four sequences selected from the group consisting of SEQ ID NOs: 39–42, 46–49, and 92–95, excluding polypeptides derived from nucleic acid molecules derived from *Nostoc punctiforme, Anabaena, Synechocystis, Zea mays, Glycine max, Arabidopsis thaliana, Oryza sativa, Trichodesmium erythraeum, Chloroflexus aurantiacus*, wheat, leek, canola, cotton, or tomato.

In another embodiment, the present invention includes polypeptides having homogentisate prenyl transferase activity and a region of conserved amino acid sequence shown in any of FIGS. 2a–2c, 3a–3c, 25a–25c, 33a–33c, 34a–34b, 35a–35b polypeptides derived from nucleic acid molecules derived from *Nostoc punctiforme, Anabaena, Synechocystis, Zea mays, Glycine max, Arabidopsis thaliana, Oryza sativa, Trichodesmium erythraeum, Chloroflexus aurantiacus*, wheat, leek, canola, cotton, or tomato. In a preferred embodiment, the present invention includes polypeptides having homogentisate prenyl transferase activity and comprising a sequence selected from the group consisting of SEQ ID NOs: 39–42, 46–49, and 92–95, excluding polypeptides derived from nucleic acid molecules derived from *Nostoc punctiforme, Anabaena, Synechocystis, Zea mays, Glycine max, Arabidopsis thaliana, Oryza sativa, Trichodesmium erythraeum, Chloroflexus aurantiacus*, wheat, leek, canola, cotton, or tomato. The present invention includes and provides said substantially purified polypeptide wherein more than one amino acid sequence is selected from the group consisting of SEQ ID NOs: 39–42, 46–49, and 92–95.

In a further preferred embodiment the present invention includes polypeptides having homogentisate prenyl transferase activity and comprising two or more, three or more, or four sequences selected from the group consisting of SEQ ID NOs: 39–42, 46–49, and 92–95, excluding polypeptides derived from nucleic acid molecules derived from *Nostoc punctiforme, Anabaena, Synechocystis, Zea mays, Glycine max, Arabidopsis thaliana, Oryza sativa, Trichodesmium erythraeum, Chloroflexus aurantiacus*, wheat, leek, canola, cotton, or tomato.

Polypeptide agents may have C-terminal or N-terminal amino acid sequence extensions. One class of N-terminal extensions employed in a preferred embodiment are plastid transit peptides. When employed, plastid transit peptides can be operatively linked to the N-terminal sequence, thereby permitting the localization of the agent polypeptides to plastids. In an embodiment of the present invention, any suitable plastid targeting sequence can be used. Where suitable, a plastid targeting sequence can be substituted for a native plastid targetting sequence, for example, for the CTP occurring natively in the tocopherol homogentisate prenyl transferase protein. In a further embodiment, a plastid targeting sequence that is heterologous to any homogentisate prenyl transferase protein or fragment described herein can be used. In a further embodiment, any suitable, modified plastid targetting sequence can be used. In another embodiment, the plastid targeting sequence is a CTP1 sequence (see WO 00/61771).

In a preferred aspect a protein of the present invention is targeted to a plastid using either a native transit peptide sequence or a heterologous transit peptide sequence. In the case of nucleic acid sequences corresponding to nucleic acid sequences of non-higher plant organisms such as cynobacteria, such nucleic acid sequences can be modified to attach the coding sequence of the protein to a nucleic acid sequence of a plastid targeting peptide.

As used herein, the terms "protein", "peptide molecule", or "polypeptide" include any molecule that comprises five or more amino acids. It is well known in the art that protein, peptide, or polypeptide molecules may undergo modification, including post-translational modifications, such as, but not limited to, disulfide bond formation, glycosylation, phosphorylation, or oligomerization. Thus, as used herein, the terms "protein", "peptide molecule", or "polypeptide" include any protein that is modified by any biological or non-biological process. The terms "amino acid" and "amino acids" refer to all naturally occurring L-amino acids. This definition is meant to include norleucine, norvaline, ornithine, homocysteine, and homoserine.

One or more of the protein or fragments thereof, peptide molecules, or polypeptide molecules may be produced via chemical synthesis, or more preferably, by expression in a suitable bacterial or eukaryotic host. Suitable methods for expression are described by Sambrook et al., In: *Molecular Cloning, A Laboratory Manual, 2nd Edition, Cold Spring Harbor Press*, Cold Spring Harbor, N.Y. (1989) or similar texts.

A "protein fragment" is a peptide or polypeptide molecule whose amino acid sequence comprises a subset of the amino acid sequence of that protein. A protein or fragment thereof that comprises one or more additional peptide regions not derived from that protein is a "fusion" protein. Such molecules may be derivatized to contain carbohydrate or other moieties (such as keyhole limpet hemocyanin). Fusion protein or peptide molecules of the present invention are preferably produced via recombinant means.

Another class of agents comprises protein, peptide molecules, or polypeptide molecules, or fragments or fusions thereof comprising SEQ ID NOs: 5, 9–11, 43–44, 57–58, and 90, and fragments thereof in which conservative, non-essential, or non-relevant amino acid residues have been added, replaced, or deleted. Computerized means for designing modifications in protein structure are known in the art (Dahiyat and Mayo, *Science*, 278:82–87 (1997)).

A protein, peptide, or polypeptide of the present invention can also be a homolog protein, peptide, or polypeptide. As used herein, a homolog protein, peptide, or polypeptide or fragment thereof is a counterpart protein, peptide, or polypeptide or fragment thereof in a second species. A homolog can also be generated by molecular evolution or DNA shuffling techniques, so that the molecule retains at least one functional or structure characteristic of the original (see, for example, U.S. Pat. No. 5,811,238).

In another embodiment, the homolog is selected from the group consisting of alfalfa, *Arabidopsis*, barley, broccoli, cabbage, canola, citrus, cotton, garlic, oat, *Allium*, flax, an ornamental plant, peanut, pepper, potato, rapeseed, rice, rye, sorghum, strawberry, sugarcane, sugarbeet, tomato, wheat, poplar, pine, fir, eucalyptus, apple, lettuce, lentils, grape, banana, tea, turf grasses, sunflower, soybean, corn, and *Phaseolus*. More particularly, preferred homologs are selected from canola, rapeseed, corn, *Brassica campestris, Brassica napus*, oilseed rape, soybean, crambe, mustard, castor bean, peanut, sesame, cottonseed, linseed, safflower, oil palm, flax, and sunflower. In an even more preferred embodiment, the homolog is selected from the group consisting of canola, rapeseed, corn, *Brassica campestris, Brassica napus*, oilseed rape, soybean, sunflower, safflower, oil palms, and peanut. In a preferred embodiment, the homolog is soybean. In a preferred embodiment, the homolog is canola. In a preferred embodiment, the homolog is oilseed rape.

In a preferred embodiment, the nucleic acid molecules of the present invention or complements and fragments of either can be utilized to obtain such homologs.

Agents of the present invention include proteins and fragments thereof comprising at least about a contiguous 10 amino acid region preferably comprising at least about a contiguous 20 amino acid region, even more preferably comprising at least about a contiguous 25, 35, 50, 75, or 100 amino acid region of a protein of the present invention. In another preferred embodiment, the proteins of the present invention include between about 10 and about 25 contiguous amino acid region, more preferably between about 20 and about 50 contiguous amino acid region, and even more preferably between about 40 and about 80 contiguous amino acid region.

Plant Constructs and Plant Transformants

One or more of the nucleic acid molecules of the present invention may be used in plant transformation or transfection. Exogenous genetic material may be transferred into a plant cell and the plant cell regenerated into a whole, fertile, or sterile plant. Exogenous genetic material is any genetic material, whether naturally occurring or otherwise, from any source that is capable of being inserted into any organism.

In a preferred aspect of the present invention the exogenous genetic material comprises a nucleic acid sequence of the present invention, more preferably one that encodes homogentisate prenyl transferase. In another preferred aspect of the present invention the exogenous genetic material of the present invention comprises a nucleic acid sequence encoding an amino acid sequence selected from the group consisting of SEQ ID NOs: 5, 9–11, 43–44, 57–58, and 90, and complements thereof and fragments of either. In a further aspect of the present invention the exogenous genetic material comprises a nucleic acid sequence encoding an amino acid sequence selected from the group consisting of SEQ ID NOs: 5, 9–11, 43–44, 57–58, and 90, and fragments of SEQ ID NOs: 5, 9–11, 43–44, 57–58, and 90.

In an embodiment of the present invention, exogenous genetic material encoding a homogentisate prenyl transferase enzyme or fragment thereof is introduced into a plant with one or more additional genes. In one embodiment, preferred combinations of genes include a nucleic acid molecule of the present invention and one or more of the following genes: tyrA (e.g., WO 02/089561 and Xia et al., *J. Gen. Microbiol.*, 138:1309–1316 (1992)), tocopherol cyclase (e.g., WO 01/79472), prephenate dehydrogenase, dxs (e.g. Lois et al., *Proc. Natl. Acad. Sci.* (*U.S.A.*), 95(5): 2105–2110 (1998)), dxr (e.g., U.S. Pub. 2002/0108814A and Takahashi et al., *Proc. Natl. Acad. Sci.* (*U.S.A.*), 95 (17), 9879–9884 (1998)), GGPPS (e.g., Bartley and Scolnik, *Plant Physiol.*, 104:1469–1470 (1994)), HPPD (e.g., Norris et al., *Plant Physiol.*, 117:1317–1323 (1998)), GMT (e.g., U.S. application Ser. No. 10/219,810, filed Aug. 16, 2002), tMT2 (e.g., U.S. application Ser. No. 10/279,029, filed Oct. 24, 2002), AANT1 (e.g., WO 02/090506), IDI (E.C.:5.3.3.2; Blanc et al., In: *Plant Gene Register*, PRG96-036; and Sato et al., *DNA Res.*, 4:215–230 (1997)), GGH (Graβes et al., *Planta.* 213–620 (2001)), or a plant ortholog and an antisense construct for homogentisic acid dioxygenase (Kridl et al., *Seed Sci. Res.*, 1:209:219 (1991); Keegstra, *Cell*, 56(2): 247–53 (1989); Nawrath, et al., *Proc. Natl. Acad. Sci.* (*U.S.A.*), 91:12760–12764 (1994); Cyanobase, www.kazusa.or.jp/cyanobase; Smith et al., *Plant J.*, 11:83–92 (1997); WO 00/32757; ExPASy Molecular Biology Server, http://us.expasy.org/enzyme; MT1 WO 00/10380; gcpE, WO 02/12478; Saint Guily et al., *Plant Physiol.*, 100(2): 1069–1071 (1992); Sato et al., *J. DNA Res.*, 7(1):31–63 (2000). In such combinations, in some crop plants, e.g., canola, a preferred promoter is a napin promoter and a preferred plastid targeting sequence is a CTP1 sequence. It is preferred that gene products are targeted to the plastid.

In a preferred combination a nucleic acid molecule encoding a homogentisate prenyl transferase polypeptide and a nucleic acid molecule encoding any of the following enzymes: tyrA, prephenate dehydrogenase, tocopherol cyclase, dxs, dxr, GGPPS, HPPD, tMT2, MT1, GCPE, AANT1, IDI, GGH, GMT, or a plant ortholog and an antisense construct for homogentisic acid dioxygenase are introduced into a plant.

For any of the above combinations, a nucleic acid molecule encoding a homogentisate prenyl transferase polypeptide encodes a polypeptide comprising a sequence selected from the group consisting of SEQ ID NOs: 5, 9–11, 43–44, 57–58, and 90. In another preferred embodiment, a nucleic acid molecule encoding a homogentisate prenyl transferase polypeptide encodes a polypeptide comprising one or more of SEQ ID NOs: 39–42, 46–49, and 92–95. In a preferred embodiment, the homogentisate prenyl transferase polypeptide does not have an amino acid sequence that is derived from a nucleic acid derived from *Nostoc punctiforme, Anabaena, Synechocystis, Zea mays, Glycine max, Arabidopsis thaliana, Oryza sativa*, wheat, leek, canola, cotton, or tomato.

Such genetic material may be transferred into either monocotyledons or dicotyledons including, but not limited to canola, corn, soybean, *Arabidopsis phaseolus*, peanut, alfalfa, wheat, rice, oat, sorghum, rapeseed, rye, tritordeum, millet, fescue, perennial ryegrass, sugarcane, cranberry, papaya, banana, safflower, oil palms, flax, muskmelon, apple, cucumber, dendrobium, gladiolus, chrysanthemum, liliacea, cotton, eucalyptus, sunflower, *Brassica campestris, Brassica napus*, oilseed rape, turfgrass, sugarbeet, coffee and dioscorea (Christou, In: *Particle Bombardment for Genetic Engineering of Plants*, Biotechnology Intelligence Unit. Academic Press, San Diego, Calif. (1996)), with canola, corn, *Brassica campestris, Brassica napus*, oilseed rape, rapeseed, soybean, crambe, mustard, castor bean, peanut, sesame, cottonseed, linseed, safflower, oil palm, flax, and sunflower preferred, and canola, rapeseed, corn, *Brassica campestris, Brassica napus*, oilseed rape, soybean, sunflower, safflower, oil palms, and peanut preferred. In a more preferred embodiment, the genetic material is transferred into canola. In another more preferred embodiment, the genetic material is transferred into oilseed rape. In another particularly preferred embodiment, the genetic material is transferred into soybean.

Transfer of a nucleic acid molecule that encodes a protein can result in expression or overexpression of that polypeptide in a transformed cell or transgenic plant. One or more of the proteins or fragments thereof encoded by nucleic acid molecules of the present invention may be overexpressed in a transformed cell or transformed plant. Such expression or overexpression may be the result of transient or stable transfer of the exogenous genetic material.

In a preferred embodiment, expression or overexpression of a polypeptide of the present invention in a plant provides in that plant, relative to an untransformed plant with a similar genetic background, an increased level of tocopherols.

In a preferred embodiment, expression or overexpression of a polypeptide of the present invention in a plant provides in that plant, relative to an untransformed plant with a similar genetic background, an increased level of α-tocopherols.

In a preferred embodiment, expression or overexpression of a polypeptide of the present invention in a plant provides in that plant, relative to an untransformed plant with a similar genetic background, an increased level of γ-tocopherols.

In a preferred embodiment, expression or overexpression of a polypeptide of the present invention in a plant provides in that plant, relative to an untransformed plant with a similar genetic background, an increased level of δ-tocopherols.

In a preferred embodiment, expression or overexpression of a polypeptide of the present invention in a plant provides in that plant, relative to an untransformed plant with a similar genetic background, an increased level of β-tocopherols.

In a preferred embodiment, expression or overexpression of a polypeptide of the present invention in a plant provides in that plant, relative to an untransformed plant with a similar genetic background, an increased level of tocotrienols.

In a preferred embodiment, expression or overexpression of a polypeptide of the present invention in a plant provides in that plant, relative to an untransformed plant with a similar genetic background, an increased level of α-tocotrienols.

In a preferred embodiment, expression or overexpression of a polypeptide of the present invention in a plant provides in that plant, relative to an untransformed plant with a similar genetic background, an increased level of γ-tocotrienols.

In a preferred embodiment, expression or overexpression of a polypeptide of the present invention in a plant provides in that plant, relative to an untransformed plant with a similar genetic background, an increased level of δ-tocotrienols.

In a preferred embodiment, expression or overexpression of a polypeptide of the present invention in a plant provides in that plant, relative to an untransformed plant with a similar genetic background, an increased level of β-tocotrienols.

In a preferred embodiment, expression or overexpression of a polypeptide of the present invention in a plant provides in that plant, relative to an untransformed plant with a similar genetic background, an increased level of plastoquinols.

In any of the embodiments described herein, an increase in γ-tocopherol, α-tocopherol, or both can lead to a decrease in the relative proportion of β-tocopherol, δ-tocopherol, or both. Similarly, an increase in γ-tocotienol, α-tocotrienol, or both can lead to a decrease in the relative proportion of β-tocotrienol, δ-tocotrienol, or both.

In another embodiment, expression overexpression of a polypeptide of the present invention in a plant provides in that plant, or a tissue of that plant, relative to an untransformed plant or plant tissue, with a similar genetic background, an increased level of a homogentisate prenyl transferase protein or fragment thereof.

In some embodiments, the levels of one or more products of the tocopherol biosynthesis pathway, including any one or more of tocopherols, α-tocopherols, γ-tocopherols, δ-tocopherols, β-tocopherols, tocotrienols, α-tocotrienols, γ-tocotrienols, δ-tocotrienols, β-tocotrienols are increased by greater than about 10%, or more preferably greater than about 25%, 35%, 50%, 75%, 80%, 90%, 100%, 150%, 200%, 1,000%, 2,000%, or 2,500%. The levels of products may be increased throughout an organism such as a plant or localized in one or more specific organs or tissues of the organism. For example, the levels of products may be increased in one or more of the tissues and organs of a plant including without limitation: roots, tubers, stems, leaves, stalks, fruit, berries, nuts, bark, pods, seeds and flowers. A preferred organ is a seed.

In some embodiments, the levels of one or more products of the tocopherol biosynthesis pathway, including any one or more of tocopherols, α-tocopherols, γ-tocopherols, δ-tocopherols, β-tocopherols, tocotrienols, α-tocotrienols, γ-tocotrienols, δ-tocotrienols, β-tocotrienols are increased so that they constitute greater than about 10%, 20%, 25%, 30%, 35%, 40%, 45%, 50%, 55%, 60%, 65%, 70%, 75%, 80%, 85%, 90%, 95%, 96%, 97%, 98%, or 99% of the total tocopherol content of the organism or tissue. The levels of products may be increased throughout an organism such as a plant or localized in one or more specific organs or tissues of the organism. For example, the levels of products may be increased in one or more of the tissues and organs of a plant including without limitation: roots, tubers, stems, leaves, stalks, fruit, berries, nuts, bark, pods, seeds and flowers. A preferred organ is a seed.

In a preferred embodiment, expression of enzymes involved in tocopherol, tocotrienol or plastoquinol synthesis in the seed will result in an increase in γ-tocopherol levels due to the absence of significant levels of GMT activity in those tissues. In another preferred embodiment, expression of enzymes involved in tocopherol, tocotrienol, or plastoquinol synthesis in photosyhthetic tissues will result in an increase in α-tocopherol due to the higher levels of GMT activity in those tissues relative to the same activity in seed tissue.

In another preferred embodiment, the expression of enzymes involved in tocopherol, tocotrienol, or plastoquinol synthesis in the seed will result in an increase in the total tocopherol, tocotrienol, or plastoquinol level in the plant.

In some embodiments, the levels of tocopherols or a species such as α-tocopherol may be altered. In some embodiments, the levels of tocotrienols may be altered. Such alteration can be compared to a plant with a similar background.

In another embodiment, either the α-tocopherol level, α-tocotrienol level, or both of plants that natively produce high levels of either α-tocopherol, α-tocotrienol or both (e.g., sunflowers), can be increased by the introduction of a gene coding for a homogentisate prenyl transferase enzyme.

In a preferred aspect, a similar genetic background is a background where the organisms being compared share about 50% or greater of their nuclear genetic material. In a more preferred aspect a similar genetic background is a background where the organisms being compared share about 75% or greater, even more preferably about 90% or greater of their nuclear genetic material. In another even more preferable aspect, a similar genetic background is a background where the organisms being compared are plants, and the plants are isogenic except for any genetic material originally introduced using plant transformation techniques.

In another preferred embodiment, expression or overexpression of a polypeptide of the present invention in a transformed plant may provide tolerance to a variety of stress, e.g. oxidative stress tolerance such as to oxygen or ozone, UV tolerance, cold tolerance, or fungal/microbial pathogen tolerance.

As used herein in a preferred aspect, a tolerance or resistance to stress is determined by the ability of a plant, when challenged by a stress such as cold to produce a plant having a higher yield than one without such tolerance or resistance to stress. In a particularly preferred aspect of the present invention, the tolerance or resistance to stress is measured relative to a plant with a similar genetic background to the tolerant or resistance plant except that the plant reduces the expression, expresses, or over expresses a protein or fragment thereof of the present invention.

Exogenous genetic material may be transferred into a host cell by the use of a DNA vector or construct designed for such a purpose. Design of such a vector is generally within the skill of the art (see, *Plant Molecular Biology: A Laboratory Manual*, Clark (ed.), Springer, N.Y. (1997)).

A construct or vector may include a plant promoter to express the polypeptide of choice. In a preferred embodiment, any nucleic acid molecules described herein can be operably linked to a promoter region which functions in a plant cell to cause the production of an mRNA molecule. For example, any promoter that functions in a plant cell to cause the production of an mRNA molecule, such as those promoters described herein, without limitation, can be used. In a preferred embodiment, the promoter is a plant promoter.

A number of promoters that are active in plant cells have been described in the literature. These include the nopaline synthase (NOS) promoter (Ebert et al., *Proc. Natl. Acad. Sci. (U.S.A.)*, 84:5745–5749 (1987)), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., *Plant Mol. Biol.*, 9:315–324 (1987)) and the CaMV 35S promoter (Odell et al., *Nature*, 313:810–812 (1985)), the figwort mosaic virus 35S-promoter, the light-inducible promoter from the small subunit of ribulose-1,5-bis-phosphate carboxylase (ssRUBISCO), the Adh promoter (Walker et al., *Proc. Natl. Acad. Sci. (U.S.A.)*, 84:6624–6628 (1987)), the sucrose synthase promoter (Yang et al., *Proc. Natl. Acad. Sci. (U.S.A.)*, 87:4144–4148 (1990)), the R gene complex promoter (Chandler et al., *The Plant Cell*, 1:1175–1183 (1989)) and the chlorophyll a/b binding protein gene promoter, etc. These promoters have been used to create DNA constructs that have been expressed in plants; see, e.g., WO 84/02913. The CaMV 35S promoters are preferred for use in plants. Promoters known or found to cause transcription of DNA in plant cells can be used in the present invention.

For the purpose of expression in source tissues of the plant, such as the leaf, seed, root or stem, it is preferred that the promoters utilized have relatively high expression in these specific tissues. Tissue-specific expression of a protein of the present invention is a particularly preferred embodiment. For this purpose, one may choose from a number of promoters for genes with tissue- or cell-specific or enhanced expression. Examples of such promoters reported in the literature include the chloroplast glutamine synthetase GS2 promoter from pea (Edwards et al., *Proc. Natl. Acad. Sci. (U.S.A.)*, 87:3459–3463 (1990)), the chloroplast fructose-1,6-biphosphatase (FBPase) promoter from wheat (Lloyd et al., *Mol. Gen. Genet.*, 225:209–216 (1991)), the nuclear photosynthetic ST-LS1 promoter from potato (Stockhaus et al., *EMBO J.*, 8:2445–2451 (1989)), the serine/threonine kinase (PAL) promoter and the glucoamylase (CHS) promoter from *Arabidopsis thaliana*. Also, reported to be active in photosynthetically active tissues are the ribulose-1,5-bisphosphate carboxylase (RbcS) promoter from eastern larch (*Larix laricina*), the promoter for the cab gene, cab6, from pine (Yamamoto et al., *Plant Cell Physiol.*, 35:773–778 (1994)), the promoter for the Cab-1 gene from wheat (Fejes et al., *Plant Mol. Biol.*, 15:921–932 (1990)), the promoter for the CAB-1 gene from spinach (Lubberstedt et al., *Plant Physiol.*, 104:997–1006 (1994)), the promoter for the cab1R gene from rice (Luan et al., *Plant Cell.*, 4:971–981 (1992)), the pyruvate, orthophosphate dikinase (PPDK) promoter from corn (Matsuoka et al., *Proc. Natl. Acad. Sci. (U.S.A.)*, 90:9586–9590 (1993)), the promoter for the tobacco Lhcb1*2 gene (Cerdan et al., *Plant Mol. Biol.*, 33:245–255 (1997)), the *Arabidopsis thaliana* SUC2 sucrose-H+ symporter promoter (Truernit et al., *Planta.*, 196:564–570 (1995)) and the promoter for the thylakoid membrane proteins from spinach (psaD, psaF, psaE, PC, FNR, atpC, atpD, cab, rbcS). Other promoters for the chlorophyll a/b-binding proteins may also be utilized in the present invention, such as the promoters for LhcB gene and PsbP gene from white mustard (*Sinapis alba*; Kretsch et al., *Plant Mol. Biol.*, 28:219–229 (1995)).

For the purpose of expression in sink tissues of the plant, such as the tuber of the potato plant, the fruit of tomato, or the seed of corn, wheat, rice and barley, it is preferred that the promoters utilized in the present invention have relatively high expression in these specific tissues. A number of promoters for genes with tuber-specific or tuber-enhanced expression are known, including the class I patatin promoter (Bevan et al., *EMBO J.*, 8:1899–1906 (1986); Jefferson et al., *Plant Mol. Biol.*, 14:995–1006 (1990)), the promoter for the potato tuber ADPGPP genes, both the large and small subunits, the sucrose synthase promoter (Salanoubat and Belliard, *Gene*, 60:47–56 (1987), Salanoubat and Belliard, *Gene*, 84:181–185 (1989)), the promoter for the major tuber proteins including the 22 kd protein complexes and protease inhibitors (Hannapel, *Plant Physiol.*, 101:703–704 (1993)), the promoter for the granule-bound starch synthase gene (GBSS) (Visser et al., *Plant Mol. Biol.*, 17:691–699 (1991)) and other class I and II patatins promoters (Koster-Topfer et al., *Mol. Gen. Genet.*, 219:390–396 (1989); Mignery et al., *Gene.*, 62:27–44 (1988)).

Other promoters can also be used to express a polypeptide in specific tissues, such as seeds or fruits. Indeed, in a preferred embodiment, the promoter used is a seed specific promoter. Examples of such promoters include the 5' regulatory regions from such genes as napin (Kridl et al., *Seed Sci. Res.*, 1:209:219 (1991)), phaseolin (Bustos et al., *Plant Cell*, 1(9):839–853 (1989)), soybean trypsin inhibitor (Riggs et al., *Plant Cell*, 1(6):609–621 (1989)), ACP (Baerson et al., *Plant Mol. Biol.*, 22(2):255–267 (1993)), stearoyl-ACP desaturase (Slocombe et al., *Plant Physiol.*, 104(4):167–176 (1994)), soybean α' subunit of β-conglycinin (soy 7s, (Chen et al., *Proc. Natl. Acad. Sci.*, 83:8560–8564 (1986))), and oleosin (see, for example, Hong et al., *Plant Mol. Biol.*, 34(3):549–555 (1997)). Further examples include the promoter for β-conglycinin (Chen et al., *Dev. Genet.*, 10:112–122 (1989)). Also included are the zeins, which are a group of storage proteins found in corn endosperm. Genomic clones for zein genes have been isolated (Pedersen et al., *Cell*, 29:1015–1026 (1982), and Russell et al., *Transgenic Res.*, 6(2):157–168) and the promoters from these clones, including the 15 kD, 16 kD, 19 kD, 22 kD, 27 kD and genes, could also be used. Other promoters known to function, for example, in corn include the promoters for the following genes: waxy, Brittle, Shrunken 2, Branching enzymes I and II, starch synthases, debranching enzymes, oleosins, glutelins and sucrose synthases. A particularly preferred promoter for corn endosperm expression is the promoter for the glutelin gene from rice, more particularly the Osgt-1 promoter (Zheng et al., *Mol. Cell Biol.*, 13:5829–5842 (1993)). Examples of promoters suitable for expression in wheat include those promoters for the ADP-glucose pyrosynthase (ADPGPP) subunits, the granule bound and other starch synthase, the branching and debranching enzymes, the embryogenesis-abundant proteins, the gliadins and the glutenins. Examples of such promoters in rice include those promoters for the ADPGPP subunits, the granule bound and other starch synthase, the branching enzymes, the debranching enzymes, sucrose synthases and the glutelins. A particularly preferred promoter is the promoter for rice glutelin, Osgt-1. Examples of such promoters for barley include those for the ADPGPP subunits, the granule bound and other starch synthase, the branching enzymes, the debranching enzymes, sucrose synthases, the hordeins, the embryo globulins and the aleurone specific proteins. A preferred promoter for expression in the seed is a napin promoter. Another preferred promoter for expression is an Arcelin 5 promoter.

Root specific promoters may also be used. An example of such a promoter is the promoter for the acid chitinase gene (Samac et al., *Plant Mol. Biol.*, 25:587–596 (1994)). Expression in root tissue could also be accomplished by utilizing the root specific subdomains of the CaMV35S promoter that have been identified (Lam et al., *Proc. Natl. Acad. Sci. (U.S.A.)*, 86:7890–7894 (1989)). Other root cell specific promoters include those reported by Conkling et al., *Plant Physiol.*, 93:1203–1211 (1990).

Other preferred promoters include 7Scα' (Beachy et al., *EMBO J.*, 4:3047 (1985); Schuler et al., *Nucleic Acid Res.*, 10(24):8225–8244 (1982)); USP 88 and enhanced USP 88 (U.S. Patent Application No. 60/377,236, filed May 3, 2002, incorporated herein by reference); and 7sα, (U.S. patent application Ser. No. 10/235,618).

Additional promoters that may be utilized are described, for example, in U.S. Pat. Nos. 5,378,619; 5,391,725; 5,428,147; 5,447,858; 5,608,144; 5,608,144; 5,614,399; 5,633,441; 5,633,435; and 4,633,436. In addition, a tissue specific enhancer may be used (Fromm et al., *The Plant Cell*, 1:977–984 (1989)).

Constructs or vectors may also include, with the coding region of interest, a nucleic acid sequence that acts, in whole or in part, to terminate transcription of that region. A number of such sequences have been isolated, including the Tr7 3' sequence and the NOS 3' sequence (Ingelbrecht et al., *The Plant Cell*, 1:671–680 (1989); Bevan et al., *Nucleic Acids Res.*, 11:369–385 (1983)). Regulatory transcript termination regions can be provided in plant expression constructs of this present invention as well. Transcript termination regions can be provided by the DNA sequence encoding the gene of interest or a convenient transcription termination region derived from a different gene source, for example, the transcript termination region that is naturally associated with the transcript initiation region. The skilled artisan will recognize that any convenient transcript termination region that is capable of terminating transcription in a plant cell can be employed in the constructs of the present invention.

A vector or construct may also include regulatory elements. Examples of such include the Adh intron 1 (Callis et al., *Genes and Develop.*, 1:1183–1200 (1987)), the sucrose synthase intron (Vasil et al., *Plant Physiol.*, 91:1575–1579 (1989)) and the TMV omega element (Gallie et al., *The Plant Cell*, 1:301–311 (1989)). These and other regulatory elements may be included when appropriate.

A vector or construct may also include a selectable marker. Selectable markers may also be used to select for plants or plant cells that contain the exogenous genetic material. Examples of such include, but are not limited to: a neo gene (Potrykus et al., *Mol. Gen. Genet.*, 199:183–188 (1985)), which codes for kanamycin resistance and can be selected for using kanamycin, RptII, G418, hpt etc.; a bar gene which codes for bialaphos resistance; a mutant EPSP synthase gene (Hinchee et al., *Bio/Technology*, 6:915–922 (1988); Reynaerts et al., Selectable and Screenable Markers. In: Gelvin and Schilperoort, Plant Molecular Biology Manual, Kluwer, Dordrecht (1988); Reynaerts et al., Selectable and Screenable Markers. In: Gelvin and Schilperoort, Plant Molecular Biology Manual, Kluwer, Dordrecht (1988)), aadA (Jones et al., *Mol. Gen. Genet.* (1987)), which encodes glyphosate resistance; a nitrilase gene which confers resistance to bromoxynil (Stalker et al., *J. Biol. Chem.*, 263:6310–6314 (1988)); a mutant acetolactate synthase gene (ALS) which confers imidazolinone or sulphonylurea resistance (EP 0 154 204 (Sep. 11, 1985)), ALS (D'Halluin et al., *Bio/Technology*, 10:309–314 (1992)), and a methotrexate resistant DHFR gene (Thillet et al., *J. Biol. Chem.*, 263:12500–12508 (1988)).

A vector or construct may also include a transit peptide. Incorporation of a suitable chloroplast transit peptide may also be employed (EP 0 218 571). Translational enhancers may also be incorporated as part of the vector DNA. DNA constructs could contain one or more 5' non-translated leader sequences, which may serve to enhance expression of the gene products from the resulting mRNA transcripts. Such sequences may be derived from the promoter selected to express the gene or can be specifically modified to increase translation of the mRNA. Such regions may also be obtained from viral RNAs, from suitable eukaryotic genes, or from a synthetic gene sequence. For a review of optimizing expression of transgenes, see Koziel et al., *Plant Mol. Biol.*, 32:393–405 (1996). A preferred transit peptide is CTP1.

A vector or construct may also include a screenable marker. Screenable markers may be used to monitor expression. Exemplary screenable markers include: a β-glucuronidase or uidA gene (GUS) which encodes an enzyme for which various chromogenic substrates are known (Jefferson, *Plant Mol. Biol, Rep.*, 5:387–405 (1987); Jefferson et al., *EMBO J.*, 6:3901–3907 (1987)); an R-locus gene, which encodes a product that regulates the production of anthocyanin pigments (red color) in plant tissues (Dellaporta et al., *Stadler Symposium*, 11:263–282 (1988)); a β-lactamase gene (Sutcliffe et al., *Proc. Natl. Acad. Sci. (U.S.A.)*, 75:3737–3741 (1978)), a gene which encodes an enzyme for which various chromogenic substrates are known (e.g., PADAC, a chromogenic cephalosporin); a luciferase gene (Ow et al., *Science*, 234:856–859 (1986)); a xylE gene (Zukowsky et al., *Proc. Natl. Acad. Sci. (U.S.A.)*, 80:1101–1105 (1983)) which encodes a catechol dioxygenase that can convert chromogenic catechols; an α-amylase gene (Ikatu et al., *Bio/Technol.*, 8:241–242 (1990)); a tyrosinase gene (Katz et al., *J. Gen. Microbiol.*, 129:2703–2714 (1983)) which encodes an enzyme capable of oxidizing tyrosine to DOPA and dopaquinone which in turn condenses to melanin; an α-galactosidase, which will turn a chromogenic α-galactose substrate.

Included within the terms "selectable or screenable marker genes" are also genes that encode a secretable marker whose secretion can be detected as a means of identifying or selecting for transformed cells. Examples include markers that encode a secretable antigen that can be identified by antibody interaction, or even secretable enzymes that can be detected catalytically. Secretable proteins fall into a number of classes, including small, diffusible proteins that are detectable, (e.g., by ELISA), small active enzymes that are detectable in extracellular solution (e.g., α-amylase, β-lactamase, phosphinothricin transferase), or proteins that are inserted or trapped in the cell wall (such as proteins that include a leader sequence such as that found in the expression unit of extension or tobacco PR-S). Other possible selectable and/or screenable marker genes will be apparent to those of skill in the art.

There are many methods for introducing transforming nucleic acid molecules into plant cells. Suitable methods are believed to include virtually any method by which nucleic acid molecules may be introduced into a cell, such as by *Agrobacterium* infection or direct delivery of nucleic acid molecules such as, for example, by PEG-mediated transformation, by electroporation or by acceleration of DNA coated particles, and the like. (Potrykus, *Ann. Rev. Plant Physiol. Plant Mol. Biol.*, 42:205–225 (1991); Vasil, *Plant Mol. Biol.*, 25:925–937 (1994)). For example, electroporation has been used to transform corn protoplasts (Fromm et al., *Nature*, 312:791–793 (1986)).

Other vector systems suitable for introducing transforming DNA into a host plant cell include but are not limited to binary artificial chromosome (BIBAC) vectors (Hamilton et al., *Gene*, 200:107–116 (1997)); and transfection with RNA viral vectors (Della-Cioppa et al., *Ann. N.Y. Acad. Sci.* (1996), 792 (Engineering Plants for Commercial Products and Applications, 57–61). Additional vector systems also include plant selectable YAC vectors such as those described in Mullen et al., *Molecular Breeding*, 4:449–457 (1988).

Technology for introduction of DNA into cells is well known to those of skill in the art. Four general methods for delivering a gene into cells have been described: (1) chemical methods (Graham and van der Eb, *Virology*, 54:536–539 (1973)); (2) physical methods such as microinjection (Capecchi, *Cell*, 22:479–488 (1980)), electroporation (Wong and Neumann, *Biochem. Biophys. Res. Commun.*, 107:584–587 (1982); Fromm et al., *Proc. Natl. Acad. Sci. (U.S.A.)*, 82:5824–5828 (1985); U.S. Pat. No. 5,384,253); the gene gun (Johnston and Tang, *Methods Cell Biol.*, 43:353–365 (1994)); and vacuum infiltration (Bechtold et al., *C.R. Acad. Sci. Paris, Life Sci.*, 316:1194–1199 (1993)); (3) viral vectors (Clapp, *Clin. Perinatol.*, 20:155–168 (1993); Lu et al., *J. Exp. Med.*, 178:2089–2096 (1993); Eglitis and Anderson, *Biotechniques*, 6:608–614 (1988)); and (4) receptor-mediated mechanisms (Curiel et al., *Hum. Gen. Ther.*, 3:147–154 (1992), Wagner et al., *Proc. Natl. Acad. Sci. (U.S.A.)*, 89:6099–6103 (1992)).

Acceleration methods that may be used include, for example, microprojectile bombardment and the like. One example of a method for delivering transforming nucleic acid molecules into plant cells is microprojectile bombardment. This method has been reviewed by Yang and Christou (eds.), *Particle Bombardment Technology for Gene Transfer*, Oxford Press, Oxford, England (1994). Non-biological particles (microprojectiles) may be coated with nucleic acids and delivered into cells by a propelling force. Exemplary particles include those comprised of tungsten, gold, platinum and the like.

A particular advantage of microprojectile bombardment, in addition to it being an effective means of reproducibly transforming monocots, is that neither the isolation of protoplasts (Cristou et al., *Plant Physiol.*, 87:671–674 (1988)) nor the susceptibility to *Agrobacterium* infection is required. An illustrative embodiment of a method for delivering DNA into corn cells by acceleration is a biolistics α-particle delivery system, which can be used to propel particles coated with DNA through a screen, such as a stainless steel or Nytex screen, onto a filter surface covered with corn cells cultured in suspension. Gordon-Kamm et al., describes the basic procedure for coating tungsten particles with DNA (Gordon-Kamm et al., *Plant Cell*, 2:603–618 (1990)). The screen disperses the tungsten nucleic acid particles so that they are not delivered to the recipient cells in large aggregates. A particle delivery system suitable for use with the present invention is the helium acceleration PDS-1000/He gun, which is available from Bio-Rad Laboratories (Bio-Rad, Hercules, Calif.) (Sanford et al., *Technique*, 3:3–16 (1991)).

For the bombardment, cells in suspension may be concentrated on filters. Filters containing the cells to be bombarded are positioned at an appropriate distance below the microprojectile stopping plate. If desired, one or more screens are also positioned between the gun and the cells to be bombarded.

Alternatively, immature embryos or other target cells may be arranged on solid culture medium. The cells to be bombarded are positioned at an appropriate distance below the microprojectile stopping plate. If desired, one or more screens are also positioned between the acceleration device and the cells to be bombarded. Through the use of techniques set forth herein one may obtain 1000 or more loci of cells transiently expressing a marker gene. The number of cells in a focus that express the exogenous gene product 48 hours post-bombardment often ranges from one to ten, and average one to three.

In bombardment transformation, one may optimize the pre-bombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment and also the nature of the transforming DNA, such as linearized DNA or intact supercoiled plasmids. It is believed that pre-bombardment manipulations are especially important for successful transformation of immature embryos.

In another alternative embodiment, plastids can be stably transformed. Methods disclosed for plastid transformation in higher plants include the particle gun delivery of DNA containing a selectable marker and targeting of the DNA to the plastid genome through homologous recombination (Svab et al., *Proc. Natl. Acad. Sci. (U.S.A.)*, 87:8526–8530 (1990); Svab and Maliga, *Proc. Natl. Acad. Sci. (U.S.A.)*, 90:913–917 (1993); Staub and Maliga, *EMBO J.*, 12:601–606 (1993); U.S. Pat. Nos. 5,451,513 and 5,545,818).

Accordingly, it is contemplated that one may wish to adjust various aspects of the bombardment parameters in small scale studies to fully optimize the conditions. One may particularly wish to adjust physical parameters such as gap distance, flight distance, tissue distance and helium pressure. One may also minimize the trauma reduction factors by modifying conditions that influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., *Bio/Technology*, 3:629–635 (1985) and Rogers et al., *Methods Enzymol.*, 153:253–277 (1987). Further, the integration of the Ti-DNA is a relatively precise process resulting in few rearrangements. The region of DNA to be transferred is defined by the border sequences and intervening DNA is usually inserted into the plant genome as described (Spielmann et al., *Mol. Gen. Genet.*, 205:34 (1986)).

Modern *Agrobacterium* transformation vectors are capable of replication in *E. coli* as well as *Agrobacterium*, allowing for convenient manipulations as described (Klee et al., In: *Plant DNA Infectious Agents*, Hohn and Schell (eds.), Springer-Verlag, NY, pp. 179–203 (1985)). Moreover, technological advances in vectors for *Agrobacterium*-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes (Rogers et al., *Methods Enzymol.*, 153:253–277 (1987)). In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

A transgenic plant formed using *Agrobacterium* transformation methods typically contains a single gene on one chromosome. Such transgenic plants can be referred to as being heterozygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant, transgenic plant that contains a single added gene, germinating some of the seed produced and analyzing the resulting plants produced for the gene of interest.

It is also to be understood that two different transgenic plants can also be mated to produce offspring that contain two independently segregating, exogenous genes. Selfing of appropriate progeny can produce plants that are homozygous for both added, exogenous genes that encode a polypeptide of interest. Back-crossing to a parental plant and out-crossing with a non-transgenic plant are also contemplated, as is vegetative propagation.

Transformation of plant protoplasts can be achieved using methods based on calcium phosphate precipitation, polyethylene glycol treatment, electroporation and combinations of these treatments (see, for example, Potrykus et al., *Mol. Gen. Genet.*, 205:193–200 (1986); Lorz et al., *Mol. Gen. Genet.*, 199:1780(1985); Fromm et al., *Nature*, 319:791 (1986); Uchimiya et al., *Mol. Gen. Genet.*, 204:204 (1986); Marcotte et al., *Nature*, 335:454–457 (1988)).

Application of these systems to different plant strains depends upon the ability to regenerate that particular plant strain from protoplasts. Illustrative methods for the regeneration of cereals from protoplasts are described (Fujimura et al., *Plant Tissue Culture Letters*, 2:74 (1985); Toriyama et al., *Theor. Appl. Genet.*, 205:34 (1986); Yamada et al., *Plant Cell Rep.*, 4:85 (1986); Abdullah et al., *Biotechnology*, 4:1087 (1986)).

To transform plant strains that cannot be successfully regenerated from protoplasts, other ways to introduce DNA into intact cells or tissues can be utilized. For example, regeneration of cereals from immature embryos or explants can be effected as described (Vasil, *Biotechnology*, 6:397 (1988)). In addition, "particle gun" or high-velocity microprojectile technology can be utilized (Vasil et al., *Bio/Technology*, 10:667 (1992)).

Using the latter technology, DNA is carried through the cell wall and into the cytoplasm on the surface of small metal particles as described (Klein et al., *Nature*, 328:70 (1987); Klein et al., *Proc. Natl. Acad. Sci. (U.S.A.)*, 85:8502–8505 (1988); McCabe et al., *Bio/Technology*, 6:923 (1988)). The metal particles penetrate through several layers of cells and thus allow the transformation of cells within tissue explants.

Other methods of cell transformation can also be used and include but are not limited to introduction of DNA into plants by direct DNA transfer into pollen (Hess et al., *Intern Rev. Cytol.*, 107:367 (1987); Luo et al., *Plant Mol. Biol. Reporter*, 6:165 (1988)), by direct injection of DNA into reproductive organs of a plant (Pena et al., *Nature*, 325:274 (1987)), or by direct injection of DNA into the cells of immature embryos followed by the rehydration of desiccated embryos (Neuhaus et al., *Theor. Appl. Genet.*, 75:30 (1987)).

The regeneration, development and cultivation of plants from single plant protoplast transformants or from various transformed explants is well known in the art (Weissbach and Weissbach, In: *Methods for Plant Molecular Biology*, Academic Press, San Diego, Calif., (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

There are a variety of methods for the regeneration of plants from plant tissue. The particular method of regeneration will depend on the starting plant tissue and the particular plant species to be regenerated.

Methods for transforming dicots, primarily by use of *Agrobacterium tumefaciens* and obtaining transgenic plants have been published for cotton (U.S. Pat. Nos. 5,004,863; 5,159,135; and 5,518,908); soybean (U.S. Pat. Nos. 5,569,834 and 5,416,011; McCabe et al., *Biotechnology*, 6:923 (1988); Christou et al., *Plant Physiol.*, 87:671–674 (1988)); Brassica (U.S. Pat. No. 5,463,174); peanut (Cheng et al., *Plant Cell Rep.*, 15:653–657 (1996), McKently et al., *Plant Cell Rep.*, 14:699–703 (1995)); papaya; pea (Grant et al., *Plant Cell Rep.*, 15:254–258 (1995)); and *Arabidopsis thaliana* (Bechtold et al., *C.R. Acad. Sci. Paris, Life Sci.*, 316:1194–1199 (1993)). The latter method for transforming *Arabidopsis thaliana* is commonly called "dipping" or vacuum infiltration or germplasm transformation.

Transformation of monocotyledons using electroporation, particle bombardment and Agrobacterium have also been reported. Transformation and plant regeneration have been achieved in asparagus (Bytebier et al., *Proc. Natl. Acad. Sci. (U.S.A.)*, 84:5354 (1987)); barley (Wan and Lemaux, *Plant*

*Physiol*, 104:37 (1994)); corn (Rhodes et al., *Science*, 240: 204 (1988); Gordon-Kamm et al., *Plant Cell*, 2:603–618 (1990); Fromm et al., *Bio/Technology*, 8:833 (1990); Koziel et al., *Bio/Technology*, 11:194 (1993); Armstrong et al., *Crop Science*, 35:550–557 (1995)); oat (Somers et al., *Bio/Technology*, 10:1589 (1992)); orchard grass (Horn et al., *Plant Cell Rep.*, 7:469 (1988)); rice (Toriyama et al., *Theor Appl. Genet.*, 205:34 (1986); Part et al., *Plant Mol. Biol.*, 32:1135–1148 (1996); Abedinia et al., *Aust. J. Plant Physiol.*, 24:133–141 (1997); Zhang and Wu, *Theor. Appl. Genet.*, 76:835 (1988); Zhang et al., *Plant Cell Rep.*, 7:379 (1988); Battraw and Hall, *Plant Sci.*, 86:191–202 (1992); Christou et al., *Bio/Technology*, 9:957 (1991)); rye (De la Pena et al., *Nature*, 325:274 (1987)); sugarcane (Bower and Birch, *Plant J.*, 2:409 (1992)); tall fescue (Wang et al., *Bio/Technology*, 10:691 (1992)); and wheat (Vasil et al., *Bio/Technology*, 10:667 (1992); U.S. Pat. No. 5,631,152).

Assays for gene expression based on the transient expression of cloned nucleic acid constructs have been developed by introducing the nucleic acid molecules into plant cells by polyethylene glycol treatment, electroporation, or particle bombardment (Marcotte et al., *Nature*, 335:454–457 (1988); Marcotte et al., *Plant Cell*, 1:523–532 (1989); McCarty et al., *Cell*, 66:895–905 (1991); Hattori et al., *Genes Dev.*, 6:609–618 (1992); Goff et al., *EMBO J.*, 9:2517–2522 (1990)). Transient expression systems may be used to functionally dissect gene constructs (see generally, Mailga et al., *Methods in Plant Molecular Biology*, Cold Spring Harbor Press, NY (1995)).

Any of the nucleic acid molecules of the present invention may be introduced into a plant cell in a permanent or transient manner in combination with other genetic elements such as vectors, promoters, enhancers, etc. Further, any of the nucleic acid molecules of the present invention may be introduced into a plant cell in a manner that allows for expression or overexpression of the protein or fragment thereof encoded by the nucleic acid molecule.

Cosuppression is the reduction in expression levels, usually at the level of RNA, of a particular endogenous gene or gene family by the expression of a homologous sense construct that is capable of transcribing mRNA of the same strandedness as the transcript of the endogenous gene (Napoli et al., *Plant Cell*, 2:279–289 (1990); van der Krol et al., *Plant Cell*, 2:291–299 (1990)). Cosuppression may result from stable transformation with a single copy nucleic acid molecule that is homologous to a nucleic acid sequence found with the cell (Prolls and Meyer, *Plant J.*, 2:465–475 (1992)) or with multiple copies of a nucleic acid molecule that is homologous to a nucleic acid sequence found with the cell (Mittlesten et al., *Mol. Gen. Genet.*, 244:325–330 (1994)). Genes, even though different, linked to homologous promoters may result in the cosuppression of the linked genes (Vaucheret, *C.R. Acad. Sci. III*, 316:1471–1483 (1993); Flavell, *Proc. Natl. Acad. Sci. (U.S.A.)*, 91:3490–3496 (1994)); van Blokland et al., *Plant J.*, 6:861–877 (1994); Jorgensen, *Trends Biotechnol.*, 8:340–344 (1990); Meins and Kunz, In: *Gene Inactivation and Homologous Recombination in Plants*, Paszkowski (ed.), pp. 335–348, Kluwer Academic, Netherlands (1994)).

It is understood that one or more of the nucleic acids of the present invention may be introduced into a plant cell and transcribed using an appropriate promoter with such transcription resulting in the cosuppression of an endogenous protein.

Antisense approaches are a way of preventing or reducing gene function by targeting the genetic material (Mol et al., *FEBS Lett.*, 268:427–430 (1990)). The objective of the antisense approach is to use a sequence complementary to the target gene to block its expression and create a mutant cell line or organism in which the level of a single chosen protein is selectively reduced or abolished. Antisense techniques have several advantages over other "reverse genetic" approaches. The site of inactivation and its developmental effect can be manipulated by the choice of promoter for antisense genes or by the timing of external application or microinjection. Antisense can manipulate its specificity by selecting either unique regions of the target gene or regions where it shares homology to other related genes (Hiatt et al., In: *Genetic Engineering*, Setlow (ed.), Vol. 11, New York: Plenum 49–63 (1989)).

Antisense RNA techniques involve introduction of RNA that is complementary to the target mRNA into cells, which results in specific RNA:RNA duplexes being formed by base pairing between the antisense substrate and the target mRNA (Green et al., *Annu. Rev. Biochem.*, 55:569–597 (1986)). Under one embodiment, the process involves the introduction and expression of an antisense gene sequence. Such a sequence is one in which part or all of the normal gene sequences are placed under a promoter in inverted orientation so that the "wrong" or complementary strand is transcribed into a noncoding antisense RNA that hybridizes with the target mRNA and interferes with its expression (Takayama and Inouye, *Crit. Rev. Biochem. Mol. Biol.*, 25:155–184 (1990)). An antisense vector is constructed by standard procedures and introduced into cells by transformation, transfection, electroporation, microinjection, infection, etc. The type of transformation and choice of vector will determine whether expression is transient or stable. The promoter used for the antisense gene may influence the level, timing, tissue, specificity, or inducibility of the antisense inhibition.

It is understood that the activity of a protein in a plant cell may be reduced or depressed by growing a transformed plant cell containing a nucleic acid molecule whose non-transcribed strand encodes a protein or fragment thereof. A preferred protein whose activity can be reduced or depressed, by any method, is a homogentisate prenyl transferase.

Posttranscriptional gene silencing (PTGS) can result in virus immunity or gene silencing in plants. PTGS is induced by dsRNA and is mediated by an RNA-dependent RNA polymerase, present in the cytoplasm, which requires a dsRNA template. The dsRNA is formed by hybridization of complementary transgene mRNAs or complementary regions of the same transcript. Duplex formation can be accomplished by using transcripts from one sense gene and one antisense gene colocated in the plant genome, a single transcript that has self-complementarity, or sense and antisense transcripts from genes brought together by crossing. The dsRNA-dependent RNA polymerase makes a complementary strand from the transgene mRNA and RNAse molecules attach to this complementary strand (cRNA). These cRNA-RNase molecules hybridize to the endogene mRNA and cleave the single-stranded RNA adjacent to the hybrid. The cleaved single-stranded RNAs are further degraded by other host RNases because one will lack a capped 5' end and the other will lack a poly (A) tail (Waterhouse et al., *PNAS*, 95:13959–13964 (1998)).

It is understood that one or more of the nucleic acids of the present invention may be introduced into a plant cell and transcribed using an appropriate promoter with such transcription resulting in the posttranscriptional gene silencing of an endogenous transcript.

Antibodies have been expressed in plants (Hiatt et al., *Nature*, 342:76–78 (1989); Conrad and Fielder, *Plant Mol. Biol.*, 26:1023–1030 (1994)). Cytoplasmic expression of a scFv (single-chain Fv antibody) has been reported to delay infection by artichoke mottled crinkle virus. Transgenic plants that express antibodies directed against endogenous proteins may exhibit a physiological effect (Philips et al., *EMBO J.*, 16:4489–4496 (1997); Marion-Poll, *Trends in Plant Science*, 2:447–448 (1997)). For example, expressed anti-abscisic antibodies have been reported to result in a general perturbation of seed development (Philips et al., *EMBO J.*, 16:4489–4496 (1997)).

Antibodies that are catalytic may also be expressed in plants (abzymes). The principle behind abzymes is that since antibodies may be raised against many molecules, this recognition ability can be directed toward generating antibodies that bind transition states to force a chemical reaction forward (Persidas, *Nature Biotechnology*, 15:1313–1315 (1997); Baca et al., *Ann. Rev. Biophys. Biomol. Struct.*, 26:461–493 (1997)). The catalytic abilities of abzymes may be enhanced by site directed mutagenesis. Examples of abzymes are, for example, set forth in U.S. Pat. Nos.: 5,658,753; 5,632,990; 5,631,137; 5,602,015; 5,559,538; 5,576,174; 5,500,358; 5,318,897; 5,298,409; 5,258,289; and 5,194,585.

It is understood that any of the antibodies of the present invention may be expressed in plants and that such expression can result in a physiological effect. It is also understood that any of the expressed antibodies may be catalytic.

The present invention also provides for parts of the plants, particularly reproductive or storage parts, of the present invention. Plant parts, without limitation, include seed, endosperm, ovule and pollen. In a particularly preferred embodiment of the present invention, the plant part is a seed. In one embodiment the seed is a constituent of animal feed.

In another embodiment, the plant part is a fruit, more preferably a fruit with enhanced shelf life. In another preferred embodiment, the fruit has increased levels of a tocopherol. In another preferred embodiment, the fruit has increased levels of a tocotrienol.

The present invention also provides a container of over about 10,000, more preferably about 20,000, and even more preferably about 40,000 seeds where over about 10%, more preferably 25%, more preferably 50%, and even more preferably 75% or 90% of the seeds are seeds derived from a plant of the present invention.

The present invention also provides a container of over about 10 kg, more preferably 25 kg, and even more preferably 50 kg seeds where over about 10%, more preferably 25%, more preferably 50%, and even more preferably 75% or 90% of the seeds are seeds derived from a plant of the present invention.

Any of the plants or parts thereof of the present invention may be processed to produce a feed, meal, protein, or oil preparation, including oil preparations high in total tocopherol content and oil preparations high in any one or more of each tocopherol component listed herein. A particularly preferred plant part for this purpose is a seed. In a preferred embodiment the feed, meal, protein or oil preparation is designed for livestock animals or humans, or both. Methods to produce feed, meal, protein and oil preparations are known in the art. See, for example, U.S. Pat. Nos. 4,957,748; 5,100,679; 5,219,596; 5,936,069; 6,005,076; 6,146,669; and 6,156,227. In a preferred embodiment, the protein preparation is a high protein preparation. Such a high protein preparation preferably has a protein content of greater than about 5% w/v, more preferably 10% w/v, and even more preferably 15% w/v. In a preferred oil preparation, the oil preparation is a high oil preparation with an oil content derived from a plant or part thereof of the present invention of greater than about 5% w/v, more preferably 10% w/v, and even more preferably 15% w/v. In a preferred embodiment the oil preparation is a liquid and of a volume greater than about 1, 5, 10, or 50 liters. The present invention provides for oil produced from plants of the present invention or generated by a method of the present invention. Such an oil may exhibit enhanced oxidative stability. Also, such oil may be a minor or major component of any resultant product. Moreover, such oil may be blended with other oils. In a preferred embodiment, the oil produced from plants of the present invention or generated by a method of the present invention constitutes greater than about 0.5%, 1%, 5%, 10%, 25%, 50%, 75%, or 90% by volume or weight of the oil component of any product. In another embodiment, the oil preparation may be blended and can constitute greater than about 10%, 25%, 35%, 50%, or 75% of the blend by volume. Oil produced from a plant of the present invention can be admixed with one or more organic solvents or petroleum distillates.

Plants of the present invention can be part of or generated from a breeding program. The choice of breeding method depends on the mode of plant reproduction, the heritability of the trait(s) being improved, and the type of cultivar used commercially (e.g., $F_1$ hybrid cultivar, pureline cultivar, etc.). Selected, non-limiting approaches, for breeding the plants of the present invention are set forth below. A breeding program can be enhanced using marker assisted selection of the progeny of any cross. It is further understood that any commercial and non-commercial cultivars can be utilized in a breeding program. Factors such as, for example, emergence vigor, vegetative vigor, stress tolerance, disease resistance, branching, flowering, seed set, seed size, seed density, standability, and threshability etc. will generally dictate the choice.

For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection. In a preferred embodiment a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Breeding lines can be tested and compared to appropriate standards in environments representative of the commercial target area(s) for two or more generations. The best lines are candidates for new commercial cultivars; those still deficient in traits may be used as parents to produce new populations for further selection.

One method of identifying a superior plant is to observe its performance relative to other experimental plants and to a widely grown standard cultivar. If a single observation is inconclusive, replicated observations can provide a better estimate of its genetic worth. A breeder can select and cross two or more parental lines, followed by repeated selfing and selection, producing many new genetic combinations.

The development of new cultivars requires the development and selection of varieties, the crossing of these varieties and the selection of superior hybrid crosses. The hybrid seed can be produced by manual crosses between selected male-fertile parents or by using male sterility systems. Hybrids are selected for certain single gene traits such as pod color, flower color, seed yield, pubescence color, or herbicide resistance, which indicate that the seed is truly a hybrid. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes. New cultivars can be evaluated to determine which have commercial potential.

Pedigree breeding is used commonly for the improvement of self-pollinating crops. Two parents who possess favorable, complementary traits are crossed to produce an $F_1$. A $F_2$ population is produced by selfing one or several $F_1$'s. Selection of the best individuals from the best families is carried out. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding.

Descriptions of other breeding methods that are commonly used for different traits and crops can be found in one of several reference books (e.g., Fehr, *Principles of Cultivar Development*, Vol. 1, pp. 2–3 (1987)).

A transgenic plant of the present invention may also be reproduced using apomixis. Apomixis is a genetically controlled method of reproduction in plants where the embryo is formed without union of an egg and a sperm. There are three basic types of apomictic reproduction: 1) apospory where the embryo develops from a chromosomally unreduced egg in an embryo sac derived from the nucleus; 2) diplospory where the embryo develops from an unreduced egg in an embryo sac derived from the megaspore mother cell; and 3) adventitious embryony where the embryo develops directly from a somatic cell. In most forms of apomixis, pseudogamy, or fertilization of the polar nuclei to produce endosperm is necessary for seed viability. In apospory, a nurse cultivar can be used as a pollen source for endosperm formation in seeds. The nurse cultivar does not affect the genetics of the aposporous apomictic cultivar since the unreduced egg of the cultivar develops parthenogenetically, but makes possible endosperm production. Apomixis is economically important, especially in transgenic plants, because it causes any genotype, no matter how heterozygous, to breed true. Thus, with apomictic reproduction, heterozygous transgenic plants can maintain their genetic fidelity throughout repeated life cycles. Methods for the production of apomictic plants are known in the art. See, U.S. Pat. No. 5,811,636.

Other Organisms

A nucleic acid of the present invention may be introduced into any cell or organism such as a mammalian cell, mammal, fish cell, fish, bird cell, bird, algae cell, algae, fungal cell, fungi, or bacterial cell. A protein of the present invention may be produced in an appropriate cell or organism. Preferred host and transformants include: fungal cells such as *Aspergillus*, yeasts, mammals, particularly bovine and porcine, insects, bacteria, and algae. Particularly preferred bacteria are *Agrobacteruim tumefaciens* and *E. coli*.

Methods to transform such cells or organisms are known in the art (EP 0 238 023; Yelton et al., *Proc. Natl. Acad. Sci. (U.S.A.)*, 81:1470–1474 (1984); Malardier et al., *Gene*, 78:147–156 (1989); Becker and Guarente, In: Abelson and Simon (eds.), *Guide to Yeast Genetics and Molecular Biology, Method Enzymol.*, Vol. 194, pp. 182–187, Academic Press, Inc., NY; Ito et al., *J. Bacteriology*, 153:163 (1983); Hinnen et al., *Proc. Natl. Acad. Sci. (U.S.A.)*, 75:1920 (1978); Bennett and LaSure (eds.), *More Gene Manipualtionins in fungi*, Academic Press, CA (1991)). Methods to produce proteins of the present invention are also known (Kudla et al., *EMBO*, 9:1355–1364 (1990); Jarai and Buxton, *Current Genetics*, 26:2238–2244 (1994); Verdier, *Yeast*, 6:271–297 (1990); MacKenzie et al., *Journal of Gen. Microbiol.*, 139:2295–2307 (1993); Hartl et al., *TIBS*, 19:20–25 (1994); Bergenron et al., *TIBS*, 19:124–128 (1994); Demolder et al., *J. Biotechnology*, 32:179–189 (1994); Craig, *Science*, 260:1902–1903 (1993); Gething and Sambrook, *Nature*, 355:33–45 (1992); Puig and Gilbert, J., *Biol. Chem.*, 269:7764–7771 (1994); Wang and Tsou, *FASEB Journal*, 7:1515–1517 (1993); Robinson et al., *Bio/Technology*, 1:381–384 (1994); Enderlin and Ogrydziak, *Yeast*, 10:67–79 (1994); Fuller et al., *Proc. Natl. Acad. Sci. (U.S.A.)*, 86:1434–1438 (1989); Julius et al., *Cell*, 37:1075–1089 (1984); Julius et al., *Cell*, 32:839–852 (1983)).

In a preferred embodiment, overexpression of a protein or fragment thereof of the present invention in a cell or organism provides in that cell or organism, relative to an untransformed cell or organism with a similar genetic background, an increased level of tocopherols.

In a preferred embodiment, overexpression of a protein or fragment thereof of the present invention in a cell or organism provides in that cell or organism, relative to an untransformed cell or organism with a similar genetic background, an increased level of α-tocopherols.

In a preferred embodiment, overexpression of a protein or fragment thereof of the present invention in a cell or organism provides in that cell or organism, relative to an untransformed cell or organism with a similar genetic background, an increased level of γ-tocopherols.

In another preferred embodiment, overexpression of a protein or fragment thereof of the present invention in a cell or organism provides in that cell or organism, relative to an untransformed cell or organism with a similar genetic background, an increased level of α-tocotrienols.

In another preferred embodiment, overexpression of a protein or fragment thereof of the present invention in a cell or organism provides in that cell or organism, relative to an untransformed cell or organism with a similar genetic background, an increased level of γ-tocotrienols.

Antibodies

One aspect of the present invention concerns antibodies, single-chain antigen binding molecules, or other proteins that specifically bind to one or more of the protein or peptide molecules of the present invention and their homologs, fusions or fragments. In a particularly preferred embodiment, the antibody specifically binds to a protein having the amino acid sequence set forth in SEQ ID NOs: 5, 9–11, 43–44, 57–58, and 90, or fragments thereof. Antibodies of the present invention may be used to quantitatively or qualitatively detect the protein or peptide molecules of the present invention, or to detect post translational modifications of the proteins. As used herein, an antibody or peptide is said to "specifically bind" to a protein or peptide molecule of the present invention if such binding is not competitively inhibited by the presence of non-related molecules.

Nucleic acid molecules that encode all or part of the protein of the present invention can be expressed, via recombinant means, to yield protein or peptides that can in turn be used to elicit antibodies that are capable of binding the expressed protein or peptide. Such antibodies may be used in immunoassays for that protein. Such protein-encoding molecules, or their fragments may be a "fusion" molecule (i.e., a part of a larger nucleic acid molecule) such that, upon expression, a fusion protein is produced. It is understood that any of the nucleic acid molecules of the present invention may be expressed, via recombinant means, to yield proteins or peptides encoded by these nucleic acid molecules.

The antibodies that specifically bind proteins and protein fragments of the present invention may be polyclonal or monoclonal and may comprise intact immunoglobulins, or antigen binding portions of immunoglobulins fragments (such as (F(ab'), F(ab')$_2$)), or single-chain immunoglobulins producible, for example, via recombinant means. It is understood that practitioners are familiar with the standard resource materials that describe specific conditions and procedures for the construction, manipulation and isolation of antibodies (see, for example, Harlow and Lane, In: *Antibodies: A Laboratory Manual*, Cold Spring Harbor Press, Cold Spring Harbor, N.Y. (1988)).

As discussed below, such antibody molecules or their fragments may be used for diagnostic purposes. Where the antibodies are intended for diagnostic purposes, it may be desirable to derivatize them, for example with a ligand group (such as biotin) or a detectable marker group (such as a fluorescent group, a radioisotope or an enzyme).

The ability to produce antibodies that bind the protein or peptide molecules of the present invention permits the identification of mimetic compounds derived from those molecules. These mimetic compounds may contain a fragment of the protein or peptide or merely a structurally similar region and nonetheless exhibits an ability to specifically bind to antibodies directed against that compound.

Exemplary Uses

Nucleic acid molecules and fragments thereof of the present invention may be employed to obtain other nucleic acid molecules from the same species (nucleic acid molecules from corn may be utilized to obtain other nucleic acid molecules from corn). Such nucleic acid molecules include the nucleic acid molecules that encode the complete coding sequence of a protein and promoters and flanking sequences of such molecules. In addition, such nucleic acid molecules include nucleic acid molecules that encode for other isozymes or gene family members. Such molecules can be readily obtained by using the above-described nucleic acid molecules or fragments thereof to screen cDNA or genomic libraries. Methods for forming such libraries are well known in the art.

Nucleic acid molecules and fragments thereof of the present invention may also be employed to obtain nucleic acid homologs. Such homologs include the nucleic acid molecules of plants and other organisms, including bacteria and fungi, including the nucleic acid molecules that encode, in whole or in part, protein homologues of other plant species or other organisms, sequences of genetic elements, such as promoters and transcriptional regulatory elements. Such molecules can be readily obtained by using the above-described nucleic acid molecules or fragments thereof to screen cDNA or genomic libraries obtained from such plant species. Methods for forming such libraries are well known in the art. Such homolog molecules may differ in their nucleotide sequences from those coding for one or more of SEQ ID NOs: 5, 9–11, 43–44, 57–58, and 90, and complements thereof because complete complementarity is not needed for stable hybridization. The nucleic acid molecules of the present invention therefore also include molecules that, although capable of specifically hybridizing with the nucleic acid molecules may lack "complete complementarity".

Any of a variety of methods may be used to obtain one or more of the above-described nucleic acid molecules (Zamechik et al., *Proc. Natl. Acad. Sci. (U.S.A.)*, 83:4143–4146 (1986); Goodchild et al., *Proc. Natl. Acad. Sci. (U.S.A.)*, 85:5507–5511 (1988); Wickstrom et al., *Proc. Natl. Acad. Sci. (U.S.A.)*, 85:1028–1032 (1988); Holt et al., *Molec. Cell. Biol.*, 8:963–973 (1988); Gerwirtz et al., *Science*, 242: 1303–1306 (1988); Anfossi et al., *Proc. Natl. Acad. Sci. (U.S.A.)*, 86:3379–3383 (1989); Becker et al., *EMBO J.*, 8:3685–3691 (1989)). Automated nucleic acid synthesizers may be employed for this purpose. In lieu of such synthesis, the disclosed nucleic acid molecules may be used to define a pair of primers that can be used with the polymerase chain reaction (Mullis et al., *Cold Spring Harbor Symp. Quant. Biol.*, 51:263–273 (1986); Erlich et al., EP 50 424; EP 84 796; EP 258 017; EP 237 362; Mullis, EP 201 184; Mullis et al., U.S. Pat. No. 4,683,202; Erlich, U.S. Pat. No. 4,582, 788; and Saiki et al., U.S. Pat. No. 4,683,194) to amplify and obtain any desired nucleic acid molecule or fragment.

Promoter sequences and other genetic elements, including but not limited to transcriptional regulatory flanking sequences, associated with one or more of the disclosed nucleic acid sequences can also be obtained using the disclosed nucleic acid sequence provided herein. In one embodiment, such sequences are obtained by incubating nucleic acid molecules of the present invention with members of genomic libraries and recovering clones that hybridize to such nucleic acid molecules thereof. In a second embodiment, methods of "chromosome walking", or inverse PCR may be used to obtain such sequences (Frohman et al., *Proc. Natl. Acad. Sci.* (*U.S.A.*), 85:8998–9002 (1988); Ohara et al., *Proc. Natl. Acad. Sci.* (*U.S.A.*), 86:5673–5677 (1989); Pang et al., *Biotechniques*, 22:1046–1048 (1977); Huang et al., *Methods Mol. Biol.*, 69:89–96 (1997); Huang et al., *Method Mol. Biol.*, 67:287–294 (1997); Benkel et al., *Genet. Anal.*, 13:123–127 (1996); Hartl et al., *Methods Mol. Biol.*, 58:293–301 (1996)). The term "chromosome walking" means a process of extending a genetic map by successive hybridization steps.

The nucleic acid molecules of the present invention may be used to isolate promoters of cell enhanced, cell specific, tissue enhanced, tissue specific, developmentally or environmentally regulated expression profiles. Isolation and functional analysis of the 5' flanking promoter sequences of these genes from genomic libraries, for example, using genomic screening methods and PCR techniques would result in the isolation of useful promoters and transcriptional regulatory elements. These methods are known to those of skill in the art and have been described (see, for example, Birren et al., *Genome Analysis: Analyzing DNA*, 1, (1997), Cold Spring Harbor Laboratory Press, Cold Spring Harbor, N.Y.). Promoters obtained utilizing the nucleic acid molecules of the present invention could also be modified to affect their control characteristics. Examples of such modifications would include but are not limited to enhancer sequences. Such genetic elements could be used to enhance gene expression of new and existing traits for crop improvement.

Another subset of the nucleic acid molecules of the present invention includes nucleic acid molecules that are markers. The markers can be used in a number of conventional ways in the field of molecular genetics. Such markers include nucleic acid molecules encoding SEQ ID NOs: 5, 9–11, 43–44, 57–58, and 90, and complements thereof, and fragments of either that can act as markers and other nucleic acid molecules of the present invention that can act as markers.

Genetic markers of the present invention include "dominant" or "codominant" markers. "Codominant markers" reveal the presence of two or more alleles (two per diploid individual) at a locus. "Dominant markers" reveal the presence of only a single allele per locus. The presence of the dominant marker phenotype (e.g., a band of DNA) is an indication that one allele is in either the homozygous or heterozygous condition. The absence of the dominant marker phenotype (e.g., absence of a DNA band) is merely evidence that "some other" undefined allele is present. In the case of populations where individuals are predominantly homozygous and loci are predominately dimorphic, dominant and codominant markers can be equally valuable. As populations become more heterozygous and multi-allelic, codominant markers often become more informative of the genotype than dominant markers. Marker molecules can be, for example, capable of detecting polymorphisms such as single nucleotide polymorphisms (SNPs).

The genomes of animals and plants naturally undergo spontaneous mutation in the course of their continuing evolution (Gusella, *Ann. Rev. Biochem.*, 55:831–854 (1986)). A "polymorphism" is a variation or difference in the sequence of the gene or its flanking regions that arises in some of the members of a species. The variant sequence and the "original" sequence co-exist in the species' population. In some instances, such co-existence is in stable or quasi-stable equilibrium.

A polymorphism is thus said to be "allelic", in that, due to the existence of the polymorphism, some members of a population may have the original sequence (i.e., the original "allele") whereas other members may have the variant sequence (i.e., the variant "allele"). In the simplest case, only one variant sequence may exist and the polymorphism is thus said to be di-allelic. In other cases, the species' population may contain multiple alleles and the polymorphism is termed tri-allelic, etc. A single gene may have multiple different unrelated polymorphisms. For example, it may have a di-allelic polymorphism at one site and a multi-allelic polymorphism at another site.

The variation that defines the polymorphism may range from a single nucleotide variation to the insertion or deletion of extended regions within a gene. In some cases, the DNA sequence variations are in regions of the genome that are characterized by short tandem repeats (STRs) that include tandem di- or tri-nucleotide repeated motifs of nucleotides. Polymorphisms characterized by such tandem repeats are referred to as "variable number tandem repeat" ("VNTR") polymorphisms. VNTRs have been used in identity analysis (Weber, U.S. Pat. No. 5,075,217; Armour et al., *FEBS Lett.*, 307:113–115 (1992); Jones et al., *Eur. J. Haematol.*, 39:144–147 (1987); Horn et al., PCT Application WO 91/14003; Jeffreys, EP 370 719; Jeffreys, U.S. Pat. No. 5,175,082; Jeffreys et al., *Amer. J. Hum. Genet.*, 39:11–24 (1986); Jeffreys et al., *Nature*, 316:76–79 (1985); Gray et al., *Proc. R. Acad. Soc. Lond.*, 243:241–253 (1991); Moore et al., *Genomics*, 10:654–660 (1991); Jeffreys et al., *Anim. Genet.*, 18:1–15 (1987); Hillel et al., *Anim. Genet.*, 20:145–155 (1989); Hillel et al., *Genet.*, 124:783–789 (1990)).

The detection of polymorphic sites in a sample of DNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis or other means.

In an alternative embodiment, such polymorphisms can be detected through the use of a marker nucleic acid molecule that is physically linked to such polymorphism(s). For this purpose, marker nucleic acid molecules comprising a nucleotide sequence of a polynucleotide located within 1 mb of the polymorphism(s) and more preferably within 100 kb of the polymorphism(s) and most preferably within 10 kb of the polymorphism(s) can be employed.

The identification of a polymorphism can be determined in a variety of ways. By correlating the presence or absence of it in a plant with the presence or absence of a phenotype, it is possible to predict the phenotype of that plant. If a polymorphism creates or destroys a restriction endonuclease cleavage site, or if it results in the loss or insertion of DNA (e.g., a VNTR polymorphism), it will alter the size or profile of the DNA fragments that are generated by digestion with that restriction endonuclease. As such, organisms that possess a variant sequence can be distinguished from those having the original sequence by restriction fragment analysis. Polymorphisms that can be identified in this manner are termed "restriction fragment length polymorphisms" (RFLPs) (Glassberg, UK Patent Application 2135774; Skolnick et al., *Cytogen. Cell Genet.,* 32:58–67 (1982); Botstein et al., *Ann. J. Hum. Genet.,* 32:314–331 (1980); Fischer et al., PCT Application WO 90/13668; Uhlen, PCT Application WO 90/11369).

Polymorphisms can also be identified by Single Strand Conformation Polymorphism (SSCP) analysis (Elles, *Methods in Molecular Medicine: Molecular Diagnosis of Genetic Diseases,* Humana Press (1996)); Orita et al., *Genomics,* 5:874–879 (1989)). A number of protocols have been described for SSCP including, but not limited to, Lee et al., *Anal. Biochem.,* 205:289–293 (1992); Suzuki et al., *Anal. Biochem.,* 192:82–84 (1991); Lo et al., *Nucleic Acids Research,* 20:1005–1009 (1992); Sarkar et al., *Genomics,* 13:441–443 (1992). It is understood that one or more of the nucleic acids of the present invention, may be utilized as markers or probes to detect polymorphisms by SSCP analysis.

Polymorphisms may also be found using a DNA fingerprinting technique called amplified fragment length polymorphism (AFLP), which is based on the selective PCR amplification of restriction fragments from a total digest of genomic DNA to profile that DNA (Vos et al., *Nucleic Acids Res.,* 23:4407–4414 (1995)). This method allows for the specific co-amplification of high numbers of restriction fragments, which can be visualized by PCR without knowledge of the nucleic acid sequence. It is understood that one or more of the nucleic acids of the present invention may be utilized as markers or probes to detect polymorphisms by AFLP analysis or for fingerprinting RNA.

Polymorphisms may also be found using random amplified polymorphic DNA (RAPD) (Williams et al., *Nucl. Acids Res.,* 18:6531–6535 (1990)) and cleaveable amplified polymorphic sequences (CAPS) (Lyamichev et al., *Science,* 260:778–783 (1993)). It is understood that one or more of the nucleic acid molecules of the present invention, may be utilized as markers or probes to detect polymorphisms by RAPD or CAPS analysis.

Single Nucleotide Polymorphisms (SNPs) generally occur at greater frequency than other polymorphic markers and are spaced with a greater uniformity throughout a genome than other reported forms of polymorphism. The greater frequency and uniformity of SNPs means that there is greater probability that such a polymorphism will be found near or in a genetic locus of interest than would be the case for other polymorphisms. SNPs are located in protein-coding regions and noncoding regions of a genome. Some of these SNPs may result in defective or variant protein expression (e.g., as a result of mutations or defective splicing). Analysis (genotyping) of characterized SNPs can require only a plus/minus assay rather than a lengthy measurement, permitting easier automation.

SNPs can be characterized using any of a variety of methods. Such methods include the direct or indirect sequencing of the site, the use of restriction enzymes (Botstein et al., *Am. J. Hum. Genet.,* 32:314–331 (1980); Konieczny and Ausubel, *Plant J.,* 4:403–410 (1993)), enzymatic and chemical mismatch assays (Myers et al., *Nature,* 313: 495–498 (1985)), allele-specific PCR (Newton et al., *Nucl. Acids Res.,* 17:2503–2516 (1989); Wu et al., *Proc. Natl. Acad. Sci. (U.S.A.),* 86:2757–2760 (1989)), ligase chain reaction (Barany, *Proc. Natl. Acad. Sci. (U.S.A.),* 88:189–193 (1991)), single-strand conformation polymorphism analysis (Labrune et al., *Am. J. Hum. Genet.,* 48:1115–1120 (1991)), single base primer extension (Kuppuswamy et al., *Proc. Natl. Acad. Sci. (U.S.A.),* 88:1143–1147 (1991), Goelet, U.S. Pat. No. 6,004,744; Goelet, U.S. Pat. No. 5,888,819), solid-phase ELISA-based oligonucleotide ligation assays (Nikiforov et al., *Nucl. Acids Res.,* 22:4167–4175 (1994)), dideoxy fingerprinting (Sarkar et al., *Genomics,* 13:441–443 (1992)), oligonucleotide fluorescence-quenching assays (Livak et al., *PCR Methods Appl.,* 4:357–362 (1995a)), 5'-nuclease allele-specific hybridization TaqMan™ assay (Livak et al., *Nature Genet.,* 9:341–342 (1995)), template-directed dye-terminator incorporation (TDI) assay (Chen and Kwok, *Nucl. Acids Res.,* 25:347–353 (1997)), allele-specific molecular beacon assay (Tyagi et al., *Nature Biotech.,* 16:49–53 (1998)), PinPoint assay (Haff and Smrnimov, *Genome Res.,* 7:378–388 (1997)), dCAPS analysis (Neff et al., *Plant J.,* 14:387–392 (1998)), pyrosequencing (Ronaghi et al., *Analytical Biochemistry,* 267:65–71 (1999); Ronaghi et al., WO 98/13523; Nyren et al., WO 98/28440; www.pyrosequencing.com), using mass spectrometry, e.g. the Masscode™ system (Howbert et al., WO 99/05319; Howbert et al., WO 97/27331; www.rapigene.com; Becker et al., WO 98/26095; Becker et al., WO 98/12355; Becker et al., WO 97/33000; Monforte et al., U.S. Pat. No. 5,965,363), invasive cleavage of oligonucleotide probes (Lyamichev et al., *Nature Biotechnology,* 17:292–296; www.twt.com), and using high density oligonucleotide arrays (Hacia et al., *Nature Genetics,* 22:164–167; www.affymetrix.com).

Polymorphisms may also be detected using allele-specific oligonucleotides (ASO), which, can be for example, used in combination with hybridization based technology including Southern, Northern, and dot blot hybridizations, reverse dot blot hybridizations and hybridizations performed on microarray and related technology.

The stringency of hybridization for polymorphism detection is highly dependent upon a variety of factors, including length of the allele-specific oligonucleotide, sequence composition, degree of complementarity (i.e., presence or absence of base mismatches), concentration of salts and other factors such as formamide and temperature. These factors are important both during the hybridization itself and during subsequent washes performed to remove target polynucleotide that is not specifically hybridized. In practice, the conditions of the final, most stringent wash are most critical. In addition, the amount of target polynucleotide that is able to hybridize to the allele-specific oligonucleotide is also governed by such factors as the concentration of both the ASO and the target polynucleotide, the presence and concentration of factors that act to "tie up" water molecules, so as to effectively concentrate the reagents (e.g., PEG, dextran, dextran sulfate, etc.), whether the nucleic acids are immobilized or in solution, and the duration of hybridization and washing steps.

Hybridizations are preferably performed below the melting temperature ($T_m$) of the ASO. The closer the hybridization and/or washing step is to the $T_m$, the higher the stringency. $T_m$ for an oligonucleotide may be approximated, for example, according to the following formula: $T_m = 81.5 + 16.6 \times (\log 10[Na+]) + 0.41 \times (\% G+C) - 675/n$; where [Na+] is the molar salt concentration of Na+ or any other suitable cation and n=number of bases in the oligonucleotide. Other formulas for approximating $T_m$ are available and are known to those of ordinary skill in the art.

Stringency is preferably adjusted so as to allow a given ASO to differentially hybridize to a target polynucleotide of the correct allele and a target polynucleotide of the incorrect allele. Preferably, there will be at least a two-fold differential between the signal produced by the ASO hybridizing to a target polynucleotide of the correct allele and the level of the signal produced by the ASO cross-hybridizing to a target polynucleotide of the incorrect allele (e.g., an ASO specific for a mutant allele cross-hybridizing to a wild-type allele). In more preferred embodiments of the present invention, there is at least a five-fold signal differential. In highly preferred embodiments of the present invention, there is at least an order of magnitude signal differential between the ASO hybridizing to a target polynucleotide of the correct allele and the level of the signal produced by the ASO cross-hybridizing to a target polynucleotide of the incorrect allele.

While certain methods for detecting polymorphisms are described herein, other detection methodologies may be utilized. For example, additional methodologies are known and set forth, in Birren et al., *Genome Analysis*, 4:135–186; *A Laboratory Manual. Mapping Genomes*, Cold Spring Harbor Laboratory Press, Cold Spring Harbor, N.Y. (1999); Maliga et al., *Methods in Plant Molecular Biology. A Laboratory Course Manual*, Cold Spring Harbor Laboratory Press, Cold Spring Harbor, N.Y. (1995); Paterson, *Biotechnology Intelligence Unit: Genome Mapping in Plants*, R. G. Landes Co., Georgetown, Tex., and Academic Press, San Diego, Calif. (1996); *The Corn Handbook*, Freeling and Walbot, (eds.), Springer-Verlag, New York, N.Y. (1994); *Methods in Molecular Medicine: Molecular Diagnosis of Genetic Diseases*, Elles, (ed.), Humana Press, Totowa, N.J. (1996); Clark, (ed.), *Plant Molecular Biology: A Laboratory Manual*, Springer-Verlag, Berlin, Germany (1997).

Factors for marker-assisted selection in a plant breeding program are: (1) the marker(s) should co-segregate or be closely linked with the desired trait; (2) an efficient means of screening large populations for the molecular marker(s) should be available; and (3) the screening technique should have high reproducibility across laboratories and preferably be economical to use and be user-friendly.

The genetic linkage of marker molecules can be established by a gene mapping model such as, without limitation, the flanking marker model reported by Lander and Botstein, *Genetics*, 121:185–199 (1989) and the interval mapping, based on maximum likelihood methods described by Lander and Botstein, *Genetics*, 121:185–199 (1989) and implemented in the software package MAPMAKER/QTL (Lincoln and Lander, *Mapping Genes Controlling Quantitative Traits Using MAPMAKER/QTL*, Whitehead Institute for Biomedical Research, MA (1990). Additional software includes Qgene, Version 2.23 (1996), Department of Plant Breeding and Biometry, 266 Emerson Hall, Cornell University, Ithaca, N.Y. Use of Qgene software is a particularly preferred approach.

A maximum likelihood estimate (MLE) for the presence of a marker is calculated, together with an MLE assuming no QTL effect, to avoid false positives. A $\log_{10}$ of an odds ratio (LOD) is then calculated as: LOD=$\log_{10}$ (MLE for the presence of a QTL/MLE given no linked QTL).

The LOD score essentially indicates how much more likely the data are to have arisen assuming the presence of a QTL than in its absence. The LOD threshold value for avoiding a false positive with a given confidence, say 95%, depends on the number of markers and the length of the genome. Graphs indicating LOD thresholds are set forth in Lander and Botstein, *Genetics*, 121:185–199 (1989) and further described by Arús and Moreno-González, *Plant Breeding*, Hayward et al., (eds.) Chapman & Hall, London, pp. 314–331 (1993).

In a preferred embodiment of the present invention the nucleic acid marker exhibits a LOD score of greater than 2.0, more preferably 2.5, even more preferably greater than 3.0 or 4.0 with the trait or phenotype of interest. In a preferred embodiment, the trait of interest is altered tocopherol levels or compositions or altered tocotrienol levels or compositions.

Additional models can be used. Many modifications and alternative approaches to interval mapping have been reported, including the use of non-parametric methods (Kruglyak and Lander, *Genetics*, 139:1421–1428 (1995)). Multiple regression methods or models can also be used, in which the trait is regressed on a large number of markers (Jansen, *Biometrics in Plant Breeding*, van Oijen and Jansen (eds.), Proceedings of the Ninth Meeting of the Eucarpia Section Biometrics in Plant Breeding, The Netherlands, pp. 116–124 (1994); Weber and Wricke, *Advances in Plant Breeding*, Blackwell, Berlin, 16 (1994)). Procedures combining interval mapping with regression analysis, whereby the phenotype is regressed onto a single putative QTL at a given marker interval and at the same time onto a number of markers that serve as "cofactors", have been reported by Jansen and Stam, *Genetics*, 136:1447–1455 (1994); and Zeng, *Genetics*, 136:1457–1468 (1994). Generally, the use of cofactors reduces the bias and sampling error of the estimated QTL positions (Utz and Melchinger, *Biometrics in Plant Breeding*, van Oijen and Jansen (eds.), Proceedings of the Ninth Meeting of the Eucarpia Section Biometrics in Plant Breeding, The Netherlands, pp. 195–204 (1994), thereby improving the precision and efficiency of QTL mapping (Zeng, *Genetics*, 136:1457–1468 (1994)). These models can be extended to multi-environment experiments to analyze genotype-environment interactions (Jansen et al., *Theo. Appl. Genet.*, 91:33–37 (1995)).

It is understood that one or more of the nucleic acid molecules of the present invention may be used as molecular markers. It is also understood that one or more of the protein molecules of the present invention may be used as molecular markers.

In a preferred embodiment, the polymorphism is present and screened for in a mapping population, e.g. a collection of plants capable of being used with markers such as polymorphic markers to map genetic position of traits. The choice of appropriate mapping population often depends on the type of marker systems employed (Tanksley et al., J. P. Gustafson and R. Appels (eds.). Plenum Press, NY, pp. 157–173 (1988)). Consideration must be given to the source of parents (adapted vs. exotic) used in the mapping population. Chromosome pairing and recombination rates can be severely disturbed (suppressed) in wide crosses (adapted× exotic) and generally yield greatly reduced linkage distances. Wide crosses will usually provide segregating populations with a relatively large number of polymorphisms when compared to progeny in a narrow cross (adapted× adapted).

An $F_2$ population is the first generation of selfing (self-pollinating) after the hybrid seed is produced. Usually a single $F_1$ plant is selfed to generate a population segregating for all the genes in Mendelian (1:2:1) pattern. Maximum genetic information is obtained from a completely classified $F_2$ population using a codominant marker system (Mather, Measurement of Linkage in Heredity: Methuen and Co., (1938)). In the case of dominant markers, progeny tests (e.g., $F_3$, $BCF_2$) are required to identify the heterozygotes, in order to classify the population. However, this procedure is often prohibitive because of the cost and time involved in progeny testing. Progeny testing of $F_2$ individuals is often used in map construction where phenotypes do not consistently reflect genotype (e.g., disease resistance) or where trait expression is controlled by a QTL. Segregation data from progeny test populations (e.g., $F_3$ or $BCF_2$) can be used in map construction. Marker-assisted selection can then be applied to cross progeny based on marker-trait map associations ($F_2$, $F_3$), where linkage groups have not been completely disassociated by recombination events (i.e., maximum disequilibrium).

Recombinant inbred lines (RIL) (genetically related lines; usually >$F_5$, developed from continuously selfing $F_2$ lines towards homozygosity) can be used as a mapping population. Information obtained from dominant markers can be maximized by using RIL because all loci are homozygous or nearly so. Under conditions of tight linkage (i.e., about <10% recombination), dominant and co-dominant markers evaluated in RIL populations provide more information per individual than either marker type in backcross populations (Reiter et al., *Proc. Natl. Acad. Sci.* (*U.S.A.*), 89:1477–1481 (1992)). However, as the distance between markers becomes larger (i.e., loci become more independent), the information in RIL populations decreases dramatically when compared to codominant markers.

Backcross populations e.g., generated from a cross between a successful variety (recurrent parent) and another variety (donor parent) carrying a trait not present in the former) can be utilized as a mapping population. A series of backcrosses to the recurrent parent can be made to recover most of its desirable traits. Thus a population is created consisting of individuals nearly like the recurrent parent but each individual carries varying amounts or mosaic of genomic regions from the donor parent. Backcross populations can be useful for mapping dominant markers if all loci in the recurrent parent are homozygous and the donor and recurrent parent have contrasting polymorphic marker alleles (Reiter et al., *Proc. Natl. Acad. Sci.* (*U.S.A.*), 89:1477–1481 (1992)). Information obtained from backcross populations using either codominant or dominant markers is less than that obtained from $F_2$ populations because one, rather than two, recombinant gamete is sampled per plant. Backcross populations, however, are more informative (at low marker saturation) when compared to RILs as the distance between linked loci increases in RIL populations (i.e., about 0.15% recombination). Increased recombination can be beneficial for resolution of tight linkages, but may be undesirable in the construction of maps with low marker saturation.

Near-isogenic lines (NIL) (created by many backcrosses to produce a collection of individuals that is nearly identical in genetic composition except for the trait or genomic region under interrogation) can be used as a mapping population. In mapping with NILs, only a portion of the polymorphic loci is expected to map to a selected region.

Bulk segregant analysis (BSA) is a method developed for the rapid identification of linkage between markers and traits of interest (Michelmore et al., *Proc. Natl. Acad. Sci.* (*U.S.A.*), 88:9828–9832 (1991)). In BSA, two bulked DNA samples are drawn from a segregating population originating from a single cross. These bulks contain individuals that are identical for a particular trait (resistant or susceptible to particular disease) or genomic region but arbitrary at unlinked regions (i.e., heterozygous). Regions unlinked to the target region will not differ between the bulked samples of many individuals in BSA.

In an aspect of the present invention, one or more of the nucleic molecules of the present invention are used to determine the level (i.e., the concentration of mRNA in a sample, etc.) in a plant (preferably canola, corn, *Brassica campestris*, oilseed rape, rapeseed, soybean, crambe, mustard, castor bean, peanut, sesame, cottonseed, linseed, safflower, oil palm, flax or sunflower) or pattern (i.e., the kinetics of expression, rate of decomposition, stability profile, etc.) of the expression of a protein encoded in part or whole by one or more of the nucleic acid molecule of the present invention (collectively, the "Expression Response" of a cell or tissue).

As used herein, the Expression Response manifested by a cell or tissue is said to be "altered" if it differs from the Expression Response of cells or tissues of plants not exhibiting the phenotype. To determine whether a Expression Response is altered, the Expression Response manifested by the cell or tissue of the plant exhibiting the phenotype is compared with that of a similar cell or tissue sample of a plant not exhibiting the phenotype. As will be appreciated, it is not necessary to re-determine the Expression Response of the cell or tissue sample of plants not exhibiting the phenotype each time such a comparison is made; rather, the Expression Response of a particular plant may be compared with previously obtained values of normal plants. As used herein, the phenotype of the organism is any of one or more characteristics of an organism (e.g., disease resistance, pest tolerance, environmental tolerance such as tolerance to abiotic stress, male sterility, quality improvement or yield etc.). A change in genotype or phenotype may be transient or permanent. Also as used herein, a tissue sample is any sample that comprises more than one cell. In a preferred aspect, a tissue sample comprises cells that share a common characteristic (e.g., Derived from root, seed, flower, leaf, stem or pollen etc.).

In one aspect of the present invention, an evaluation can be conducted to determine whether a particular mRNA molecule is present. One or more of the nucleic acid molecules of the present invention are utilized to detect the presence or quantity of the mRNA species. Such molecules are then incubated with cell or tissue extracts of a plant under conditions sufficient to permit nucleic acid hybridization. The detection of double-stranded probe-mRNA hybrid molecules is indicative of the presence of the mRNA; the amount of such hybrid formed is proportional to the amount of mRNA. Thus, such probes may be used to ascertain the level and extent of the mRNA production in a plant's cells or tissues. Such nucleic acid hybridization may be conducted under quantitative conditions (thereby providing a numerical value of the amount of the mRNA present). Alternatively, the assay may be conducted as a qualitative assay that indicates either that the mRNA is present, or that its level exceeds a user set, predefined value.

A number of methods can be used to compare the expression response between two or more samples of cells or tissue. These methods include hybridization assays, such as northerns, RNAse protection assays, and in situ hybridization. Alternatively, the methods include PCR-type assays. In a preferred method, the expression response is compared by hybridizing nucleic acids from the two or more samples to an array of nucleic acids. The array contains a plurality of suspected sequences known or suspected of being present in the cells or tissue of the samples.

An advantage of in situ hybridization over more conventional techniques for the detection of nucleic acids is that it allows an investigator to determine the precise spatial population (Angerer et al., *Dev. Biol.*, 101:477–484 (1984); Angerer et al., *Dev. Biol.*, 112:157–166 (1985); Dixon et al., *EMBO J.*, 10:1317–1324 (1991)). In situ hybridization may be used to measure the steady-state level of RNA accumulation (Hardin et al., *J. Mol. Biol.*, 202:417–431 (1989)). A number of protocols have been devised for in situ hybridization, each with tissue preparation, hybridization and washing conditions (Meyerowitz, *Plant Mol. Biol. Rep.*, 5:242–250 (1987); Cox and Goldberg, In: *Plant Molecular Biology: A Practical Approach*, Shaw (ed.), pp. 1–35, IRL Press, Oxford (1988); Raikhel et al., *In situ RNA hybridization in plant tissues*, In: *Plant Molecular Biology Manual*, Vol. B9:1–32, Kluwer Academic Publisher, Dordrecht, Belgium (1989)).

In situ hybridization also allows for the localization of proteins within a tissue or cell (Wilkinson, *In Situ Hybridization*, Oxford University Press, Oxford (1992); Langdale, *In Situ Hybridization* In: *The Corn Handbook*, Freeling and Walbot (eds.), pp. 165–179, Springer-Verlag, NY (1994)). It is understood that one or more of the molecules of the present invention, preferably one or more of the nucleic acid molecules or fragments thereof of the present invention or one or more of the antibodies of the present invention may be utilized to detect the level or pattern of a protein or mRNA thereof by in situ hybridization.

Fluorescent in situ hybridization allows the localization of a particular DNA sequence along a chromosome, which is useful, among other uses, for gene mapping, following chromosomes in hybrid lines, or detecting chromosomes with translocations, transversions or deletions. In situ hybridization has been used to identify chromosomes in several plant species (Griffor et al., *Plant Mol. Biol.*, 17:101–109 (1991); Gustafson et al., *Proc. Natl. Acad. Sci. (U.S.A.)*, 87:1899–1902 (1990); Mukai and Gill, *Genome*, 34:448–452 (1991); Schwarzacher and Heslop-Harrison, *Genome*, 34:317–323 (1991); Wang et al., *Jpn. J. Genet.*, 66:313–316 (1991); Parra and Windle, *Nature Genetics*, 5:17–21 (1993)). It is understood that the nucleic acid molecules of the present invention may be used as probes or markers to localize sequences along a chromosome.

Another method to localize the expression of a molecule is tissue printing. Tissue printing provides a way to screen, at the same time on the same membrane many tissue sections from different plants or different developmental stages (Yomo and Taylor, *Planta*, 112:35–43 (1973); Harris and Chrispeels, *Plant Physiol.*, 56:292–299 (1975); Cassab and Varner, *J. Cell. Biol.*, 105:2581–2588 (1987); Spruce et al., *Phytochemistry*, 26:2901–2903 (1987); Barres et al., *Neuron*, 5:527–544 (1990); Reid and Pont-Lezica, *Tissue Printing: Tools for the Study of Anatomy, Histochemistry and Gene Expression*, Academic Press, New York, N.Y. (1992); Reid et al., *Plant Physiol.*, 93:160–165 (1990); Ye et al., *Plant J.*, 1:175–183 (1991)).

One skilled in the art can refer to general reference texts for detailed descriptions of known techniques discussed herein or equivalent techniques. These texts include *Current Protocols in Molecular Biology*, Ausubel et al., (eds.), John Wiley & Sons, NY (1989), and supplements through September (1998), *Molecular Cloning, A Laboratory Manual*, Sambrook et al., 2$^{nd}$ Ed., Cold Spring Harbor Press, Cold Spring Harbor, N.Y. (1989), *Genome Analysis: A Laboratory Manual 1: Analyzing DNA*, Birren et al., Cold Spring Harbor Press, Cold Spring Harbor, N.Y. (1997); *Genome Analysis: A Laboratory Manual 2: Detecting Genes*, Birren et al., Cold Spring Harbor Press, Cold Spring Harbor, N.Y. (1998); *Genome Analysis: A Laboratory Manual 3: Cloning Systems*, Birren et al., Cold Spring Harbor Press, Cold Spring Harbor, N.Y. (1999); *Genome Analysis: A Laboratory Manual 4: Mapping Genomes*, Birren et al., Cold Spring Harbor Press, Cold Spring Harbor, N.Y. (1999); *Plant Molecular Biology: A Laboratory Manual*, Clark, Springer-Verlag, Berlin, (1997); *Methods in Plant Molecular Biology*, Maliga et al., Cold Spring Harbor Press, Cold Spring Harbor, N.Y. (1995). These texts can, of course, also be referred to in making or using any aspect of the present invention. It is understood that any of the agents of the present invention can be substantially purified and/or be biologically active and/or recombinant.

Having now generally described the present invention, the same will be more readily understood through reference to the following examples that are provided by way of illustration, and are not intended to be limiting of the present invention, unless specified.

EXAMPLE 1

Identification of Homogentisate Prenyl Transferase Sequences

This example sets forth methods used to analyze homogentisate prenyl transferase sequences from various sources in order to identify motifs common to homogentisate prenyl transferase that are contained therein.

Homogentisate prenyl transferase sequences from Soy, *Arabidopsis*, Corn and *Cuphea* (partial) are cloned and sequenced from EST sequences found in an EST database. *Synechocystis*, *Nostoc*, and *Anabaena* are obtained from Genbank. These sequences (representing SEQ ID NOs: 1–8) are then aligned with respect to each other using the multiple alignment software ClustalX, which is described by Thompson et al., *Nucleic Acids Research*, 24:4876–4882 (1997). The multiple alignment of the protein sequences is visualized and edited using Genedoc, which is described by Nicholas et al., EMBNEW.NEWS, 4:14 (1997).

Figure 2B:
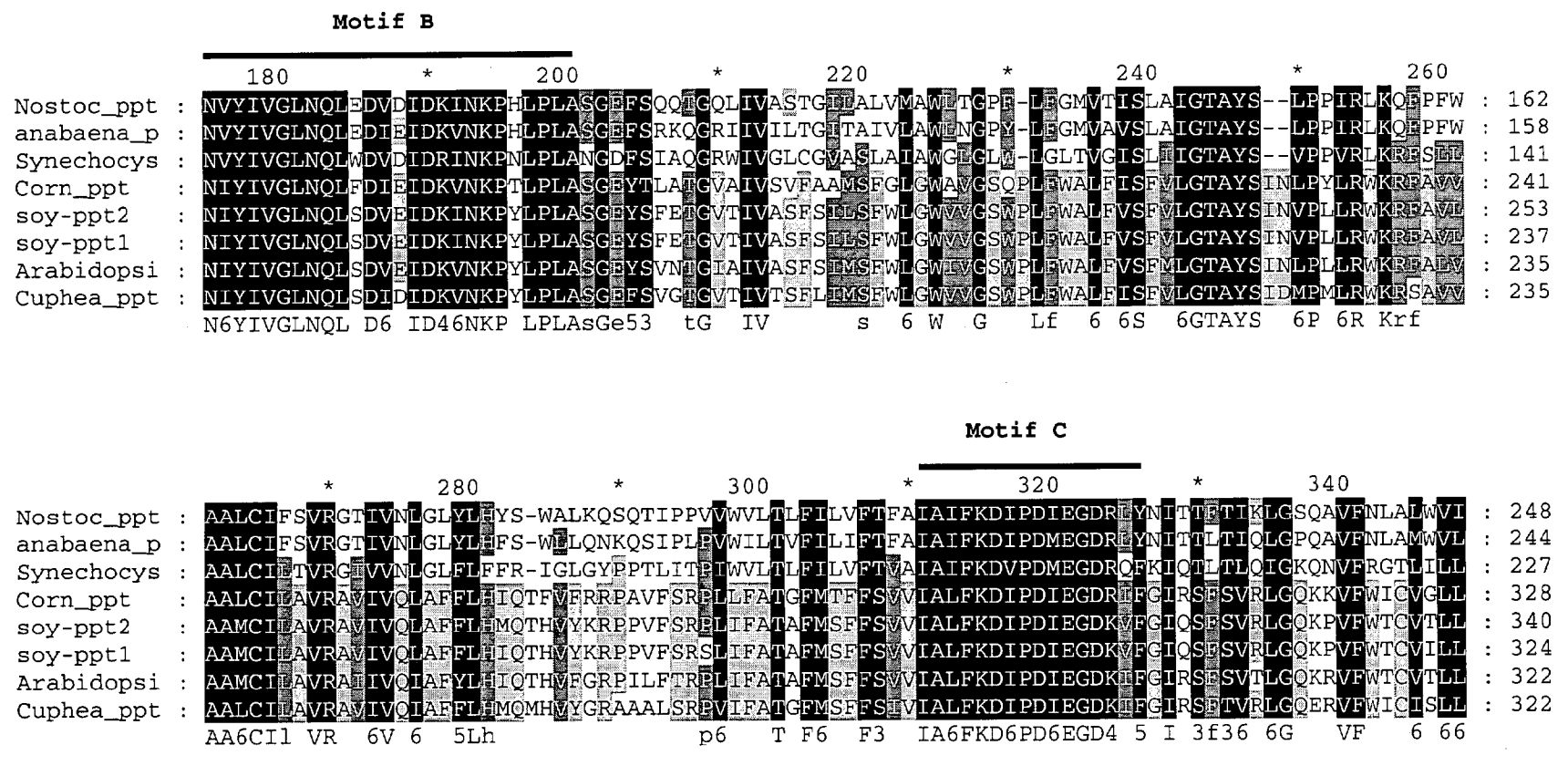

Using the aforementioned multiple alignment tool, four motifs (A–D) are identified, as shown in FIGS. 2a–2c, wherein motifs A–D are set forth. These motifs are represented by SEQ ID NOs: 12–15. The Cuphea sequence is removed from motif D because the sequence had multiple errors towards the 3' end that generated apparent frame shift errors.

Figure 3B:
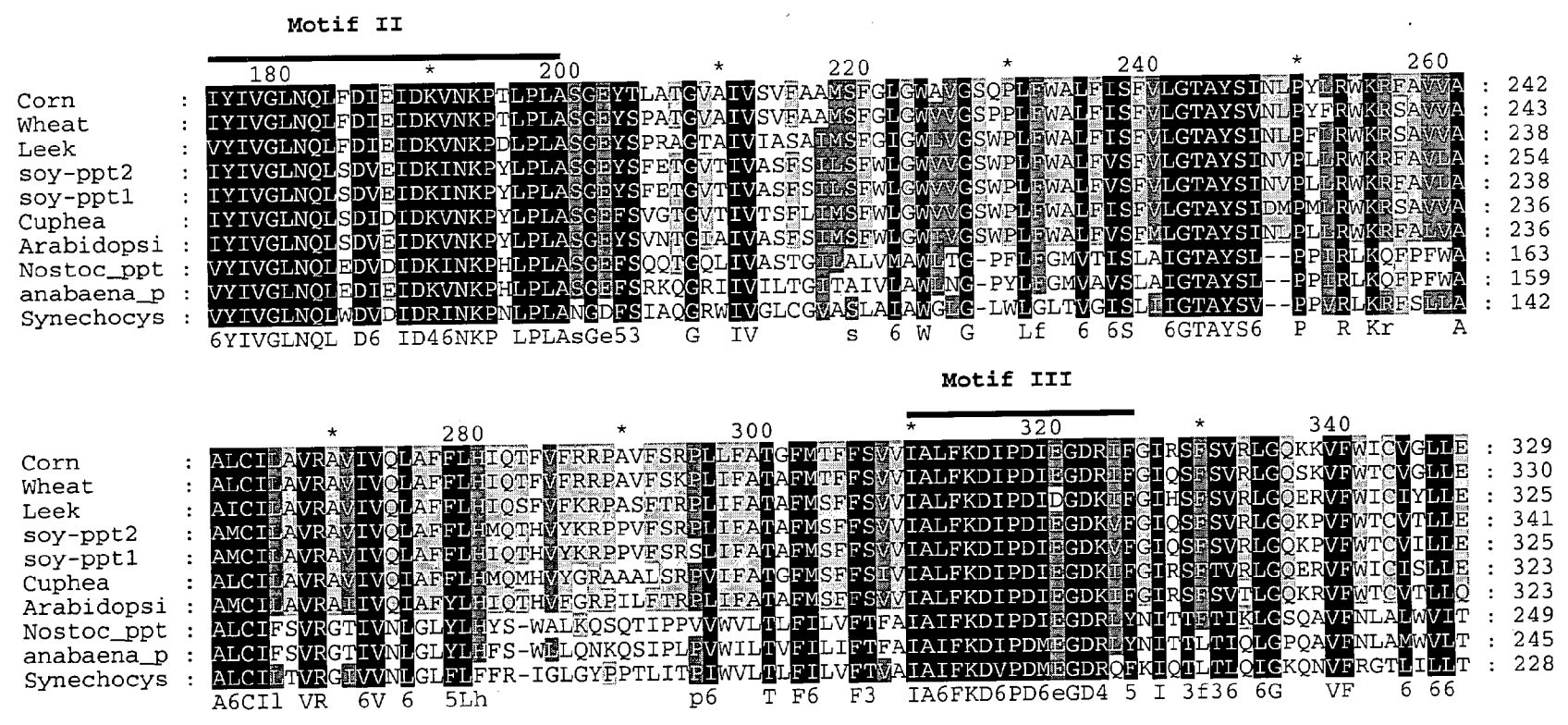
Figure 3C:
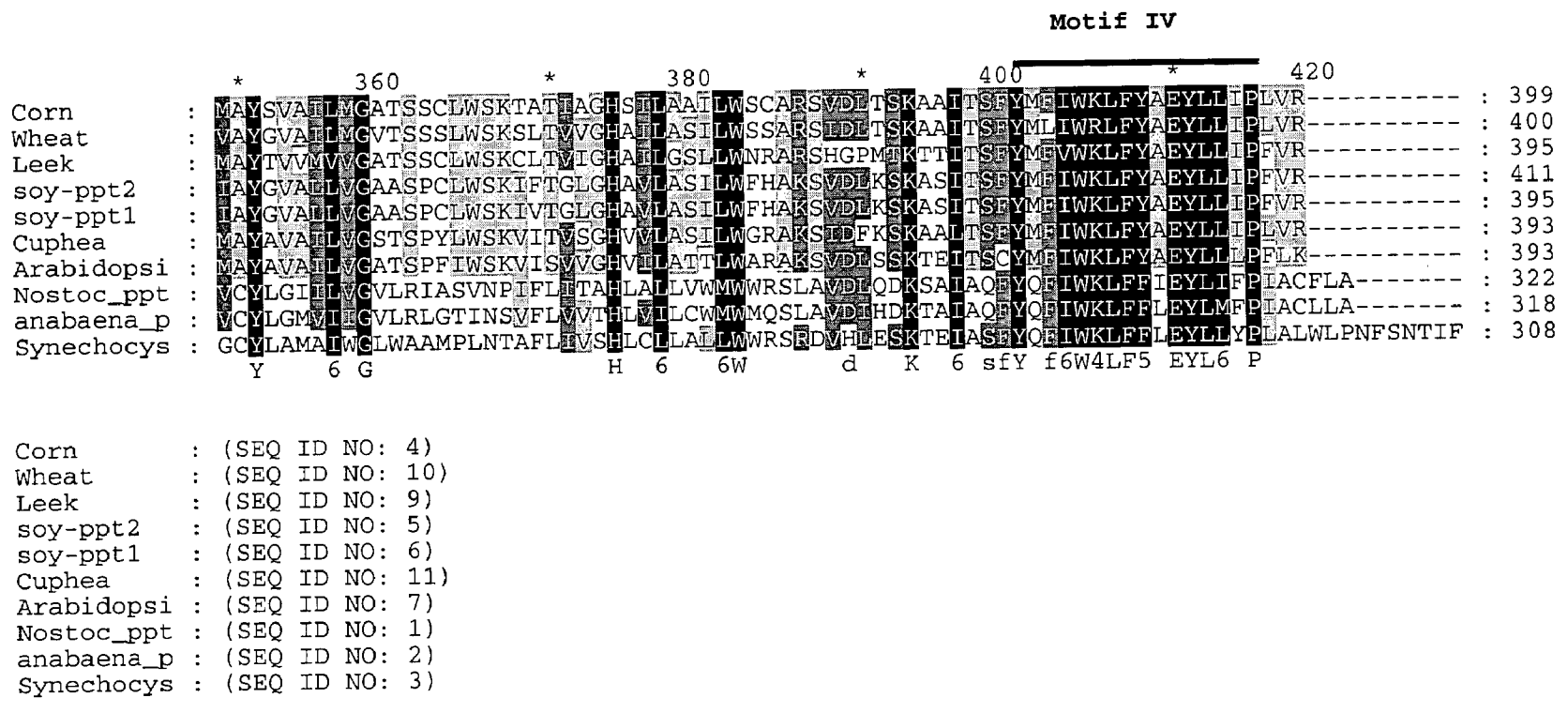

The specificity of these motifs is demonstrated using a Hidden Markov Model (HMM) that is built using an HMMER(version 2.2 g) software package (Eddy, *Bioinformatics*, 14:755–763 (1998)). A HMM search is performed on a cDNA sequence database containing full insert sequence from different plant species. This search identifies two new homogentisate prenyl transferase sequences (SEQ ID NOs: 9–10) in addition to several partial homogentisate prenyl transferase sequences. The two new homogentisate prenyl transferase sequences identified are from leek and wheat. This search also identifies a complete *Cuphea* sequence (SEQ ID NO: 11) with no errors. A second alignment is generated using the aforementioned multiple alignment tool, as shown in FIGS. 3a–3c. This alignment has the leek, wheat, and full *Cuphea* sequences incorporated. Motifs I-IV (SEQ ID NOs: 39–42) are shown.

Specificity is also tested by using each motif sequence to search the non-redundant amino acid database downloaded from Genbank available through NCBI. All four motifs identify three homogentisate prenyl transferase found in the aforementioned non-redundant amino acid database, as follows: *Nostoc*, *Synechocystis*, *Arabidopsis*. Motifs II and IV also identified some genomic variants of an uncharacterized *Arabidopsi*s protein. Motifs I and III only identified known homogentisate prenyl transferase at an E value of 0.001 or lower.

EXAMPLE 2

Preparation of Expression Constructs

A plasmid containing the napin cassette derived from pCGN3223 (described in U.S. Pat. No. 5,639,790, the entirety of which is incorporated herein by reference) is modified to make it more useful for cloning large DNA fragments containing multiple restriction sites, and to allow the cloning of multiple napin fusion genes into plant binary transformation vectors. An adapter comprised of the self annealed oligonucleotide of sequence CGCGATTTAAATG-GCGCGCCCTGCAGGCGGCCGCCTG-CAGGGCGCGCCATTTAAA T (SEQ ID NO: 16) is ligated into the cloning vector pBC SK+ (Stratagene) after digestion with the restriction endonuclease BssHII to construct vector pCGN7765. Plasmids pCGN3223 and pCGN7765 are digested with NotI and ligated together. The resultant vector, pCGN7770, contains the pCGN7765 backbone with the napin seed specific expression cassette from pCGN3223.

The cloning cassette pCGN7787 comprises essentially the same regulatory elements as pCGN7770, with the exception that the napin regulatory regions of pCGN7770 have been replaced with the double CAMV 35S promoter and the polyadenylation and transcriptional termination region.

A binary vector for plant transformation, pCGN5139, is constructed from pCGN1558 (McBride and Summerfelt, *Plant Molecular Biology*, 14:269–276 (1990)). The polylinker of pCGN1558 is replaced as a HindIII/Asp718 fragment with a polylinker containing unique restriction endonuclease sites, AscI, PacI, XbaI, SwaI, BamHI, and NotI. The Asp718 and HindIII restriction endonuclease sites are retained in pCGN5139.

A series of binary vectors are constructed to allow for the rapid cloning of DNA sequences into binary vectors containing transcriptional initiation regions (promoters) and transcriptional termination regions.

The plasmid pCGN8618 is constructed by ligating oligonucleotides 5'-TCGAGGATCCGCGGCCGCAAGCTTC-CTGCAGG-3' (SEQ ID NO: 17) and 5'-TCGACCTGCAG-GAAGCTTGCGGCCGCGGATCC-3' (SEQ ID NO: 18) into SalII/XhoI-digested pCGN7770. A fragment containing the napin promoter, polylinker and napin 3' region is excised from pCGN8618 by digestion with Asp718I; the fragment is blunt-ended by filling in the 5' overhangs with Klenow fragment then ligated into pCGN5139 that is digested with Asp7181 and HindIII and blunt-ended by filling in the 5' overhangs with Klenow fragment. A plasmid containing the insert oriented so that the napin promoter is closest to the blunted Asp718I site of pCGN5139 and the napin 3' is closest to the blunted HindIII site is subjected to sequence analysis to confirm both the insert orientation and the integrity of cloning junctions. The resulting plasmid is designated pCGN8622.

The plasmid pCGN8619 is constructed by ligating oligonucleotides 5'-TCGACCTGCAGGAAGCTTGCGGC-CGCGGATCC-3' (SEQ ID NO: 19) and 5'-TCGAGGATC-CGCGGCCGCAAGCTTCCTGCAGG-3' (SEQ ID NO: 20) into SalI/XhoI-digested pCGN7770. A fragment containing the napin promoter, polylinker and napin 3' region is removed from pCGN8619 by digestion with Asp718I; the fragment is blunt-ended by filling in the 5' overhangs with Klenow fragment then ligated into pCGN5139 that is digested with Asp7181 and HindIII and blunt-ended by filling in the 5' overhangs with Klenow fragment. A plasmid containing the insert oriented so that the napin promoter is closest to the blunted Asp7181 site of pCGN5139 and the napin 3' is closest to the blunted HindIII site is subjected to sequence analysis to confirm both the insert orientation and the integrity of cloning junctions. The resulting plasmid is designated pCGN8623.

The plasmid pCGNS620 is constructed by ligating oligonucleotides 5'-TCGAGGATCCGCGGCCGCAAGCTTC-CTGCAGGAGCT-3' (SEQ ID NO: 21) and 5'-CCTGCAG-GAAGCTTGCGGCCGCGGATCC-3' (SEQ ID NO: 22) into SalI/SacI-digested pCGN7787. A fragment containing the d35S promoter, polylinker and trial 3' region is removed from pCGN8620 by complete digestion with Asp718I and partial digestion with NotI. The fragment is blunt-ended by filling in the 5' overhangs with Klenow fragment then ligated into pCGN5139 that is digested with Asp718I and HindIII and blunt-ended by filling in the 5' overhangs with Klenow fragment. A plasmid containing the insert oriented so that the d35S promoter is closest to the blunted Asp718I site of pCGN5139 and the tml 3' is closest to the blunted HindIII site is subjected to sequence analysis to confirm both the insert orientation and the integrity of cloning junctions. The resulting plasmid is designated pCGN8624.

The plasmid pCGN8621 is constructed by ligating oligonucleotides 5'-TCGACCTGCAGGAAGCTTGCGGC-CGCGGATCCAGCT-3' (SEQ ID NO: 23) and 5'-GGATC-CGCGGCCGCAAGCTTCCTGCAGG-3' (SEQ ID NO: 24) into SalI/SacI-digested pCGN7787. A fragment containing the d35S promoter, polylinker and tml 3' region is removed from pCGN8621 by complete digestion with Asp718I and partial digestion with NotI.

The fragment is blunt-ended by filling in the 5' overhangs with Klenow fragment then ligated into pCGN5139 that had been digested with Asp718I and HindIII and blunt-ended by filling in the 5' overhangs with Klenow fragment. A plasmid containing the insert oriented so that the d35S promoter is closest to the blunted Asp718I site of pCGN5139 and the tml 3' is closest to the blunted HindIII site is subjected to sequence analysis to confirm both the insert orientation and the integrity of cloning junctions. The resulting plasmid is designated pCGN8625.

The plasmid construct pCGN8640 is a modification of pCGN8624 described above. A 938 bp PstI fragment isolated from transposon Tn7 which encodes bacterial spectinomycin and streptomycin resistance (Fling et al., *Nucleic Acids Research*, 13(19):7095–7106 (1985)), a determinant for *E. coli* and Agrobacterium selection, is blunt-ended with Pfu polymerase. The blunt-ended fragment is ligated into pCGN8624 that had been digested with SpeI and blunt-ended with Pfu polymerase. The region containing the PstI fragment is sequenced to confirm both the insert orientation and the integrity of cloning junctions.

The spectinomycin resistance marker is introduced into pCGN8622 and pCGN8623 as follows. A 7.7 Kbp AvrII-SnaBI fragment from pCGN8640 is ligated to a 10.9 Kbp AvrII-SnaBI fragment from pCGN8623 or pCGN8622, described above. The resulting plasmids are pCGN8641 and pCGN8643, respectively.

The plasmid pCGN8644 is constructed by ligating oligonucleotides 5'-GATCACCTGCAGGAAGCTTGCGGC-CGCGGATCCAATGCA-3' (SEQ ID NO: 25) and 5' TTG-GATCCGCGGCCGCAAGCTTCCTGCAGGT-3' (SEQ ID NO: 26) into BamHI-PstI digested pCGN8640.

Synthetic oligonucleotides are designed for use in Polymerase Chain Reactions (PCR) to amplify the coding sequences of each of the nucleic acids that encode the polypeptides of SEQ ID NOs: 1–7, 9–11, 43–44, 57–58, and 90 for the preparation of expression constructs.

The coding sequences of each of the nucleic acids that encode the polypeptides of SEQ ID NOs: 1–7, 9–11, 43–44, 57–58, and 90 are all amplified and cloned into the TopoTA vector (Invitrogen). Constructs containing the respective homogentisate prenyl transferase sequences are digested with NotI and Sse83871 and cloned into the turbobinary vectors described above.

Synthetic oligonucleotides were designed for use in Polymerase Chain Reactions (PCR) to amplify SEQ ID NO: 33 for the preparation of expression constructs and are provided in the table below:

| Restriction Site | Sequence | SEQ ID NO: |
|---|---|---|
| 5' NotI | GGATCCGCGGCCGCACAATGG AGTCTCTGCTCTCTAGTTCT | 37 |
| 3' SseI | GGATCCTGCAGGTCACTTCAAA AAAGGTAACAGCAAGT | 38 |

SEQ ID NO: 33 was amplified using the respective PCR primers shown in the table above and cloned into the TopoTA vector (Invitrogen). Constructs containing the respective homogentisate prenyl transferase sequences were digested with NotI and Sse83871 and cloned into the turbobinary vectors described above.

Figure 4:
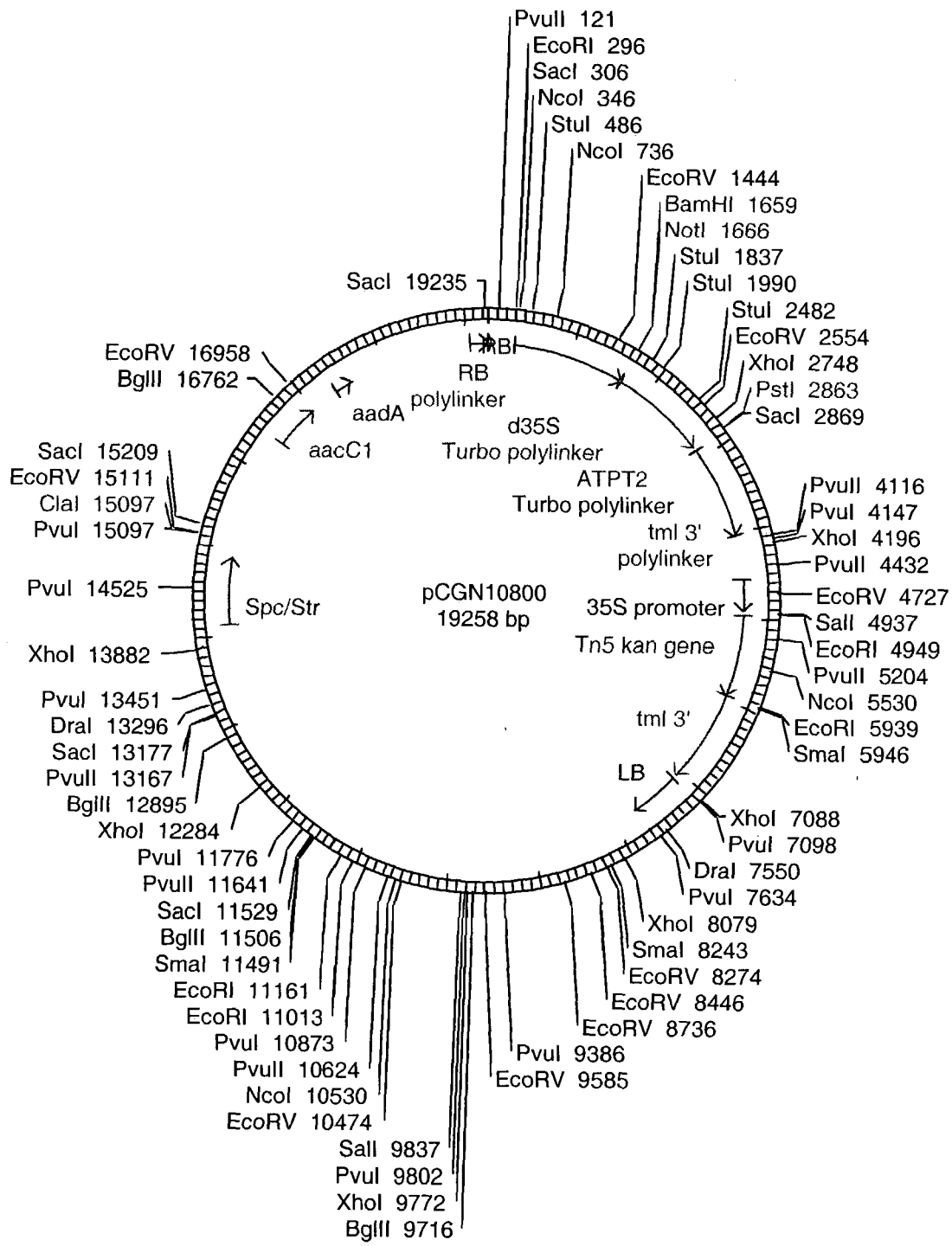
FIG. 4 provides a schematic of the expression construct pCGN10800.

SEQ ID NO: 33 was cloned in the sense orientation into pCGN8640 to produce the plant transformation construct pCGN10800 (FIG. 4). SEQ ID NO: 33 is under control of the enhanced 35S promoter.

Figure 5:
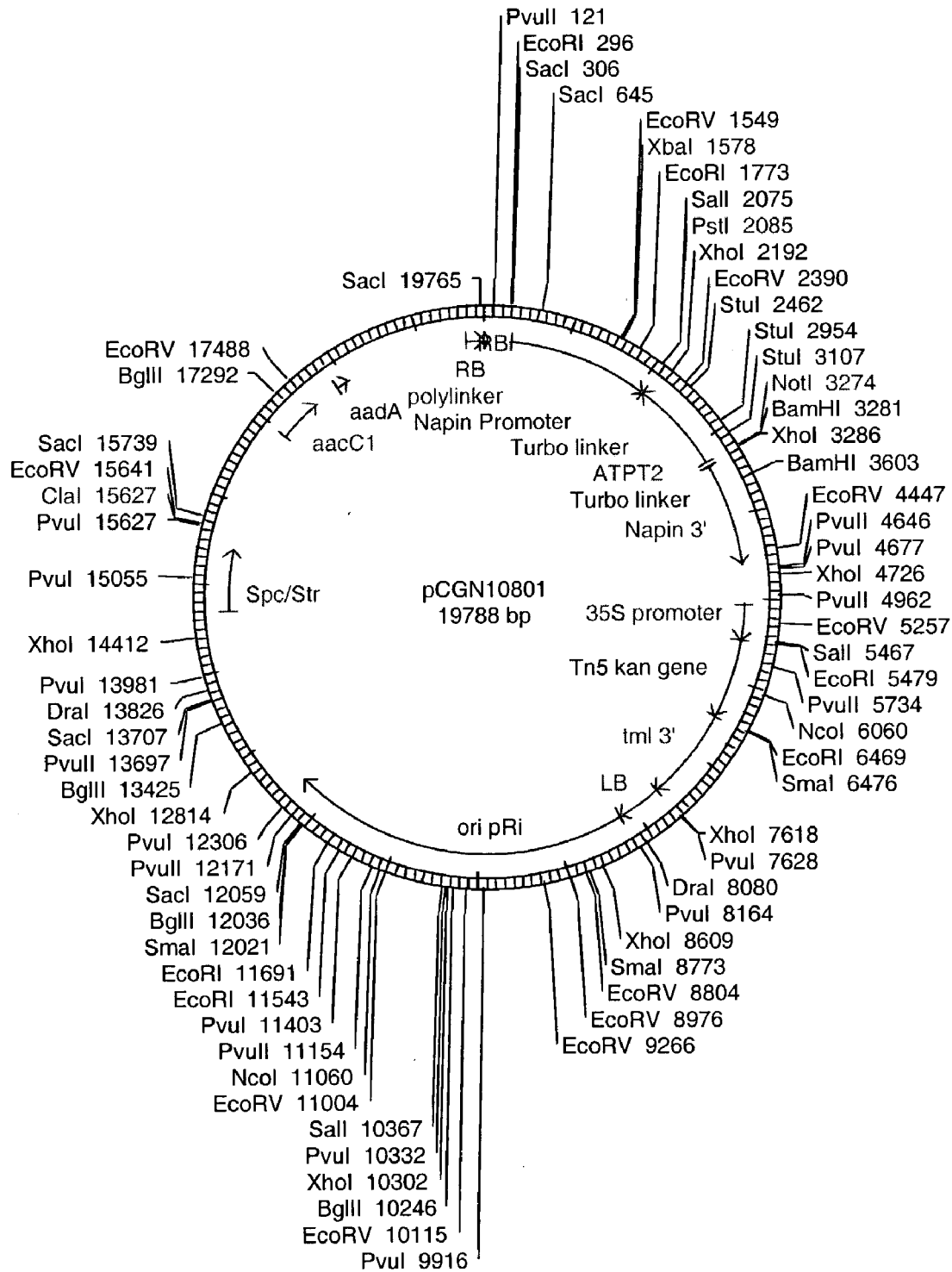
FIG. 5 provides a schematic of the expression construct pCGN10801.

SEQ ID NO: 33 was also cloned in the antisense orientation into the construct pCGN8641 to create pCGN10801 (FIG. 5). This construct provides for the antisense expression of SEQ ID NO: 33 from the napin promoter.

Figure 7:
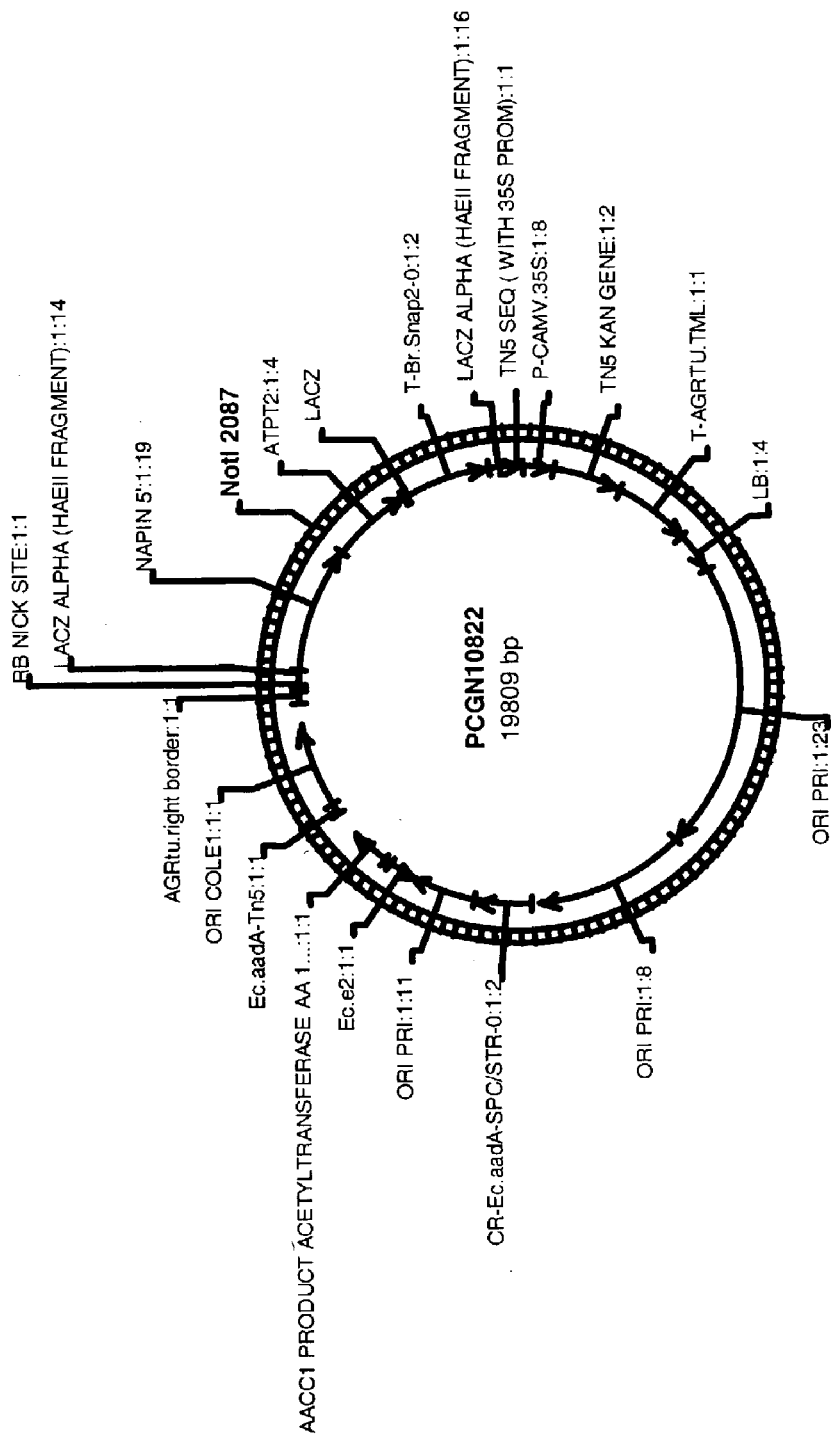
FIG. 7 provides a schematic of the expression construct pCGN10822.

SEQ ID NO: 33 was also cloned in the sense orientation into the vector pCGN8643 to create the plant transformation construct pCGN10822 (FIG. 7). This construct provides for the sense expression of SEQ ID NO: 33 from the napin promoter.

Figure 6:
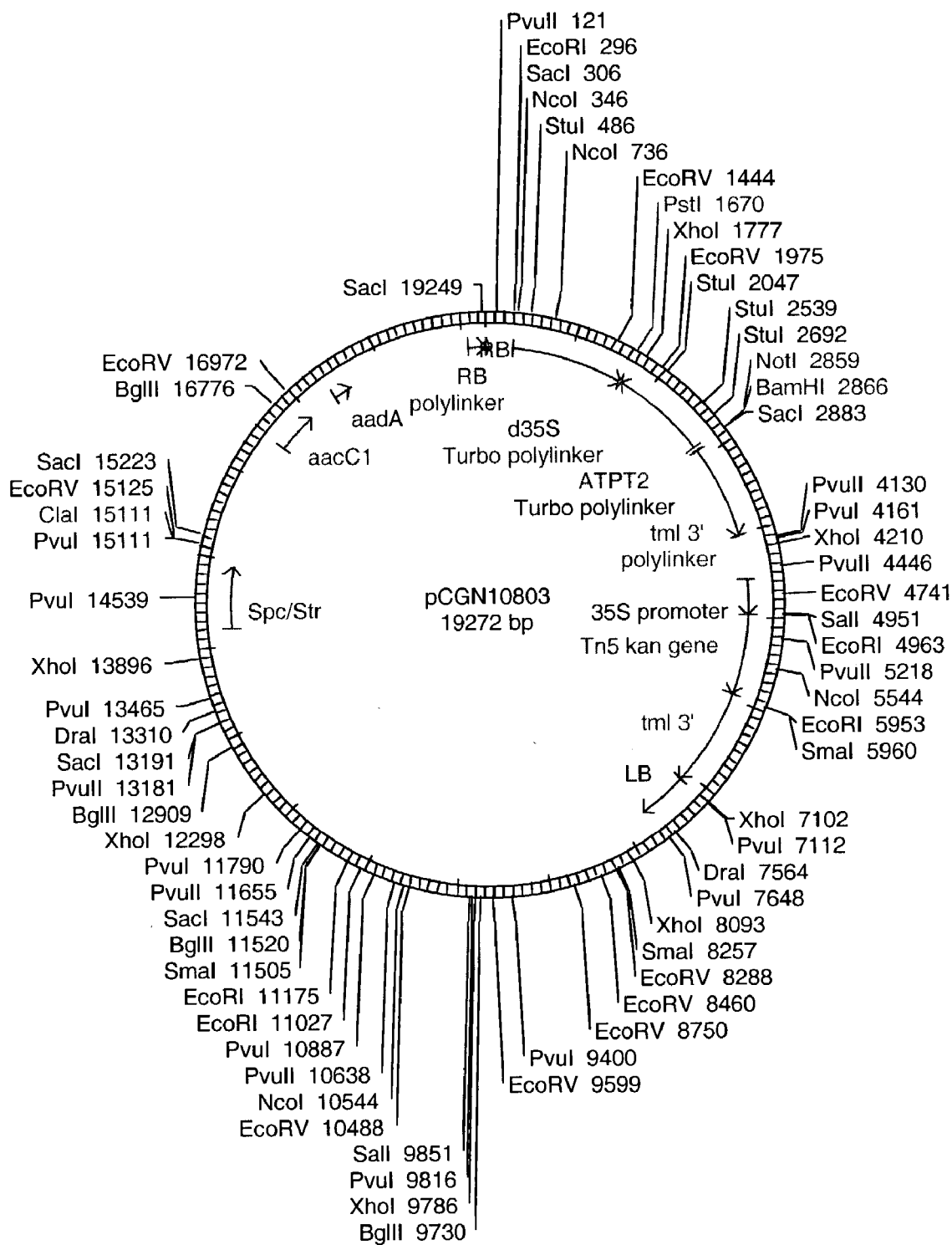
FIG. 6 provides a schematic of the expression construct pCGN10803.

SEQ ID NO: 33 was also cloned in the antisense orientation into the vector pCGN8644 to create the plant transformation construct pCGN10803 (FIG. 6). This construct provides for the antisense expression of SEQ ID NO: 33 from the enhanced 35S promoter.

EXAMPLE 3

Plant Transformation

Transgenic Brassica plants are obtained by *Agrobacterium*-mediated transformation as described by Radke et al., *Theor. Appl. Genet.*, 75:685–694 (1988); *Plant Cell Reports*, 11:499–505 (1992). Transgenic *Arabidopsis thaliana* plants may be obtained by *Agrobacterium*-mediated transformation as described by Valverkens et al., *Proc. Nat. Acad. Sci.*, 85:5536–5540 (1988), or as described by Bent et al., *Science*, 265:1856–1860 (1994), or Bechtold et al., *C.R. Acad. Sci. Life Sciences*, 316:1194–1199 (1993). Other plant species may be similarly transformed using related techniques.

Alternatively, microprojectile bombardment methods, such as described by Klein et al., *Bio/Technology*, 10:286–291 may also be used to obtain nuclear transformed plants.

EXAMPLE 4

Identification of Additional Homogentisate Prenyl Transferase

In order to identify additional homogentisate prenyl transferase, motifs identified through sequence homology are used to search a database of cDNA sequences containing full insert sequences. The cDNA database is first translated in all six frames and then a HMM search is done using a HMM model built for the motifs. All HMM hits are annotated by performing a blast search against a non-redundant amino acid database. All motifs are sensitive and identify homogentisate prenyl transferase sequences present in the database. Novel homogentisate prenyl transferase sequences are thereby discovered.

EXAMPLE 5

Transgenic Plant Analysis

*Arabidopsis* plants transformed with constructs for the sense or antisense expression of the homogentisate prenyl transferase proteins are analyzed by High Performance Liquid Chromatography (HPLC) for altered levels of total tocopherols and tocotrienols, as well as altered levels of specific tocopherols and tocotrienols (e.g. α, β, γ, and δ-tocopherol/tocotrienol).

Extracts of leaves and seeds are prepared for HPLC as follows. For seed extracts, 1-mg of seed is added to 1 g of MICROBEADS (glass beads) (Biospec) in a sterile microfuge tube to which 500 ul 1% pyrogallol (Sigma Chem)/ethanol is added. The mixture is shaken for 3 minutes in a mini Beadbeater (Biospec) on "fast" speed. The extract is filtered through a 0.2 um filter into an autosampler tube. The filtered extracts are then used in HPLC analysis described below.

Leaf extracts are prepared by mixing 30–50 mg of leaf tissue with 1 g microbeads and freezing in liquid nitrogen until extraction. For extraction, 500 ul 1% pyrogallol in ethanol is added to the leaf/bead mixture and shaken for 1 minute on a Beadbeater (Biospec) on "fast" speed. The resulting mixture is centrifuged for 4 minutes at 14,000 rpm and filtered as described above prior to HPLC analysis.

HPLC is performed on a ZORBAX (material used for chromatography) silica HPLC column (4.6 mm×250 mm), using a fluorescent detection monitor, with excitation and emission spectra set at 290 nm and 336 nm, respectively. Solvent A is hexane and solvent B is methyl-t-butyl ether. The injection volume is 20 ul, the flow rate is 1.5 ml/min, the run time is 12 mm (40° C.) using the table below:

| Time | Solvent A | Solvent B |
|---|---|---|
| 0 min. | 90% | 10% |
| 10 min. | 90% | 10% |
| 11 min. | 25% | 75% |
| 12 min. | 90% | 10% |

Tocopherol standards in 1% pyrogallol/ethanol are also run for comparison (alpha tocopherol, gamma tocopherol, beta tocopherol, delta tocopherol, and tocopherol (tocol) (all from Matreya, State College, Pa., or Calbiochem, La Jolla, Calif.)).

Standard curves for alpha, beta, delta, and gamma tocopherol are calculated using CHEMSTATION (software for analyzing chromatography data) software. The absolute amount of component x is: Absolute amount of x=Responses$_x$×RF$_x$×silution factor where Response$_x$ is the area of peak x, RF$_x$, is the response factor for component x (Amount$_x$/Response$_x$) and the dilution factor is 500 ul. The ng/mg tissue is found by: total ng component/mg plant tissue.

Figure 8:
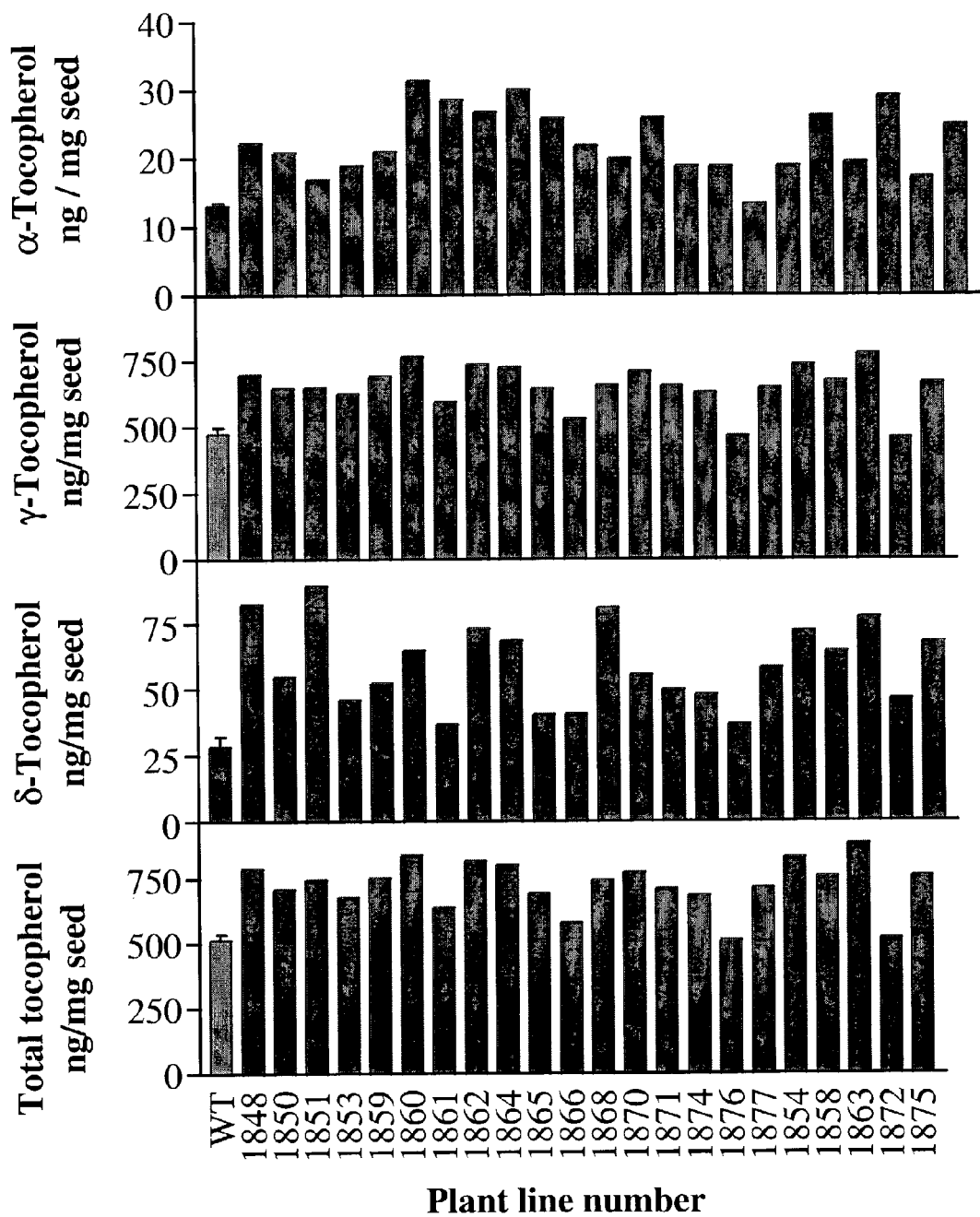
FIG. 8 provides bar graphs of HPLC data obtained from seed extracts of transgenic *Arabidopsis* containing pCGN10822, which provides of the expression of the ATPT2 sequence (SEQ ID NO: 33), in the sense orientation, from the napin promoter. Provided are graphs for α, β, and δ-tocopherols, as well as total tocopherol for 22 transformed lines, as well as a nontransformed (wild-type) control.

Results of the HPLC analysis of seed extracts of transgenic *Arabidopsis* lines containing pMON10822 for the expression of SEQ ID NO: 33 from the napin promoter are provided in FIG. 8.

HPLC analysis results of *Arabidopsis* seed tissue expressing the SEQ ID NO: 33 sequence from the napin promoter (pMON10822) demonstrates an increased level of tocopherols in the seed. Total tocopherol levels are increased as much as 50 to 60% over the total tocopherol levels of non-transformed (wild-type) *Arabidopsis* plants (FIG. 8).

Figure 9:
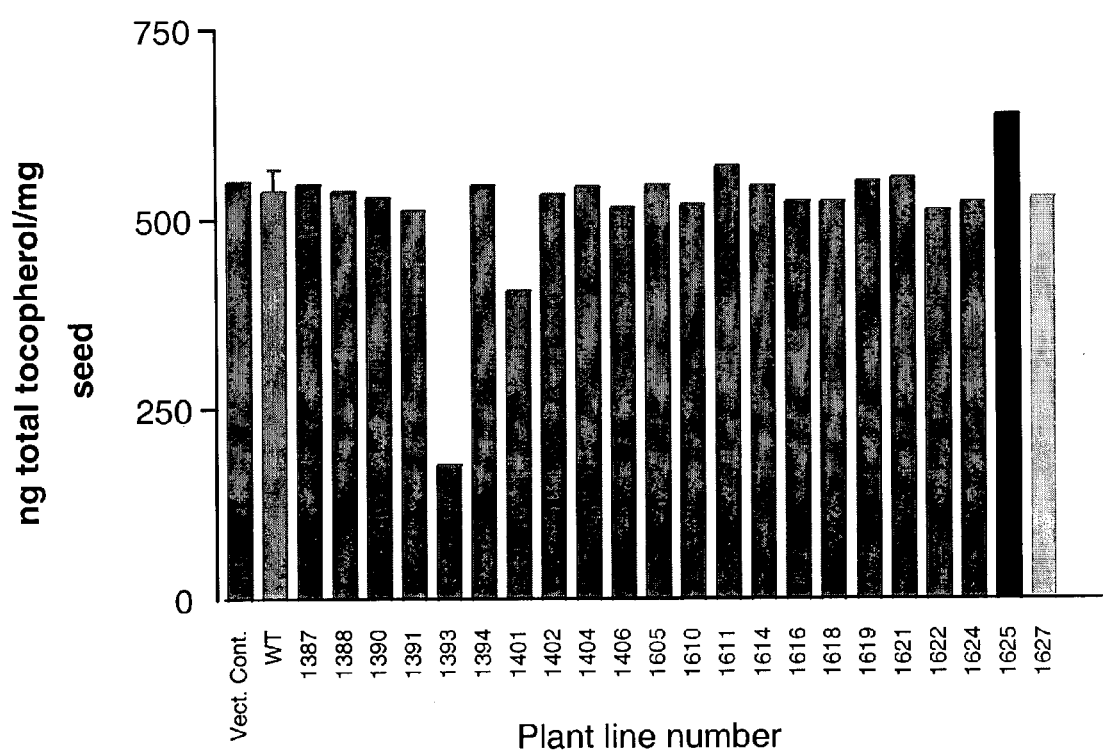
FIG. 9 provides a bar graph of HPLC analysis of seed extracts from *Arabidopsis* plants transformed with a pCGN10803 (lines 1387 through 1624, enhanced 35S-ATPT2, in the antisense orientation), a nontransformed (wt) control, and an empty vector transformed control.

Results of the HPLC analysis of seed extracts of transgenic *Arabidopsis* lines 1387–1624 containing pMON10803 for the antisense expression of SEQ ID NO: 33 from the enhanced 35S promoter are provided in FIG. 9. Two lines, 1393 and 1401, show a substantial reduction in overall tocopherol levels, supporting the position that HPT is a homogentisate prenyl transferase involved in the synthesis of tocopherol.

Results of the HPLC analysis of seed extracts of transgenic *Arabidopsis* lines containing constructs for the expression of SEQ ID NOs: 5, 9–11, 43–44, 57–58, and 90 are obtained.

Results of the HPLC analysis of seed extracts of transgenic *Arabidopsis* lines containing constructsfor the expression of SEQ ID NOs: 5, 9–11, 43–44, 57–58, and 90 from the enhanced 35S promoter are obtained.

EXAMPLE 6

Figure 10:
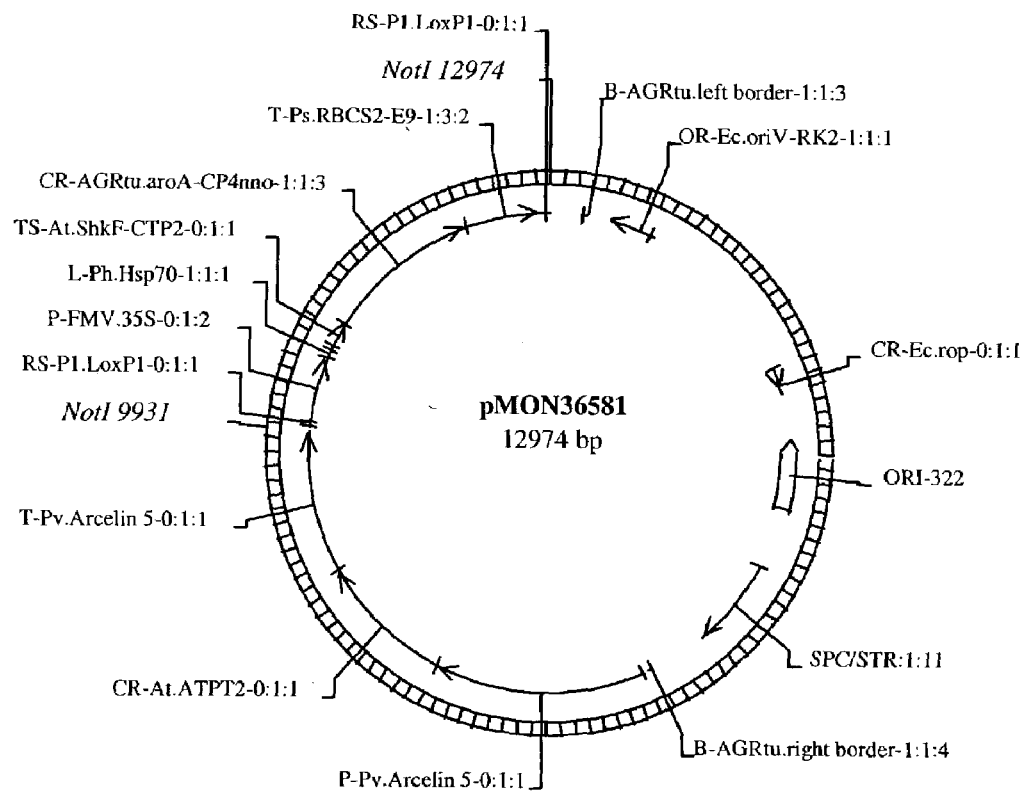
FIG. 10 provides a schematic of the expression construct pMON36581.
Figure 11:
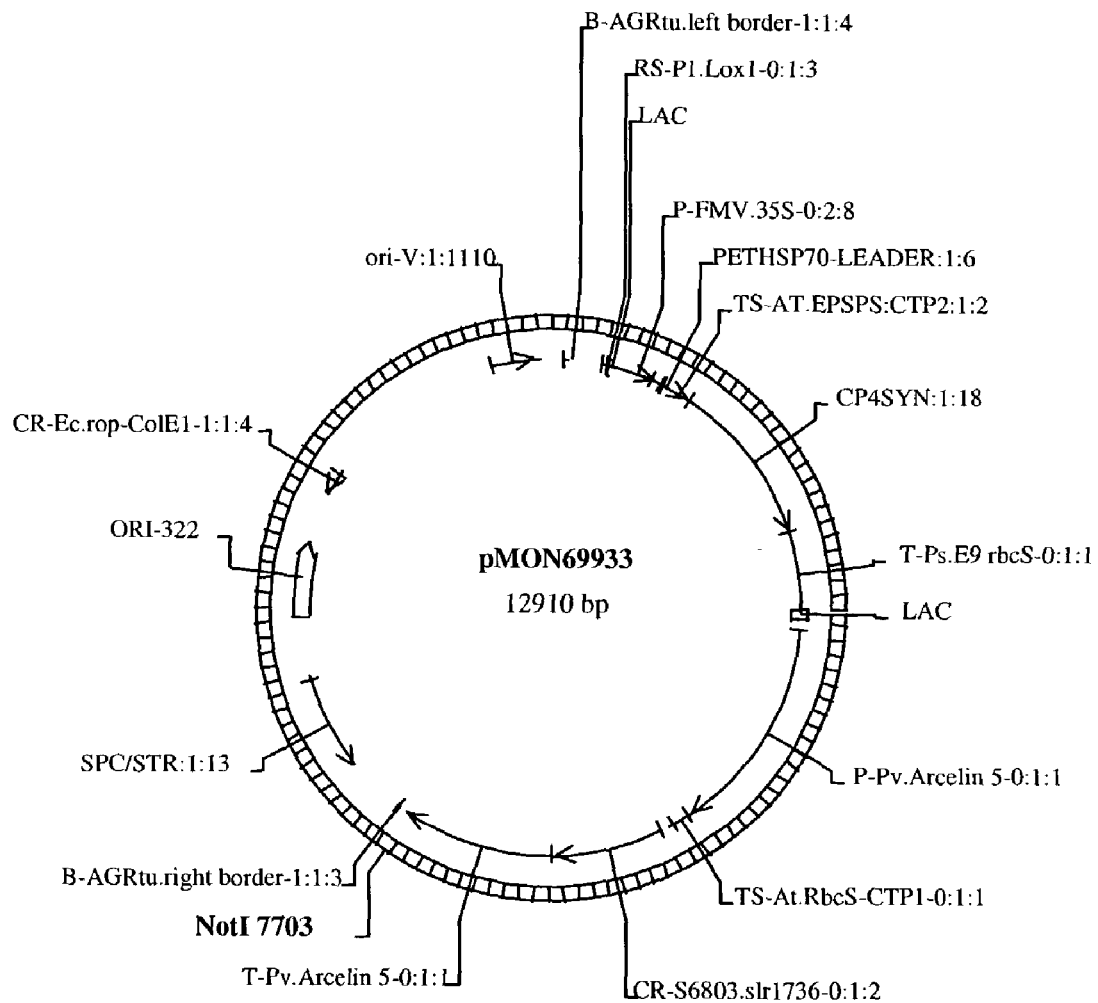
FIG. 11 provides a schematic of the expression construct pMON69933.
Figure 12:
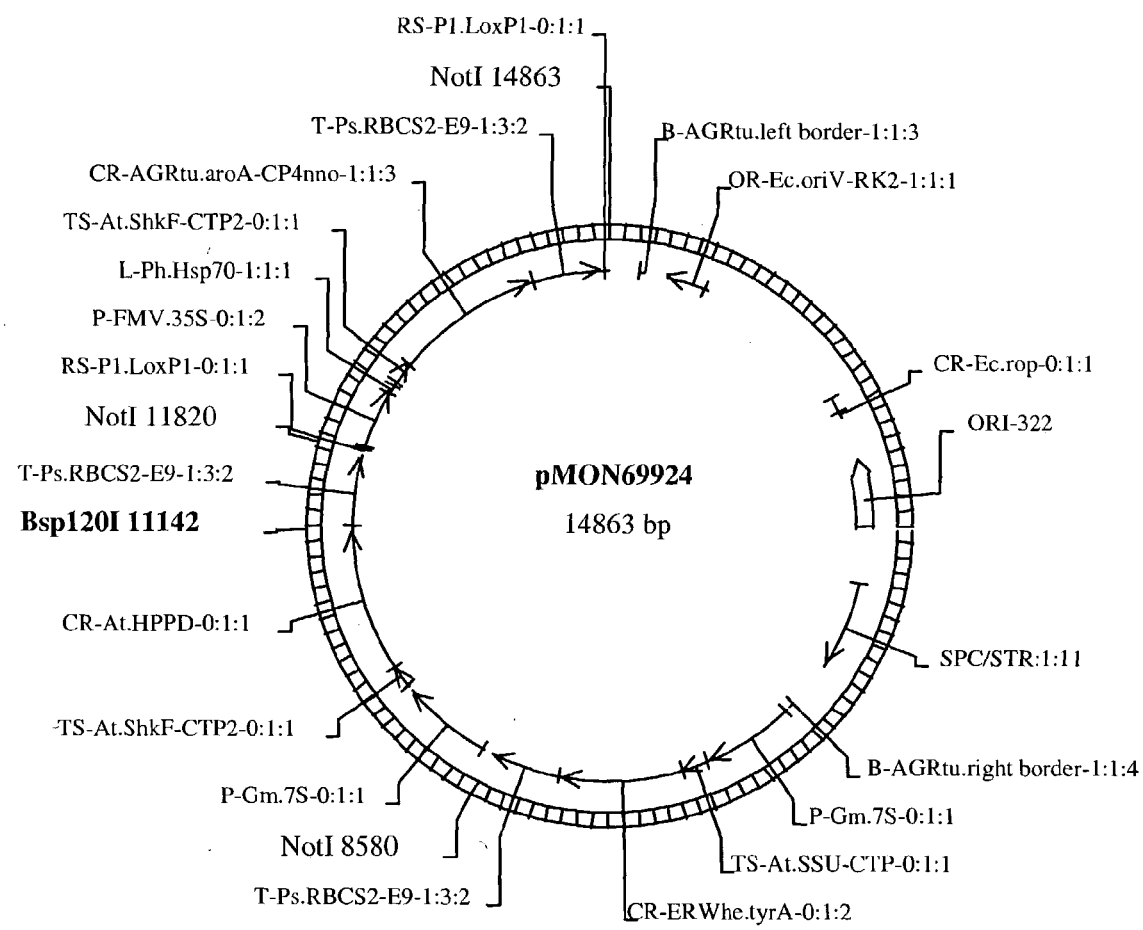
FIG. 12 provides a schematic of the expression construct pMON69924.

Expression of a Homogentisate Prenyl Transferase as Single Gene, and in Combination with HPPD and tyrA in Soy The *Arabidopsis* homogentisate prenyl transferase (ATPT2) (SEQ ID NO: 33) was cloned in a soy binary vector harboring an Arcelin 5 expression cassette. This expression cassette consisted of an Arcelin 5-promoter, a multi cloning site, and the Arcelin 5 3'-untranslated sequence in the order as described. Vector construction for this construct and the following constructs was performed using standard cloning techniques well established in the art and described in lab manuals such as (Sambrook et al. 2001). The resulting binary vector for soy seed-specific expression of ATPT2 was designated pMON36581 (FIG. 10). Similarly the *Synechocystis* homogentisate prenyl transferase (slr1736) (SEQ ID NO: 29) was fused to a chloroplast target peptide (CTP1), and cloned into the Arcelin 5 soy seed-specific expression cassette. The resulting binary plasmid was designated pMON69933 (FIG. 11). An additional binary plasmid for seed-specific co-expression of the *Arabidopsis* p-hydroxyphenylpyruvate dioxygenase (HPPD$_{At}$) and the bifunctional prephenate dehydrogenase from *Erwinia herbicola* (tyrA$_{Eh}$) (see WO 02/089561) was constructed by fusing the HPPD$_{At}$-gene and the tyrA$_{Eh}$-gene to the chloroplast target peptides, CTP2, and CTP1, respectively. These fusion genes were subsequently cloned into the multi cloning site of soy seed-specific expression cassettes consisting of the p7Sα'-promoter, a multi cloning site, and the E9 3'-untranslated region. The HPPD$_{At}$ expression cassette was cloned into a binary vector downstream of the tyrA$_{Eh}$ expression cassette resulting in the formation of pMON69924 (FIG. 12).

Figure 13:
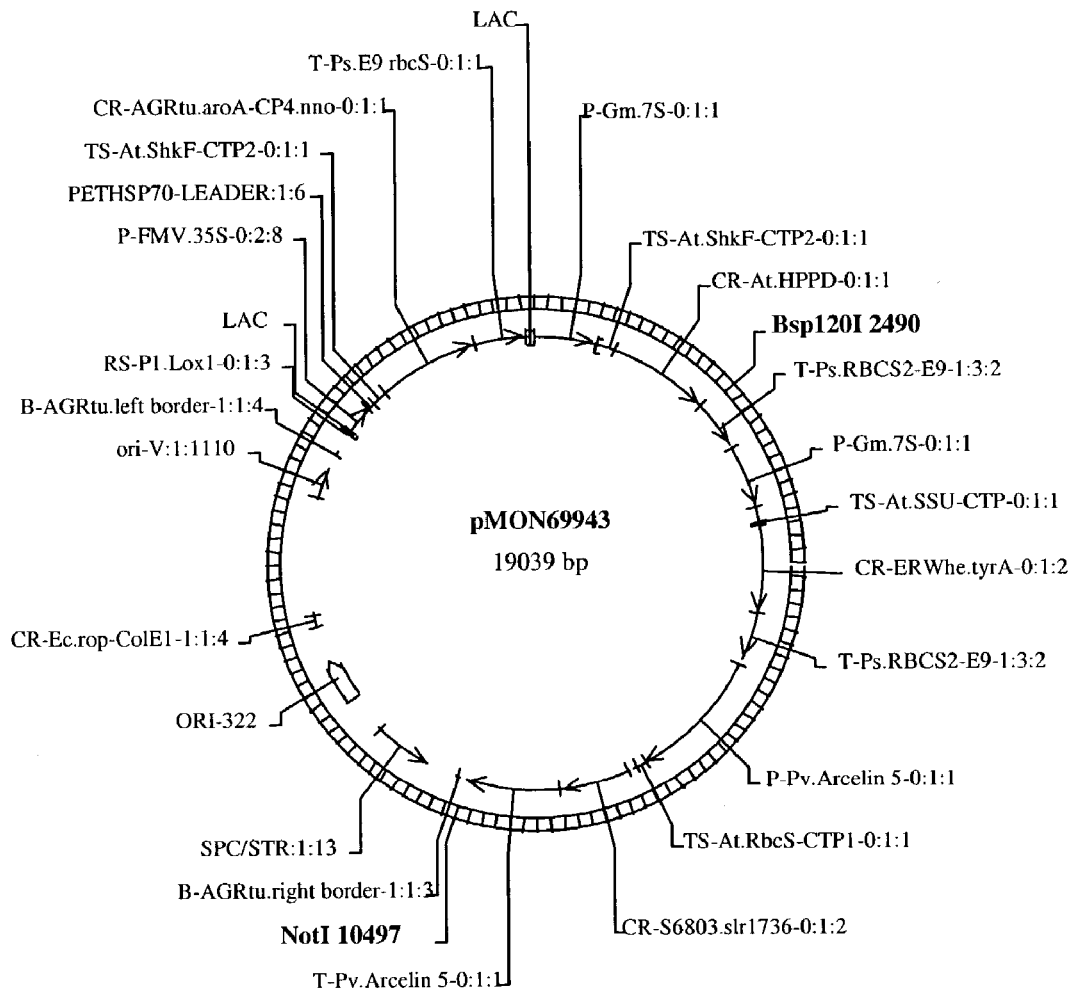
FIG. 13 provides a schematic of the expression construct pMON69943.

A fourth plasmid was constructed by cloning the Arcelin 5-expression cassette for slr1736 (SEQ ID NO: 29), downstream of the HPPD$_{At}$, and the tyrA$_{Eh}$ expression cassettes, resulting in the formation of pMON69943 (FIG. 13).

Figure 14:
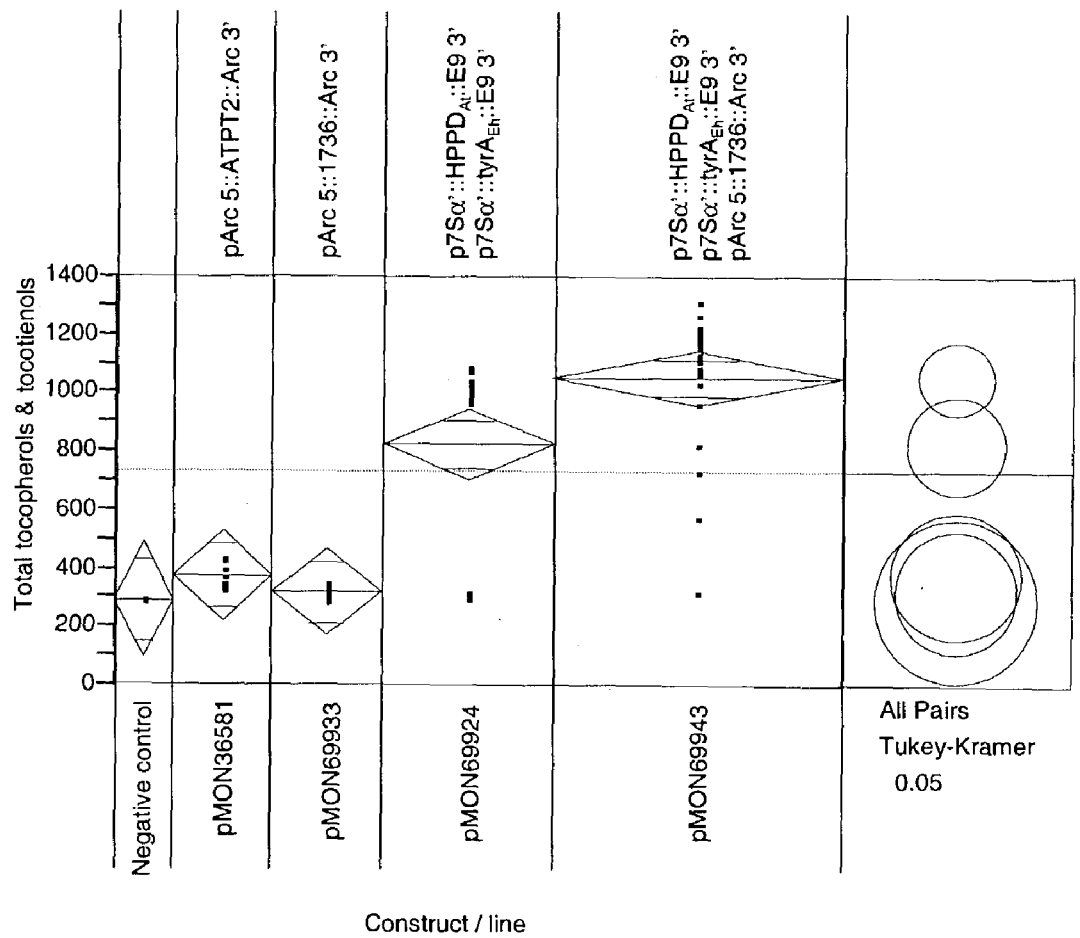
FIG. 14 depicts results of total tocopherol levels in recombinant soy lines.

Each of these binary constructs was transformed into soybean. R1 seed pools from plants harboring these constructs were analyzed for tocopherol content and composition. For constructs pMON36581 and pMON69933, the seed for analysis were chosen at random. Seed from plants transformed with pMON69924 and pMON69943 showed a segregating dark phenotype. This phenotype has been associated with the presence of increased levels of homogentisic acid as a result of the expression of trans genes HPPD and tyrA. Seed without dark coloration did have wild-type tocopherol levels and were not transgenic. For this reason colored seed were chosen for analysis of plants transformed with pMON69924 or pMON69943. For the impact of the HPT expression on total tocopherol accumulation in a single gene vector, or in a multi gene vector, seed from non-transformed soy, or seed transformed with pMON69924 served as controls, respectively. FIG. 14 summarizes the tocopherol data obtained from these experiments. While expression of ATPT2 or slr1736 increased total tocopherol and tocotrienol levels in soy moderately, the impact of HPT expression in the context of a multi gene vector was much more pronounced. FIG. 14 demonstrates a significantly increased level of tocopherol and tocotrienol accumulation for pMON69943 compared to pMON69924 lines. These data suggest that combination of an HPT with tyrA, and HPPD can substantially enhance tocopherol biosynthesis in soy.

Western analysis is carried out to detect the transgene expression in tissues harboring the gene of interest (GOI) expression cassette using the GOI protein specific antibody. Northern analysis is done for detecting the mRNA level of the transgene using the GOI sequence specific radiolabelled probe.

EXAMPLE 7

Identification of Additional Homogentisate Prenyl Transferase Sequences

In an analysis of the non-redundant amino acid database, Motifs II and IV (SEQ ID NOs: 40 and 42 identified in addition to HPT sequences, two genomic variants of *Arabidopsis thaliana* sequence related to HPTs (SEQ ID NOs: 61–62). These sequences are based on insillico prediction from genomic sequence by gene prediction algorithms. Further bioinformatic analysis showed that these sequences encoded an additional homogentisate prenyl transferase related to HPT. Both sequences (SEQ ID NOs: 61–62) were used to search the non-redundant amino acid database. The BLAST search results indicated that these sequences are related most to HPT sequences from cyanobacteria (SEQ ID NOs: 1–3) and *Arabidopsis* (SEQ ID NO: 7).

Alignment of gi15229898 (970 aa)(SEQ ID NO: 61) and gi10998133 (441 aa) (SEQ ID NO: 62) showed that:

a) C terminal half of gi15229898 (SEQ ID NO: 61) overlaps with gi10998133 (SEQ ID NO: 62);

b) the last 40–50 aa in the C terminal portions of these two proteins do not align; and c) the N terminal of gi 15229898 does not align also with HPTs (SEQ ID NOs: 1–7, and 9–11). These findings indicate discrepancy in the coding sequence prediction reported in Genbank.

In order to verify the predicted sequence, the BAC sequence of the *Arabidopsis* genome corresponding to the region was downloaded from Genbank (gi|12408742|gb|AC016795.6|ATAC016795, 100835 bp). Coding sequences were predicted from this BAC clone using the FGENESH (Solovyev V.V. (2001) Statistical approaches in Eukaryotic gene prediction: in Handbook of Statistical genetics (eds. Balding D. et al.), John Wiley & Sons, Ltd., p. 83–127) gene prediction program. FGENESH predicted 28 proteins from this BAC clone. To identify new homogentisate prenyl transferase proteins among 28 FGENESH predicted proteins, all 28 predicted proteins were blasted against the non-redundant amino acid database. FGENESH predicted protein No. 25 (402aa) (SEQ ID NO: 45) was most similar to gi10998133 (441 aa) (SEQ ID NO: 62), C terminal half of gi15229898 (970 aa) (SEQ ID NO: 61) and HPTs (SEQ ID NOs: 1–7, and 9–11.)

To provide functional and transcriptional evidence and to confirm the coding sequence for this gene, plant EST sequences database comprising proprietary and public sequence was searched. We found several ESTs (SEQ ID NOs: 63–72) which match the N terminal and C terminal portions of this gene. The new gene was named HPT2 (SEQ ID NO: 59) from *Arabidopsis*. The HPT2 (SEQ ID NO: 57) sequence is quite distinct from HPT1 (SEQ ID NO: 7).

HPT2 (SEQ ID NO: 57) from *Arabidopsis* is also known as Tocopherol Synthase (TS). Present data suggests that the overexpression of TS leads to a similar increase in the amount of overall tocopherol, over the wild type, as with HPT1 (SEQ ID NO: 33). However, the enzymes may have different biochemical characteristics because the overexpression of TS results in less production of the delta tocopherol than the overexpression of HPT1 (SEQ ID NO: 33).

The presence of chloroplast transit peptide in the HPT2 *Arabidopsis* sequence (SEQ ID NOs: 45 and 57) was verified using ChloroP program (Olof Emanuelsson1, Henrik Nielsen1, 2, and Gunnar von Heijne1 ChloroP, a neural network-based method for predicting chloroplast transit peptides and their cleavage sites. Protein Science: 8: 978–984, 1999).

Figure 26:
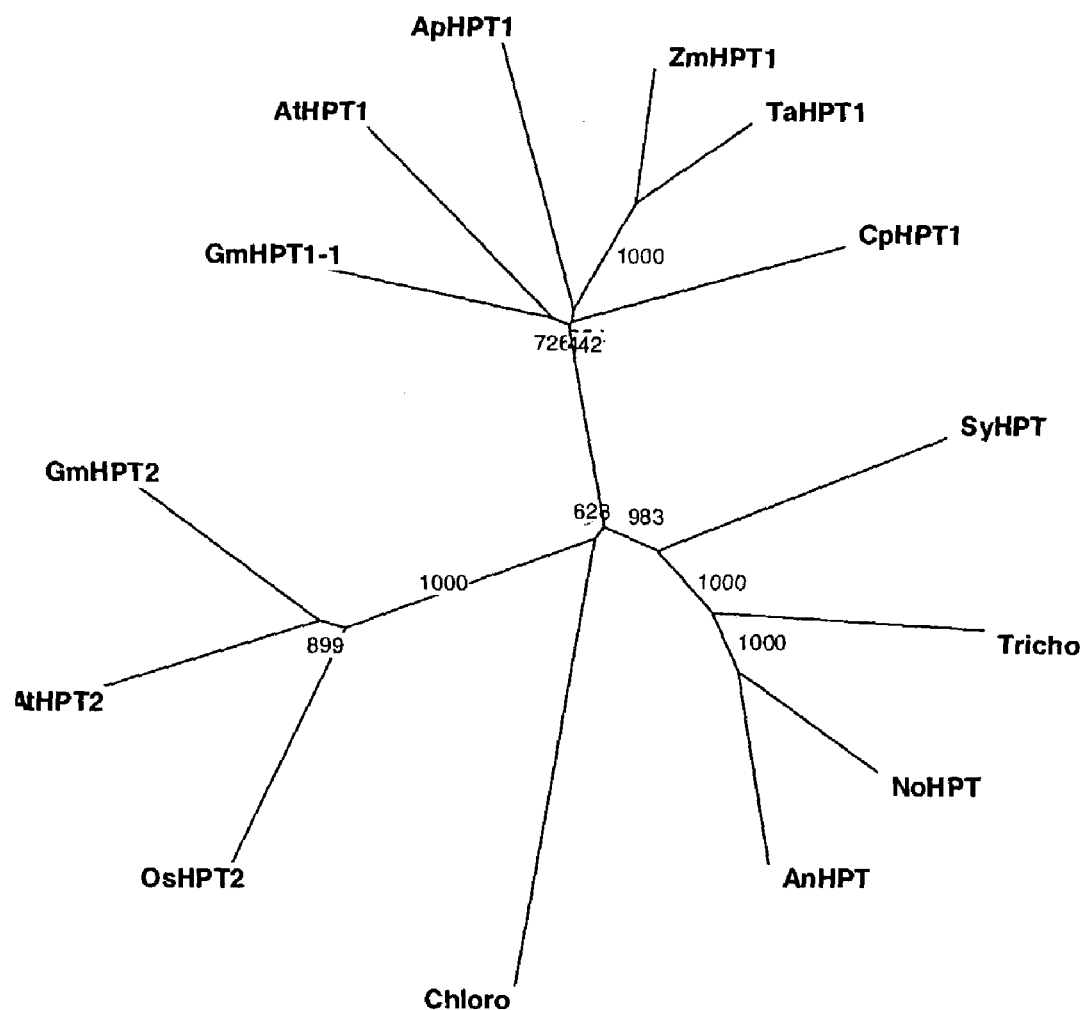
FIG. 26 depicts a sequence tree derived from a multiple alignment shown from SEQ ID NOs: 1–7, 9–11, 43, 44, 57–58, and 90.

In addition to SEQ ID NOs: 1, 7, and 9–11(HPT), SEQ ID NOs: 57–58, and 90 (HPT2) were added to the alignment, see FIGS. 24–25 and the resulting motifs analyzed. Motif V (SEQ ID NO: 46), VII (SEQ ID NO: 48), and vm (SEQ ID NO: 49) are specific to HPT and HPT2 sequences. A HMM search of the non-redundant amino acid database using these motifs identified only cyanobacteria (SEQ ID NOs: 1–3, and 43), photobacteria (SEQ ID NO: 44), and plant HPTs (SEQ ID NOs: 7, and 61–62). Motif VII (SEQ ID NO: 48) identified distantly related ubiA prenyl transerase from bacteria in addtion to homogentisate prenyl transferase. However, the sensitivity of Motif VII to homogentisate prenyl transferase was higher. Homogentisate prenyl transferases had lower e-values by several orders and hihger alignment score (higher than 30). HPT2 sequences are distinct from HPT and cyanobacterial HPTs as demonstrated by the sequence dendogram in FIG. 26.

Figure 33C:
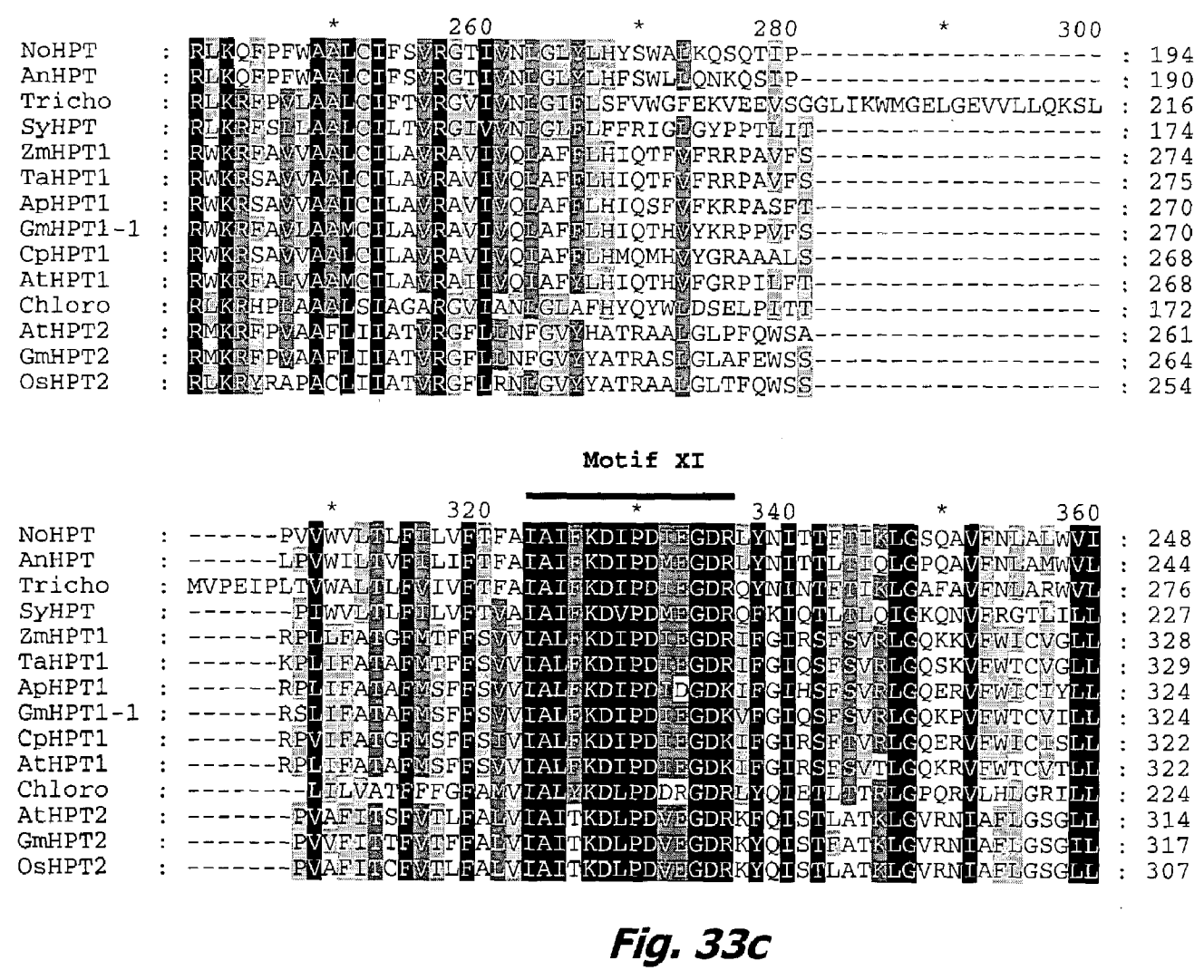
Figure 33D:
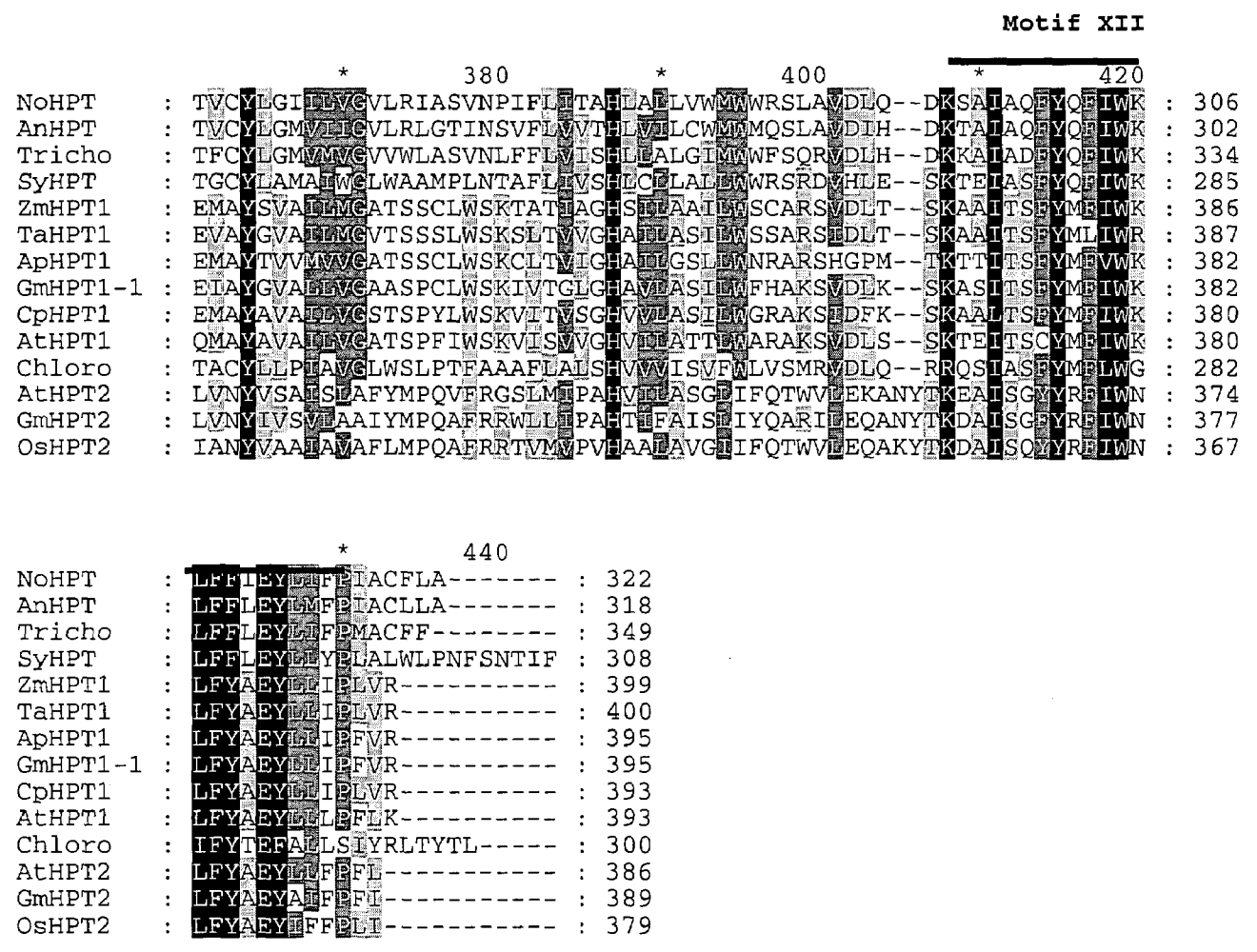

SEQ ID NOs: 43–44 were added to an alignment with SEQ ID NOs: 1–4, 6–7, 9–11, 57–58, and 91, see FIGS. 33–34, and the resulting motifs (SEQ ID NOs: 92–95, Motifs IX–XII) were analyzed. Specificity of these motifs to homogentisate prenyl transferases was confirmed by HMM search. A non redundant database containing more than 1.34M sequence was searched using HMM models built from the alignments shown in FIG. 34 for Motifs IX–XII. E value limits for the search was set at 1.0. All four motifs identified only homogentisate prenyl transferase from cyanobacteria, photobacteria and *Arabidopsis*. Upper E values limits for Motif IX, X, XI, and XII were 0.9, $11E10^{-11}$, 0.03, $8E10^{-8}$ respectively. The small size of motifs resulted in higher E values for Motif IX and XI.

EXAMPLE 8

Transformation and Expression of a Wild Type *Arabidopsis* HPT2 Gene in Sense and Antisense Orientations with Respect to Seed-specific and Constitutive Promoters in *Arabidopsis thialiana*

Figure 15:
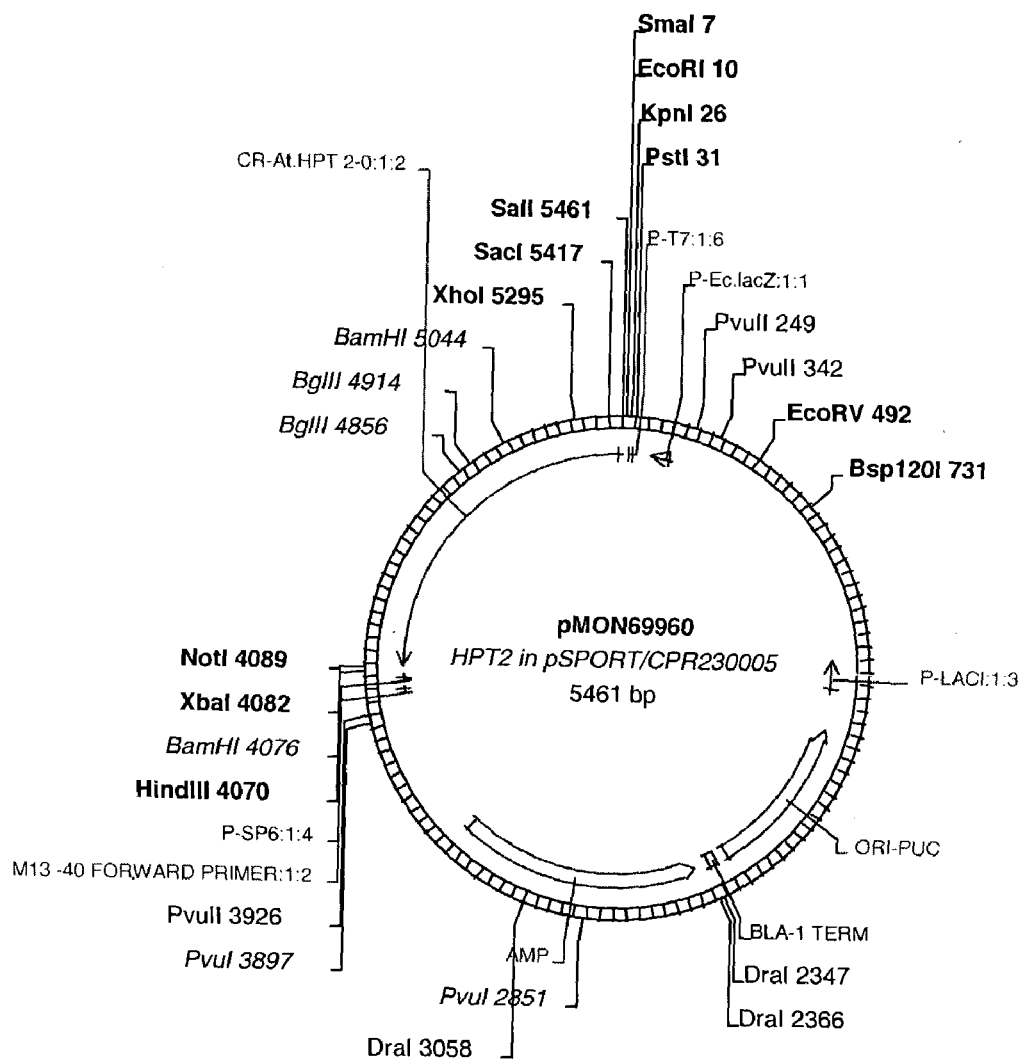
FIG. 15 depicts pMON 69960.
Figure 16:
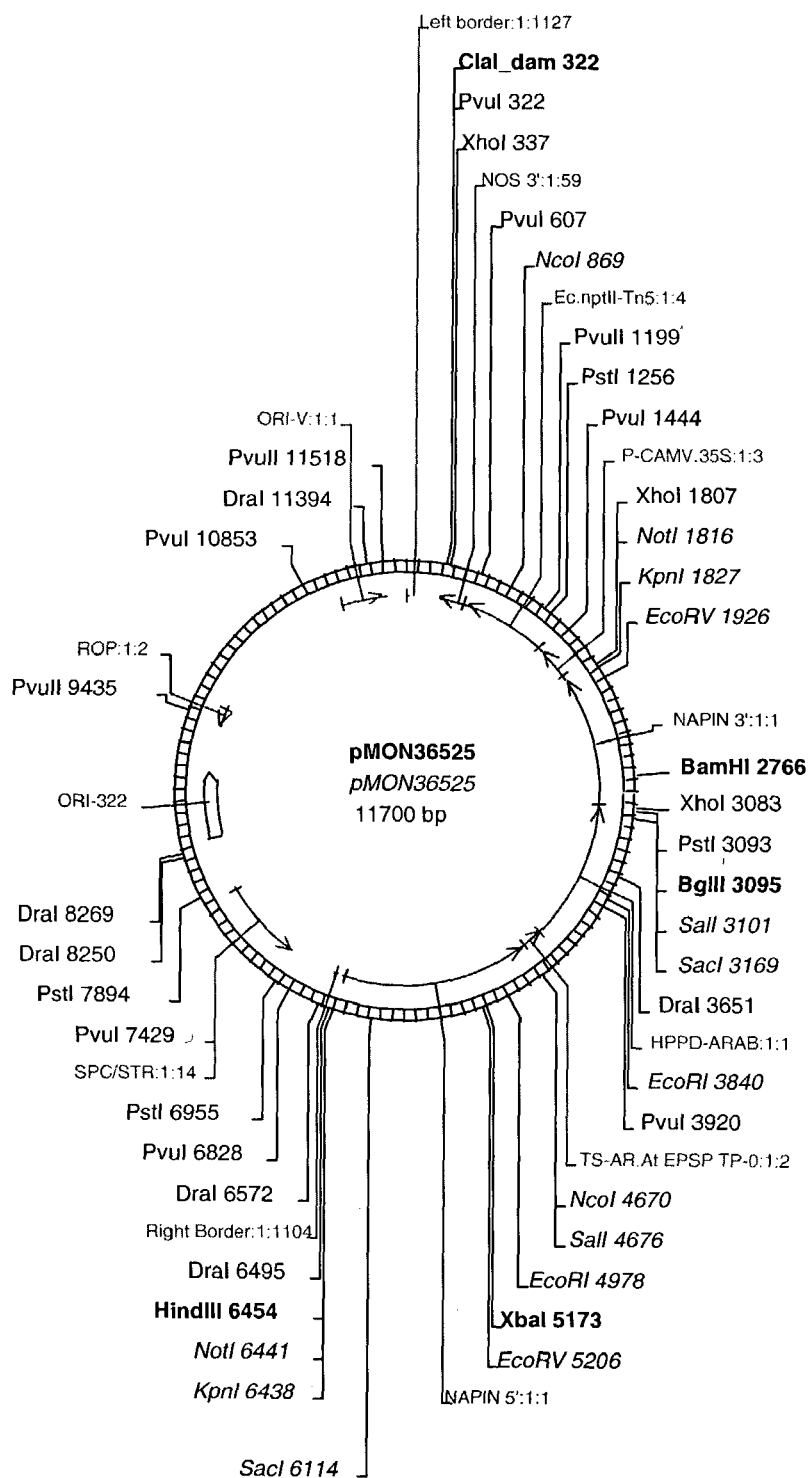
FIG. 16 depicts pMON 36525.
Figure 17:
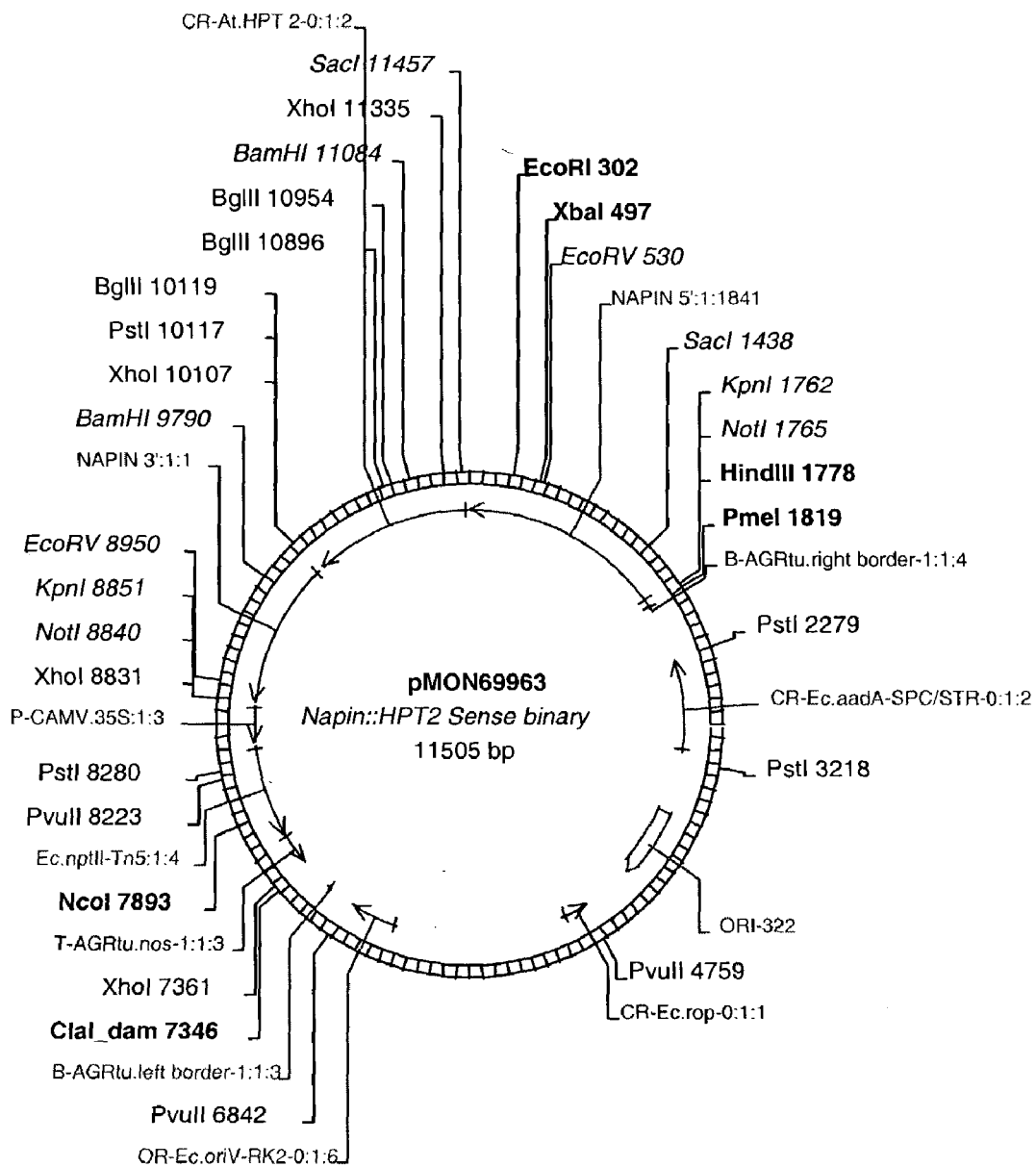
FIG. 17 depicts pMON 69963.
Figure 18:
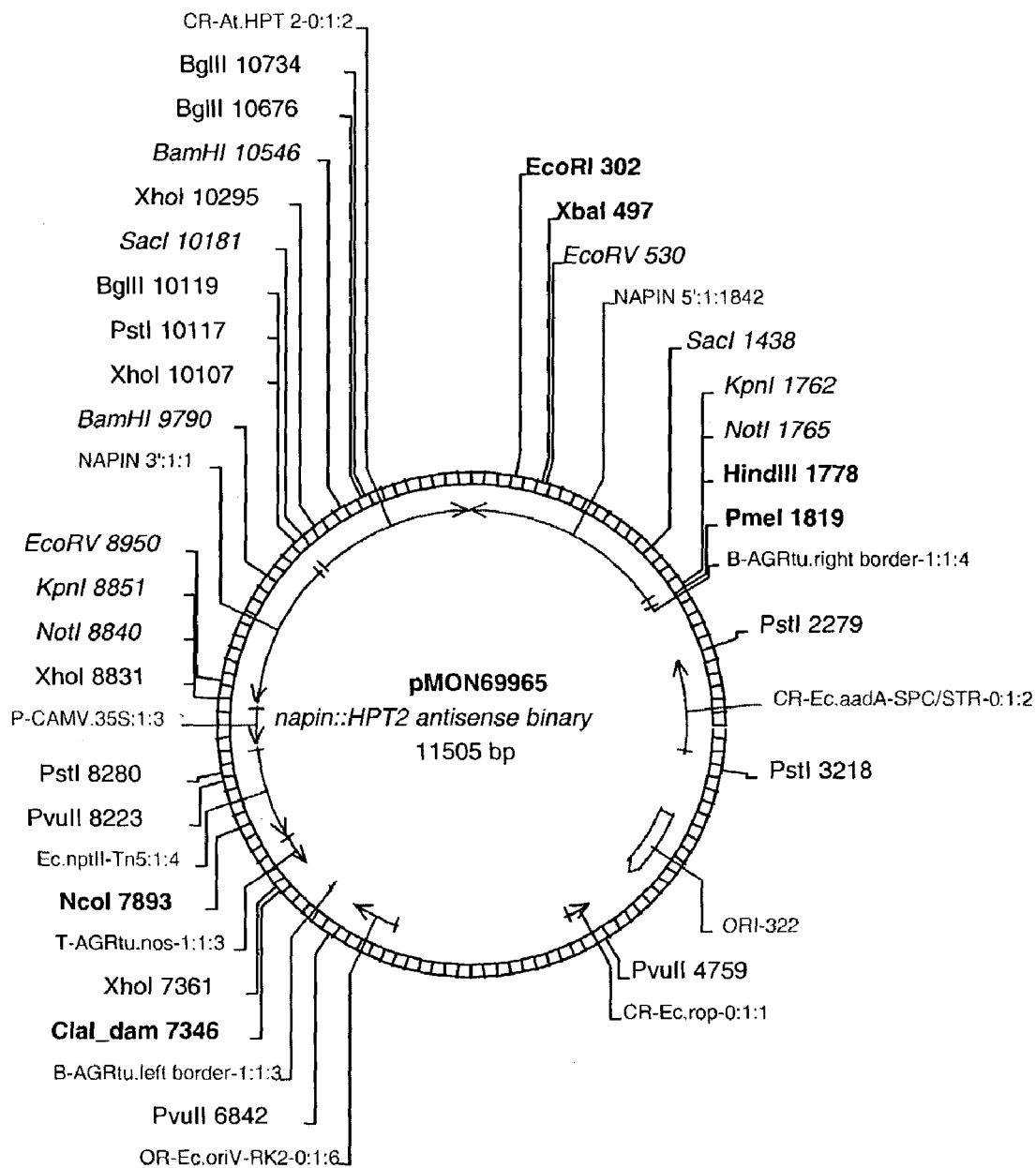
FIG. 18 depicts pMON 69965.
Figure 19:
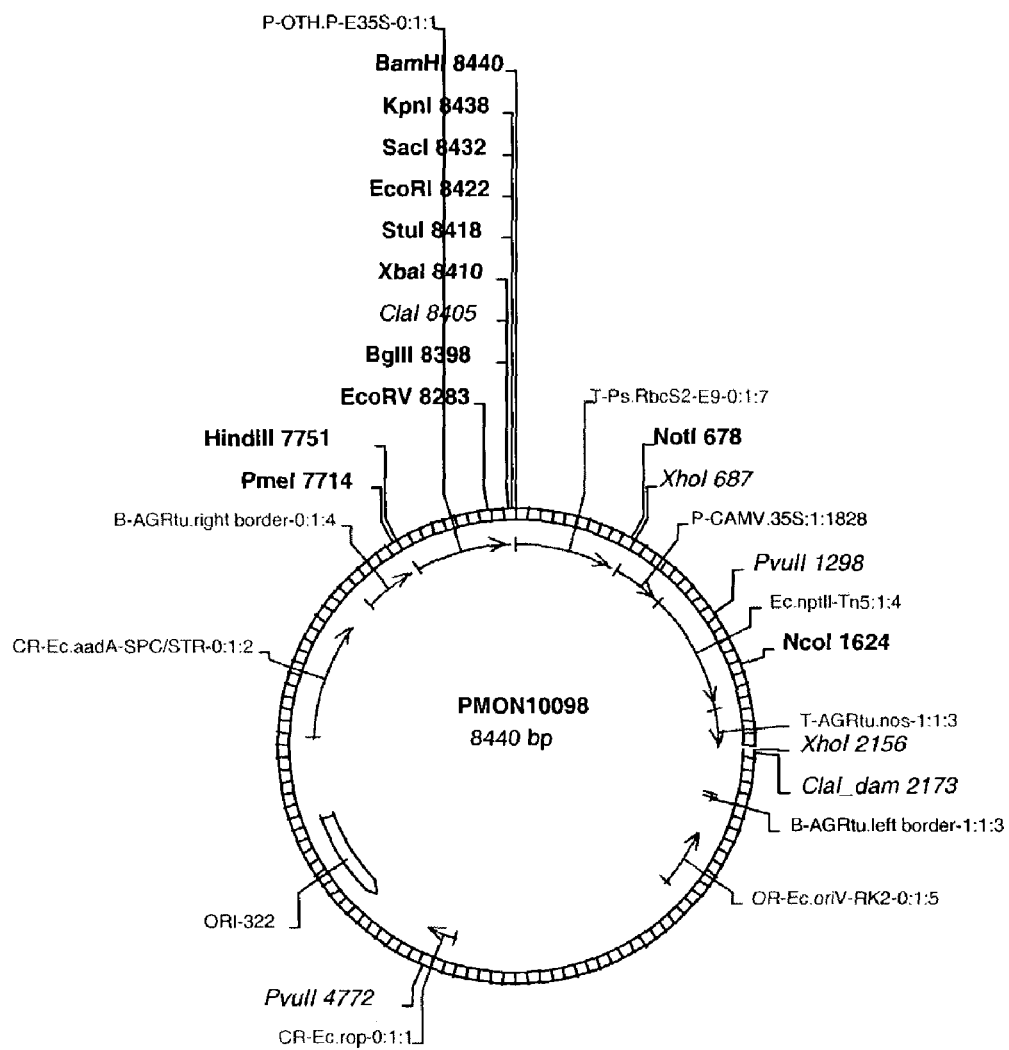
FIG. 19 depicts pMON 10098.
Figure 20:
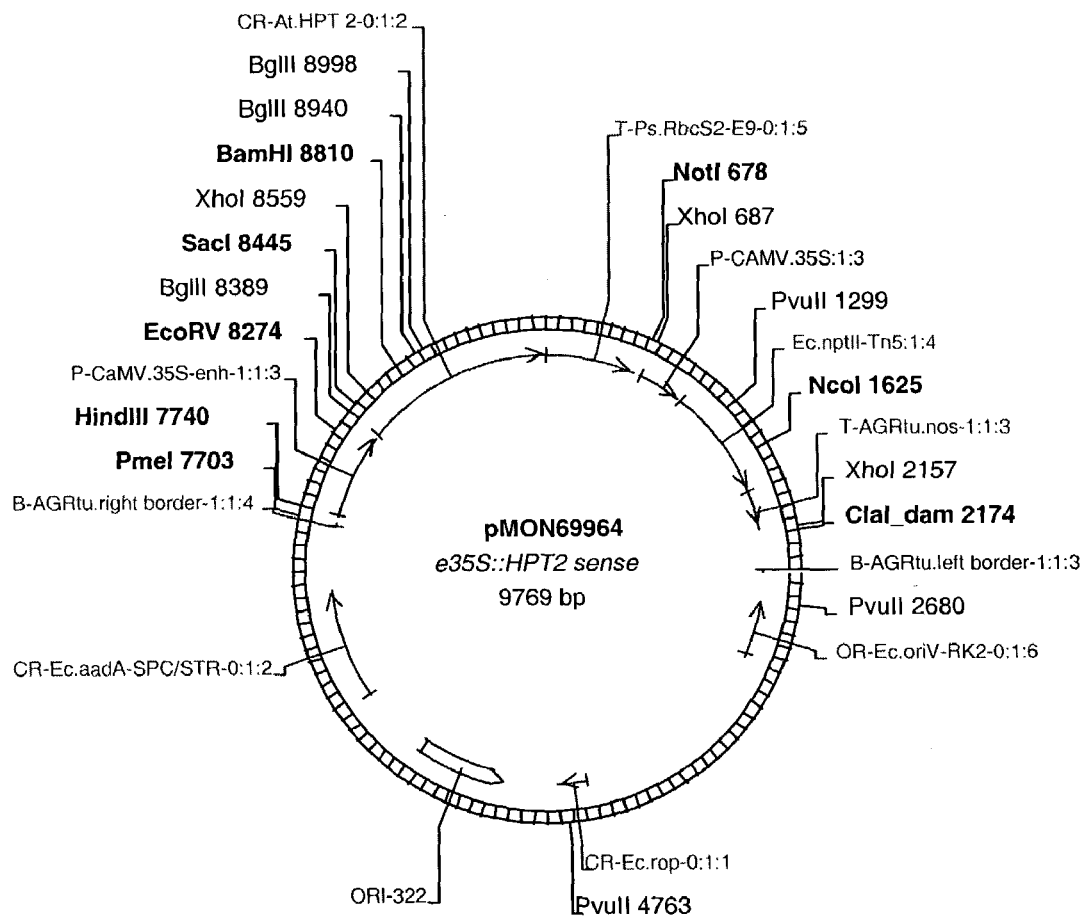
FIG. 20 depicts pMON 69964.
Figure 21:
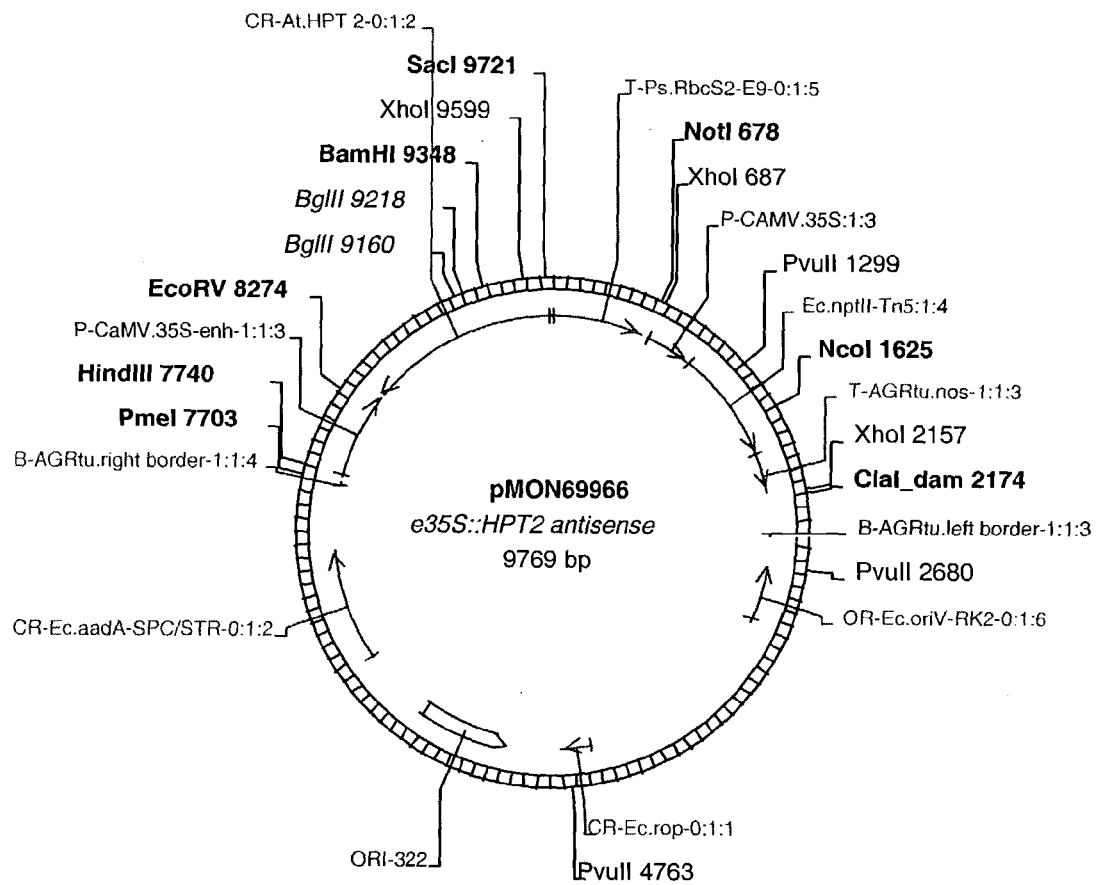
FIG. 21 depicts pMON 69966.

The HPT2 full-length cDNA (SEQ ID NO: 59) is excised from an EST clone, CPR230005 (pMON69960-FIG. 15), with SalI and NotI enzymes, blunt-ended and cloned in between the napin promoter and napin 3' end at blunt-ended SalI site in sense and antisense orientations with respect to the napin promoter in pMON36525 (FIG. 16) to generate recombinant binary vectors pMON69963 (FIG. 17) and pMON69965 (FIG. 18), respectively. The sequence of the HlPT2 cDNA is confirmed by sequencing with napin 5'-sense (5'-GTGGCTCGGCTTCACTTTTTAC-3') (SEQ ID NO: 50) and napin 3'-antisense (5'-CCACACTCATAT-CACCGTGG-3') (SEQ ID NO: 51) primers using standard sequencing methodology. The HPT2 cDNA used to generate the pMON69963 and pMON69965 is also cloned in between the enhanced 35S promoter and E9-3' end at blunt-ended BglII and BamHI sites of pMON10098 (FIG. 19) to generate the pMON69964 (FIG. 20) and pMON69966 (FIG. 21) in sense and antisense orientations with respect to the enhanced 35S promoter, respectively. Additional HPT2 internal primers synthesized to completely sequence the whole HPT2 cDNA are listed in the table below:

A list of primers used for confirming the HPT2 cDNA sequence.

| Primer | Description | Sequence |
| --- | --- | --- |
| BXK 169 | HPT2/CPR23005/sense | 5'-CAGTGCTGGATAGAATTGCCCGGTTCC-3' (SEQ ID NO: 52) |
| BXK 170 | HPT2/CPR23005/sense | 5'-GAGATCTATCAGTGCAGTCTGCTTGG-3' (SEQ ID NO: 53) |
| BXK 171 | HPT2/CPR23005/antisense | 5'-GGGACAAGCATTTTTATTGCAAG-3' (SEQ ID NO: 54) |

-continued

A list of primers used for confirming the HPT2 cDNA sequence.

| Primer | Description | Sequence |
|---|---|---|
| BXK 172 | HPT2/CPR23005/antisense | 5'-GCCAAGATCACATGTGCAGGAATC-3' (SEQ ID NO: 55) |
| BXK 173 | HPT2/CPR23005/sense | 5'-GTGGAGTGCACCTGTGGCGTTCATC-3' (SEQ ID NO: 56) |

Figure 22:
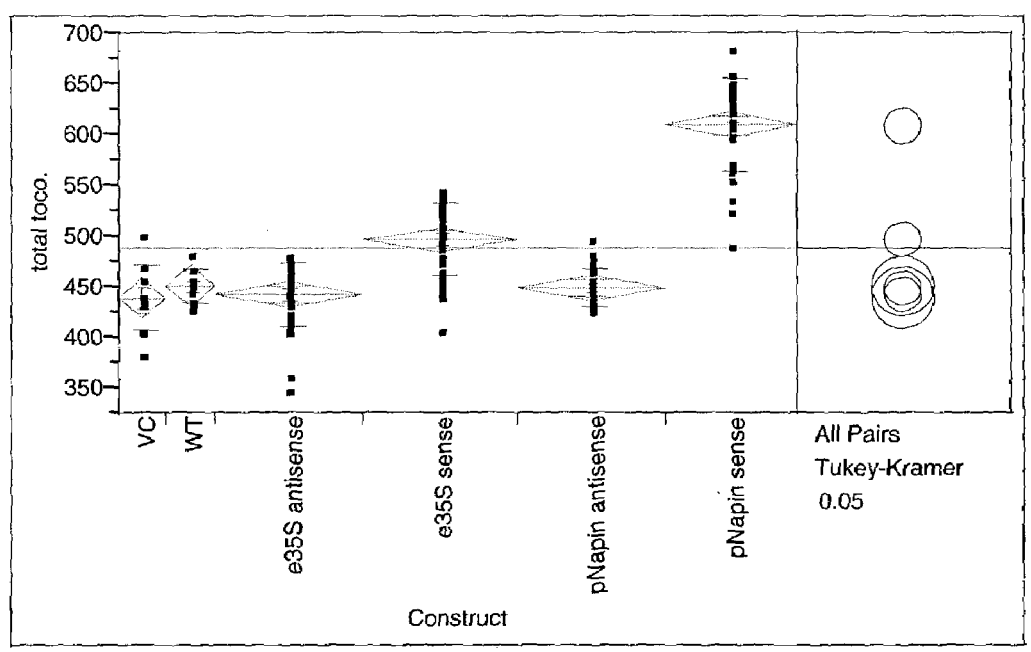
FIG. 22 depicts results of seed total tocopherol analysis.
Figure 23:
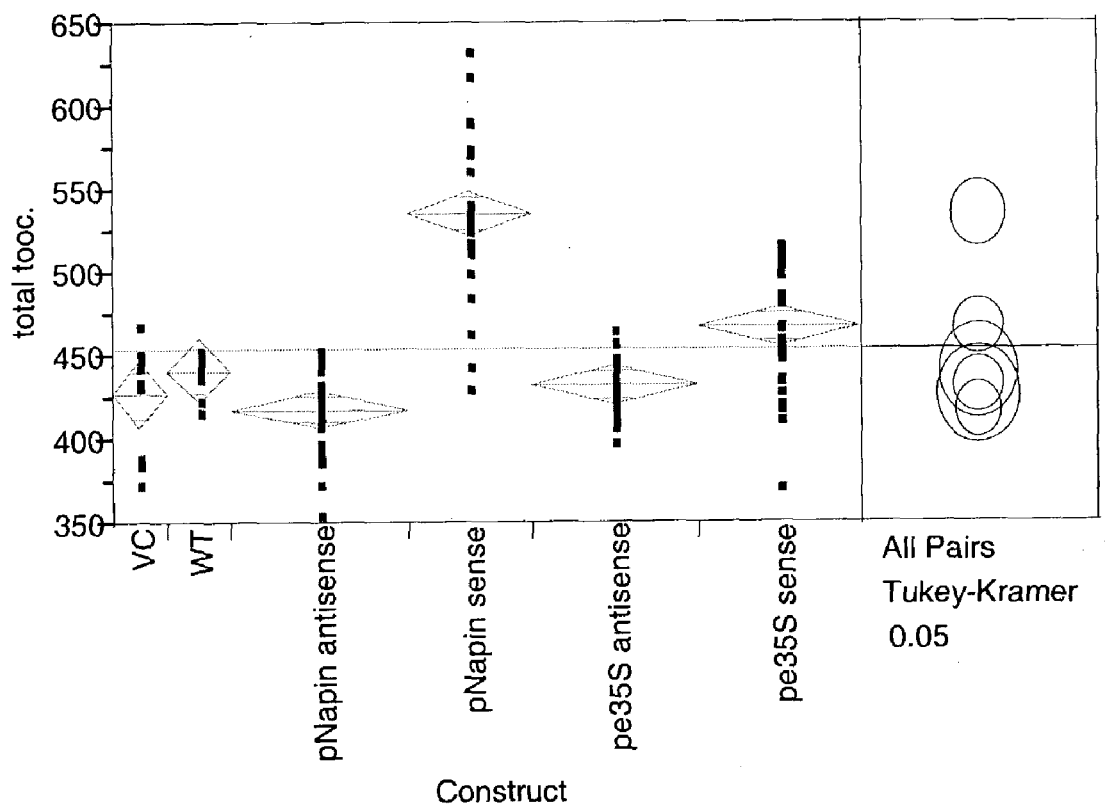
FIG. 23 depicts results of seed total tocopherol analysis.

The plant binary vectors pMON69963, and pMON69965 are used in *Arabidopsis thaliana* plant transformation to direct the sense and antisense expression of the HPT2, in the embryo. The binary vectors pMON69964, and pMON69966 are used in *Arabidopsis thaliana* plant transformation for sense and antisense expression of the HPT2 in whole plant. The binary vectors are transformed into ABI strain *Agrobacterium* cells by electroporation (Bio-Rad Electroprotocol Manual, Dower et al., *Nucleic Acids Res.*, 16:6127–6145 (1988)). Transgenic *Arabidopsis thaliana* plants are obtained by *Agrobacterium*-mediated transformation as described by Valverkens et al., *Proc. Nat. Acad. Sci.*, 85:5536–5540 (1988), Bent et al., *Science*, 265:1856–1860 (1994), and Bechtold et al., *C.R. Acad. Sci., Life Sciences*, 316:1194–1199 (1993). Transgenic plants are selected by sprinkling the transformed $T_1$ seeds onto the selection plates containing MS basal salts (4.3 g/L), Gamborg'a B-5, 500× (2.0 g/L), sucrose (10 g/L), MES (0.5 g/L), phytagar (8 g/L), carbenicillin (250 mg/L), cefotaxime (100 mg/L), plant preservation medium (2 ml/L), and kanamycin (60 mg/L) and then vernalizing them at 4° C. in the absence of light for 2–4 days. The seeds are transferred to 23° C., and 16/8 hours light/dark cycle for 5–10 days until seedlings emerge. Once one set of true leaves are formed on the kanamycin resistant seedlings, they are transferred to soil and grown to maturity. The transgenic lines generated through kanamycin selection are grown under two different light conditions. One set of the transgenic lines are grown under 16 hrs light and 8 hrs dark and another set of the transgenic lines are grown under 24 hrs light to study the effect of light on seed tocopherol levels. The $T_2$ seed harvested from the transformants is analyzed for tocopherol content. The results from the seed total tocopherol analysis from lines grown under both normal and high light conditions are presented in FIGS. 22 and 23. Seed-specific overexpression of HPT2 under normal and high light conditions produced a significant 1.6- and 1.5-fold increase in total tocopherol levels (alpha=0.05; Tukey-Kramer HSD) (SAS institute, 2002, JPM version 5.0).

Expression of HPT2 using the constitutive promoter, e35S, produced about 20% increase in seed total tocopherol levels as compared to control under both light conditions. Maximum tocopherol level reduction in lines harboring the enhanced 35S::HPT2 antisense construct was 20%. Overall, the significant increase in seed total tocopherol level in the *Arabidopsis thaliana* lines harboring the HPT2 driven by the napin promoter suggests that HPT2 plays a key role in tocopherol biosynthesis.

Western analysis is carried out to detect the transgene expression in tissues harboring the gene of interest (GOI) expression cassette using the GOI protein specific antibody. Northern analysis is done for detecting the mRNA level of the transgene using the GOI sequence specific radiolabelled probe.

EXAMPLE 9

Figure 27:
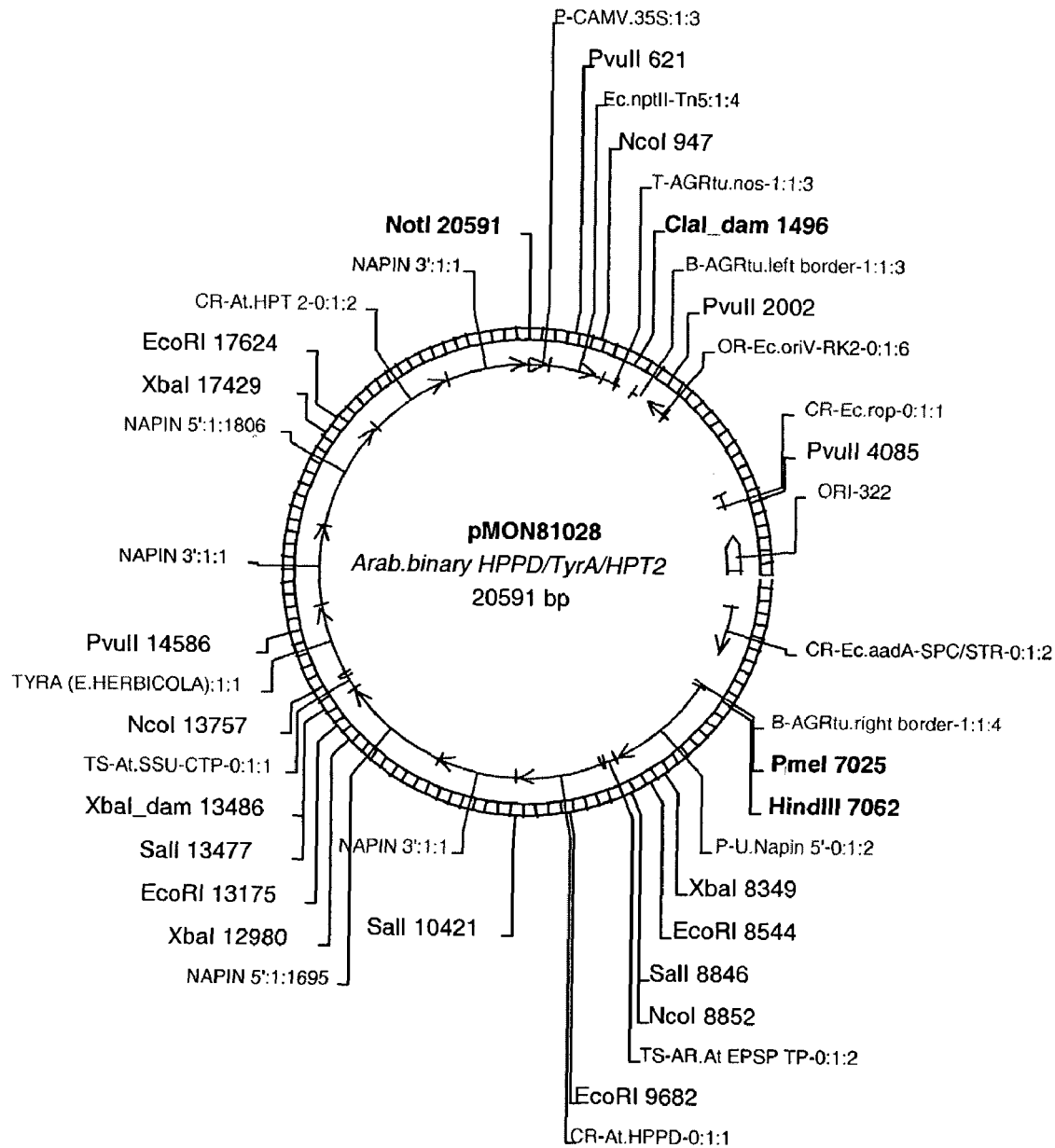
FIG. 27 depicts pMON81028.
Figure 28:
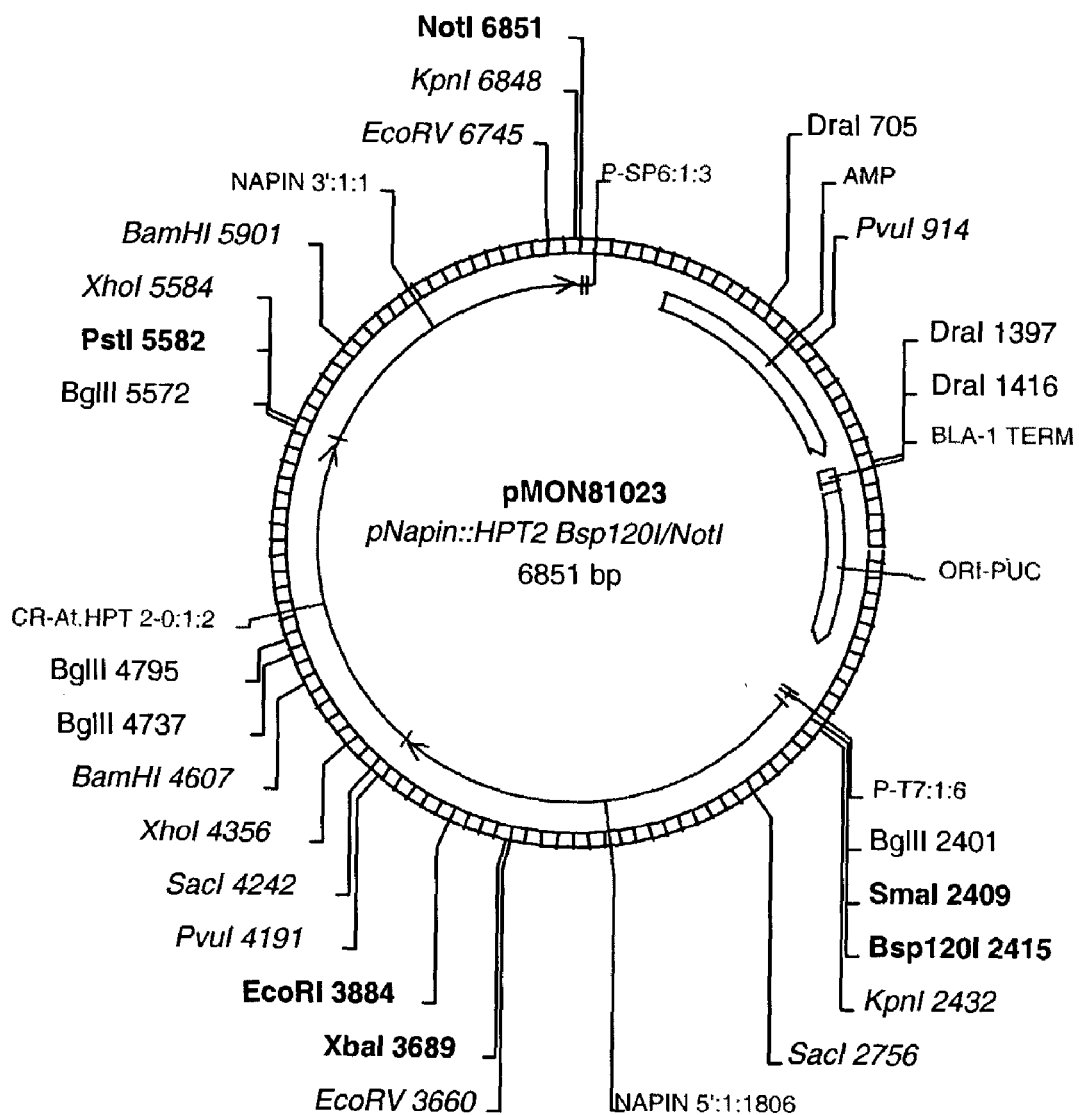
FIG. 28 depicts pMON81023.
Figure 29:
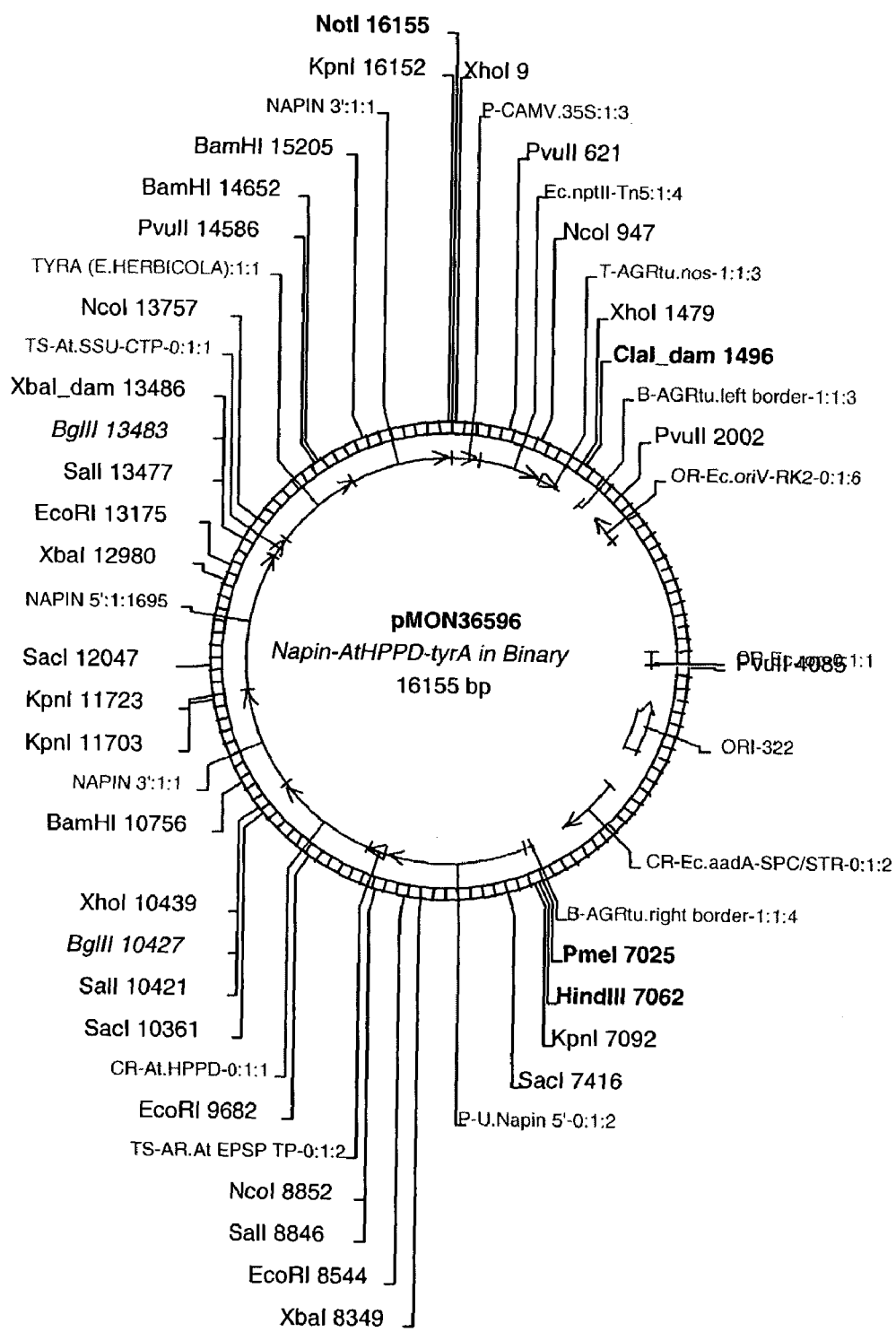
FIG. 29 depicts pMON36596.

Preparation of Plant Binary Vector for Expression of HPT2 from *Arabidopsis* in Combination with Tocopherol Pathway Genes To investigate the combinatorial effect of HPT2 with other key enzymes in the pathway, a plant binary vector containing seed-specifically expressed hydroxyphenylpyruvate dioxygenase (HPPD), bifunctional prephenate dehydrogenase tyrA, and HPT2 (pMON81028—FIG. 27) is prepared. The pMON81028 is made by exercising the pNapin::HPT2::Napin 3' expression cassette from pMON81023 (FIG. 28) with Bsp120I and NotI enzymes and ligating it to pMON36596 (FIG. 29) at NotI site. The pMON36596 contains the pNapin::CTP2::HPPD::Napin 3' and pNapin::CTP1::TyrA::Napin 3' expression cassettes. The pMON81028 is transformed into *Arabidopsis thaliana* plant using the method described in Example 8.

EXAMPLE 10

Preparation of Construct for Bacterial Expression of HPT2 from *Arabidopsis*

Figure 30:
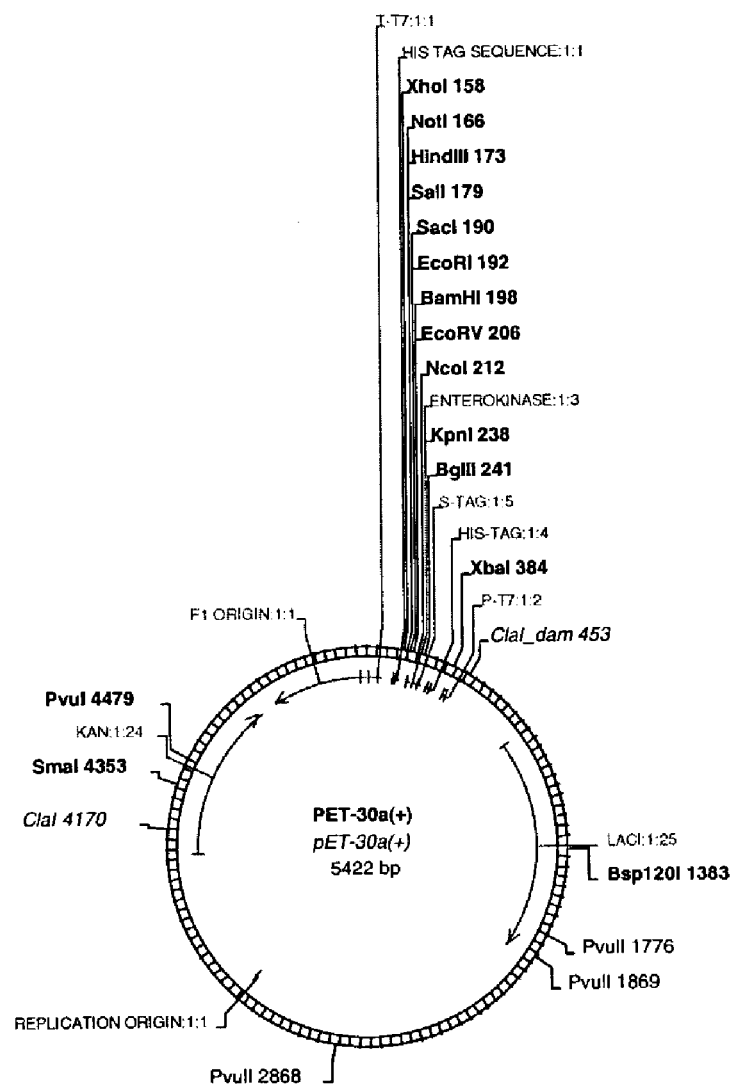
FIG. 30 depicts pET30a(+) vector.
Figure 31:
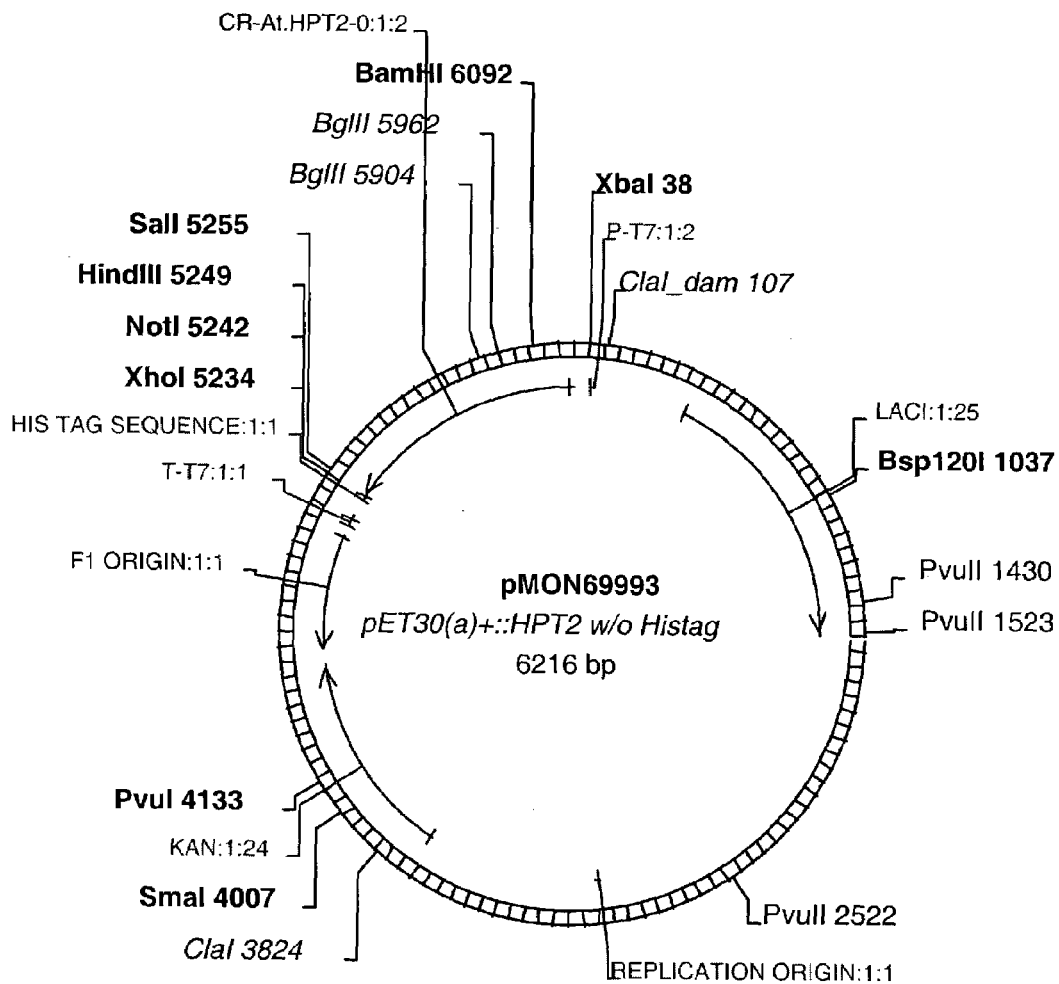
FIG. 31 depicts pMON69993.
Figure 32:
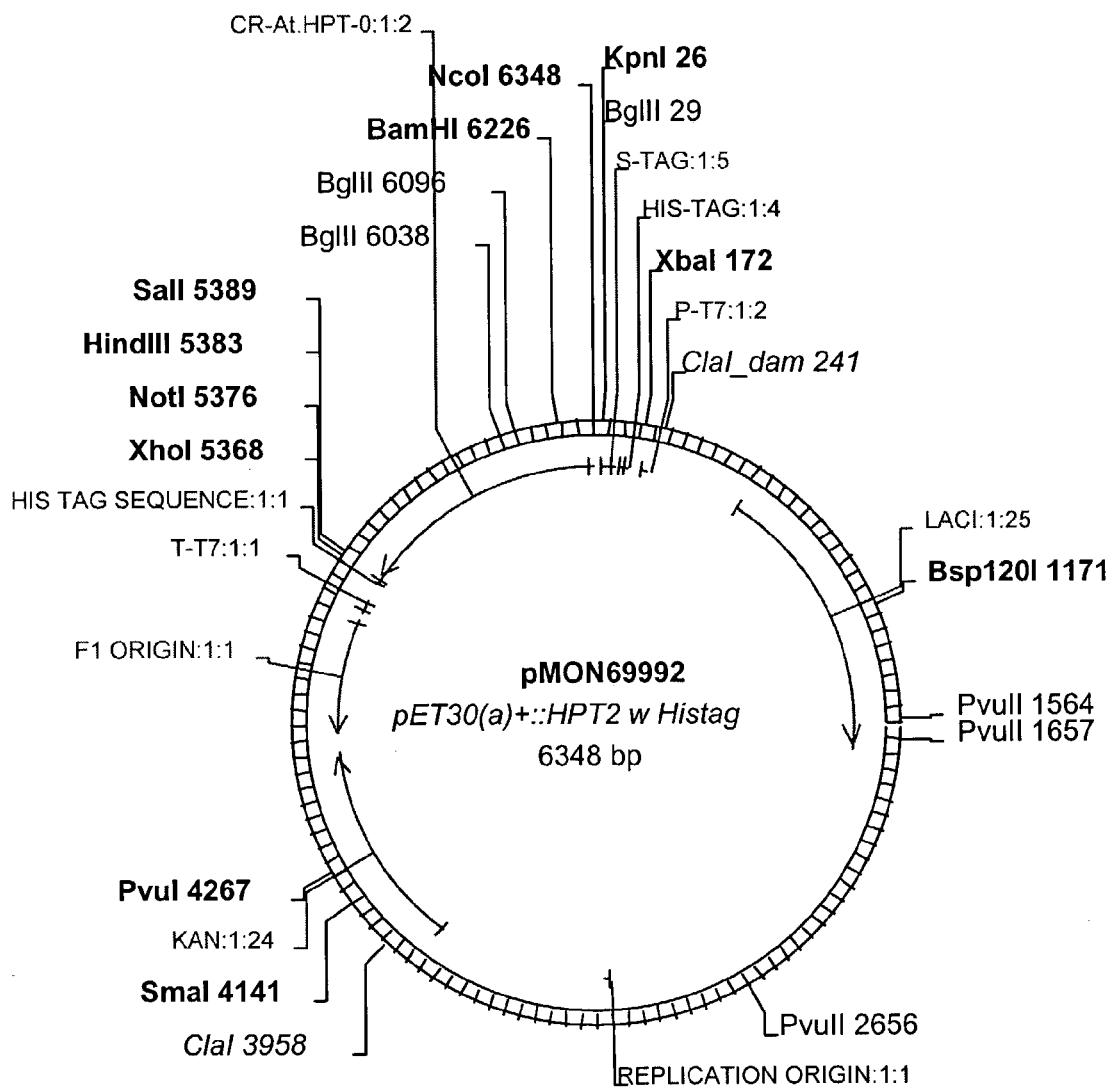
FIG. 32 depicts pMON69992.

The EST clone CPR23005 containing the HPT2 full length cDNA is used as a template for PCR to amplify the HPT2 cDNA fragment codes for the mature form of the HPT2 protein. Two sets of PCR products are generated to clone at the pET30a(+) vector (Novagen, Inc.) (FIG. 30) to produce HPT2 protein with and without his tag. The primer set BXK174 (5'-CACATATGGCATGTTCTCAGGTTGGTGCTGC-3') (SEQ ID NO: 84) and BXK176 (5'-GCGTCGACCTAGAGGAAGGGGAATAACAG-3') (SEQ ID NO: 85) is used for cloning HPT2 at the NdeI and SalI sites of pET30a(+), behind the T7 promoter to generate mature HPT2 protein without the his tag. The resulting recobmbinant vector is named pMON69993 (FIG. 31). The primer set BXK175 (5'-CAACCATGGCATGTTCTCAGGTTGGTGCTGC-3') (SEQ ID NO: 86) and BXK176 (5'-GCGTCGACCTAGAGGAAGGGGAATAACAG-3') (SEQ ID NO: 87) is used to generate HPT2 PCR product to clone at the NcoI and SalI sites of pET30a(+) to produce mature HPT2 with his tag. The recombinant vector is named as pMON69992 (FIG. 32). The pMON69993 and pMON69992 is used for producing bacterial expressed HPT2 to carry out enzyme assays to confirm its homogentisate prenyl transferase activity and specificity towards geranylgeranyl pyrophosphate, phytyl pyrophophaste and solanyl pyrophosphate substrates.

What is claimed is:

1. An isolated nucleic acid molecule encoding the amino acid sequence of SEQ ID NO:57.

2. A transformed plant comprising an introduced nucleic acid molecule encoding a polypeptide comprising the amino acid sequence of SEQ ID NO:57, wherein said nucleic acid molecule is operably linked to a promoter that functions in plants.

3. The transformed plant of claim 2, wherein said plant is selected from the group consisting of alfalfa, *Arabidopsis thaliana*, barley, *Brassica napus, Brassica campestris*, oilseed rape, broccoli, cabbage, citrus, canola, cotton, garlic, oat, Allium, flax, an ornamental plant, peanut, pepper, potato, rapeseed, rice, rye, sorghum, strawberry, sugarcane, sugar beet, tomato, wheat, poplar, pine, fir, eucalyptus, apple, lettuce, lentils, grape, banana, tea, turf grasses, sunflower, soybean, chick peas, corn, Phaseolus, crambe, mustard, castor bean, sesame, cottonseed, linseed, safflower, and oil palm.

4. The transformed plant of claim 2, wherein said plant is selected from the group consisting of oilseed rape, soybean and canola.

5. The transformed plant of claim 2, wherein said transformed plant comprises tissue with at least one of an increased total tocopherol level and an increased tocotrienol level relative to a plant with the same genetic background but lacking said introduced nucleic acid molecule.

6. The transformed plant of claim 2, wherein said transformed plant produces a seed with at least one of an increased total tocopherol level and an increased total tocotrienol level relative to a plant with the same genetic background but lacking said introduced nucleic acid molecule.

7. The transformed plant of claim 2, wherein said nucleic acid molecule is operably linked to a heterologous promoter.

8. The transformed plant of claim 7, wherein said promoter is a seed-specific promoter.

9. The transformed plant of claim 8, wherein said promoter is selected from the promoters consisting of: napin, 7S alpha, 7S alpha', USP 88, enhanced USP 88, Arcelin 5, and Oleosin.

10. A transformed plant comprising an introduced first nucleic acid molecule encoding a polypeptide comprising the amino acid sequence of SEQ ID NO:57, and an introduced second nucleic acid molecule encoding an enzyme selected from the group consisting of tyrA, prephenate dehydrogenase, tocopherol, cylase, dxs, dxr, GGPPS, HPPD, AANT1, ID, GGH, GMT tMT2, MT1, GCPE, and complements thereof, wherein said first nucleic acid molecule and said second nucleic acid molecule are each operably linked to a promoter that functions in plants.

11. The transformed plant of claim 10, wherein said plant is selected from the group consisting of alfalfa, *Arabidopsis thaliana*, barley, *Brassica napus, Brassica campestris*, oilseed rape, broccoli, cabbage, citrus, canola, cotton, garlic, oat, Allium, flax, an ornamental plant, peanut, pepper, potato, rapeseed, rice, rye, sorghum, strawberry, sugarcane, sugar beet, tomato, wheat, poplar, pine, fir, eucalyptus, apple, lettuce, lentils, grape, banana, tea, turf grasses, sunflower, soybean, chick peas, corn, Phaseolus, crambe, mustard, castor bean, sesame, cottonseed, linseed, safflower, and oil palm.

12. The transformed plant of claim 10, wherein said plant is selected from the group consisting of canola, oilseed rape, and soybean.

13. The transformed plant of claim 10, wherein said transformed plant comprises tissue with at least one of an increased total tocopherol level and an increased tocotrienol level relative to a plant with the same genetic background but lacking said introduced nucleic acid molecules.

14. The transformed plant of claim 10, wherein said transformed plant produces a seed with at least one of an increased total tocopherol level and an increased tocotrienol level relative to a plant with the same genetic background but lacking said introduced nucleic acid molecules.

15. The transformed plant of claim 10, wherein at least one of said first and second nucleic acids molecule is operably linked to a heterologous promoter.

16. The transformed plant of claim 15, wherein said promoter is a seed specific promoter.

17. The transformed plant of claim 16, wherein said promoter is selected from the promoters consisting of: napin, 7S alpha, 7S alpha', USP 88, enhanced USP 88, Arcelin 5, and Oleosin.

18. A method of producing a plant having a seed with an increased total tocopherol level comprising: (A) transforming said plant with an introduced nucleic acid molecule encoding a polypeptide comprising the amino acid sequence of SEQ ID NO:57, wherein said nucleic acid is operably linked to a promoter that functions in plants, and (B) growing said transformed plant.

19. The method of producing a plant of claim 18, wherein said plant is selected from the group consisting of alfalfa, *Arabidopsis thaliana*, barley, *Brassica napus, Brassica campestris*, oilseed rape, broccoli, cabbage, canola, citrus, cotton, garlic, oat, Allium, flax, an ornamental plant, peanut, pepper, potato, rapeseed, rice, rye, sorghum, strawberry, sugarcane, sugar beet, tomato, wheat, poplar, pine, fir, eucalyptus, apple, lettuce, lentils, grape, banana, tea, turf grasses, sunflower, soybean, corn, Phaseolus, crambe, mustard, castor bean, sesame, cottonseed, linseed, safflower, and oil palm.

20. The method of claim 18, wherein said plant is selected from the group consisting of canola, oilseed rape, and soybean.

21. The method of claim 18, wherein the plant is transformed with an introduced second nucleic acid molecule encoding an enzyme selected from the group consisting of tyrA, prephenate dehydrogenase, tocopherol cyclase, dxs, dxr, GGPPS, HPPD, AANT1, ID1, GGH, tMT2, GMT, MT1, GCPE, and complements thereof, wherein said second nucleic acid molecule is operably linked to a promoter that functions in plants.

22. A seed derived from a transformed plant comprising an introduced nucleic acid molecule encoding a polypeptide comprising the amino acid sequence of SEQ ID NO:57, wherein said nucleic acid molecule is operably linked to a promoter that functions in plants, and wherein said seed comprises said nucleic acid.

23. The seed of claim 22, wherein said seed has at least one of an increased total tocopherol level and an increased tocotrienol level relative to a plant with the same genetic background but lacking said introduced nucleic acid molecule.

24. A seed derived from a transformed plant comprising an introduced first nucleic acid molecule encoding an introduced polypeptide comprising the amino acid sequence of SEQ ID NO:57 and an introduced second nucleic acid encoding an enzyme selected from the group consisting of tyrA, prephenate dehydrogenase, tocopherol cyclase, dxs, dxr, GGPPS, HPPD, AANT1, ID1, GGH, tMT2, MT1, GCPE, GMT, and complements thereof, wherein said nucleic acid molecules are each operably linked to a promoter that functions in plants, and wherein said seed comprises said nucleic acid molecules.

25. The seed of claim 24, wherein said seed has at least one of an increased total tocopherol level and an increased tocotrienol level relative to a seed from a plant having the same genetic background but lacking said introduced nucleic acid molecule.

26. The nucleic acid molecule of claim 1, wherein the nucleic acid molecule comprises the sequence of SEQ ID NO:59.

27. The transformed plant of claim 2, wherein the nucleic acid molecule comprises the sequence of SEQ ID NO:59.

28. The transformed plant of claim 10, wherein the first nucleic acid molecule comprises the sequence of SEQ ID NO:59.

29. The method of claim 18, wherein the introduced nucleic acid molecule comprises the sequence of SEQ ID NO:59.

30. The seed of claim 22, wherein the introduced nucleic acid molecule comprises the sequence of SEQ ID NO:59.

31. The seed of claim 24, wherein the first nucleic acid molecule comprises the sequence of SEQ ID NO:59.

* * * * *

UNITED STATES PATENT AND TRADEMARK OFFICE
CERTIFICATE OF CORRECTION

| | | |
|---|---|---|
| PATENT NO. | : 7,112,717 B2 | Page 1 of 1 |
| APPLICATION NO. | : 10/391363 | |
| DATED | : September 26, 2006 | |
| INVENTOR(S) | : Valentin et al. | |

It is certified that error appears in the above-identified patent and that said Letters Patent is hereby corrected as shown below:

Column 161, line 58, delete ", cylase" and insert --cyclase-- therefor.

Column 161, line 59, delete "ID," and insert --ID1,-- therefor.

Column 161, line 59, after "GMT" insert --, -- therefor.

Signed and Sealed this

Thirtieth Day of January, 2007

JON W. DUDAS
*Director of the United States Patent and Trademark Office*

SEQUENCE LISTING

<160> NUMBER OF SEQ ID NOS: 95

<210> SEQ ID NO 1
<211> LENGTH: 322
<212> TYPE: PRT
<213> ORGANISM: Nostoc punctiforme

<400> SEQUENCE: 1

```
Met Ser Gln Ser Ser Gln Asn Ser Pro Leu Pro Arg Lys Pro Val Gln
1               5                   10                  15

Ser Tyr Phe His Trp Leu Tyr Ala Phe Trp Lys Phe Ser Arg Pro His
            20                  25                  30

Thr Ile Ile Gly Thr Ser Leu Ser Val Leu Ser Leu Tyr Leu Ile Ala
        35                  40                  45

Ile Ala Ile Ser Asn Asn Thr Ala Ser Leu Phe Thr Thr Pro Gly Ser
50                  55                  60

Leu Ser Pro Leu Phe Gly Ala Trp Ile Ala Cys Leu Cys Gly Asn Val
65                  70                  75                  80

Tyr Ile Val Gly Leu Asn Gln Leu Glu Asp Val Asp Ile Asp Lys Ile
                85                  90                  95

Asn Lys Pro His Leu Pro Leu Ala Ser Gly Glu Phe Ser Gln Gln Thr
            100                 105                 110

Gly Gln Leu Ile Val Ala Ser Thr Gly Ile Leu Ala Leu Val Met Ala
        115                 120                 125

Trp Leu Thr Gly Pro Phe Leu Phe Gly Met Val Thr Ile Ser Leu Ala
    130                 135                 140

Ile Gly Thr Ala Tyr Ser Leu Pro Pro Ile Arg Leu Lys Gln Phe Pro
145                 150                 155                 160

Phe Trp Ala Ala Leu Cys Ile Phe Ser Val Arg Gly Thr Ile Val Asn
                165                 170                 175

Leu Gly Leu Tyr Leu His Tyr Ser Trp Ala Leu Lys Gln Ser Gln Thr
            180                 185                 190

Ile Pro Pro Val Val Trp Val Leu Thr Leu Phe Ile Leu Val Phe Thr
        195                 200                 205

Phe Ala Ile Ala Ile Phe Lys Asp Ile Pro Asp Ile Glu Gly Asp Arg
    210                 215                 220

Leu Tyr Asn Ile Thr Thr Phe Thr Ile Lys Leu Gly Ser Gln Ala Val
225                 230                 235                 240

Phe Asn Leu Ala Leu Trp Val Ile Thr Val Cys Tyr Leu Gly Ile Ile
                245                 250                 255

Leu Val Gly Val Leu Arg Ile Ala Ser Val Asn Pro Ile Phe Leu Ile
            260                 265                 270

Thr Ala His Leu Ala Leu Leu Val Trp Met Trp Trp Arg Ser Leu Ala
        275                 280                 285

Val Asp Leu Gln Asp Lys Ser Ala Ile Ala Gln Phe Tyr Gln Phe Ile
    290                 295                 300

Trp Lys Leu Phe Phe Ile Glu Tyr Leu Ile Phe Pro Ile Ala Cys Phe
305                 310                 315                 320

Leu Ala
```

<210> SEQ ID NO 2
<211> LENGTH: 318
<212> TYPE: PRT
<213> ORGANISM: Anabaena sp.

```
<400> SEQUENCE: 2

Met Asn Gln Ser Ser Gln Asp Arg Pro Leu Arg Pro Lys Pro Leu Gln
1               5                   10                  15

Ser Ser Phe Gln Trp Leu Tyr Ala Phe Trp Lys Phe Ser Arg Pro His
            20                  25                  30

Thr Ile Ile Gly Thr Ser Leu Ser Val Leu Gly Leu Tyr Leu Ile Ser
        35                  40                  45

Ile Ala Val Ser Ser Thr Gly Phe Ala Leu Thr Gln Ile Asn Ser Val
50                  55                  60

Leu Gly Ala Trp Leu Ala Cys Leu Cys Gly Asn Val Tyr Ile Val Gly
65                  70                  75                  80

Leu Asn Gln Leu Glu Asp Ile Glu Ile Asp Lys Val Asn Lys Pro His
                85                  90                  95

Leu Pro Leu Ala Ser Gly Glu Phe Ser Arg Lys Gln Gly Arg Ile Ile
            100                 105                 110

Val Ile Leu Thr Gly Ile Thr Ala Ile Val Leu Ala Trp Leu Asn Gly
        115                 120                 125

Pro Tyr Leu Phe Gly Met Val Ala Val Ser Leu Ala Ile Gly Thr Ala
130                 135                 140

Tyr Ser Leu Pro Pro Ile Arg Leu Lys Gln Phe Pro Phe Trp Ala Ala
145                 150                 155                 160

Leu Cys Ile Phe Ser Val Arg Gly Thr Ile Val Asn Leu Gly Leu Tyr
                165                 170                 175

Leu His Phe Ser Trp Leu Leu Gln Asn Lys Gln Ser Ile Pro Leu Pro
            180                 185                 190

Val Trp Ile Leu Thr Val Phe Ile Leu Ile Phe Thr Phe Ala Ile Ala
        195                 200                 205

Ile Phe Lys Asp Ile Pro Asp Met Glu Gly Asp Arg Leu Tyr Asn Ile
210                 215                 220

Thr Thr Leu Thr Ile Gln Leu Gly Pro Gln Ala Val Phe Asn Leu Ala
225                 230                 235                 240

Met Trp Val Leu Thr Val Cys Tyr Leu Gly Met Val Ile Ile Gly Val
                245                 250                 255

Leu Arg Leu Gly Thr Ile Asn Ser Val Phe Leu Val Val Thr His Leu
            260                 265                 270

Val Ile Leu Cys Trp Met Trp Met Gln Ser Leu Ala Val Asp Ile His
        275                 280                 285

Asp Lys Thr Ala Ile Ala Gln Phe Tyr Gln Phe Ile Trp Lys Leu Phe
290                 295                 300

Phe Leu Glu Tyr Leu Met Phe Pro Ile Ala Cys Leu Leu Ala
305                 310                 315

<210> SEQ ID NO 3
<211> LENGTH: 308
<212> TYPE: PRT
<213> ORGANISM: Synechocystis sp.

<400> SEQUENCE: 3

Met Ala Thr Ile Gln Ala Phe Trp Arg Phe Ser Arg Pro His Thr Ile
1               5                   10                  15

Ile Gly Thr Thr Leu Ser Val Trp Ala Val Tyr Leu Leu Thr Ile Leu
            20                  25                  30

Gly Asp Gly Asn Ser Val Asn Ser Pro Ala Ser Leu Asp Leu Val Phe
        35                  40                  45
```

```
Gly Ala Trp Leu Ala Cys Leu Leu Gly Asn Val Tyr Ile Val Gly Leu
         50                  55                  60

Asn Gln Leu Trp Asp Val Asp Ile Asp Arg Ile Asn Lys Pro Asn Leu
 65                  70                  75                  80

Pro Leu Ala Asn Gly Asp Phe Ser Ile Ala Gln Gly Arg Trp Ile Val
                 85                  90                  95

Gly Leu Cys Gly Val Ala Ser Leu Ala Ile Ala Trp Gly Leu Gly Leu
            100                 105                 110

Trp Leu Gly Leu Thr Val Gly Ile Ser Leu Ile Gly Thr Ala Tyr
            115                 120                 125

Ser Val Pro Pro Val Arg Leu Lys Arg Phe Ser Leu Leu Ala Ala Leu
        130                 135                 140

Cys Ile Leu Thr Val Arg Gly Ile Val Val Asn Leu Gly Leu Phe Leu
145                 150                 155                 160

Phe Phe Arg Ile Gly Leu Gly Tyr Pro Pro Thr Leu Ile Thr Pro Ile
                165                 170                 175

Trp Val Leu Thr Leu Phe Ile Leu Val Phe Thr Val Ala Ile Ala Ile
            180                 185                 190

Phe Lys Asp Val Pro Asp Met Glu Gly Asp Arg Gln Phe Lys Ile Gln
        195                 200                 205

Thr Leu Thr Leu Gln Ile Gly Lys Gln Asn Val Phe Arg Gly Thr Leu
210                 215                 220

Ile Leu Leu Thr Gly Cys Tyr Leu Ala Met Ala Ile Trp Gly Leu Trp
225                 230                 235                 240

Ala Ala Met Pro Leu Asn Thr Ala Phe Leu Ile Val Ser His Leu Cys
                245                 250                 255

Leu Leu Ala Leu Leu Trp Trp Arg Ser Arg Asp Val His Leu Glu Ser
            260                 265                 270

Lys Thr Glu Ile Ala Ser Phe Tyr Gln Phe Ile Trp Lys Leu Phe Phe
        275                 280                 285

Leu Glu Tyr Leu Leu Tyr Pro Leu Ala Leu Trp Leu Pro Asn Phe Ser
290                 295                 300

Asn Thr Ile Phe
305

<210> SEQ ID NO 4
<211> LENGTH: 399
<212> TYPE: PRT
<213> ORGANISM: Zea mays

<400> SEQUENCE: 4

Met Asp Ala Leu Arg Leu Arg Pro Ser Leu Leu Pro Val Arg Pro Gly
1               5                   10                  15

Ala Ala Arg Pro Arg Asp His Phe Leu Pro Pro Cys Cys Ser Ile Gln
                20                  25                  30

Arg Asn Gly Glu Gly Arg Ile Cys Phe Ser Ser Gln Arg Thr Gln Gly
            35                  40                  45

Pro Thr Leu His His His Gln Lys Phe Phe Glu Trp Lys Ser Ser Tyr
        50                  55                  60

Cys Arg Ile Ser His Arg Ser Leu Asn Thr Ser Val Asn Ala Ser Gly
65                  70                  75                  80

Gln Gln Leu Gln Ser Glu Pro Glu Thr His Asp Ser Thr Thr Ile Trp
                85                  90                  95

Arg Ala Ile Ser Ser Ser Leu Asp Ala Phe Tyr Arg Phe Ser Arg Pro
```

```
                100             105             110
His Thr Val Ile Gly Thr Ala Leu Ser Ile Val Ser Val Ser Leu Leu
        115                 120                 125

Ala Val Gln Ser Leu Ser Asp Ile Ser Pro Leu Phe Leu Thr Gly Leu
130                 135                 140

Leu Glu Ala Val Val Ala Leu Phe Met Asn Ile Tyr Ile Val Gly
145                 150                 155                 160

Leu Asn Gln Leu Phe Asp Ile Glu Ile Asp Lys Val Asn Lys Pro Thr
                165                 170                 175

Leu Pro Leu Ala Ser Gly Glu Tyr Thr Leu Ala Thr Gly Val Ala Ile
                180                 185                 190

Val Ser Val Phe Ala Ala Met Ser Phe Gly Leu Gly Trp Ala Val Gly
                195                 200                 205

Ser Gln Pro Leu Phe Trp Ala Leu Phe Ile Ser Phe Val Leu Gly Thr
            210                 215                 220

Ala Tyr Ser Ile Asn Leu Pro Tyr Leu Arg Trp Lys Arg Phe Ala Val
225                 230                 235                 240

Val Ala Ala Leu Cys Ile Leu Ala Val Arg Ala Val Ile Val Gln Leu
                245                 250                 255

Ala Phe Phe Leu His Ile Gln Thr Phe Val Phe Arg Arg Pro Ala Val
                260                 265                 270

Phe Ser Arg Pro Leu Leu Phe Ala Thr Gly Phe Met Thr Phe Phe Ser
            275                 280                 285

Val Val Ile Ala Leu Phe Lys Asp Ile Pro Asp Ile Glu Gly Asp Arg
            290                 295                 300

Ile Phe Gly Ile Arg Ser Phe Ser Val Arg Leu Gly Gln Lys Lys Val
305                 310                 315                 320

Phe Trp Ile Cys Val Gly Leu Leu Glu Met Ala Tyr Ser Val Ala Ile
                325                 330                 335

Leu Met Gly Ala Thr Ser Ser Cys Leu Trp Ser Lys Thr Ala Thr Ile
                340                 345                 350

Ala Gly His Ser Ile Leu Ala Ala Ile Leu Trp Ser Cys Ala Arg Ser
            355                 360                 365

Val Asp Leu Thr Ser Lys Ala Ala Ile Thr Ser Phe Tyr Met Phe Ile
            370                 375                 380

Trp Lys Leu Phe Tyr Ala Glu Tyr Leu Leu Ile Pro Leu Val Arg
385                 390                 395
```

<210> SEQ ID NO 5
<211> LENGTH: 411
<212> TYPE: PRT
<213> ORGANISM: Glycine max (ppt2)

<400> SEQUENCE: 5

```
Met Asp Ser Leu Leu Arg Ser Phe Pro Asn Ile Asn Asn Ala Ser
1               5                   10                  15

Ser Leu Thr Thr Thr Gly Ala Asn Phe Ser Arg Thr Lys Ser Phe Ala
            20                  25                  30

Asn Ile Tyr His Ala Ser Ser Tyr Val Pro Asn Ala Ser Trp His Asn
            35                  40                  45

Arg Lys Ile Gln Lys Glu Tyr Asn Phe Leu Arg Phe Arg Trp Pro Ser
        50                  55                  60

Leu Asn His His Tyr Lys Gly Ile Glu Gly Ala Cys Thr Cys Lys Lys
65                  70                  75                  80
```

```
Cys Asn Ile Lys Phe Val Val Lys Ala Thr Ser Glu Lys Ser Leu Glu
                85                  90                  95

Ser Glu Pro Gln Ala Phe Asp Pro Lys Ser Ile Leu Asp Ser Val Lys
            100                 105                 110

Asn Ser Leu Asp Ala Phe Tyr Arg Phe Ser Arg Pro His Thr Val Ile
        115                 120                 125

Gly Thr Ala Leu Ser Ile Ile Ser Val Ser Leu Leu Ala Val Glu Lys
    130                 135                 140

Ile Ser Asp Ile Ser Pro Leu Phe Phe Thr Gly Val Leu Glu Ala Val
145                 150                 155                 160

Val Ala Ala Leu Phe Met Asn Ile Tyr Ile Val Gly Leu Asn Gln Leu
                165                 170                 175

Ser Asp Val Glu Ile Asp Lys Ile Asn Lys Pro Tyr Leu Pro Leu Ala
            180                 185                 190

Ser Gly Glu Tyr Ser Phe Glu Thr Gly Val Thr Ile Val Ala Ser Phe
        195                 200                 205

Ser Ile Leu Ser Phe Trp Leu Gly Trp Val Gly Ser Trp Pro Leu
    210                 215                 220

Phe Trp Ala Leu Phe Val Ser Phe Val Leu Gly Thr Ala Tyr Ser Ile
225                 230                 235                 240

Asn Val Pro Leu Leu Arg Trp Lys Arg Phe Ala Val Leu Ala Ala Met
                245                 250                 255

Cys Ile Leu Ala Val Arg Ala Val Ile Val Gln Leu Ala Phe Phe Leu
            260                 265                 270

His Met Gln Thr His Val Tyr Lys Arg Pro Val Phe Ser Arg Pro
        275                 280                 285

Leu Ile Phe Ala Thr Ala Phe Met Ser Phe Phe Ser Val Val Ile Ala
    290                 295                 300

Leu Phe Lys Asp Ile Pro Asp Ile Glu Gly Asp Lys Val Phe Gly Ile
305                 310                 315                 320

Gln Ser Phe Ser Val Arg Leu Gly Gln Lys Pro Val Phe Trp Thr Cys
                325                 330                 335

Val Thr Leu Leu Glu Ile Ala Tyr Gly Val Ala Leu Leu Val Gly Ala
            340                 345                 350

Ala Ser Pro Cys Leu Trp Ser Lys Ile Phe Thr Gly Leu Gly His Ala
        355                 360                 365

Val Leu Ala Ser Ile Leu Trp Phe His Ala Lys Ser Val Asp Leu Lys
    370                 375                 380

Ser Lys Ala Ser Ile Thr Ser Phe Tyr Met Phe Ile Trp Lys Leu Phe
385                 390                 395                 400

Tyr Ala Glu Tyr Leu Leu Ile Pro Phe Val Arg
                405                 410

<210> SEQ ID NO 6
<211> LENGTH: 395
<212> TYPE: PRT
<213> ORGANISM: Glycine max (ppt1)

<400> SEQUENCE: 6

Met Asp Ser Met Leu Leu Arg Ser Phe Pro Asn Ile Asn Asn Ala Ser
1               5                   10                  15

Ser Leu Ala Thr Thr Gly Ser Tyr Leu Pro Asn Ala Ser Trp His Asn
            20                  25                  30

Arg Lys Ile Gln Lys Glu Tyr Asn Phe Leu Arg Phe Arg Trp Pro Ser
        35                  40                  45
```

```
Leu Asn His His Tyr Lys Ser Ile Glu Gly Gly Cys Thr Cys Lys Lys
 50                  55                  60

Cys Asn Ile Lys Phe Val Val Lys Ala Thr Ser Glu Lys Ser Phe Glu
 65                  70                  75                  80

Ser Glu Pro Gln Ala Phe Asp Pro Lys Ser Ile Leu Asp Ser Val Lys
                 85                  90                  95

Asn Ser Leu Asp Ala Phe Tyr Arg Phe Ser Arg Pro His Thr Val Ile
            100                 105                 110

Gly Thr Ala Leu Ser Ile Ile Ser Val Ser Leu Leu Ala Val Glu Lys
            115                 120                 125

Ile Ser Asp Ile Ser Pro Leu Phe Phe Thr Gly Val Leu Glu Ala Val
130                 135                 140

Val Ala Ala Leu Phe Met Asn Ile Tyr Ile Val Gly Leu Asn Gln Leu
145                 150                 155                 160

Ser Asp Val Glu Ile Asp Lys Ile Asn Lys Pro Tyr Leu Pro Leu Ala
                165                 170                 175

Ser Gly Glu Tyr Ser Phe Glu Thr Gly Val Thr Ile Val Ala Ser Phe
            180                 185                 190

Ser Ile Leu Ser Phe Trp Leu Gly Trp Val Gly Ser Trp Pro Leu
            195                 200                 205

Phe Trp Ala Leu Phe Val Ser Phe Val Leu Gly Thr Ala Tyr Ser Ile
210                 215                 220

Asn Val Pro Leu Leu Arg Trp Lys Arg Phe Ala Val Leu Ala Ala Met
225                 230                 235                 240

Cys Ile Leu Ala Val Arg Ala Val Ile Val Gln Leu Ala Phe Phe Leu
                245                 250                 255

His Ile Gln Thr His Val Tyr Lys Arg Pro Pro Val Phe Ser Arg Ser
            260                 265                 270

Leu Ile Phe Ala Thr Ala Phe Met Ser Phe Phe Ser Val Val Ile Ala
            275                 280                 285

Leu Phe Lys Asp Ile Pro Asp Ile Glu Gly Asp Lys Val Phe Gly Ile
290                 295                 300

Gln Ser Phe Ser Val Arg Leu Gly Gln Lys Pro Val Phe Trp Thr Cys
305                 310                 315                 320

Val Ile Leu Leu Glu Ile Ala Tyr Gly Val Ala Leu Leu Val Gly Ala
                325                 330                 335

Ala Ser Pro Cys Leu Trp Ser Lys Ile Val Thr Gly Leu Gly His Ala
            340                 345                 350

Val Leu Ala Ser Ile Leu Trp Phe His Ala Lys Ser Val Asp Leu Lys
            355                 360                 365

Ser Lys Ala Ser Ile Thr Ser Phe Tyr Met Phe Ile Trp Lys Leu Phe
            370                 375                 380

Tyr Ala Glu Tyr Leu Leu Ile Pro Phe Val Arg
385                 390                 395

<210> SEQ ID NO 7
<211> LENGTH: 393
<212> TYPE: PRT
<213> ORGANISM: Arabidopsis thaliana

<400> SEQUENCE: 7

Met Glu Ser Leu Leu Ser Ser Ser Ser Leu Val Ser Ala Ala Gly Gly
 1               5                  10                  15

Phe Cys Trp Lys Lys Gln Asn Leu Lys Leu His Ser Leu Ser Glu Ile
```

```
                    20                  25                  30
Arg Val Leu Arg Cys Asp Ser Ser Lys Val Ala Lys Pro Lys Phe
            35                  40                  45

Arg Asn Asn Leu Val Arg Pro Asp Gly Gln Gly Ser Ser Leu Leu Leu
 50                  55                  60

Tyr Pro Lys His Lys Ser Arg Phe Arg Val Asn Ala Thr Ala Gly Gln
 65                  70                  75                  80

Pro Glu Ala Phe Asp Ser Asn Ser Lys Gln Lys Ser Phe Arg Asp Ser
            85                  90                  95

Leu Asp Ala Phe Tyr Arg Phe Ser Arg Pro His Thr Val Ile Gly Thr
            100                 105                 110

Val Leu Ser Ile Leu Ser Val Ser Phe Leu Ala Val Glu Lys Val Ser
            115                 120                 125

Asp Ile Ser Pro Leu Leu Phe Thr Gly Ile Leu Glu Ala Val Val Ala
            130                 135                 140

Ala Leu Met Met Asn Ile Tyr Ile Val Gly Leu Asn Gln Leu Ser Asp
145                 150                 155                 160

Val Glu Ile Asp Lys Val Asn Lys Pro Tyr Leu Pro Leu Ala Ser Gly
                165                 170                 175

Glu Tyr Ser Val Asn Thr Gly Ile Ala Ile Val Ala Ser Phe Ser Ile
                180                 185                 190

Met Ser Phe Trp Leu Gly Trp Ile Val Gly Ser Trp Pro Leu Phe Trp
            195                 200                 205

Ala Leu Phe Val Ser Phe Met Leu Gly Thr Ala Tyr Ser Ile Asn Leu
            210                 215                 220

Pro Leu Leu Arg Trp Lys Arg Phe Ala Leu Val Ala Ala Met Cys Ile
225                 230                 235                 240

Leu Ala Val Arg Ala Ile Ile Val Gln Ile Ala Phe Tyr Leu His Ile
                245                 250                 255

Gln Thr His Val Phe Gly Arg Pro Ile Leu Phe Thr Arg Pro Leu Ile
            260                 265                 270

Phe Ala Thr Ala Phe Met Ser Phe Phe Ser Val Ile Ala Leu Phe
            275                 280                 285

Lys Asp Ile Pro Asp Ile Glu Gly Asp Lys Ile Phe Gly Ile Arg Ser
290                 295                 300

Phe Ser Val Thr Leu Gly Gln Lys Arg Val Phe Trp Thr Cys Val Thr
305                 310                 315                 320

Leu Leu Gln Met Ala Tyr Ala Val Ala Ile Leu Val Gly Ala Thr Ser
                325                 330                 335

Pro Phe Ile Trp Ser Lys Val Ile Ser Val Val Gly His Val Ile Leu
                340                 345                 350

Ala Thr Thr Leu Trp Ala Arg Ala Lys Ser Val Asp Leu Ser Ser Lys
            355                 360                 365

Thr Glu Ile Thr Ser Cys Tyr Met Phe Ile Trp Lys Leu Phe Tyr Ala
            370                 375                 380

Glu Tyr Leu Leu Leu Pro Phe Leu Lys
385                 390

<210> SEQ ID NO 8
<211> LENGTH: 361
<212> TYPE: PRT
<213> ORGANISM: Cuphea pulcherrima

<400> SEQUENCE: 8
```

```
Met Arg Met Glu Ser Leu Leu Asn Ser Phe Ser Pro Ser Pro Ala
1               5                   10                  15

Gly Gly Lys Ile Cys Arg Ala Asp Thr Tyr Lys Ala Tyr Phe Ala
            20                  25              30

Thr Ala Arg Cys Asn Thr Leu Asn Ser Leu Asn Lys Asn Thr Gly Glu
        35                  40                  45

Tyr His Leu Ser Arg Thr Arg Gln Arg Phe Thr Phe His Gln Asn Gly
    50                  55                  60

His Arg Thr Tyr Leu Val Lys Ala Val Ser Gly Gln Ser Leu Glu Ser
65                  70                  75                  80

Glu Pro Glu Ser Tyr Pro Asn Asn Arg Trp Asp Tyr Val Lys Ser Ala
                85                  90                  95

Ala Asp Ala Phe Tyr Arg Phe Ser Arg Pro His Thr Ile Ile Gly Thr
                100                 105                 110

Ala Leu Ser Ile Val Ser Val Ser Leu Leu Ala Val Glu Lys Leu Pro
            115                 120                 125

Glu Leu Asn Ser Met Phe Phe Thr Gly Leu Leu Glu Val Ile Leu Ala
    130                 135                 140

Ala Leu Phe Met Asn Ile Tyr Ile Val Gly Leu Asn Gln Leu Ser Asp
145                 150                 155                 160

Ile Asp Ile Asp Lys Val Asn Lys Pro Tyr Leu Pro Leu Ala Ser Gly
                165                 170                 175

Glu Phe Ser Val Gly Thr Gly Val Thr Ile Val Thr Ser Phe Leu Ile
            180                 185                 190

Met Ser Phe Trp Leu Gly Trp Val Gly Ser Trp Pro Leu Phe Trp
    195                 200                 205

Ala Leu Phe Ile Ser Phe Val Leu Gly Thr Ala Tyr Ser Ile Asp Met
210                 215                 220

Pro Met Leu Arg Trp Lys Arg Ser Ala Val Val Ala Ala Leu Cys Ile
225                 230                 235                 240

Leu Ala Val Arg Ala Val Ile Val Gln Ile Ala Phe Phe Leu His Met
                245                 250                 255

Gln Met His Val Tyr Gly Arg Ala Ala Leu Ser Arg Pro Val Ile
                260                 265                 270

Phe Ala Thr Gly Phe Met Ser Phe Ser Ile Val Ile Ala Leu Phe
            275                 280                 285

Lys Asp Ile Pro Asp Ile Glu Gly Asp Lys Ile Phe Gly Ile Arg Ser
                290                 295                 300

Phe Thr Val Arg Leu Gly Gln Glu Arg Val Phe Trp Ile Cys Ile Ser
305                 310                 315                 320

Leu Leu Glu Met Ala Tyr Ala Val Ala Leu Trp Val Leu Arg Ala Arg
                325                 330                 335

Gly Arg Lys Lys His Ala Asp Gly Val Ser Ala Ser Glu Phe Phe Leu
                340                 345                 350

Ser Ile Ser Gly Gly Arg Lys Asn Leu
    355                 360
```

<210> SEQ ID NO 9
<211> LENGTH: 395
<212> TYPE: PRT
<213> ORGANISM: Allium porrum

<400> SEQUENCE: 9

```
Met Leu Ser Met Asp Ser Leu Leu Thr Lys Pro Val Val Ile Pro Leu
1               5                   10                  15
```

Pro Ser Pro Val Cys Ser Leu Pro Ile Leu Arg Gly Ser Ser Ala Pro
            20                  25                  30

Gly Gln Tyr Ser Cys Arg Asn Tyr Asn Pro Ile Arg Ile Gln Arg Cys
        35                  40                  45

Leu Val Asn Tyr Glu His Val Lys Pro Arg Phe Thr Thr Cys Ser Arg
        50                  55                  60

Ser Gln Lys Leu Gly His Val Lys Ala Thr Ser Glu His Ser Leu Glu
65                  70                  75                  80

Ser Gly Ser Glu Gly Tyr Thr Pro Arg Ser Ile Trp Glu Ala Val Leu
                85                  90                  95

Ala Ser Leu Asn Val Leu Tyr Lys Phe Ser Arg Pro His Thr Ile Ile
            100                 105                 110

Gly Thr Ala Met Gly Ile Met Ser Val Ser Leu Leu Val Val Glu Ser
            115                 120                 125

Leu Ser Asp Ile Ser Pro Leu Phe Phe Val Gly Leu Leu Glu Ala Val
130                 135                 140

Val Ala Ala Leu Phe Met Asn Val Tyr Ile Val Gly Leu Asn Gln Leu
145                 150                 155                 160

Phe Asp Ile Glu Ile Asp Lys Val Asn Lys Pro Asp Leu Pro Leu Ala
                165                 170                 175

Ser Gly Glu Tyr Ser Pro Arg Ala Gly Thr Ala Ile Val Ile Ala Ser
            180                 185                 190

Ala Ile Met Ser Phe Gly Ile Gly Trp Leu Val Gly Ser Trp Pro Leu
            195                 200                 205

Phe Trp Ala Leu Phe Ile Ser Phe Val Leu Gly Thr Ala Tyr Ser Ile
210                 215                 220

Asn Leu Pro Phe Leu Arg Trp Lys Arg Ser Ala Val Val Ala Ala Ile
225                 230                 235                 240

Cys Ile Leu Ala Val Arg Ala Val Ile Val Gln Leu Ala Phe Phe Leu
                245                 250                 255

His Ile Gln Ser Phe Val Phe Lys Arg Pro Ala Ser Phe Thr Arg Pro
            260                 265                 270

Leu Ile Phe Ala Thr Ala Phe Met Ser Phe Ser Val Val Ile Ala
            275                 280                 285

Leu Phe Lys Asp Ile Pro Asp Ile Asp Gly Asp Lys Ile Phe Gly Ile
            290                 295                 300

His Ser Phe Ser Val Arg Leu Gly Gln Glu Arg Val Phe Trp Ile Cys
305                 310                 315                 320

Ile Tyr Leu Leu Glu Met Ala Tyr Thr Val Val Met Val Val Gly Ala
                325                 330                 335

Thr Ser Ser Cys Leu Trp Ser Lys Cys Leu Thr Val Ile Gly His Ala
            340                 345                 350

Ile Leu Gly Ser Leu Leu Trp Asn Arg Ala Arg Ser His Gly Pro Met
            355                 360                 365

Thr Lys Thr Thr Ile Thr Ser Phe Tyr Met Phe Val Trp Lys Leu Phe
370                 375                 380

Tyr Ala Glu Tyr Leu Leu Ile Pro Phe Val Arg
385                 390                 395

<210> SEQ ID NO 10
<211> LENGTH: 400
<212> TYPE: PRT
<213> ORGANISM: Triticum sp.

<400> SEQUENCE: 10

```
Met Asp Ser Leu Arg Leu Arg Pro Ser Ser Leu Arg Ser Ala Pro Gly
1               5                   10                  15

Ala Ala Ala Arg Arg Arg Asp His Ile Leu Pro Ser Phe Cys Ser
            20                  25                  30

Ile Gln Arg Asn Gly Lys Gly Arg Val Thr Leu Ser Ile Gln Ala Ser
                35                  40                  45

Lys Gly Pro Thr Ile Asn His Cys Lys Lys Phe Leu Asp Trp Lys Tyr
    50                  55                  60

Ser Asn His Arg Ile Ser His Gln Ser Ile Asn Thr Ser Ala Lys Ala
65                  70                  75                  80

Gly Gln Ser Leu Gln Pro Glu Thr Glu Ala His Asp Pro Ala Ser Phe
                85                  90                  95

Trp Lys Pro Ile Ser Ser Ser Leu Asp Ala Phe Tyr Arg Phe Ser Arg
                100                 105                 110

Pro His Thr Ile Ile Gly Thr Ala Leu Ser Ile Val Ser Val Ser Leu
                115                 120                 125

Leu Ala Val Glu Ser Leu Ser Asp Ile Ser Pro Leu Phe Leu Thr Gly
130                 135                 140

Leu Leu Glu Ala Val Ala Ala Leu Phe Met Asn Ile Tyr Ile Val
145                 150                 155                 160

Gly Leu Asn Gln Leu Phe Asp Ile Glu Ile Asp Lys Val Asn Lys Pro
                165                 170                 175

Thr Leu Pro Leu Ala Ser Gly Glu Tyr Ser Pro Ala Thr Gly Val Ala
                180                 185                 190

Ile Val Ser Val Phe Ala Ala Met Ser Phe Gly Leu Gly Trp Val Val
                195                 200                 205

Gly Ser Pro Pro Leu Phe Trp Ala Leu Phe Ile Ser Phe Val Leu Gly
    210                 215                 220

Thr Ala Tyr Ser Val Asn Leu Pro Tyr Phe Arg Trp Lys Arg Ser Ala
225                 230                 235                 240

Val Val Ala Ala Leu Cys Ile Leu Ala Val Arg Ala Val Ile Val Gln
                245                 250                 255

Leu Ala Phe Phe Leu His Ile Gln Thr Phe Val Phe Arg Arg Pro Ala
                260                 265                 270

Val Phe Ser Lys Pro Leu Ile Phe Ala Thr Ala Phe Met Thr Phe Phe
                275                 280                 285

Ser Val Val Ile Ala Leu Phe Lys Asp Ile Pro Asp Ile Glu Gly Asp
    290                 295                 300

Arg Ile Phe Gly Ile Gln Ser Phe Ser Val Arg Leu Gly Gln Ser Lys
305                 310                 315                 320

Val Phe Trp Thr Cys Val Gly Leu Leu Glu Val Ala Tyr Gly Val Ala
                325                 330                 335

Ile Leu Met Gly Val Thr Ser Ser Leu Trp Ser Lys Ser Leu Thr
                340                 345                 350

Val Val Gly His Ala Ile Leu Ala Ser Ile Leu Trp Ser Ser Ala Arg
                355                 360                 365

Ser Ile Asp Leu Thr Ser Lys Ala Ala Ile Thr Ser Phe Tyr Met Leu
    370                 375                 380

Ile Trp Arg Leu Phe Tyr Ala Glu Tyr Leu Leu Ile Pro Leu Val Arg
385                 390                 395                 400
```

<210> SEQ ID NO 11

<211> LENGTH: 393
<212> TYPE: PRT
<213> ORGANISM: Cuphea pulcherrima

<400> SEQUENCE: 11

```
Met Arg Met Glu Ser Leu Leu Leu Asn Ser Phe Ser Pro Ser Pro Ala
1               5                   10                  15

Gly Gly Lys Ile Cys Arg Ala Asp Thr Tyr Lys Lys Ala Tyr Phe Ala
            20                  25                  30

Thr Ala Arg Cys Asn Thr Leu Asn Ser Leu Asn Lys Asn Thr Gly Glu
        35                  40                  45

Tyr His Leu Ser Arg Thr Arg Gln Arg Phe Thr Phe His Gln Asn Gly
    50                  55                  60

His Arg Thr Tyr Leu Val Lys Ala Val Ser Gly Gln Ser Leu Glu Ser
65                  70                  75                  80

Glu Pro Glu Ser Tyr Pro Asn Asn Arg Trp Asp Tyr Val Lys Ser Ala
                85                  90                  95

Ala Asp Ala Phe Tyr Arg Phe Ser Arg Pro His Thr Ile Ile Gly Thr
            100                 105                 110

Ala Leu Ser Ile Val Ser Val Ser Leu Leu Ala Val Glu Lys Leu Pro
        115                 120                 125

Glu Leu Asn Ser Met Phe Phe Thr Gly Leu Leu Glu Val Ile Leu Ala
    130                 135                 140

Ala Leu Phe Met Asn Ile Tyr Ile Val Gly Leu Asn Gln Leu Ser Asp
145                 150                 155                 160

Ile Asp Ile Asp Lys Val Asn Lys Pro Tyr Leu Pro Leu Ala Ser Gly
                165                 170                 175

Glu Phe Ser Val Gly Thr Gly Val Thr Ile Val Thr Ser Phe Leu Ile
            180                 185                 190

Met Ser Phe Trp Leu Gly Trp Val Val Gly Ser Trp Pro Leu Phe Trp
        195                 200                 205

Ala Leu Phe Ile Ser Phe Val Leu Gly Thr Ala Tyr Ser Ile Asp Met
    210                 215                 220

Pro Met Leu Arg Trp Lys Arg Ser Ala Val Ala Ala Leu Cys Ile
225                 230                 235                 240

Leu Ala Val Arg Ala Val Ile Val Gln Ile Ala Phe Phe Leu His Met
                245                 250                 255

Gln Met His Val Tyr Gly Arg Ala Ala Ala Leu Ser Arg Pro Val Ile
            260                 265                 270

Phe Ala Thr Gly Phe Met Ser Phe Phe Ser Ile Val Ile Ala Leu Phe
        275                 280                 285

Lys Asp Ile Pro Asp Ile Glu Gly Asp Lys Ile Phe Gly Ile Arg Ser
    290                 295                 300

Phe Thr Val Arg Leu Gly Gln Glu Arg Val Phe Trp Ile Cys Ile Ser
305                 310                 315                 320

Leu Leu Glu Met Ala Tyr Ala Val Ala Ile Leu Val Gly Ser Thr Ser
                325                 330                 335

Pro Tyr Leu Trp Ser Lys Val Ile Thr Val Ser Gly His Val Val Leu
            340                 345                 350

Ala Ser Ile Leu Trp Gly Arg Ala Lys Ser Ile Asp Phe Lys Ser Lys
        355                 360                 365

Ala Ala Leu Thr Ser Phe Tyr Met Phe Ile Trp Lys Leu Phe Tyr Ala
    370                 375                 380

Glu Tyr Leu Leu Ile Pro Leu Val Arg
```

```
385            390

<210> SEQ ID NO 12
<211> LENGTH: 14
<212> TYPE: PRT
<213> ORGANISM: artificial sequence
<220> FEATURE:
<223> OTHER INFORMATION: Conserved Motif
<220> FEATURE:
<221> NAME/KEY: MISC_FEATURE
<222> LOCATION: (3)..(3)
<223> OTHER INFORMATION: x = w or y
<220> FEATURE:
<221> NAME/KEY: MISC_FEATURE
<222> LOCATION: (4)..(4)
<223> OTHER INFORMATION: x = k or r
<220> FEATURE:
<221> NAME/KEY: MISC_FEATURE
<222> LOCATION: (11)..(11)
<223> OTHER INFORMATION: x = i or v

<400> SEQUENCE: 12

Ala Phe Xaa Xaa Phe Ser Arg Pro His Thr Xaa Ile Gly Thr
1               5                   10

<210> SEQ ID NO 13
<211> LENGTH: 26
<212> TYPE: PRT
<213> ORGANISM: artificial sequence
<220> FEATURE:
<223> OTHER INFORMATION: Conserved Motif
<220> FEATURE:
<221> NAME/KEY: MISC_FEATURE
<222> LOCATION: (2)..(2)
<223> OTHER INFORMATION: x = v or i
<220> FEATURE:
<221> NAME/KEY: MISC_FEATURE
<222> LOCATION: (11)..(11)
<223> OTHER INFORMATION: x = e, w, f, or s
<220> FEATURE:
<221> NAME/KEY: MISC_FEATURE
<222> LOCATION: (13)..(13)
<223> OTHER INFORMATION: x = v or i
<220> FEATURE:
<221> NAME/KEY: MISC_FEATURE
<222> LOCATION: (14)..(14)
<223> OTHER INFORMATION: x = d or e
<220> FEATURE:
<221> NAME/KEY: MISC_FEATURE
<222> LOCATION: (17)..(17)
<223> OTHER INFORMATION: x = k or r
<220> FEATURE:
<221> NAME/KEY: MISC_FEATURE
<222> LOCATION: (18)..(18)
<223> OTHER INFORMATION: x = i or v
<220> FEATURE:
<221> NAME/KEY: MISC_FEATURE
<222> LOCATION: (22)..(22)
<223> OTHER INFORMATION: x = h, n, t or y

<400> SEQUENCE: 13

Asn Xaa Tyr Ile Val Gly Leu Asn Gln Leu Xaa Asp Xaa Xaa Ile Asp
1               5                   10                  15

Xaa Xaa Asn Lys Pro Xaa Leu Pro Leu Ala
            20                  25

<210> SEQ ID NO 14
<211> LENGTH: 16
<212> TYPE: PRT
<213> ORGANISM: artificial sequence
<220> FEATURE:
<223> OTHER INFORMATION: Conserved Motif
<220> FEATURE:
```

```
<221> NAME/KEY: MISC_FEATURE
<222> LOCATION: (3)..(3)
<223> OTHER INFORMATION: x = i or l
<220> FEATURE:
<221> NAME/KEY: MISC_FEATURE
<222> LOCATION: (7)..(7)
<223> OTHER INFORMATION: x = i or v
<220> FEATURE:
<221> NAME/KEY: MISC_FEATURE
<222> LOCATION: (10)..(10)
<223> OTHER INFORMATION: x = i or m
<220> FEATURE:
<221> NAME/KEY: MISC_FEATURE
<222> LOCATION: (14)..(14)
<223> OTHER INFORMATION: x = r or k
<220> FEATURE:
<221> NAME/KEY: MISC_FEATURE
<222> LOCATION: (15)..(15)
<223> OTHER INFORMATION: x = l, q, i, or v
<220> FEATURE:
<221> NAME/KEY: MISC_FEATURE
<222> LOCATION: (16)..(16)
<223> OTHER INFORMATION: x = y or f

<400> SEQUENCE: 14

Ile Ala Xaa Phe Lys Asp Xaa Pro Asp Xaa Glu Gly Asp Xaa Xaa Xaa
1               5                   10                  15

<210> SEQ ID NO 15
<211> LENGTH: 17
<212> TYPE: PRT
<213> ORGANISM: artificial sequence
<220> FEATURE:
<223> OTHER INFORMATION: Conserved Motif
<220> FEATURE:
<221> NAME/KEY: MISC_FEATURE
<222> LOCATION: (1)..(1)
<223> OTHER INFORMATION: x = f or c
<220> FEATURE:
<221> NAME/KEY: MISC_FEATURE
<222> LOCATION: (3)..(3)
<223> OTHER INFORMATION: x = q or m
<220> FEATURE:
<221> NAME/KEY: MISC_FEATURE
<222> LOCATION: (10)..(10)
<223> OTHER INFORMATION: x = f or y
<220> FEATURE:
<221> NAME/KEY: MISC_FEATURE
<222> LOCATION: (11)..(11)
<223> OTHER INFORMATION: x = i, l, or a
<220> FEATURE:
<221> NAME/KEY: MISC_FEATURE
<222> LOCATION: (15)..(15)
<223> OTHER INFORMATION: x = i, m, or l
<220> FEATURE:
<221> NAME/KEY: MISC_FEATURE
<222> LOCATION: (16)..(16)
<223> OTHER INFORMATION: x = f, y, i, or l

<400> SEQUENCE: 15

Xaa Tyr Xaa Phe Ile Trp Lys Leu Phe Xaa Xaa Glu Tyr Leu Xaa Xaa
1               5                   10                  15
Pro

<210> SEQ ID NO 16
<211> LENGTH: 56
<212> TYPE: DNA
<213> ORGANISM: artificial sequence
<220> FEATURE:
<223> OTHER INFORMATION: Synthetic Primer Sequence

<400> SEQUENCE: 16
cgcgatttaa atggcgcgcc ctgcaggcgg ccgcctgcag ggcgcgccat ttaaat      56
```

<210> SEQ ID NO 17
<211> LENGTH: 32
<212> TYPE: DNA
<213> ORGANISM: artificial sequence
<220> FEATURE:
<223> OTHER INFORMATION: Synthetic Primer Sequence

<400> SEQUENCE: 17
tcgaggatcc gcggccgcaa gcttcctgca gg            32

<210> SEQ ID NO 18
<211> LENGTH: 32
<212> TYPE: DNA
<213> ORGANISM: artificial sequence
<220> FEATURE:
<223> OTHER INFORMATION: Synthetic Primer Sequence

<400> SEQUENCE: 18
tcgacctgca ggaagcttgc ggccgcggat cc            32

<210> SEQ ID NO 19
<211> LENGTH: 32
<212> TYPE: DNA
<213> ORGANISM: artificial sequence
<220> FEATURE:
<223> OTHER INFORMATION: Synthetic Primer Sequence

<400> SEQUENCE: 19
tcgacctgca ggaagcttgc ggccgcggat cc            32

<210> SEQ ID NO 20
<211> LENGTH: 32
<212> TYPE: DNA
<213> ORGANISM: artificial sequence
<220> FEATURE:
<223> OTHER INFORMATION: Synthetic Primer Sequence

<400> SEQUENCE: 20
tcgaggatcc gcggccgcaa gcttcctgca gg            32

<210> SEQ ID NO 21
<211> LENGTH: 36
<212> TYPE: DNA
<213> ORGANISM: artificial sequence
<220> FEATURE:
<223> OTHER INFORMATION: Synthetic Primer Sequence

<400> SEQUENCE: 21
tcgaggatcc gcggccgcaa gcttcctgca ggagct       36

<210> SEQ ID NO 22
<211> LENGTH: 28
<212> TYPE: DNA
<213> ORGANISM: artificial sequence
<220> FEATURE:
<223> OTHER INFORMATION: Synthetic Primer Sequence

<400> SEQUENCE: 22
cctgcaggaa gcttgcggcc gcggatcc                 28

<210> SEQ ID NO 23
<211> LENGTH: 36
<212> TYPE: DNA
<213> ORGANISM: artificial sequence
<220> FEATURE:

<223> OTHER INFORMATION: Synthetic Primer Sequence

<400> SEQUENCE: 23
tcgacctgca ggaagcttgc ggccgcggat ccagct                                    36

<210> SEQ ID NO 24
<211> LENGTH: 28
<212> TYPE: DNA
<213> ORGANISM: artificial sequence
<220> FEATURE:
<223> OTHER INFORMATION: Synthetic Primer Sequence

<400> SEQUENCE: 24
ggatccgcgg ccgcaagctt cctgcagg                                             28

<210> SEQ ID NO 25
<211> LENGTH: 39
<212> TYPE: DNA
<213> ORGANISM: artificial sequence
<220> FEATURE:
<223> OTHER INFORMATION: Synthetic Primer Sequence

<400> SEQUENCE: 25
gatcacctgc aggaagcttg cggccgcgga tccaatgca                                 39

<210> SEQ ID NO 26
<211> LENGTH: 31
<212> TYPE: DNA
<213> ORGANISM: artificial sequence
<220> FEATURE:
<223> OTHER INFORMATION: Synthetic Primer Sequence

<400> SEQUENCE: 26
ttggatccgc ggccgcaagc ttcctgcagg t                                         31

<210> SEQ ID NO 27
<211> LENGTH: 969
<212> TYPE: DNA
<213> ORGANISM: Nostoc punctiforme

<400> SEQUENCE: 27
atgagccaga gttctcaaaa cagcccttg ccacgcaaac ctgttcaatc atatttccat           60
tggttatacg ctttctggaa attctctcgc cctcacacga ttattggtac aagtctgagt          120
gtgttgagtt tgtatttaat tgctattgcc attagtaata ataccgcttc tttattcact          180
actcccggct ccctaagccc tctcttcggc gcatggattg cttgtctatg tggcaatgtt          240
tacattgtag gctgaatca attagaagat gttgatattg acaagattaa taaacctcat           300
ttaccgttgg catcaggtga gttttctcaa cagacgggac aattaattgt tgcatctact          360
gggatttttgg cactagttat ggcgtggcta actgggccat tcttgtttgg catggtaaca        420
attagtttgg ccattggtac tgcttattct ttaccgccaa ttcgcttaaa acagtttccc          480
ttttgggcag cgctgtgtat tttttcggta cgcggcacga ttgttaattt aggattgtat          540
ttgcactata gttgggcgct gaaacaaagc caaacaattc cgcctgtggt gtgggtgctg          600
acattgttta ttttggtgtt taccttgcg atcgcaatct ttaaagatat cccagatata           660
gaaggcgatc gcctctacaa tattactact ttcacgatta aactagggtc ccaagctgtg          720
tttaatctag ctctttgggt gataactgtc tgttatctag gataattct ggtaggagtg          780
ctacgcatcg cttcagttaa ccccattttt ctgataactg ctcatttggc gctgttggtt         840
tggatgtggt ggcggagttt ggcggtagac ttacaagata aaagtgcgat cgctcaattc          900

```
taccaattta tctggaaact ctttttttata gaatatctaa ttttttcctat cgcctgcttt    960 ttggcttag                                                              969
```

<210> SEQ ID NO 28
<211> LENGTH: 957
<212> TYPE: DNA
<213> ORGANISM: Anabaena sp.

<400> SEQUENCE: 28

```
atgaaccaaa gttcccaaga cagaccgttg cgacctaaac cattgcaatc atcttttcag     60
tggctttatg cttttttggaa attttcccgc ccacacacaa ttattggcac aagtctcagt    120
gttttgggct tatatttaat ttctatcgcc gtcagttcca ccggttttgc cctgacgcag    180
ataaactccg ttttaggagc atggctggcc tgtctctgtg caatgtttta tattgtgggg    240
ttaaatcaat tagaagatat tgaaattgat aaagttaata aacctcattt acctctagct    300
tcgggagaat ttagccgcaa acaaggacgg ataattgtaa ttctcacggg aattaccgcc    360
atagtattag cttggttaaa tggcccttat ttatttggta tggtggcggt gagtttagcc    420
attggtactg cctattcttt accaccaatt cgtttaaaac agtttcccctt ttgggcggcc    480 ttgtgtattt tttcagtaag gggaacgatt gttaatttag gattatatct gcacttcagt    540
tggctactac agaataaaca gtcaattcct ctacctgtat ggatattaac ggtatttatt    600
ttaatattta cctttgcgat cgccatcttt aaagatatcc ctgatatgga aggcgatcgc    660
ctctacaata ttaccactct caccatccaa ctagggccac aagctgtctt taattttggca   720 atgtgggtat taacggtttg ctacttgggt atggtgataa ttggtgtgct gcggctaggt    780
acaattaact cagtgtttct ggtcgtgact catttagtaa ttctctgttg gatgtggatg    840
cagagtttag ccgtagacat acatgacaaa acggcgatcg ctcaattcta tcaatttatt    900
tggaagctct ttttcctaga atatttaatg tttcccattg cctgtctttt agcttaa       957
```

<210> SEQ ID NO 29
<211> LENGTH: 927
<212> TYPE: DNA
<213> ORGANISM: Synechocystis sp.

<400> SEQUENCE: 29

```
atggcaacta tccaagcttt ttggcgcttc tcccgccccc ataccatcat tggtacaact     60
ctgagcgtct gggctgtgta tctgttaact attctcgggg atggaaactc agttaactcc    120
cctgcttccc tggatttagt gttcggcgct tggctggcct gcctgttggg taatgtgtac    180
attgtcggcc tcaaccaatt gtgggatgtg acattgacc gcatcaataa gccgaatttg    240
cccctagcta acggagattt ttctatcgcc cagggccgtt ggattgtggg actttgtggc    300
gttgcttcct tggcgatcgc ctggggatta gggctatggc tggggctaac ggtgggcatt    360
agtttgatta ttggcacggc ctattcggtg ccgccagtga ggttaaagcg ctttccctg    420 ctggcggccc tgtgtattct gacggtgcgg ggaattgtgg ttaacttggg cttattttta    480
ttttttagaa ttggtttagg ttatccccccc actttaataa ccccccatctg ggttttgact    540 ttatttatct tagttttcac cgtggcgatc gccattttta aagatgtgcc agatatggaa    600
ggcgatcggc aatttaagat tcaaacttta acttgcaaa tcggcaaaca aaacgttttt    660
cggggaacct taatttttact cactggttgt tatttagcca tggcaatctg ggcttatgg    720 gcggctatgc ctttaaatac tgctttcttg attgtttccc atttgtgctt attagcctta    780
```

```
ctctggtggc ggagtcgaga tgtacactta gaaagcaaaa ccgaaattgc tagttttat    840 cagtttattt ggaagctatt tttcttagag tacttgctgt atcccttggc tctgtggtta    900
cctaattttt ctaatactat tttttag                                        927

<210> SEQ ID NO 30
<211> LENGTH: 1569
<212> TYPE: DNA
<213> ORGANISM: Zea mays

<400> SEQUENCE: 30
ccacgcgtcc gcccggccaa gggatggacg cgcttcgcct acggccgtcc ctcctctccg     60
tgcggcccgg cgcggcccgc ccgcgagatc attttctacc accatgttgt tccatacaac    120
gaaatggtga aggacgaatt tgcttttcta gccaaaggac ccaaggtcct accttgcatc    180
accatcagaa attcttcgaa tggaaatcct cctattgtag gatatcacat cgatcattaa    240
atacttctgt taatgcttcg gggcaacagc tgcagtctga acctgaaaca catgattcta    300
caaccatctg gagggcaata tcatcttctc tagatgcatt ttacagattt tcccggccac    360
atactgtcat aggaacagca ttaagcatag tctcagtttc ccttctagct gtccagagct    420
tgtctgatat atcacctttg ttcctcactg gtttgctgga ggcagtggta gctgcccttt    480
tcatgaatat ctatattgtt ggactgaacc agttattcga cattgagata gacaaggtta    540
acaagccaac tcttccattg gcatctgggg aatacacccc tgcaactggg gttgcaatag    600
tttcggtctt tgccgctatg agctttggcc ttggatgggc tgttggatca caacctctgt    660
tttgggctct tttcataagc tttgttcttg ggactgcata ttcaatcaat ctgccgtacc    720
ttcgatggaa gagatttgct gttgttgcag cactgtgcat attagcagtc cgtgcagtga    780
ttgttcagct ggccttttt ctccacattc agacttttgt tttcaggaga ccggcagtgt    840
tttctaggcc attattattt gcaactggat ttatgacgtt cttctctgtt gtaatagcac    900
tattcaagga tatacctgac atcgaaggag accgcatatt cgggatccga tccttcagcg    960
tccggttagg gcaaaagaag gtctttttgga tctgcgttgg cttgcttgag atggcctaca   1020
gcgttgcgat actgatggga gctacctctt cctgtttgtg gagcaaaaca gcaaccatcg   1080
ctggccattc catacttgcc gcgatcctat ggagctgcgc gcgatcggtg gacctgacga   1140
gcaaagccgc aataacgtcc ttctacatgt tcatctggaa gctgttctac gcggagtacc   1200
tgctcatccc tctggtgcgg tgagcgcgag gcgaggtggt ggcagacgga tcggcgtcgg   1260
cggggcggca acaactcca cgggagaact tgagtgccgg aagtaaactc ccgtttgaaa    1320
gttgaagcgt gcaccaccgg caccgggcag agagagacac ggtggctgga tggatacgga   1380 tggcccccc aataaattcc cccgtgcatg gtaccccacg ctgcttgatg atatcccatg   1440
tgtccgggtg atcgtctcta gagagattgg ttgcacaacg tccaacatag cccgtaggta   1500
ttgctaccac tgctagtatg atactccttc ctagtccttg ccaaaaaaaa aaaaaaaaa   1560 aaaaaaaag                                                           1569

<210> SEQ ID NO 31
<211> LENGTH: 1236
<212> TYPE: DNA
<213> ORGANISM: Glycine max (ppt2)

<400> SEQUENCE: 31
atggattcac tgcttcttcg atctttccct aatattaata acgcctcttc tctcaccacc     60
actggtgcaa atttctccag gactaaatct ttcgccaaca tttaccatgc aagttcttat    120
```

-continued

```
gtgccaaatg cttcatggca caataggaaa atccaaaaag aatataattt tttgaggttt    180
cggtggccaa gtttgaacca tcattacaaa ggcattgagg gagcgtgtac atgtaaaaaa    240
tgtaatataa aatttgttgt gaaagcgacc tctgaaaaat ctcttgagtc tgaacctcaa    300
gcttttgatc caaaaagcat tttggactct gtcaagaatt ccttggatgc tttctacagg    360
ttttccaggc ctcacacagt tattggcaca gcattaagca taatttctgt gtctcttctt    420
gctgttgaga aaatatcaga tatatctcca ttatttttta ctggtgtgtt ggaggctgtg    480
gttgctgccc tgtttatgaa tatttatatt gttggtttga atcaattgtc tgatgttgaa    540
atagacaaga taaacaagcc gtatcttcca ttagcatctg gggaatattc ctttgaaact    600
ggtgtcacta ttgttgcatc ttttttcaatt ctgagttttt ggcttggctg ggttgtaggt    660
tcatggccat tattttgggc cctttttgta agctttgtgc taggaactgc ttattcaatc    720
aatgtgcctc tgttgagatg gaagaggttt gcagtgcttg cagcgatgtg cattctagct    780
gttcgggcag taatagttca acttgcattt ttccttcaca tgcagactca tgtgtacaag    840
aggccacctg tctttttcaag accattgatt tttgctactg cattcatgag cttcttctct    900
gtagttatag cactgtttaa ggatatacct gacattgaag gagataaagt atttggcatc    960
caatcttttt cagtgcgttt aggtcagaag ccggtgttct ggacttgtgt tacccttctt   1020
gaaatagctt atggagtcgc cctcctggtg ggagctgcat ctccttgtct ttggagcaaa   1080
attttcacgg gtctgggaca cgctgtgctg gcttcaattc tctggtttca tgccaaatct   1140
gtagatttga aaagcaaagc ttcgataaca tccttctata tgtttatttg gaagctattt   1200
tatgcagaat acttactcat tcctttttgtt agatga                             1236
```

<210> SEQ ID NO 32
<211> LENGTH: 1188
<212> TYPE: DNA
<213> ORGANISM: Glycine max (ppt1)

<400> SEQUENCE: 32

```
atggattcga tgcttcttcg atcttttcct aatattaaca acgcttcttc tctcgccacc     60
actggttctt atttgccaaa tgcttcatgg cacaatagga aatccaaaaa agaatataat    120
tttttgaggt ttcggtggcc aagtttgaac caccattaca aaagcattga aggagggtgt    180
acatgtaaaa aatgtaatat aaaatttgtt gtgaaagcga cctctgaaaa atcttttgag    240
tctgaacccc aagcttttga tccaaaaagc attttggact ctgtcaagaa ttccttggat    300
gctttctaca ggttttccag acctcacaca gttattggca cagcattaag cataatttct    360
gtgtccctcc ttgctgttga gaaaatatca gatatatctc cattattttt tactggtgtg    420
ttggaggctg tggttgctgc cctgtttatg aatatttata ttgttggttt gaatcaattg    480
tctgatgttg aaatagacaa gataaacaag ccgtatcttc cattagcatc tggggaatat    540 tccttttgaaa ctggtgtcac tattgttgca tcttttttcaa ttctgagttt ttggcttggc    600
tgggttgtag gttcatggcc attattttgg gcccttttttg taagctttgt gctaggaact    660
gcttattcaa tcaatgtgcc tctgttgaga tggaagaggt ttgcagtgct tgcagcgatg    720
tgcattctag ctgttcgggc agtaatagtt caacttgcat ttttccttca catccagact    780
catgtataca agaggccacc tgtcttttca agatcattga ttttttgctac tgcattcatg    840 agcttcttct ctgtagttat agcactgttt aaggatatac ctgacattga aggagataaa    900
gtatttggca tccaatcttt ttcagtgcgt ttaggtcaga agccggtatt ctggacttgt    960
```

| gttatccttc ttgaaatagc ttatggagtc gccctcctgg tgggagctgc atctccttgt | 1020 |
| ctttggagca aaattgtcac gggtctggga cacgctgttc tggcttcaat tctctggttt | 1080 |
| catgccaaat ctgtagattt gaaaagcaaa gcttcgataa catccttcta tatgtttatt | 1140 |
| tggaagctat tttatgcaga atacttactc attccttttg ttagatga | 1188 |

<210> SEQ ID NO 33
<211> LENGTH: 1182
<212> TYPE: DNA
<213> ORGANISM: Arabidopsis thaliana

<400> SEQUENCE: 33

| atggagtctc tgctctctag ttcttctctt gtttccgctg ctggtgggtt ttgttggaag | 60 |
| aagcagaatc taaagctcca ctctttatca gaaatccgag ttctgcgttg tgattcgagt | 120 |
| aaagttgtcg caaaaccgaa gtttaggaac atcttgtta ggcctgatgg tcaaggatct | 180 |
| tcattgttgt tgtatccaaa acataagtcg agatttcggg ttaatgccac tgcgggtcag | 240 |
| cctgaggctt cgactcgaa tagcaaacag aagtctttta gagactcgtt agatgcgttt | 300 |
| tacaggtttt ctaggcctca tacagttatt ggcacagtgc ttagcatttt atctgtatct | 360 |
| ttcttagcag tagagaaggt ttctgatata tctcctttac ttttcactgg catcttggag | 420 |
| gctgttgttg cagctctcat gatgaacatt tacatagttg ggctaaatca gttgtctgat | 480 |
| gttgaaatag ataaggttaa caagccctat cttccattgg catcaggaga atattctgtt | 540 |
| aacaccggca ttgcaatagt agcttccttc tccatcatga gtttctggct tgggtggatt | 600 |
| gttggttcat ggccattgtt ctgggctctt tttgtgagtt tcatgctcgg tactgcatac | 660 |
| tctatcaatt tgccactttt acggtggaaa agatttgcat tggttgcagc aatgtgtatc | 720 |
| ctcgctgtcc gagctattat tgttcaaatc gccttttatc tacatattca gacacatgtg | 780 |
| tttggaagac caatcttgtt cactaggcct cttattttcg ccactgcgtt tatgagcttt | 840 |
| ttctctgtcg ttattgcatt gtttaaggat atacctgata tcgaagggga taagatattc | 900 |
| ggaatccgat cattctctgt aactctgggt cagaaacggg tgttttggac atgtgttaca | 960 |
| ctacttcaaa tggcttacgc tgttgcaatt ctagttggag ccacatctcc attcatatgg | 1020 |
| agcaaagtca tctcggttgt gggtcatgtt atactcgcaa caactttgtg ggctcgagct | 1080 |
| aagtccgttg atctgagtag caaaaccgaa ataacttcat gttatatgtt catatggaag | 1140 |
| ctcttttatg cagagtactt gctgttacct tttttgaagt ga | 1182 |

<210> SEQ ID NO 34
<211> LENGTH: 1374
<212> TYPE: DNA
<213> ORGANISM: Cuphea pulcherrima

<400> SEQUENCE: 34

| ccacgcgtcc ggctggtttg tgggttttgc gagcacgagg aaggaaaaaa catgcggatg | 60 |
| gagtctctgc ttctgaattc tttctctcca tctccggcgg gaggaaaaat ttgtagggcc | 120 |
| gatacttaca agaaggccta cttcgcaact gcgaggtgca acacattgaa cagcctcaac | 180 |
| aagaatacag gtgaatatca tctcagcaga acccgacaac ggttcacatt tcaccaaaat | 240 |
| ggtcacagaa cttacctagt caaggcagtg tccgggcagt ccctggagtc tgagcccgaa | 300 |
| agttacccta acaataggtg ggattatgtc aaaagtgctg ctgatgcctt ctaccggttt | 360 |
| tctcgtcccc acacaattat aggcactgcg ttgagcatag tatcggtttc gcttcttgct | 420 |
| gtagagaagt tgcctgaatt gaattcaatg ttttttcactg gcttattgga ggtgattttg | 480 |

-continued

```
gctgccctct tcatgaatat atatattgtc ggtttgaatc agttgtctga tatagacatt      540
gacaaggtaa acaagccgta tcttcccctg gcatcaggag aattctcggt tggaactggg      600
gttaccattg taacatcctt cttgattatg agcttttggc tggggtgggt tgtcggttca      660
tggcccttgt tttgggccct tttcatcagt tttgtgcttg aacagcata ctcaatcgat       720 atgccaatgc tcagatggaa gagatctgca gttgtggctg cactgtgcat tctagctgtt      780
cgggccgtga ttgttcagat agcgtttttt ttgcacatgc agatgcatgt gtatggaaga      840
gcagctgcac tttctcggcc tgtaatattt gccacaggct ttatgagctt cttttctatt      900
gttattgcgt tgtttaagga cattcctgac atagaaggtg ataaaatatt tgggatccgg      960
tcattcactg ttcgtctggg ccaagaacgg gttttctgga tatgcatatc acttctcgaa     1020
atggcttatg ctgttgcgat tcttgttggg tcgacgtctc cctatctttg gagcaaagtc     1080
atcacggttt cgggtcatgt tgtgttggcc tccatactat ggggacgagc caagtctatc     1140
gactttaaga gcaaagcagc actaacctcc ttctacatgt ttatttggaa gctatttac      1200 gcagaatact tgcttatacc gcttgtacga tgagctttcg ggatcagaac attacattat     1260
cgtaaactga acaatttaga attgcatatt gttcagatga cagctccatc ttggcaataa     1320
aatttgatat gaatgtctct gatccaaaaa aaaaaaaaaa aaaaaaaaaa aaag           1374
```

<210> SEQ ID NO 35
<211> LENGTH: 1486
<212> TYPE: DNA
<213> ORGANISM: Allium porrum

<400> SEQUENCE: 35

```
gcacgagttt tgaagaatgt taagcatgga ctccctcctt accaagccag ttgtaatacc       60
tctgccttct ccagtttgtt cactaccaat cttgcgaggc agttctgcac cagggcagta     120
ttcatgtaga aactacaatc caataagaat tcaaaggtgc ctcgtaaatt atgaacatgt     180
gaaaccaagg tttacaacat gtagtaggtc tcaaaaactt ggtcatgtaa agccacatc      240 cgagcattct ttagaatctg gatccgaagg atacactcct agaagcatat gggaagccgt     300
actagcttca ctgaatgttc tatacaaatt ttcacgacct cacacaataa taggaacagc     360
aatgggcata atgtcagttt ctttgcttgt tgtcgagagc ctatccgata tttctcctct     420
gttttttgtg ggattattag aggctgtggt tgctgcattg tttatgaatg tttacattgt     480
aggtctgaat caattatttg acatagaaat agacaaggtc aataaacctg atcttcctct     540
tgcatctgga gaatactcac caagagctgg tactgctatt gtcattgctt cagccatcat     600
gagctttggc attggatggt tagttggctc ttggccatta ttctgggcgc tttttattag     660
tttcgttctt ggcactgcat attcaatcaa tctaccattt ctaagatgga agagatccgc     720
cgttgttgca gcaatatgta tccttgctgt acgagcagtt atagtccagc tcgccttttt     780
cttacacata cagagttttg ttttcaaaag accagcaagt ttcacaaggc cattgatatt     840
tgcaactgcc ttcatgagct tcttctcagt tgttattgct ctatttaagg atatacctga     900
tatagacgga gacaaaatat ttggcatcca ttctttcagc gtgcgccttg gccaggagag     960
ggtgttttgg atatgtatat atctccttga gatggcctac actgttgtca tggttgttgg    1020
agctacttcc tcatgcctat ggagcaaatg cttaacagtg ataggtcatg caattcttgg    1080
gtcgttactt tggaatcgtg ctagatctca tggaccaatg accaaaacca ctattacatc    1140
tttttatatg ttcgtgtgga agctcttcta tgctgagtac ttgctcattc cttttgtaag    1200
```

-continued

```
atgagggttt atgacctaca tggaaaagaa tcgcaagaga agatgagtag ataatggagg    1260
cagaaatggc tggaattaac aacgctttaa ttgtcatctt aaaaacggag agttctttca    1320
acaattgcag atcatttctc cttaattata ttcatgttgt atgttgtgtt aaagattatc    1380
attgaatgac aatagcctat gttgaattta ggatatccag tggttttctt tgttcttttt    1440
taagaattta ttcacagaaa aatgaagtaa aaaaaaaaaa aaaaaa                    1486
```

<210> SEQ ID NO 36
<211> LENGTH: 1670
<212> TYPE: DNA
<213> ORGANISM: Triticum sp.

<400> SEQUENCE: 36

```
ccacgcgtcc ggtcccactg cccgcccccc acccgcgcgc cgccgcggcg atggactcgc      60
tccgcctccg gccgtcctcg ctccgctccg cgccggcgc cgccgccgcc cgccggcgag     120
atcatattct accatcattt tgttcgatcc aacgaaatgg taaagggcga gttactttgt     180
ccatccaagc atccaaggcc cctaccatta tcactgtaa aaagttcttg gattggaaat     240
attccaacca taggatatca catcaatcaa taaatacttc tgcaaaagct gggcaatcgc     300
tacagcctga aactgaagca cacgatcctg caagcttctg gaagccaata tcatcttctc     360
tggacgcgtt ctacaggttt tctcggccac ataccatcat aggaacagca ctaagcatag     420
tctcagtttc ccttctagct gtcgagagct tatctgatat ttcgcccttg ttcctcactg     480
gtttgctgga ggcagtggtg gctgctcttt ttatgaacat ctatattgtt ggattgaatc     540
agttgttcga cattgaaatt gacaaggtta acaagccaac tcttccacta gcatctgggg     600
aatactctcc tgcaactgga gttgcaatag tgtcagtatt tgcagccatg agctttggcc     660
ttggatgggt tgttggatca ccacctctgt tttgggctct ttttattagc tttgttcttg     720
gaactgctta ttcagtcaat ctgccgtact ttcgatggaa gagatctgct gttgttgcag     780
cactctgcat attagcagtg cgtgcggtga ttgttcaact ggcattttt ctccacattc     840 agacatttgt tttcagaagg ccggcagtct tttcaaagcc attgatattt gcaactgcct     900
tcatgacatt cttctcagtt gtaatagcat tattcaagga tatacccgat attgaagggg     960
accgcatctt tggaattcaa tcttttagtg ttagattagg tcaaagcaag gttttctgga    1020
cttgtgttgg tctacttgag gttgcctacg gtgttgcgat actgatgggg gtaacttctt    1080
ccagtttgtg gagcaaatct ctaactgttg tgggccatgc aatcctcgcc agcatcttgt    1140
ggagcagcgc acggtccatc gacttgacaa gcaaagctgc gataacatcc ttctacatgc    1200
tcatctggag gctgttctac gcggagtacc tgctcatccc tctggtgaga tgaggaccga    1260
caagcagccc acgaagaac ttcagtgccg gagtacagct gtgcgaatcc atttgaattt    1320
cggatggtca cggaccgcgc ccaataaaac tcccagagcc ttgccccggt acatcgttga    1380
ttttccagcc atgaatggtg agatcaccac ctaaagatga taacctccc catgtaccca    1440 agctgggcca ggtgagctgt agtttagttg atgctagcga gcaacaactc ctgcagcagg    1500
cacgcggctg cctggaaaat aaggctcccc actcccaatt acattctgtt gtacggtttt    1560
agtacttgtg aattttgctc tggtccgttg ttgtctagga tgtttggaac attgcgcaga    1620
ctttcttata tcttaccggg agggtgaat tggcaaaaaa aaaaaaaaag               1670
```

<210> SEQ ID NO 37
<211> LENGTH: 41
<212> TYPE: DNA
<213> ORGANISM: artificial sequence

```
<220> FEATURE:
<223> OTHER INFORMATION: Primer Sequence

<400> SEQUENCE: 37
ggatccgcgg ccgcacaatg gagtctctgc tctctagttc t          41

<210> SEQ ID NO 38
<211> LENGTH: 38
<212> TYPE: DNA
<213> ORGANISM: artificial sequence
<220> FEATURE:
<223> OTHER INFORMATION: Primer Sequence

<400> SEQUENCE: 38
ggatcctgca ggtcacttca aaaaggtaa cagcaagt              38

<210> SEQ ID NO 39
<211> LENGTH: 14
<212> TYPE: PRT
<213> ORGANISM: artificial sequence
<220> FEATURE:
<223> OTHER INFORMATION: Conserved Motif
<220> FEATURE:
<221> NAME/KEY: MISC_FEATURE
<222> LOCATION: (1)..(1)
<223> OTHER INFORMATION: x = a or v
<220> FEATURE:
<221> NAME/KEY: MISC_FEATURE
<222> LOCATION: (2)..(2)
<223> OTHER INFORMATION: x = f or l
<220> FEATURE:
<221> NAME/KEY: MISC_FEATURE
<222> LOCATION: (3)..(3)
<223> OTHER INFORMATION: x = w or y
<220> FEATURE:
<221> NAME/KEY: MISC_FEATURE
<222> LOCATION: (4)..(4)
<223> OTHER INFORMATION: x = k or r
<220> FEATURE:
<221> NAME/KEY: MISC_FEATURE
<222> LOCATION: (11)..(11)
<223> OTHER INFORMATION: x = i or v

<400> SEQUENCE: 39

Xaa Xaa Xaa Xaa Phe Ser Arg Pro His Thr Xaa Ile Gly Thr
1               5                   10

<210> SEQ ID NO 40
<211> LENGTH: 26
<212> TYPE: PRT
<213> ORGANISM: artificial sequence
<220> FEATURE:
<223> OTHER INFORMATION: Conserved Motif
<220> FEATURE:
<221> NAME/KEY: MISC_FEATURE
<222> LOCATION: (2)..(2)
<223> OTHER INFORMATION: x = i or l
<220> FEATURE:
<221> NAME/KEY: MISC_FEATURE
<222> LOCATION: (11)..(11)
<223> OTHER INFORMATION: x = w, e, s, or f
<220> FEATURE:
<221> NAME/KEY: MISC_FEATURE
<222> LOCATION: (13)..(13)
<223> OTHER INFORMATION: x = v or i
<220> FEATURE:
<221> NAME/KEY: MISC_FEATURE
<222> LOCATION: (14)..(14)
<223> OTHER INFORMATION: x = d or e
<220> FEATURE:
<221> NAME/KEY: MISC_FEATURE
<222> LOCATION: (17)..(17)
<223> OTHER INFORMATION: x = r or k
```

```
<220> FEATURE:
<221> NAME/KEY: MISC_FEATURE
<222> LOCATION: (18)..(18)
<223> OTHER INFORMATION: x = i or v
<220> FEATURE:
<221> NAME/KEY: MISC_FEATURE
<222> LOCATION: (23)..(23)
<223> OTHER INFORMATION: x = n, h, y, t, or d

<400> SEQUENCE: 40

Asn Xaa Tyr Ile Val Gly Leu Asn Gln Leu Xaa Asp Xaa Xaa Ile Asp
1               5                   10                  15

Xaa Xaa Asn Lys Pro Xaa Leu Pro Leu Ala
            20                  25

<210> SEQ ID NO 41
<211> LENGTH: 16
<212> TYPE: PRT
<213> ORGANISM: artificial sequence
<220> FEATURE:
<223> OTHER INFORMATION: Conserved Motif
<220> FEATURE:
<221> NAME/KEY: MISC_FEATURE
<222> LOCATION: (3)..(3)
<223> OTHER INFORMATION: x = i or l
<220> FEATURE:
<221> NAME/KEY: MISC_FEATURE
<222> LOCATION: (7)..(7)
<223> OTHER INFORMATION: x = v or i
<220> FEATURE:
<221> NAME/KEY: MISC_FEATURE
<222> LOCATION: (10)..(10)
<223> OTHER INFORMATION: x = m or i
<220> FEATURE:
<221> NAME/KEY: MISC_FEATURE
<222> LOCATION: (11)..(11)
<223> OTHER INFORMATION: x = e or d
<220> FEATURE:
<221> NAME/KEY: MISC_FEATURE
<222> LOCATION: (14)..(14)
<223> OTHER INFORMATION: x = r or k
<220> FEATURE:
<221> NAME/KEY: MISC_FEATURE
<222> LOCATION: (15)..(15)
<223> OTHER INFORMATION: x = i, v, l, or q
<220> FEATURE:
<221> NAME/KEY: MISC_FEATURE
<222> LOCATION: (16)..(16)
<223> OTHER INFORMATION: x = y or f

<400> SEQUENCE: 41

Ile Ala Xaa Phe Lys Asp Xaa Pro Asp Xaa Xaa Gly Asp Xaa Xaa Xaa
1               5                   10                  15

<210> SEQ ID NO 42
<211> LENGTH: 17
<212> TYPE: PRT
<213> ORGANISM: artificial sequence
<220> FEATURE:
<223> OTHER INFORMATION: Conserved Motif
<220> FEATURE:
<221> NAME/KEY: MISC_FEATURE
<222> LOCATION: (1)..(1)
<223> OTHER INFORMATION: x = f or c
<220> FEATURE:
<221> NAME/KEY: MISC_FEATURE
<222> LOCATION: (3)..(3)
<223> OTHER INFORMATION: x = m or q
<220> FEATURE:
<221> NAME/KEY: MISC_FEATURE
<222> LOCATION: (4)..(4)
<223> OTHER INFORMATION: x = f or l
<220> FEATURE:
<221> NAME/KEY: MISC_FEATURE
```

-continued

```
<222> LOCATION: (5)..(5)
<223> OTHER INFORMATION: x = i or v
<220> FEATURE:
<221> NAME/KEY: MISC_FEATURE
<222> LOCATION: (7)..(7)
<223> OTHER INFORMATION: x = k or r
<220> FEATURE:
<221> NAME/KEY: MISC_FEATURE
<222> LOCATION: (10)..(10)
<223> OTHER INFORMATION: x = f or y
<220> FEATURE:
<221> NAME/KEY: MISC_FEATURE
<222> LOCATION: (11)..(11)
<223> OTHER INFORMATION: x = l, i or a
<220> FEATURE:
<221> NAME/KEY: MISC_FEATURE
<222> LOCATION: (15)..(15)
<223> OTHER INFORMATION: x = l, m, or i
<220> FEATURE:
<221> NAME/KEY: MISC_FEATURE
<222> LOCATION: (16)..(16)
<223> OTHER INFORMATION: x = f, y, l, or i

<400> SEQUENCE: 42

Xaa Tyr Xaa Xaa Xaa Trp Xaa Leu Phe Xaa Xaa Glu Tyr Leu Xaa Xaa
 1               5                  10                  15

Pro

<210> SEQ ID NO 43
<211> LENGTH: 349
<212> TYPE: PRT
<213> ORGANISM: Trichodesmium erythraeum

<400> SEQUENCE: 43

Met Gly Lys Ile Ala Gly Ser Gln Gln Gly Lys Ile Thr Thr Asn Trp
 1               5                  10                  15

Leu Gln Lys Tyr Val Pro Trp Leu Tyr Ser Phe Trp Lys Phe Ala Arg
                20                  25                  30

Pro His Thr Ile Ile Gly Thr Ser Leu Ser Val Leu Ala Leu Tyr Ile
            35                  40                  45

Ile Ala Met Gly Asp Arg Ser Asn Phe Phe Asp Lys Tyr Phe Phe Leu
        50                  55                  60

Tyr Ser Leu Ile Leu Leu Ile Thr Trp Ile Ser Cys Leu Cys Gly
 65                 70                  75                  80

Asn Ile Tyr Ile Val Gly Leu Asn Gln Leu Glu Asp Ile Glu Ile Asp
                85                  90                  95

Arg Ile Asn Lys Pro His Leu Pro Ile Ala Ala Gly Glu Phe Ser Arg
            100                 105                 110

Phe Ser Gly Gln Ile Ile Val Val Ile Thr Gly Ile Leu Ala Leu Ser
        115                 120                 125

Phe Ala Gly Leu Gly Gly Pro Phe Leu Leu Gly Thr Val Gly Ile Ser
    130                 135                 140

Leu Ala Ile Gly Thr Ala Tyr Ser Leu Pro Pro Ile Arg Leu Lys Arg
145                 150                 155                 160

Phe Pro Val Leu Ala Ala Leu Cys Ile Phe Thr Val Arg Gly Val Ile
                165                 170                 175

Val Asn Leu Gly Ile Phe Leu Ser Phe Val Trp Gly Phe Glu Lys Val
            180                 185                 190

Glu Glu Val Ser Gly Gly Leu Ile Lys Trp Met Gly Glu Leu Gly Glu
        195                 200                 205

Val Val Leu Leu Gln Lys Ser Leu Met Val Pro Glu Ile Pro Leu Thr
    210                 215                 220
```

-continued

Val Trp Ala Leu Thr Leu Phe Val Ile Val Phe Thr Phe Ala Ile Ala
225                 230                 235                 240

Ile Phe Lys Asp Ile Pro Asp Ile Glu Gly Asp Arg Gln Tyr Asn Ile
                245                 250                 255

Asn Thr Phe Thr Ile Lys Leu Gly Ala Phe Ala Val Phe Asn Leu Ala
                260                 265                 270

Arg Trp Val Leu Thr Phe Cys Tyr Leu Gly Met Val Met Val Gly Val
            275                 280                 285

Val Trp Leu Ala Ser Val Asn Leu Phe Phe Leu Val Ile Ser His Leu
        290                 295                 300

Leu Ala Leu Gly Ile Met Trp Trp Phe Ser Gln Arg Val Asp Leu His
305                 310                 315                 320

Asp Lys Lys Ala Ile Ala Asp Phe Tyr Gln Phe Ile Trp Lys Leu Phe
                325                 330                 335

Phe Leu Glu Tyr Leu Ile Phe Pro Met Ala Cys Phe Phe
            340                 345

<210> SEQ ID NO 44
<211> LENGTH: 300
<212> TYPE: PRT
<213> ORGANISM: Chloroflexus aurantiacus

<400> SEQUENCE: 44

Met Arg Lys Gln Leu Arg Leu Leu Ile Glu Phe Ala Arg Pro His Thr
1               5                   10                  15

Val Ile Ala Thr Ser Val Gln Val Leu Thr Met Leu Ile Ile Val Ile
                20                  25                  30

Gly Trp His Pro Pro Thr Leu Glu Leu Val Gly Leu Val Gly Val Thr
            35                  40                  45

Leu Val Val Cys Leu Ala Leu Asn Leu Tyr Val Val Gly Val Asn Gln
        50                  55                  60

Leu Thr Asp Val Ala Ile Asp Arg Ile Asn Lys Pro Trp Leu Pro Val
65                  70                  75                  80

Ala Ala Gly Gln Leu Ser Ser Asp Ala Ala Gln Arg Ile Val Ile Ser
                85                  90                  95

Ala Leu Phe Ile Ala Leu Thr Gly Ala Ala Met Leu Gly Pro Pro Leu
                100                 105                 110

Trp Trp Thr Val Ser Ile Ile Ala Leu Ile Gly Ser Leu Tyr Ser Leu
            115                 120                 125

Pro Pro Leu Arg Leu Lys Arg His Pro Leu Ala Ala Ala Leu Ser Ile
        130                 135                 140

Ala Gly Ala Arg Gly Val Ile Ala Asn Leu Gly Leu Ala Phe His Tyr
145                 150                 155                 160

Gln Tyr Trp Leu Asp Ser Glu Leu Pro Ile Thr Thr Leu Ile Leu Val
                165                 170                 175

Ala Thr Phe Phe Phe Gly Phe Ala Met Val Ile Ala Leu Tyr Lys Asp
                180                 185                 190

Leu Pro Asp Asp Arg Gly Asp Arg Leu Tyr Gln Ile Glu Thr Leu Thr
            195                 200                 205

Thr Arg Leu Gly Pro Gln Arg Val Leu His Leu Gly Arg Ile Leu Leu
        210                 215                 220

Thr Ala Cys Tyr Leu Leu Pro Ile Ala Val Gly Leu Trp Ser Leu Pro
225                 230                 235                 240

Thr Phe Ala Ala Ala Phe Leu Ala Leu Ser His Val Val Val Ile Ser

```
                    245                 250                 255
Val Phe Trp Leu Val Ser Met Arg Val Asp Leu Gln Arg Arg Gln Ser
            260                 265                 270

Ile Ala Ser Phe Tyr Met Phe Leu Trp Gly Ile Phe Tyr Thr Glu Phe
            275                 280                 285

Ala Leu Leu Ser Ile Tyr Arg Leu Thr Tyr Thr Leu
            290                 295                 300

<210> SEQ ID NO 45
<211> LENGTH: 402
<212> TYPE: PRT
<213> ORGANISM: Arabidopsis thaliana

<400> SEQUENCE: 45

Met Glu Leu Ser Ile Ser Gln Ser Pro Arg Val Arg Phe Ser Ser Leu
1               5                   10                  15

Ala Pro Arg Phe Leu Ala Ala Ser His His Arg Pro Ser Val His
            20                  25                  30

Leu Ala Gly Lys Phe Ile Ser Leu Pro Arg Asp Val Arg Phe Thr Ser
            35                  40                  45

Leu Ser Thr Ser Arg Met Arg Ser Lys Phe Val Ser Thr Asn Tyr Arg
        50                  55                  60

Lys Ile Ser Ile Arg Ser Val Cys Ala Phe Cys Asn Gly Thr His Lys
65                  70                  75                  80

Ser Arg Tyr Tyr Gln Ala Cys Ser Gln Val Gly Ala Ala Glu Ser Asp
            85                  90                  95

Asp Pro Val Leu Asp Arg Ile Ala Arg Phe Gln Asn Ala Cys Trp Arg
            100                 105                 110

Phe Leu Arg Pro His Thr Ile Arg Gly Thr Ala Leu Gly Ser Thr Ala
            115                 120                 125

Leu Val Thr Arg Ala Leu Ile Glu Asn Thr His Leu Ile Lys Trp Ser
130                 135                 140

Leu Val Leu Lys Ala Leu Ser Gly Leu Leu Ala Leu Ile Cys Gly Asn
145                 150                 155                 160

Gly Tyr Ile Val Gly Ile Asn Gln Ile Tyr Asp Ile Gly Ile Asp Lys
            165                 170                 175

Val Asn Lys Pro Tyr Leu Pro Ile Ala Ala Gly Asp Leu Ser Val Gln
            180                 185                 190

Ser Ala Trp Leu Leu Val Ile Phe Phe Ala Ile Ala Gly Leu Leu Val
            195                 200                 205

Val Gly Phe Asn Phe Gly Pro Phe Ile Thr Ser Leu Tyr Ser Leu Gly
            210                 215                 220

Leu Phe Leu Gly Thr Ile Tyr Ser Val Pro Pro Leu Arg Met Lys Arg
225                 230                 235                 240

Phe Pro Val Ala Ala Phe Leu Ile Ile Ala Thr Val Arg Gly Phe Leu
            245                 250                 255

Leu Asn Phe Gly Val Tyr His Ala Thr Arg Ala Ala Leu Gly Leu Pro
            260                 265                 270

Phe Gln Trp Ser Ala Pro Val Ala Phe Ile Thr Ser Phe Val Thr Leu
            275                 280                 285

Phe Ala Leu Val Ile Ala Ile Thr Lys Asp Leu Pro Asp Val Glu Gly
            290                 295                 300

Asp Arg Lys Phe Gln Ile Ser Thr Leu Ala Thr Lys Leu Gly Val Arg
305                 310                 315                 320
```

```
Asn Ile Ala Phe Leu Gly Ser Gly Leu Leu Val Asn Tyr Val Ser
            325                 330                 335

Ala Ile Ser Leu Ala Phe Tyr Met Pro Gln Val Phe Arg Gly Ser Leu
            340                 345                 350

Met Ile Pro Ala His Val Ile Leu Ala Ser Gly Leu Ile Phe Gln Thr
            355                 360                 365

Trp Val Leu Glu Lys Ala Asn Tyr Thr Lys Glu Ala Ile Ser Gly Tyr
        370                 375                 380

Tyr Arg Phe Ile Trp Asn Leu Phe Tyr Ala Glu Tyr Leu Leu Phe Pro
385                 390                 395                 400

Phe Leu

<210> SEQ ID NO 46
<211> LENGTH: 12
<212> TYPE: PRT
<213> ORGANISM: Artificial
<220> FEATURE:
<223> OTHER INFORMATION: Conserved Motif
<220> FEATURE:
<221> NAME/KEY: MISC_FEATURE
<222> LOCATION: (1)..(1)
<223> OTHER INFORMATION: x = w or y
<220> FEATURE:
<221> NAME/KEY: MISC_FEATURE
<222> LOCATION: (2)..(2)
<223> OTHER INFORMATION: x = r or k
<220> FEATURE:
<221> NAME/KEY: MISC_FEATURE
<222> LOCATION: (4)..(4)
<223> OTHER INFORMATION: x = l or s
<220> FEATURE:
<221> NAME/KEY: MISC_FEATURE
<222> LOCATION: (9)..(9)
<223> OTHER INFORMATION: x = i or v
<220> FEATURE:
<221> NAME/KEY: MISC_FEATURE
<222> LOCATION: (10)..(10)
<223> OTHER INFORMATION: x = i or r

<400> SEQUENCE: 46

Xaa Xaa Phe Xaa Arg Pro His Thr Xaa Xaa Gly Thr
1               5                   10

<210> SEQ ID NO 47
<211> LENGTH: 26
<212> TYPE: PRT
<213> ORGANISM: Artificial
<220> FEATURE:
<223> OTHER INFORMATION: Conserved Motif
<220> FEATURE:
<221> NAME/KEY: MISC_FEATURE
<222> LOCATION: (2)..(2)
<223> OTHER INFORMATION: x = v, i, or g
<220> FEATURE:
<221> NAME/KEY: MISC_FEATURE
<222> LOCATION: (7)..(7)
<223> OTHER INFORMATION: x = i or l
<220> FEATURE:
<221> NAME/KEY: MISC_FEATURE
<222> LOCATION: (10)..(10)
<223> OTHER INFORMATION: x = i or l
<220> FEATURE:
<221> NAME/KEY: MISC_FEATURE
<222> LOCATION: (11)..(11)
<223> OTHER INFORMATION: x = s, f, y, or e
<220> FEATURE:
<221> NAME/KEY: MISC_FEATURE
<222> LOCATION: (13)..(13)
<223> OTHER INFORMATION: x = v or i
<220> FEATURE:
<221> NAME/KEY: MISC_FEATURE
```

```
<222> LOCATION: (14)..(14)
<223> OTHER INFORMATION: x = r, s, g, e, or d
<220> FEATURE:
<221> NAME/KEY: MISC_FEATURE
<222> LOCATION: (17)..(17)
<223> OTHER INFORMATION: x = k or r
<220> FEATURE:
<221> NAME/KEY: MISC_FEATURE
<222> LOCATION: (18)..(18)
<223> OTHER INFORMATION: x = v or i
<220> FEATURE:
<221> NAME/KEY: MISC_FEATURE
<222> LOCATION: (22)..(22)
<223> OTHER INFORMATION: x = y, d, t, n, or h
<220> FEATURE:
<221> NAME/KEY: MISC_FEATURE
<222> LOCATION: (25)..(25)
<223> OTHER INFORMATION: x = i or l

<400> SEQUENCE: 47

Asn Xaa Tyr Ile Val Gly Xaa Asn Gln Xaa Xaa Asp Xaa Xaa Ile Asp
1               5                   10                  15

Xaa Xaa Asn Lys Pro Xaa Leu Pro Xaa Ala
            20                  25

<210> SEQ ID NO 48
<211> LENGTH: 14
<212> TYPE: PRT
<213> ORGANISM: Arabidopsis thaliana
<220> FEATURE:
<221> NAME/KEY: MISC_FEATURE
<222> LOCATION: (3)..(3)
<223> OTHER INFORMATION: x = l or i
<220> FEATURE:
<221> NAME/KEY: MISC_FEATURE
<222> LOCATION: (4)..(4)
<223> OTHER INFORMATION: x = f or t
<220> FEATURE:
<221> NAME/KEY: MISC_FEATURE
<222> LOCATION: (7)..(7)
<223> OTHER INFORMATION: x = l, i, or v
<220> FEATURE:
<221> NAME/KEY: MISC_FEATURE
<222> LOCATION: (10)..(10)
<223> OTHER INFORMATION: x = i, v, or m
<220> FEATURE:
<221> NAME/KEY: MISC_FEATURE
<222> LOCATION: (11)..(11)
<223> OTHER INFORMATION: x = e or d

<400> SEQUENCE: 48

Ile Ala Xaa Xaa Lys Asp Xaa Pro Asp Xaa Xaa Gly Asp Arg
1               5                   10

<210> SEQ ID NO 49
<211> LENGTH: 23
<212> TYPE: PRT
<213> ORGANISM: Artificial
<220> FEATURE:
<223> OTHER INFORMATION: Conserved Motif
<220> FEATURE:
<221> NAME/KEY: MISC_FEATURE
<222> LOCATION: (2)..(2)
<223> OTHER INFORMATION: x = d, e, t, a, or s
<220> FEATURE:
<221> NAME/KEY: MISC_FEATURE
<222> LOCATION: (3)..(3)
<223> OTHER INFORMATION: x = a, e, s, or t
<220> FEATURE:
<221> NAME/KEY: MISC_FEATURE
<222> LOCATION: (4)..(4)
<223> OTHER INFORMATION: x = i or l
<220> FEATURE:
<221> NAME/KEY: MISC_FEATURE
```

```
<222> LOCATION: (5)..(5)
<223> OTHER INFORMATION: x = s, t, or a
<220> FEATURE:
<221> NAME/KEY: MISC_FEATURE
<222> LOCATION: (6)..(6)
<223> OTHER INFORMATION: x = q, g, or s
<220> FEATURE:
<221> NAME/KEY: MISC_FEATURE
<222> LOCATION: (7)..(7)
<223> OTHER INFORMATION: x = f, y, or c
<220> FEATURE:
<221> NAME/KEY: MISC_FEATURE
<222> LOCATION: (9)..(9)
<223> OTHER INFORMATION: x = q, m, or r
<220> FEATURE:
<221> NAME/KEY: MISC_FEATURE
<222> LOCATION: (10)..(10)
<223> OTHER INFORMATION: x = f or l
<220> FEATURE:
<221> NAME/KEY: MISC_FEATURE
<222> LOCATION: (11)..(11)
<223> OTHER INFORMATION: x = i or v
<220> FEATURE:
<221> NAME/KEY: MISC_FEATURE
<222> LOCATION: (13)..(13)
<223> OTHER INFORMATION: x = n or k
<220> FEATURE:
<221> NAME/KEY: MISC_FEATURE
<222> LOCATION: (16)..(16)
<223> OTHER INFORMATION: x = y or f
<220> FEATURE:
<221> NAME/KEY: MISC_FEATURE
<222> LOCATION: (17)..(17)
<223> OTHER INFORMATION: x = a, l, or i
<220> FEATURE:
<221> NAME/KEY: MISC_FEATURE
<222> LOCATION: (21)..(21)
<223> OTHER INFORMATION: x = f, i, l, or m
<220> FEATURE:
<221> NAME/KEY: MISC_FEATURE
<222> LOCATION: (22)..(22)
<223> OTHER INFORMATION: x = f, l, i, or y
<220> FEATURE:
<221> NAME/KEY: MISC_FEATURE
<222> LOCATION: (20)..(20)
<223> OTHER INFORMATION: x = a, i, or l

<400> SEQUENCE: 49

Lys Xaa Xaa Xaa Xaa Xaa Xaa Tyr Xaa Xaa Xaa Trp Xaa Leu Phe Xaa
1               5                   10                  15

Xaa Glu Tyr Xaa Xaa Xaa Pro
            20

<210> SEQ ID NO 50
<211> LENGTH: 22
<212> TYPE: DNA
<213> ORGANISM: Artificial
<220> FEATURE:
<223> OTHER INFORMATION: Primer

<400> SEQUENCE: 50
gtggctcggc ttcactttttt ac                                          22

<210> SEQ ID NO 51
<211> LENGTH: 20
<212> TYPE: DNA
<213> ORGANISM: Artificial
<220> FEATURE:
<223> OTHER INFORMATION: Primer

<400> SEQUENCE: 51
ccacactcat atcaccgtgg                                              20
```

<210> SEQ ID NO 52
<211> LENGTH: 27
<212> TYPE: DNA
<213> ORGANISM: Artificial
<220> FEATURE:
<223> OTHER INFORMATION: Primer

<400> SEQUENCE: 52
cagtgctgga tagaattgcc cggttcc                                    27

<210> SEQ ID NO 53
<211> LENGTH: 26
<212> TYPE: DNA
<213> ORGANISM: Artificial
<220> FEATURE:
<223> OTHER INFORMATION: Primer

<400> SEQUENCE: 53
gagatctatc agtgcagtct gcttgg                                     26

<210> SEQ ID NO 54
<211> LENGTH: 23
<212> TYPE: DNA
<213> ORGANISM: Artificial
<220> FEATURE:
<223> OTHER INFORMATION: Primer

<400> SEQUENCE: 54
gggacaagca tttttattgc aag                                        23

<210> SEQ ID NO 55
<211> LENGTH: 24
<212> TYPE: DNA
<213> ORGANISM: Artificial
<220> FEATURE:
<223> OTHER INFORMATION: Primer

<400> SEQUENCE: 55
gccaagatca catgtgcagg aatc                                       24

<210> SEQ ID NO 56
<211> LENGTH: 24
<212> TYPE: DNA
<213> ORGANISM: Artificial
<220> FEATURE:
<223> OTHER INFORMATION: Primer

<400> SEQUENCE: 56
gccaagatca catgtgcagg aatc                                       24

<210> SEQ ID NO 57
<211> LENGTH: 386
<212> TYPE: PRT
<213> ORGANISM: Arabidopsis thaliana

<400> SEQUENCE: 57

Met Glu Leu Ser Ile Ser Gln Ser Pro Arg Val Arg Phe Ser Ser Leu
1               5                   10                  15

Ala Pro Arg Phe Leu Ala Ala Ser His His Arg Pro Ser Val His
            20                  25                  30

Leu Ala Gly Lys Phe Ile Ser Leu Pro Arg Asp Val Arg Phe Thr Ser
        35                  40                  45

Leu Ser Thr Ser Arg Met Arg Ser Lys Phe Val Ser Thr Asn Tyr Arg
    50                  55                  60

-continued

```
Lys Ile Ser Ile Arg Ala Cys Ser Gln Val Gly Ala Ala Glu Ser Asp
 65                  70                  75                  80

Asp Pro Val Leu Asp Arg Ile Ala Arg Phe Gln Asn Ala Cys Trp Arg
                 85                  90                  95

Phe Leu Arg Pro His Thr Ile Arg Gly Thr Ala Leu Gly Ser Thr Ala
            100                 105                 110

Leu Val Thr Arg Ala Leu Ile Glu Asn Thr His Leu Ile Lys Trp Ser
        115                 120                 125

Leu Val Leu Lys Ala Leu Ser Gly Leu Leu Ala Leu Ile Cys Gly Asn
    130                 135                 140

Gly Tyr Ile Val Gly Ile Asn Gln Ile Tyr Asp Ile Gly Ile Asp Lys
145                 150                 155                 160

Val Asn Lys Pro Tyr Leu Pro Ile Ala Ala Gly Asp Leu Ser Val Gln
                165                 170                 175

Ser Ala Trp Leu Leu Val Ile Phe Phe Ala Ile Ala Gly Leu Leu Val
            180                 185                 190

Val Gly Phe Asn Phe Gly Pro Phe Ile Thr Ser Leu Tyr Ser Leu Gly
        195                 200                 205

Leu Phe Leu Gly Thr Ile Tyr Ser Val Pro Pro Leu Arg Met Lys Arg
    210                 215                 220

Phe Pro Val Ala Ala Phe Leu Ile Ile Ala Thr Val Arg Gly Phe Leu
225                 230                 235                 240

Leu Asn Phe Gly Val Tyr His Ala Thr Arg Ala Ala Leu Gly Leu Pro
                245                 250                 255

Phe Gln Trp Ser Ala Pro Val Ala Phe Ile Thr Ser Phe Val Thr Leu
            260                 265                 270

Phe Ala Leu Val Ile Ala Ile Thr Lys Asp Leu Pro Asp Val Glu Gly
        275                 280                 285

Asp Arg Lys Phe Gln Ile Ser Thr Leu Ala Thr Lys Leu Gly Val Arg
    290                 295                 300

Asn Ile Ala Phe Leu Gly Ser Gly Leu Leu Val Asn Tyr Val Ser
305                 310                 315                 320

Ala Ile Ser Leu Ala Phe Tyr Met Pro Gln Val Phe Arg Gly Ser Leu
                325                 330                 335

Met Ile Pro Ala His Val Ile Leu Ala Ser Gly Leu Ile Phe Gln Thr
            340                 345                 350

Trp Val Leu Glu Lys Ala Asn Tyr Thr Lys Glu Ala Ile Ser Gly Tyr
        355                 360                 365

Tyr Arg Phe Ile Trp Asn Leu Phe Tyr Ala Glu Tyr Leu Leu Phe Pro
    370                 375                 380

Phe Leu
385

<210> SEQ ID NO 58
<211> LENGTH: 379
<212> TYPE: PRT
<213> ORGANISM: Oryza sativa

<400> SEQUENCE: 58

Met Ala Ser Leu Ala Ser Pro Pro Leu Pro Cys Arg Ala Ala Ala Thr
  1               5                  10                  15

Ala Ser Arg Ser Gly Arg Pro Ala Pro Arg Leu Leu Gly Pro Pro Pro
                 20                  25                  30

Pro Pro Ala Ser Pro Leu Leu Ser Ser Ala Ser Ala Arg Phe Pro Arg
```

-continued

```
                  35                  40                  45
Ala Pro Cys Asn Ala Ala Arg Trp Ser Arg Arg Asp Ala Val Arg Val
 50                  55                  60
Cys Ser Gln Ala Gly Ala Ala Gly Pro Ala Pro Leu Ser Lys Thr Leu
 65                  70                  75                  80
Ser Asp Leu Lys Asp Ser Cys Trp Arg Phe Leu Arg Pro His Thr Ile
                 85                  90                  95
Arg Gly Thr Ala Leu Gly Ser Ile Ala Leu Val Ala Arg Ala Leu Ile
                100                 105                 110
Glu Asn Pro Gln Leu Ile Asn Trp Trp Leu Val Phe Lys Ala Phe Tyr
            115                 120                 125
Gly Leu Val Ala Leu Ile Cys Gly Asn Gly Tyr Ile Val Gly Ile Asn
130                 135                 140
Gln Ile Tyr Asp Ile Arg Ile Asp Lys Val Asn Lys Pro Tyr Leu Pro
145                 150                 155                 160
Ile Ala Ala Gly Asp Leu Ser Val Gln Thr Ala Trp Leu Leu Val Val
                165                 170                 175
Leu Phe Ala Ala Ala Gly Phe Ser Ile Val Val Thr Asn Phe Ile Leu
            180                 185                 190
Phe Ile Thr Ser Leu Tyr Cys Leu Ala Leu Phe Leu Gly Thr Ile Tyr
        195                 200                 205
Ser Val Pro Pro Phe Arg Leu Lys Arg Tyr Arg Ala Pro Ala Cys Leu
    210                 215                 220
Ile Ile Ala Thr Val Arg Gly Phe Leu Arg Asn Leu Gly Val Tyr Tyr
225                 230                 235                 240
Ala Thr Arg Ala Ala Leu Gly Leu Thr Phe Gln Trp Ser Ser Pro Val
                245                 250                 255
Ala Phe Ile Thr Cys Phe Val Thr Leu Phe Ala Leu Val Ile Ala Ile
            260                 265                 270
Thr Lys Asp Leu Pro Asp Val Glu Gly Asp Arg Lys Tyr Gln Ile Ser
        275                 280                 285
Thr Leu Ala Thr Lys Leu Gly Val Arg Asn Ile Ala Phe Leu Gly Ser
    290                 295                 300
Gly Leu Leu Ile Ala Asn Tyr Val Ala Ile Ala Val Ala Phe Leu
305                 310                 315                 320
Met Pro Gln Ala Phe Arg Arg Thr Val Met Val Pro Val His Ala Ala
                325                 330                 335
Leu Ala Val Gly Ile Ile Phe Gln Thr Trp Val Leu Glu Gln Ala Lys
            340                 345                 350
Tyr Thr Lys Asp Ala Ile Ser Gln Tyr Tyr Arg Phe Ile Trp Asn Leu
        355                 360                 365
Phe Tyr Ala Glu Tyr Ile Phe Phe Pro Leu Ile
    370                 375

<210> SEQ ID NO 59
<211> LENGTH: 1423
<212> TYPE: DNA
<213> ORGANISM: Arabidopsis thaliana

<400> SEQUENCE: 59
ctctcactac agaacataca caagtataat tcgtcgatcg acccacgcgt ccggcagagc     60
aaagagtttt tgtgtggcta gtggcatcaa tggagctctc gatctcacaa tcaccgcgtg    120
ttcggttctc gtctctggcg cctcgtttct tagcagcttc tcatcatcat cgtccttctg    180
```

-continued

| | |
|---|---|
| tgcatttagc tgggaagttt ataagcctcc ctcgagatgt tcgcttcacg agcttatcaa | 240 |
| cttcaagaat gcggtccaaa tttgtttcaa ccaattatag aaaaatctca atccgggcat | 300 |
| gttctcaggt tggtgctgct gagtctgatg atccagtgct ggatagaatt gcccggttcc | 360 |
| aaaatgcttg ctggagattt cttagacccc atacaatccg cggaacagct ttaggatcca | 420 |
| ctgccttggt gacaagagct tgatagaga cactcattt gatcaaatgg agtcttgtac | 480 |
| taaaggcact ttcaggtctt cttgctctta tttgtgggaa tggttatata gtcggcatca | 540 |
| atcagatcta cgacattgga atcgacaaag tgaacaaacc atacttgcca atagcagcag | 600 |
| gagatctatc agtgcagtct gcttggttgt tagtgatatt ttttgcgata gcagggcttt | 660 |
| tagttgtcgg atttaacttt ggtccattca ttacaagcct atactctctt ggcctttttc | 720 |
| tgggaaccat ctattctgtt ccaccctca gaatgaaaag attcccagtt gcagcattc | 780 |
| ttattattgc cacggtacga ggtttccttc ttaactttgg tgtgtaccat gctacaagag | 840 |
| ctgctcttgg acttccattt cagtggagtg cacctgtggc gttcatcaca tcttttgtga | 900 |
| cactgtttgc actggtcatt gctattacaa aggaccttcc tgatgttgaa ggagatcgaa | 960 |
| agttccaaat atcaaccctg caacaaaac ttggagtgag aaacattgca ttcctcggtt | 1020 |
| ctggacttct gctagtaaat tatgtttcag ccatatcact agctttctac atgcctcagg | 1080 |
| tttttagagg tagcttgatg attcctgcac atgtgatctt ggcttcaggc ttaattttcc | 1140 |
| agacatgggt actagaaaaa gcaaactaca ccaaggaagc tatctcagga tattatcggt | 1200 |
| ttatatggaa tctcttctac gcagagtatc tgttattccc cttcctctag ctttcaattt | 1260 |
| catggtgagg atatgcagtt ttctttgtat atcattcttc ttcttctttg tagcttggag | 1320 |
| tcaaaatcgg ttccttcatg tacatacatc aaggatatgt ccttctgaat ttttatatct | 1380 |
| tgcaataaaa atgcttgtcc caaaaaaaaa aaaaaaaaaa aaa | 1423 |

<210> SEQ ID NO 60
<211> LENGTH: 1841
<212> TYPE: DNA
<213> ORGANISM: Oryza sativa

<400> SEQUENCE: 60

| | |
|---|---|
| ctcaccgaca ccatccgtag gtcttccagg agctccttcc tgccacgtca tcaatggcga | 60 |
| tgatgggtgg ctgacagtca aacgctcccc acgcctcctc cccttccccc ctctctccct | 120 |
| ccatggcttc cctcgcctcc cctcctctcc cctgccgcgc cgccgccacc gccagccgca | 180 |
| gcgggcgtcc tgctccgcgc ctcctcggcc ctccgccgcc gcccgcttcc cctctcctct | 240 |
| cctccgcttc ggcgcgcttc ccgcgtgccc cctgcaacgc cgcacgctgg agccggcgcg | 300 |
| acgccgtgcg ggtttgctct caagctggtg cagctggacc agccccatta tcgaagacat | 360 |
| tgtcagacct caaggattcc tgctggagat ttttacggcc acatacaatt cgaggaactg | 420 |
| ccttgggatc catagcatta gttgctagag cttttgataga gaaccccccaa ctgataaatt | 480 |
| ggtggttggt attcaaagcg ttctatgggc tcgtggcgtt aatctgtggc aatggttaca | 540 |
| tcgttgggat caatcagatc tatgacatta gaatcgataa ggtaaacaag ccatatttac | 600 |
| caattgctgc cggtgatctc tcagttcaga cagcatggtt attggtggta ttatttgcag | 660 |
| ctgcgggatt tcaattgtt gtgacaaact ttatactttt cattacctct ctatactgcc | 720 |
| ttgctctatt tcttggcacc atatactctg ttcctccatt cagacttaag agatatcgtg | 780 |
| cgcctgcatg cctcatcatt gcaacggtcc gcggttttct ccgcaacttg ggtgtgtact | 840 |
| atgctactag agcagcactg ggtcttacat tccaatggag ctcgcctgtt gctttcatta | 900 |

-continued

```
catgcttcgt gactttattt gctttggtca ttgctataac caaagatctc ccagatgttg    960
aagggatcg gaagtatcaa atatcaactt tggcgacaaa gctcggtgtc agaaacattg   1020
catttcttgg ctctggttta ttgatagcaa attatgttgc tgctattgct gtagcttttc   1080
tcatgcctca ggctttcagg cgcactgtaa tggtgcctgt gcatgctgcc cttgccgttg   1140
gtataatttt ccagacatgg gttctggagc aagcaaaata tactaaggat gctatttcac   1200
agtactaccg gttcatttgg aatctcttct atgctgaata catcttcttc ccgttgatat   1260
agagaccaag caatctgata tggtctgcat gttgagtgcg gcaaaaacta gaagcccata   1320
tgaacagtgg gagtaaggga acgaacatgc catccatggg aagactctga taactctctc   1380
tcgcccgggc tgtaaagggt aagcactgtt gtgcatatat atgaaaggaa ggtgataaag   1440
cagggatgct aaattgctac tgggatcctc aaaggcttat agtggtcatc agtggaatgt   1500
gccttaataa tttggttacc tagcagagca agttttttgca ggttattagg taatatcttt   1560
gagggaatga acttagattt cattgtttta aggtctggtc acacaacggg tagtagtgct   1620
ggagcggcaa aagacgacct tgttttacac taccaaggga ggttaactct agttttcatg   1680
tgaccactta ccttgagagt tgagaccatg gaatcacttg tcgactcctc ggcttgtata   1740
tttctagtgt cagcatttgc attctcctcc acacttgtac ttgaagagtt gaagacaact   1800
tttttgtttg tgtatttctg gagtgtcagc atttgcattc                         1841
```

<210> SEQ ID NO 61
<211> LENGTH: 970
<212> TYPE: PRT
<213> ORGANISM: Arabidopsis thaliana

<400> SEQUENCE: 61

```
Met Asp Pro Pro Val Ser Asp Leu Glu Ser Ile Glu Asp Gln Lys Glu
1               5                   10                  15

Gly Gly Pro Ser Phe His Cys Asp Leu Tyr Asp Thr Gln Val Val His
            20                  25                  30

Lys Ile Ala Gln Val Phe Leu Pro Gly Leu Ala Thr Ala Cys Val Asp
        35                  40                  45

Asn Thr Thr Gly Asp Ile Phe Arg Ser Pro Gly Ser Val Ala Ala Asp
    50                  55                  60

Ile Arg Lys Glu Met Ile Glu Tyr Leu Thr Arg Arg Ser Glu Thr Phe
65                  70                  75                  80

Val Ala Glu His Ile Val Leu Gln Gly Gly Ser Glu Ile Glu Ala Ser
                85                  90                  95

His Asp Pro Phe Asp Ile Ile Ser Asp Phe Ile Asp Asp Phe Ala Thr
            100                 105                 110

Ser Lys Arg Asn Leu Phe Ser Arg Val Ser Gly Trp Met Leu Ser Glu
        115                 120                 125

Arg Arg Glu Asp Asn Ile Asp Asp Phe Ala Gln Glu Met Glu Ile Ser
    130                 135                 140

Gly Phe Trp Leu Thr Asp His Arg Glu Gly Ile Ala Gln Thr Leu Leu
145                 150                 155                 160

Lys Asn Val Asp Phe Lys Ser Ser Ala His Cys Glu Met Lys Phe Gln
                165                 170                 175

Thr Glu Gly Glu Leu Ala Glu His Ala Met Asn Cys Gly Tyr Arg Thr
            180                 185                 190

Met Asn Cys Glu Asn Glu Gly Cys Thr Ala Val Phe Cys Ala Asn Gln
        195                 200                 205
```

-continued

```
Met Glu Asn His Asp Ser Val Cys Pro Phe Lys Ile Ile Pro Cys Glu
    210                 215                 220
Gln Asn Cys Ser Glu Ser Ile Met Arg Arg Asp Met Asp Arg His Cys
225                 230                 235                 240
Ile Thr Val Cys Pro Met Lys Leu Val Asn Cys Pro Phe His Ser Val
                245                 250                 255
Gly Cys Leu Ser Asp Val His Gln Cys Glu Val Gln Gln His His Leu
                260                 265                 270
Asp Asn Val Ser Ser His Leu Met Tyr Ile Leu Arg Ser Ile Tyr Lys
            275                 280                 285
Glu Ala Ser Leu Asp Asp Leu Lys Pro Arg Ala Glu Gln Ile Gln Gln
290                 295                 300
Leu Ser Thr Arg Leu Ser Glu Ala Arg Asn Ala Arg Ser Leu Thr Asn
305                 310                 315                 320
Leu Val Lys Glu Ile Asp Gly Lys Leu Gly Pro Leu Glu Ile Lys Pro
                325                 330                 335
Lys Ile Val Thr Asp Ser Glu Ser Asp Lys Pro Glu Asn Thr Glu Lys
                340                 345                 350
Lys Ala Leu Glu Glu Ala Glu Ile Lys Glu Lys Pro Glu Thr Ser Asn
            355                 360                 365
Leu Lys Ala Val Thr Leu Glu Gln Thr Ala Arg Glu Ala Pro Glu Asp
        370                 375                 380
Lys Leu Val Ser Lys Glu Val Asp Ala Ala Met Val Lys Glu Ala Ala
385                 390                 395                 400
Lys Lys Val Ser Glu Ala Glu Ile Ala Asp Asn Val Asn Glu Glu Gly
                405                 410                 415
Glu Leu Lys Ala Gln Lys Leu Leu Glu Ile Gly Glu Phe Ile Lys Glu
            420                 425                 430
Gly Asp Asn Asn Ser Ala Asp Asp Leu Ser Glu Arg Thr Glu Thr Lys
        435                 440                 445
Ala Pro Glu Val Val Met Asp Glu Ala Arg Glu Glu Asp Ser
450                 455                 460
Val Glu Thr Lys Asp Thr Arg Thr Tyr Glu Thr Ile Arg Gly Leu Glu
465                 470                 475                 480
Ile Glu Ala Asn Glu Met Ile Asp Glu Glu Thr Lys Lys Ser Thr Glu
                485                 490                 495
Thr Lys Thr Glu Ala Pro Ser Arg Ile Val Met Asp Lys Glu Gly Asp
            500                 505                 510
Glu Glu Thr Lys Lys Ser Thr Glu Thr Glu Thr Glu Ala Pro Ser Arg
        515                 520                 525
Ile Val Met Glu Thr Glu Lys Asp Glu Glu Thr Met Asn Ser Arg Ala
530                 535                 540
Arg Ala Ser Asp Glu Ala Glu Ala Leu Ser Lys Ser Ser Gln Val Ala
545                 550                 555                 560
Ser Met Glu Leu Ser Ile Ser Gln Ser Pro Arg Val Arg Phe Ser Ser
                565                 570                 575
Leu Ala Pro Arg Phe Leu Ala Ala Ser His His Arg Pro Ser Val
            580                 585                 590
His Leu Ala Gly Lys Phe Ile Ser Leu Pro Arg Asp Val Arg Phe Thr
        595                 600                 605
Ser Leu Ser Thr Ser Arg Met Arg Ile Leu Ala Val Ala Leu Thr Phe
610                 615                 620
```

```
Lys Ser Arg Cys Val Tyr Val Asn Tyr Glu Ile Pro Lys Asp Gln Ile
625                 630                 635                 640

Leu Val Gly Ala Ala Glu Ser Asp Asp Pro Val Leu Asp Arg Ile Ala
                645                 650                 655

Arg Phe Gln Asn Ala Cys Trp Arg Phe Leu Arg Pro His Thr Ile Arg
            660                 665                 670

Gly Thr Ala Leu Gly Ser Thr Ala Leu Val Thr Arg Ala Leu Ile Glu
        675                 680                 685

Asn Thr His Leu Ile Lys Trp Ser Leu Val Leu Lys Ala Leu Ser Gly
    690                 695                 700

Leu Leu Ala Leu Ile Cys Gly Asn Gly Tyr Ile Val Gly Ile Asn Gln
705                 710                 715                 720

Ile Tyr Asp Ile Gly Ile Asp Lys Val Asn Lys Pro Tyr Leu Pro Ile
                725                 730                 735

Ala Ala Gly Asp Leu Ser Val Gln Ser Ala Trp Leu Leu Val Ile Phe
            740                 745                 750

Phe Ala Ile Ala Gly Leu Leu Val Gly Phe Asn Phe Gly Pro Phe
        755                 760                 765

Ile Thr Ser Leu Tyr Ser Leu Gly Leu Phe Leu Gly Thr Ile Tyr Ser
770                 775                 780

Val Pro Pro Leu Arg Met Lys Arg Phe Pro Val Ala Ala Phe Leu Ile
785                 790                 795                 800

Ile Ala Thr Val Arg Gly Phe Leu Leu Asn Phe Gly Val Tyr His Ala
                805                 810                 815

Thr Arg Ala Ala Leu Gly Leu Pro Phe Gln Trp Ser Ala Pro Val Ala
            820                 825                 830

Phe Ile Thr Ser Phe Val Thr Leu Phe Ala Leu Val Ile Ala Ile Thr
        835                 840                 845

Lys Asp Leu Pro Asp Val Glu Gly Asp Arg Lys Phe Gln Ile Ser Thr
    850                 855                 860

Leu Ala Thr Lys Leu Gly Val Arg Asn Ile Ala Phe Leu Gly Ser Gly
865                 870                 875                 880

Leu Leu Leu Val Asn Tyr Val Ser Ala Ile Ser Leu Ala Phe Tyr Met
                885                 890                 895

Pro Gln Tyr Ala Ala Leu Lys Arg Pro Thr Leu Leu Ser Phe Asn Asn
            900                 905                 910

Glu Gln Val Phe Arg Gly Ser Leu Met Ile Pro Ala His Val Ile Leu
        915                 920                 925

Ala Ser Gly Leu Ile Phe Gln Thr Trp Val Leu Glu Lys Ala Asn Tyr
    930                 935                 940

Thr Lys Glu Ala Ile Ser Gly Tyr Tyr Arg Phe Ile Trp Asn Leu Phe
945                 950                 955                 960

Tyr Ala Glu Tyr Leu Leu Phe Pro Phe Leu
                965                 970

<210> SEQ ID NO 62
<211> LENGTH: 441
<212> TYPE: PRT
<213> ORGANISM: Arabidopsis thaliana

<400> SEQUENCE: 62

Met Glu Leu Ser Ile Ser Gln Ser Pro Arg Val Arg Phe Ser Ser Leu
1               5                   10                  15

Ala Pro Arg Phe Leu Ala Ala Ser His His Arg Pro Ser Val His
                20                  25                  30
```

-continued

```
Leu Ala Gly Lys Phe Ile Ser Leu Pro Arg Asp Val Arg Phe Thr Ser
        35                  40                  45

Leu Ser Thr Ser Arg Met Arg Ser Lys Phe Val Ser Thr Asn Tyr Arg
    50                  55                  60

Lys Ile Ser Ile Arg Ser Val Cys Ala Phe Cys Asn Gly Thr His Lys
65                  70                  75                  80

Ser Arg Tyr Tyr Gln Ala Cys Ser Gln Val Gly Ala Ala Glu Ser Asp
                85                  90                  95

Asp Pro Val Leu Asp Arg Ile Ala Arg Phe Gln Asn Ala Cys Trp Arg
                100                 105                 110

Phe Leu Arg Pro His Thr Ile Arg Gly Thr Ala Leu Gly Ser Thr Ala
            115                 120                 125

Leu Val Thr Arg Ala Leu Ile Glu Asn Thr His Leu Ile Lys Trp Ser
        130                 135                 140

Leu Val Leu Lys Ala Leu Ser Gly Leu Leu Ala Leu Ile Cys Gly Asn
145                 150                 155                 160

Gly Tyr Ile Val Gly Ile Asn Gln Ile Tyr Asp Ile Gly Ile Asp Lys
                165                 170                 175

Val Asn Lys Pro Tyr Leu Pro Ile Ala Ala Gly Asp Leu Ser Val Gln
                180                 185                 190

Ser Ala Trp Leu Leu Val Ile Phe Phe Ala Ile Ala Gly Leu Leu Val
            195                 200                 205

Val Gly Phe Asn Phe Gly Pro Phe Ile Thr Ser Leu Tyr Ser Leu Gly
        210                 215                 220

Leu Phe Leu Gly Thr Ile Tyr Ser Val Pro Pro Leu Arg Met Lys Arg
225                 230                 235                 240

Phe Pro Val Ala Ala Phe Leu Ile Ile Ala Thr Val Arg Gly Phe Leu
                245                 250                 255

Leu Asn Phe Gly Val Tyr His Ala Thr Arg Ala Ala Leu Gly Leu Pro
                260                 265                 270

Phe Gln Trp Ser Ala Pro Val Ala Phe Ile Thr Ser Phe Val Thr Leu
            275                 280                 285

Phe Ala Leu Val Ile Ala Ile Thr Lys Asp Leu Pro Asp Val Glu Gly
        290                 295                 300

Asp Arg Lys Phe Gln Ile Ser Thr Leu Ala Thr Lys Leu Gly Val Arg
305                 310                 315                 320

Asn Ile Ala Phe Leu Gly Ser Gly Leu Leu Val Asn Tyr Val Ser
                325                 330                 335

Ala Ile Ser Leu Ala Phe Tyr Met Pro Gln Tyr Ala Ala Leu Lys Arg
            340                 345                 350

Pro Thr Leu Leu Ser Phe Asn Asn Glu Gln Val Phe Arg Gly Ser Leu
        355                 360                 365

Met Ile Pro Ala His Val Ile Leu Ala Ser Gly Leu Ile Phe Gln Thr
    370                 375                 380

Trp Val Leu Glu Lys Ala Asn Tyr Thr Lys Ser Ile Cys Tyr Ser Pro
385                 390                 395                 400

Ser Ser Ser Phe Gln Phe His Gly Glu Asp Met Gln Phe Ser Leu Tyr
                405                 410                 415

Ile Ile Leu Leu Leu Cys Ser Leu Glu Ser Lys Ser Val Pro Ser
                420                 425                 430

Cys Thr Tyr Ile Lys Asp Met Ser Phe
            435                 440
```

<210> SEQ ID NO 63
<211> LENGTH: 155
<212> TYPE: DNA
<213> ORGANISM: Arabidopsis thaliana

<400> SEQUENCE: 63

| | | | | | |
|---|---|---|---|---|---|
| gtgtggctag | tggcatcaat | ggagctctcg | atctcacaat | caccgcgtgt | tcggttctcg | 60 |
| tctctggcgc | ctcgtttctt | agcagcttct | catcatcatc | gtccttctgt | gcatttagct | 120 |
| gggaagttta | taagcctccc | tcgagatgtt | cgctt | | | 155 |

<210> SEQ ID NO 64
<211> LENGTH: 626
<212> TYPE: DNA
<213> ORGANISM: Medicago truncatula

<400> SEQUENCE: 64

| | | | | | |
|---|---|---|---|---|---|
| gctccttatg | gagctctcta | cttcttcatc | atcttctctt | cattcacatt | ccataattcc | 60 |
| cacatggaat | tccaaaaact | actactcttt | caaaccaccc | atttcagcta | agtccacaac | 120 |
| cccaaaatct | tccaaacggt | ttggttcaat | gggctgcac | catcatcatc | acacaagttt | 180 |
| ctctgctcat | gtttcaaaac | cgaagagaca | gtgtaaaccc | atttccatca | gggcctgcag | 240 |
| tgaagttgga | gctgctggat | ctgatcgtcc | atttgctgac | aaagttttag | attttaaaga | 300 |
| tgcattctgg | agatttttaa | ggccacatac | tatccgtggg | acagcattag | gctcttttgc | 360 |
| tttggtgtca | agagcgttga | ttgagaactc | aaatctgata | aagtggtctc | ttttgttgaa | 420 |
| agcactctct | ggactttttg | ctctgatttg | tgggaatggt | tatatagttg | gcatcaatca | 480 |
| aatatatgat | atcggcattg | acaaggtaaa | caaaccttat | ttacctatag | ctgcaggaga | 540 |
| tctttctgtc | caatctgcat | ggtacttggt | tatattcttt | gcagcagctg | gccttttgac | 600 |
| tgtaggattg | aactttggat | cttttta | | | | 626 |

<210> SEQ ID NO 65
<211> LENGTH: 651
<212> TYPE: DNA
<213> ORGANISM: Medicago truncatula

<400> SEQUENCE: 65

| | | | | | |
|---|---|---|---|---|---|
| cttcagctcc | ttatggagct | ctctacttct | tcatcatctt | ctcttcattc | acattccata | 60 |
| attcccacat | ggaattccaa | aaactactac | tctttcaaac | cacccatttc | agctaagtcc | 120 |
| acaaccccaa | aatcttccaa | acggtttggt | tcaattgggc | tgcaccatca | tcatcacaca | 180 |
| agtttctctg | ctcatgtttc | aaaaccgaag | agacagtgta | aacccatttc | catcagggcc | 240 |
| tgcagtgaag | ttggagctgc | tggatctgat | cgtccatttg | ctgacaaagt | tttagatttt | 300 |
| aaagatgcat | tctggagatt | tttaaggcca | catactatcc | gtgggacagc | attaggctct | 360 |
| tttgctttgg | tgtcaagagc | gttgattgag | aactcaaatc | tgataaagtg | gtctcttttg | 420 |
| ttgaaagcac | tctctggact | ttttgctctg | atttgtggga | atggttatat | agttggcatc | 480 |
| aatcaaatat | atgatatcgg | cattgacaag | gtaaacaaac | cttatttacc | tatagctgca | 540 |
| ggagatcttt | ctgtccaatc | tgcatggtac | ttggttatat | tctttgcagc | agctggcctt | 600 |
| ttgactgtag | gattgaactt | tggatcttta | ttttttctct | ttactccttc | g | 651 |

<210> SEQ ID NO 66
<211> LENGTH: 651
<212> TYPE: DNA
<213> ORGANISM: Medicago truncatula -continued

<400> SEQUENCE: 66

| cttcagctcc ttatggagct ctctacttct tcatcatctt ctcttcattc acattccata | 60 |
| aattcccacat ggaattccaa aaactactac tctttcaaac cacccatttc agctaagtcc | 120 |
| acaaccccaa aatcttccaa acggtttggt tcaattgggc tgcaccatca tcatcacaca | 180 |
| agtttctctg ctcatgtttc aaaaccgaag agacagtgta aacccatttc catcagggcc | 240 |
| tgcagtgaag ttggagctgc tggatctgat cgtccatttg ctgacaaagt tttagatttt | 300 |
| aaagatgcat tctggagatt tttaaggcca catactatcc gtgggacagc attaggctct | 360 |
| tttgctttgg tgtcaagagc gttgattgag aactcaaatc tgataaagtg gtctcttttg | 420 |
| ttgaaagcac tctctggact ttttgctctg atttgtggga atggttatat agttggcatc | 480 |
| aatcaaatat atgatatcgg cattgacaag gtaaacaaac cttatttacc tatagctgca | 540 |
| ggagatcttt ctgtccaatc tgcatggtac ttggttatat tctttgcagc agctggcctt | 600 |
| ttgactgtag gattgaactt tggatctttta ttttttctct ttactccttc g | 651 |

<210> SEQ ID NO 67
<211> LENGTH: 614
<212> TYPE: DNA
<213> ORGANISM: Medicago truncatula

<400> SEQUENCE: 67

| gttgagtgtt gcttcagctc cttatggagc tctctacttc ttcatcatct tctcttcatt | 60 |
| cacattccat aattcccaca tggaattcca aaaactacta ctctttcaaa ccacccattt | 120 |
| cagctaagtc cacaaccca aatcttccaa acggtttggt tcaattggg ctgcaccatc | 180 |
| atcatcacac aagtttctct gctcatgttt caaaaccgaa gagacagtgt aaacccattt | 240 |
| ccatcagggc tgcagtgaa gttggagctg ctggatctga tcgtccattt gctgacaaag | 300 |
| ttttagattt taaagatgca ttctggagat ttttaaggcc acatactatc cgtgggacag | 360 |
| cattaggctc ttttgctttg gtgtcaagag cgttgattga aactcaaat ctgataaagt | 420 |
| ggtctctttt gttgaaagca ctctctggac ttttgctct gatttgtggg aatggttata | 480 |
| tagttggcat caatcaaata tatgatatcg gcattgacaa ggtaaacaaa ccttatttac | 540 |
| ctatagctgc aggagatctt tctgtaccaa tctgcatggt acttggttat attctttgca | 600 |
| acagctggcc tttt | 614 |

<210> SEQ ID NO 68
<211> LENGTH: 560
<212> TYPE: DNA
<213> ORGANISM: Solanum tuberosum

<400> SEQUENCE: 68

| gaccctttttc ccatatattt atccacttac caccttatcc tcttgaggtt gaacaaattc | 60 |
| attcttcctt tggtatggag atacagggtg ttacaataga caaaattgac tcacacaaga | 120 |
| aacattccat ctcctaagga tagattgatg aatttcctaa gaatatacaa caacaggata | 180 |
| aataaattct ccatccccccc catctctata gacaattttc ctttgcaaac cagaaagaaa | 240 |
| acttgcattt cttcgaggtc catcgaacaa aaaccttat caagtagatt ttagatgaaa | 300 |
| ggaaagatga tgtactccgc atagaaaaga ttccatataa atctatagta tgctgagatt | 360 |
| gcttccttgg tgtaatttgc tctttccaac aaccatgcct ggaaaactaa acacgatgct | 420 |
| aagatgacat gtacaggtat catcaagcta cacctgaatg cttggggcat gtatattgct | 480 |

```
gcaactacag caccaatgta atttgttaat aatagaccag aaccaaggaa tgctatgttt    540
ctcacaccaa gctttgttgc                                                560
```

<210> SEQ ID NO 69
<211> LENGTH: 371
<212> TYPE: DNA
<213> ORGANISM: Arabidopsis thaliana

<400> SEQUENCE: 69

```
caattggtac aagcattttt attgcaagat ataaaaattc agaaggacat atccttgatg     60
tatgtacatg aaggaaccga ttttgactcc aagctacaaa aagaagaag aatgatatac    120 aaagaaaact gcatatcctc accatgaaat tgaaagctag aggaagggga ataacagata    180
ctctgcgtag aagagattcc atataaaccg ataatatcct gagatagctt ccttggtgta    240
gtttgctttt tctagtaccc atgtctggaa aattaagcct gaagccaaga tcacatgtgc    300
aggaatcatc aagctacctc taaaaacctg aggcatgtag aaagctagtg atatggctga    360
aacataattt a                                                         371
```

<210> SEQ ID NO 70
<211> LENGTH: 357
<212> TYPE: DNA
<213> ORGANISM: Arabidopsis thaliana

<400> SEQUENCE: 70

```
ggtacaagca tttttattgc aagatataaa aattcagaag gacatatcct tgatgtatgt     60
acatgaagga accgattttg actccaagct acaagaaga agaagaatga tatacaaaga    120
aaactgcata tcctcaccat gaaattgaaa gctagaggaa ggggaataac agatactctg    180
cgtagaagag attccatata aaccgataat atcctgagat agcttccttg gtgtagtttg    240 cttttttctag tacccatgtc tggaaaatta gcctgaagc caagatcaca ctggttgcag    300
gaactcatca agctaccctc taaaaaaacc gtgaggcaac tgctaggaaa acaggcc       357
```

<210> SEQ ID NO 71
<211> LENGTH: 560
<212> TYPE: DNA
<213> ORGANISM: Medicago truncatula
<220> FEATURE:
<221> NAME/KEY: misc_feature
<222> LOCATION: (537)..(537)
<223> OTHER INFORMATION: unknown

<400> SEQUENCE: 71

```
tgccacaggc tttcaggaga tggttactga taccagctca tgcaatattt gcttcaagct     60
taatttacca ggtgcagata ttagaaaaag caaattatac aaaggaagca atatcaggat    120
tctatcgatt catatggaat ctgttctatg ccgagtatgc attatttcct ttcatctagc    180
aaactgtgct acatttttac ttggaaaaat tgcacacatg catccaaaaa tgcagcggtt    240
gcttgaccaa agccggtcaa taagacaaag ccgttcaata agaaaatct tagttatatc    300 gagtatctat tctaaagta ttaacaattt tttttaatgg tttgagtaaa ttttgtata    360 tagtatagtg cttccttta atgagatgta ttgccatgag aattgtatac aacggccaga    420
tttcatttgt gttggaacaa attccactgg tgaatgtgat aatatactca tgtgaactct    480 acccaaaat aaaataaat aaaaaaaaaa aaaaaaaaa aaaataaaaa aaaaannaaa       540
aataaaaaaa cgtcgagggg                                                560
```

```
<210> SEQ ID NO 72
<211> LENGTH: 713
<212> TYPE: DNA
<213> ORGANISM: Glycine max
<220> FEATURE:
<221> NAME/KEY: misc_feature
<222> LOCATION: (13)..(13)
<223> OTHER INFORMATION: unknown
<220> FEATURE:
<221> NAME/KEY: misc_feature
<222> LOCATION: (679)..(679)
<223> OTHER INFORMATION: unknown
<220> FEATURE:
<221> NAME/KEY: misc_feature
<222> LOCATION: (681)..(683)
<223> OTHER INFORMATION: unknown
<220> FEATURE:
<221> NAME/KEY: misc_feature
<222> LOCATION: (686)..(693)
<223> OTHER INFORMATION: unknown
<220> FEATURE:
<221> NAME/KEY: misc_feature
<222> LOCATION: (28)..(29)
<223> OTHER INFORMATION: unknown
<220> FEATURE:
<221> NAME/KEY: misc_feature
<222> LOCATION: (634)..(635)
<223> OTHER INFORMATION: unknown
<220> FEATURE:
<221> NAME/KEY: misc_feature
<222> LOCATION: (637)..(637)
<223> OTHER INFORMATION: unknown
<220> FEATURE:
<221> NAME/KEY: misc_feature
<222> LOCATION: (643)..(643)
<223> OTHER INFORMATION: unknown
<220> FEATURE:
<221> NAME/KEY: misc_feature
<222> LOCATION: (658)..(660)
<223> OTHER INFORMATION: unknown
<220> FEATURE:
<221> NAME/KEY: misc_feature
<222> LOCATION: (664)..(664)
<223> OTHER INFORMATION: unknown
<220> FEATURE:
<221> NAME/KEY: misc_feature
<222> LOCATION: (669)..(670)
<223> OTHER INFORMATION: unknown
<220> FEATURE:
<221> NAME/KEY: misc_feature
<222> LOCATION: (672)..(674)
<223> OTHER INFORMATION: unknown

<400> SEQUENCE: 72
aaatgcgatg ganagccgat gacgcctnna tatacaaaaa tactcattaa aaaaatagct      60
agtttactaa ttgatacttg agacaacaaa gaagatctct ctaactatgc acgtatgcac     120
cttttcccaa gaaaatgta gcaaggcttg ctatatgaaa ggaaatattg catactcagc      180
atagaacaga ttccatatga atcgatagaa tcctgatatt gcatccttgg tataatttgc     240
ttgttctaat atccatgcct ggtaaatcaa gcttattgca aaaatcgtat gagccggtat     300
gagtaaccaa cgcctgaaag cctgaggcat ataaattgct gccaaaacag aaacaatata     360
gttcaccaac aaaattccag aaccaaggaa agcaatgttc cgaactccta attttgtggc     420
aaaggttgat atctgatact tgcgatctcc ttcaacatca ggaagatctt ttgttatagc     480
aattaccagt gcgaaaaatg ttacaaatgt tgtgataaaa accacaggag agctccattc     540
aaatgcaagc ccaagggcag ctctagtggc atagtacaca ccaaagttaa agagaaaacc     600
ccgaaccgtg gcaattataa gaatgctgc aacnngnaag cgnttcattc taaatggnnn      660
aacngaattn annntaccna nnnaannnnn nnntgtgtaa agagaaaaaa tga            713
```

<210> SEQ ID NO 73
<211> LENGTH: 56
<212> TYPE: DNA
<213> ORGANISM: Artificial
<220> FEATURE:
<223> OTHER INFORMATION: Primer

<400> SEQUENCE: 73
cgcgatttaa atggcgcgcc ctgcaggcgg ccgcctgcag ggcgcgccat ttaaat      56

<210> SEQ ID NO 74
<211> LENGTH: 32
<212> TYPE: DNA
<213> ORGANISM: Artificial
<220> FEATURE:
<223> OTHER INFORMATION: Primer

<400> SEQUENCE: 74
tcgaggatcc gcggccgcaa gcttcctgca gg      32

<210> SEQ ID NO 75
<211> LENGTH: 32
<212> TYPE: DNA
<213> ORGANISM: Artificial
<220> FEATURE:
<223> OTHER INFORMATION: Primer

<400> SEQUENCE: 75
tcgacctgca ggaagcttgc ggccgcggat cc      32

<210> SEQ ID NO 76
<211> LENGTH: 32
<212> TYPE: DNA
<213> ORGANISM: Artificial
<220> FEATURE:
<223> OTHER INFORMATION: Primer

<400> SEQUENCE: 76
tcgacctgca ggaagcttgc ggccgcggat cc      32

<210> SEQ ID NO 77
<211> LENGTH: 32
<212> TYPE: DNA
<213> ORGANISM: Artificial
<220> FEATURE:
<223> OTHER INFORMATION: Primer

<400> SEQUENCE: 77
tcgaggatcc gcggccgcaa gcttcctgca gg      32

<210> SEQ ID NO 78
<211> LENGTH: 36
<212> TYPE: DNA
<213> ORGANISM: Artificial
<220> FEATURE:
<223> OTHER INFORMATION: Primer

<400> SEQUENCE: 78
tcgaggatcc gcggccgcaa gcttcctgca ggagct      36

<210> SEQ ID NO 79
<211> LENGTH: 28
<212> TYPE: DNA
<213> ORGANISM: Artificial
<220> FEATURE:
<223> OTHER INFORMATION: Primer

```
<400> SEQUENCE: 79
cctgcaggaa gcttgcggcc gcggatcc                                              28

<210> SEQ ID NO 80
<211> LENGTH: 36
<212> TYPE: DNA
<213> ORGANISM: Artificial
<220> FEATURE:
<223> OTHER INFORMATION: Primer

<400> SEQUENCE: 80
tcgacctgca ggaagcttgc ggccgcggat ccagct                                     36

<210> SEQ ID NO 81
<211> LENGTH: 28
<212> TYPE: DNA
<213> ORGANISM: Artificial
<220> FEATURE:
<223> OTHER INFORMATION: Primer

<400> SEQUENCE: 81
ggatccgcgg ccgcaagctt cctgcagg                                              28

<210> SEQ ID NO 82
<211> LENGTH: 39
<212> TYPE: DNA
<213> ORGANISM: Artificial
<220> FEATURE:
<223> OTHER INFORMATION: Primer

<400> SEQUENCE: 82
gatcacctgc aggaagcttg cggccgcgga tccaatgca                                  39

<210> SEQ ID NO 83
<211> LENGTH: 31
<212> TYPE: DNA
<213> ORGANISM: Artificial
<220> FEATURE:
<223> OTHER INFORMATION: Primer

<400> SEQUENCE: 83
ttggatccgc ggccgcaagc ttcctgcagg t                                          31

<210> SEQ ID NO 84
<211> LENGTH: 31
<212> TYPE: DNA
<213> ORGANISM: Artificial
<220> FEATURE:
<223> OTHER INFORMATION: Primer

<400> SEQUENCE: 84
cacatatggc atgttctcag gttggtgctg c                                          31

<210> SEQ ID NO 85
<211> LENGTH: 29
<212> TYPE: DNA
<213> ORGANISM: Artificial
<220> FEATURE:
<223> OTHER INFORMATION: Primer

<400> SEQUENCE: 85
gcgtcgacct agaggaaggg gaataacag                                             29

<210> SEQ ID NO 86
```

```
<211> LENGTH: 31
<212> TYPE: DNA
<213> ORGANISM: Artificial
<220> FEATURE:
<223> OTHER INFORMATION: Primer

<400> SEQUENCE: 86
caaccatggc atgttctcag gttggtgctg c                              31

<210> SEQ ID NO 87
<211> LENGTH: 29
<212> TYPE: DNA
<213> ORGANISM: Artificial
<220> FEATURE:
<223> OTHER INFORMATION: Primer

<400> SEQUENCE: 87
gcgtcgacct agaggaaggg gaataacag                                 29

<210> SEQ ID NO 88
<211> LENGTH: 1290
<212> TYPE: DNA
<213> ORGANISM: Trichodesmium erythraeum

<400> SEQUENCE: 88
atgggaaaaa ttgctggttc tcaacaggga aaaattacaa cgaattggct acaaaaatat    60
gtgccatggc tttatagttt ttggaagttt gctcgcccac atacgattat tggtacatcg   120
ttaagtgtgc tggctttata tataattgcc atgggcgatc gctctaattt ttttgacaaa   180 tattttttt tatacagctt aattctgtta ttgataactt ggattagttg tttatgtgga   240
atgggaaaaa ttgctggttc tcaacaggga aaaattacaa cgaattggct acaaaaatat   300
gtgccatggc tttatagttt ttggaagttt gctcgcccac atacgattat tggtacatcg   360
ttaagtgtgc tggctttata tataattgcc atgggcgatc gctctaattt ttttgacaaa   420 tattttttt tatacagctt aattctgtta ttgataactt ggattagttg tttatgtgga   480
aatatttata tagtaggatt aaatcaatta gaggatatag aaatagatag gattaataag   540
cctcatctcc ctatagctgc tggtgagttt tctcgttttt ctggtcaaat aattgtggta   600
ataacgggta ttttggcttt gagttttgcc gggttggggg gacctttttt gttgggtaca   660
gtggggataa gtttggcaat tggtacggct tattctttac ctcctattcg attaaaaaga   720
tttcctgttt tggccgcatt atgtattttt actgtgcggg gagttattgt taatttgggt   780 atattttaa gctttgtttg ggggtttgaa aaggttgagg aggtttcagg aggtttaatt   840
aaatggatgg gtgagttggg tgaggttgtt ctacttcaaa aaagcttgat ggttccagaa   900
attcctctga cggtatgggc tttaactttg tttgtgatag tatttacttt tgctattgct   960
atttttaagg atattccaga tattgagggt gaccgtcaat ataatattaa tacgtttacg  1020
attaagttgg gagcatttgc tgtttttaat ttggcaaggt gggtattgac ttttttgctat  1080 ctgggtatgg tgatggtggg tgtagtttgg ttggcgagtg ttaatttatt tttttttggtg  1140 attagtcatt tattggcttt gggtataatg tggtggttta gtcaaagggt agatctgcat  1200
gataaaaagg cgatcgctga ttttatcaa tttatttgga aattatttt cctggaatat   1260 ctaatttttc ctatggcttg ttttttttaa                                  1290

<210> SEQ ID NO 89
<211> LENGTH: 903
<212> TYPE: DNA
<213> ORGANISM: Chloroflexus aurantiacus
```

-continued

```
<400> SEQUENCE: 89
atgcgcaaac agctacgcct gctcattgaa tttgcccgtc cccacaccgt cattgctacc      60
agcgtccagg ttctgaccat gctgatcatc gtgatcggct ggcacccacc aacgctcgaa    120
ctggtgggac tggtcggggt gacgctcgtt gtctgtctgg cgctcaatct ctacgtagtc    180
ggcgtgaatc aactgaccga tgtggcgatt gatcggatca acaagccatg gctaccggtt    240
gctgccggtc agctttcatc ggatgctgcg caacgtattg ttatcagtgc cctgtttatt    300
gccctgaccg gtgcggctat gctcggccca ccgctctggt ggacggtgag tatcatcgcg    360
ctgatcggtt cactctactc gctcccccg ctgcgcttga agcgtcatcc cctcgctgcg    420
gccctcagta ttgccggtgc ccgcggggtg attgccaatc tcggcctggc cttccactat    480
cagtactggt tagatagcga attgccgatc acgaccctga tcctggtggc aaccttcttt    540
ttcggtttcg ctatggtgat cgcgctctat aaagacttgc ccgatgatcg cggtgatcgg    600
ttgtatcaga tcgagaccct gaccacgcgc ctcggcccgc agcgagtgct gcacctgggc    660
agaatcttgc tcaccgcctg ttatctgctt ccgattgccg tcggtctctg gtcgctgccg    720
acttttgccg ccgcgttcct ggccctcagc catgtggtcg ttatcagtgt tttctggctg    780
gtcagtatgc gcgttgatct gcaacgccgg caatcgattg ccagttttta tatgtttctg    840
tgggggattt tttataccga atttgccctg cttagcattt atcgtctgac gtataccctc    900
tga                                                                    903

<210> SEQ ID NO 90
<211> LENGTH: 389
<212> TYPE: PRT
<213> ORGANISM: Glycine max

<400> SEQUENCE: 90

Met Glu Leu Ser Leu Ser Pro Thr Ser His Arg Val Pro Ser Thr Ile
1               5                   10                  15

Pro Thr Leu Asn Ser Ala Lys Leu Ser Ser Thr Lys Ala Thr Lys Ser
            20                  25                  30

Gln Gln Pro Leu Phe Leu Gly Phe Ser Lys His Phe Asn Ser Ile Gly
        35                  40                  45

Leu His His His Ser Tyr Arg Cys Cys Ser Asn Ala Val Pro Glu Arg
    50                  55                  60

Pro Gln Arg Pro Ser Ser Ile Arg Ala Cys Thr Gly Val Gly Ala Ser
65                  70                  75                  80

Gly Ser Asp Arg Pro Leu Ala Glu Arg Leu Leu Asp Leu Lys Asp Ala
                85                  90                  95

Cys Trp Arg Phe Leu Arg Pro His Thr Ile Arg Gly Thr Ala Leu Gly
            100                 105                 110

Ser Phe Ala Leu Val Ala Arg Ala Leu Ile Glu Asn Thr Asn Leu Ile
        115                 120                 125

Lys Trp Ser Leu Phe Phe Lys Ala Phe Cys Gly Leu Phe Ala Leu Ile
    130                 135                 140

Cys Gly Asn Gly Tyr Ile Val Gly Ile Asn Gln Ile Tyr Asp Ile Ser
145                 150                 155                 160

Ile Asp Lys Val Asn Lys Pro Tyr Leu Pro Ile Ala Ala Gly Asp Leu
                165                 170                 175

Ser Val Gln Ser Ala Trp Phe Leu Val Ile Phe Phe Ala Ala Ala Gly
            180                 185                 190
```

```
                                                                         -continued Leu Ser Ile Ala Gly Leu Asn Phe Gly Pro Phe Ile Phe Ser Leu Tyr
            195                 200                 205
Thr Leu Gly Leu Phe Leu Gly Thr Ile Tyr Ser Val Pro Pro Leu Arg
    210                 215                 220
Met Lys Arg Phe Pro Val Ala Ala Phe Leu Ile Ile Ala Thr Val Arg
225                 230                 235                 240
Gly Phe Leu Leu Asn Phe Gly Val Tyr Tyr Ala Thr Arg Ala Ser Leu
                245                 250                 255
Gly Leu Ala Phe Glu Trp Ser Ser Pro Val Val Phe Ile Thr Thr Phe
            260                 265                 270
Val Thr Phe Phe Ala Leu Val Ile Ala Ile Thr Lys Asp Leu Pro Asp
        275                 280                 285
Val Glu Gly Asp Arg Lys Tyr Gln Ile Ser Thr Phe Ala Thr Lys Leu
    290                 295                 300
Gly Val Arg Asn Ile Ala Phe Leu Gly Ser Gly Ile Leu Leu Val Asn
305                 310                 315                 320
Tyr Ile Val Ser Val Leu Ala Ala Ile Tyr Met Pro Gln Ala Phe Arg
                325                 330                 335
Arg Trp Leu Leu Ile Pro Ala His Thr Ile Phe Ala Ile Ser Leu Ile
            340                 345                 350
Tyr Gln Ala Arg Ile Leu Glu Gln Ala Asn Tyr Thr Lys Asp Ala Ile
        355                 360                 365
Ser Gly Phe Tyr Arg Phe Ile Trp Asn Leu Phe Tyr Ala Glu Tyr Ala
    370                 375                 380
Ile Phe Pro Phe Ile
385

<210> SEQ ID NO 91
<211> LENGTH: 1427
<212> TYPE: DNA
<213> ORGANISM: Glycine max

<400> SEQUENCE: 91
ttgcaatgta acattatgaa atatgttaat ggcattacgt caaagtaaaa ggaaatagta       60
tcacatttat atacaacaat actcatttta aaaaaataat gatagctagt ttaccaattg      120
acacttgata acaaagatc tctctaacta tgcacgtatg caccttttcc caagaaaaaa       180
gtagcaaggt ttgctatatg aaaggaaata ttgcatactc agcatagaac agattccata      240
tgaatcgata gaatcctgat attgcatcct tggtataatt tgcttgttct aatattcgtg      300
cctggtaaat caagcttatt gcaaaaattg tatgagctgg tatgagtaac caacgcctga      360
aagcctgagg catataaatt gctgccaaaa cagaaacaat ataattcacc agcaaaattc      420
cagaaccaag gaaagcaatg ttccgaactc ctaattttgt agcaaaggtt gatatctgat      480
acttgcgatc accttcaaca tcaggaagat cttttgttat agcaattacc agtgcgaaaa      540
atgttacaaa tgttgtgata aaaccacag gagagctcca ttcaaatgca agcccaaggg       600
aagctctagt ggcatagtac acaccaaagt taaggagaaa accacgtacc gtggcaatta      660
taagaaatgc tgcaacagga aagcgtttca tcctcaatgg aggaacagaa tagatggttc      720
ccaagaaaag gccaagtgtg taagagaaa aaatgaaagg cccaagttc aaccctgcaa        780 tcgacaggcc agctgctgca aaaatataa ccaagaacca tgcagattgg acagaaagat       840
ctccagcagc tataggtaaa taggtttgt ttaccttgtc aatgctaatg tcatagattt       900
gattgatgcc aactatataa ccattcccac aaatcagggg aaaagacca cagaaagctt       960
```

```
tgaaaaaaag agaccacttt atcaaattcg tgttctcaat caatgctctt gccaccaaag   1020
caaatgaacc tagtgctgta ccacgtatag tatgtggcct taaaaatctc caacaagcat   1080
ctttcaaatc taaaagtctt tcagctaatg gacgatcaga tccagaagct ccaactccag   1140
tgcaagccct tatggaactg ggtctttggg gtctctcggg aacagcattt gagcagcatc   1200
tgtaactgtg atggtgcaac ccaattgagt tgaagtgttt ggaaaatcct aagaacaaag   1260
gttgttgtga cttggtggcc ttagtggatg atagtttagc ggaattcaaa gtgggaattg   1320
tggaaggaac acgatgtgaa gttggagaga gtgagagctc cataaggagc tgagcacagc   1380
aaacgagaaa acactccaaa tttcagacgc aacgcaaggc aaaaacc                1427
```

```
<210> SEQ ID NO 92
<211> LENGTH: 12
<212> TYPE: PRT
<213> ORGANISM: Artificial
<220> FEATURE:
<223> OTHER INFORMATION: Conserved Motif
<220> FEATURE:
<221> NAME/KEY: MISC_FEATURE
<222> LOCATION: (1)..(1)
<223> OTHER INFORMATION: x = w, i, or y
<220> FEATURE:
<221> NAME/KEY: MISC_FEATURE
<222> LOCATION: (2)..(2)
<223> OTHER INFORMATION: x = r, e, or k
<220> FEATURE:
<221> NAME/KEY: MISC_FEATURE
<222> LOCATION: (4)..(4)
<223> OTHER INFORMATION: x = l, a, or s
<220> FEATURE:
<221> NAME/KEY: MISC_FEATURE
<222> LOCATION: (4)..(4)
<223> OTHER INFORMATION: x = l, a, or s
<220> FEATURE:
<221> NAME/KEY: MISC_FEATURE
<222> LOCATION: (9)..(9)
<223> OTHER INFORMATION: x = i or v
<220> FEATURE:
<221> NAME/KEY: MISC_FEATURE
<222> LOCATION: (10)..(10)
<223> OTHER INFORMATION: x = i or r
<220> FEATURE:
<221> NAME/KEY: MISC_FEATURE
<222> LOCATION: (11)..(11)
<223> OTHER INFORMATION: x = g or a

<400> SEQUENCE: 92

Xaa Xaa Phe Xaa Arg Pro His Thr Xaa Xaa Xaa Thr
1               5                   10

<210> SEQ ID NO 93
<211> LENGTH: 26
<212> TYPE: PRT
<213> ORGANISM: Artificial
<220> FEATURE:
<223> OTHER INFORMATION: Conserved Motif
<220> FEATURE:
<221> NAME/KEY: MISC_FEATURE
<222> LOCATION: (2)..(2)
<223> OTHER INFORMATION: x = v, i, l, or g
<220> FEATURE:
<221> NAME/KEY: MISC_FEATURE
<222> LOCATION: (7)..(7)
<223> OTHER INFORMATION: x = i, l, or v
<220> FEATURE:
<221> NAME/KEY: MISC_FEATURE
<222> LOCATION: (10)..(10)
<223> OTHER INFORMATION: x = i or l
<220> FEATURE:
<221> NAME/KEY: MISC_FEATURE
<222> LOCATION: (11)..(11)
```

```
<223> OTHER INFORMATION: x = s, f, y, e, w, or t
<220> FEATURE:
<221> NAME/KEY: MISC_FEATURE
<222> LOCATION: (13)..(13)
<223> OTHER INFORMATION: x = v or i
<220> FEATURE:
<221> NAME/KEY: MISC_FEATURE
<222> LOCATION: (14)..(14)
<223> OTHER INFORMATION: x = r, s, g, e, d, or a
<220> FEATURE:
<221> NAME/KEY: MISC_FEATURE
<222> LOCATION: (17)..(17)
<223> OTHER INFORMATION: x = k or r
<220> FEATURE:
<221> NAME/KEY: MISC_FEATURE
<222> LOCATION: (18)..(18)
<223> OTHER INFORMATION: x = v or i
<220> FEATURE:
<221> NAME/KEY: MISC_FEATURE
<222> LOCATION: (22)..(22)
<223> OTHER INFORMATION: x = y, d, t, w, n, or h
<220> FEATURE:
<221> NAME/KEY: MISC_FEATURE
<222> LOCATION: (25)..(25)
<223> OTHER INFORMATION: x = i, v, or l

<400> SEQUENCE: 93

Asn Xaa Tyr Ile Val Gly Xaa Asn Gln Xaa Xaa Asp Xaa Xaa Ile Asp
1               5                   10                  15

Xaa Xaa Asn Lys Pro Xaa Leu Pro Xaa Ala
            20                  25

<210> SEQ ID NO 94
<211> LENGTH: 14
<212> TYPE: PRT
<213> ORGANISM: Artificial
<220> FEATURE:
<223> OTHER INFORMATION: Conserved Motif
<220> FEATURE:
<221> NAME/KEY: MISC_FEATURE
<222> LOCATION: (3)..(3)
<223> OTHER INFORMATION: x = l or i
<220> FEATURE:
<221> NAME/KEY: MISC_FEATURE
<222> LOCATION: (4)..(4)
<223> OTHER INFORMATION: x = f, t, or y
<220> FEATURE:
<221> NAME/KEY: MISC_FEATURE
<222> LOCATION: (7)..(7)
<223> OTHER INFORMATION: x = l, i, or v
<220> FEATURE:
<221> NAME/KEY: MISC_FEATURE
<222> LOCATION: (10)..(10)
<223> OTHER INFORMATION: x = i, v, m, or d
<220> FEATURE:
<221> NAME/KEY: MISC_FEATURE
<222> LOCATION: (11)..(11)
<223> OTHER INFORMATION: x = e, d, or r
<220> FEATURE:
<221> NAME/KEY: MISC_FEATURE
<222> LOCATION: (14)..(14)
<223> OTHER INFORMATION: x = r or k

<400> SEQUENCE: 94

Ile Ala Xaa Xaa Lys Asp Xaa Pro Asp Xaa Xaa Gly Asp Xaa
1               5                   10

<210> SEQ ID NO 95
<211> LENGTH: 23
<212> TYPE: PRT
<213> ORGANISM: Artificial
<220> FEATURE:
<223> OTHER INFORMATION: Conserved Motif
<220> FEATURE:
```

-continued

```
<221> NAME/KEY: MISC_FEATURE
<222> LOCATION: (1)..(1)
<223> OTHER INFORMATION: x = k or r
<220> FEATURE:
<221> NAME/KEY: MISC_FEATURE
<222> LOCATION: (2)..(2)
<223> OTHER INFORMATION: x = d, e, q, t, a, k, or s
<220> FEATURE:
<221> NAME/KEY: MISC_FEATURE
<222> LOCATION: (3)..(3)
<223> OTHER INFORMATION: x = a, e, s, or t
<220> FEATURE:
<221> NAME/KEY: MISC_FEATURE
<222> LOCATION: (4)..(4)
<223> OTHER INFORMATION: x = i or l
<220> FEATURE:
<221> NAME/KEY: MISC_FEATURE
<222> LOCATION: (5)..(5)
<223> OTHER INFORMATION: x = s, t, or a
<220> FEATURE:
<221> NAME/KEY: MISC_FEATURE
<222> LOCATION: (6)..(6)
<223> OTHER INFORMATION: x = q, g, d, or s
<220> FEATURE:
<221> NAME/KEY: MISC_FEATURE
<222> LOCATION: (7)..(7)
<223> OTHER INFORMATION: x = f, y, or c
<220> FEATURE:
<221> NAME/KEY: MISC_FEATURE
<222> LOCATION: (9)..(9)
<223> OTHER INFORMATION: x = q, m, or r
<220> FEATURE:
<221> NAME/KEY: MISC_FEATURE
<222> LOCATION: (10)..(10)
<223> OTHER INFORMATION: x = f or l
<220> FEATURE:
<221> NAME/KEY: MISC_FEATURE
<222> LOCATION: (11)..(11)
<223> OTHER INFORMATION: i, v, or l
<220> FEATURE:
<221> NAME/KEY: MISC_FEATURE
<222> LOCATION: (13)..(13)
<223> OTHER INFORMATION: x = n, k, or g
<220> FEATURE:
<221> NAME/KEY: MISC_FEATURE
<222> LOCATION: (14)..(14)
<223> OTHER INFORMATION: x = l or i
<220> FEATURE:
<221> NAME/KEY: MISC_FEATURE
<222> LOCATION: (16)..(16)
<223> OTHER INFORMATION: x = y or f
<220> FEATURE:
<221> NAME/KEY: MISC_FEATURE
<222> LOCATION: (17)..(17)
<223> OTHER INFORMATION: x = a, l, i, or t
<220> FEATURE:
<221> NAME/KEY: MISC_FEATURE
<222> LOCATION: (19)..(19)
<223> OTHER INFORMATION: x = y or f
<220> FEATURE:
<221> NAME/KEY: MISC_FEATURE
<222> LOCATION: (20)..(20)
<223> OTHER INFORMATION: x = a, i, or l
<220> FEATURE:
<221> NAME/KEY: MISC_FEATURE
<222> LOCATION: (21)..(21)
<223> OTHER INFORMATION: x = f, i, l, or m
<220> FEATURE:
<221> NAME/KEY: MISC_FEATURE
<222> LOCATION: (22)..(22)
<223> OTHER INFORMATION: x = f, l, i, or y
<220> FEATURE:
<221> NAME/KEY: MISC_FEATURE
<222> LOCATION: (23)..(23)
<223> OTHER INFORMATION: x = p or s
```

```
<400> SEQUENCE: 95

Xaa Xaa Xaa Xaa Xaa Xaa Xaa Tyr Xaa Xaa Xaa Trp Xaa Xaa Phe Xaa
1               5                   10                  15

Xaa Glu Xaa Xaa Xaa Xaa Xaa
            20
```